US011038121B2

(12) United States Patent
Xia

(10) Patent No.: US 11,038,121 B2
(45) Date of Patent: Jun. 15, 2021

(54) 9 MEMBERED RING CARBAZOLE COMPOUNDS

(71) Applicant: BEIJING SUMMER SPROUT TECHNOLOGY CO., LTD., Beijing (CN)

(72) Inventor: Chuanjun Xia, Lawrenceville, NJ (US)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 104 days.

(21) Appl. No.: 16/378,559

(22) Filed: Apr. 8, 2019

(65) Prior Publication Data

US 2019/0312214 A1 Oct. 10, 2019

Related U.S. Application Data

(60) Provisional application No. 62/655,219, filed on Apr. 9, 2018.

(51) Int. Cl.

| | |
|---|---|
| ***H01L 51/00*** | (2006.01) |
| ***C07D 487/04*** | (2006.01) |
| ***C07D 495/04*** | (2006.01) |
| ***H01L 51/50*** | (2006.01) |

(52) U.S. Cl.

CPC ........ *H01L 51/0072* (2013.01); *C07D 487/04* (2013.01); *C07D 495/04* (2013.01); *H01L 51/006* (2013.01); *H01L 51/0061* (2013.01); *H01L 51/0067* (2013.01); *H01L 51/0073* (2013.01); *H01L 51/0074* (2013.01); *H01L 51/5016* (2013.01); *H01L 51/5056* (2013.01); *H01L 51/5072* (2013.01); *H01L 51/5096* (2013.01)

(58) Field of Classification Search

CPC .. C07D 487/04; C07D 487/06; C07D 495/04; C07D 495/16; H01L 51/006; H01L 51/0061; H01L 51/0067; H01L 51/0072; H01L 51/0073; H01L 51/0074; H01L 51/5012; H01L 51/5016; H01L 51/5056; H01L 51/5072; H01L 51/5096

See application file for complete search history.

(56) References Cited

U.S. PATENT DOCUMENTS

| | | | |
|---|---|---|---|
| 5,703,436 | A | 12/1997 | Forrest et al. |
| 5,707,745 | A | 1/1998 | Forrest et al. |
| 5,844,363 | A | 12/1998 | Gu et al. |
| 6,097,147 | A | 8/2000 | Baldo et al. |
| 6,303,238 | B1 | 10/2001 | Thompson et al. |
| 7,279,704 | B2 | 10/2007 | Walters et al. |
| 7,968,146 | B2 | 6/2011 | Wagner et al. |
| 2003/0230980 | A1 | 12/2003 | Forrest et al. |
| 2004/0174116 | A1 | 9/2004 | Lu et al. |
| 2015/0349273 | A1 | 12/2015 | Hung et al. |
| 2016/0163998 | A1 | 6/2016 | Saito et al. |
| 2016/0359122 | A1 | 12/2016 | Boudreault et al. |
| 2017/0018721 | A1 | 1/2017 | Tsang et al. |
| 2018/0331301 | A1 | 11/2018 | Parham et al. |

FOREIGN PATENT DOCUMENTS

CN 111269239 A * 6/2020

OTHER PUBLICATIONS

Google Patents translation for CN 111269239 A (publication date Jun. 2020). (Year: 2020).*

C.W. Tang et al. "Organic electroluminescent diodes", Appl. Phys. Ltt. 51, 913 (1987); doi: 10.1063/1.98799.

Hiroki Uoyama et al. "Highli efficient organic light-emitting diodes from delayed fluorescence", Nature, vol. 492, Dec. 13, 2012. doi:10.1038/nature11687, 234.

* cited by examiner

*Primary Examiner* — Dawn L Garrett

(74) *Attorney, Agent, or Firm* — Alston & Bird LLP

(57) ABSTRACT

Novel 9 membered ring carbazole compounds are disclosed, which can be used as host materials etc. in an electroluminescent device. Compared with the existing host materials etc., these novel compounds can effectively modulate the charge transporting properties in the above materials and give OLEDs better performance. Also disclosed are an electroluminescent device and a formulation.

17 Claims, 2 Drawing Sheets

9 MEMBERED RING CARBAZOLE COMPOUNDS

This application claims the benefit of U.S. Provisional Application No. 62/655,219, filed Apr. 9, 2018, the entire content of which is incorporated herein by reference.

FIELD OF THE INVENTION

The present invention relates to compounds for organic electronic devices, such as organic light emitting devices. More specifically, the present invention relates to 9 membered ring carbazole compounds, an organic electroluminescent device and a formulation comprising the compounds.

BACKGROUND ART

An organic electronic device is preferably selected from the group consisting of organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This invention laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since OLED is a self-emitting solid state device, it offers tremendous potential for display and lighting applications. In addition, the inherent properties of organic materials, such as their flexibility, may make them well suited for particular applications such as fabrication on flexible substrates.

OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of a fluorescent OLED is only 25%. This limitation hindered the commercialization of OLED. In 1997, Forrest and Thompson reported phosphorescent OLED, which uses triplet emission from heave metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. Small molecule refers to any organic or organometallic material that is not a polymer. The molecular weight of a small molecule can be large as long as it has well defined structure. Dendrimers with well-defined structures are considered as small molecules. Polymer OLEDs include conjugated polymers and non-conjugated polymers with pendant emitting groups. Small molecule OLED can become a polymer OLED if post polymerization occurred during the fabrication process.

There are various methods for OLED fabrication. Small molecule OLEDs are generally fabricated by vacuum thermal evaporation. Polymer OLEDs are fabricated by solution process, such as spin-coating, ink-jet printing, and nozzle printing. Small molecule OLEDs can also be fabricated by solution process if the materials can be dissolved or dispersed in solvents.

The emitting color of an OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent emitters still suffer from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

Host materials play a key role in the OLED device, such as the hole and electron transporting balance and the effective dispersion of light-emitting materials. The charge-transfer performance of the host materials often directly affects the driving voltage and efficiency of the OLED device. The 9 membered ring carbazole compounds herein are capable of effectively regulating their charge transporting properties, especially for electrons. The present invention provides a series of novel 9 membered ring carbazole compounds. These compounds can effectively modulate the charge transporting properties in the host materials and give OLEDs better performance.

SUMMARY OF THE INVENTION

The present invention aims to provide a new series of 9 membered ring carbazole compounds to solve at least part of the above problems. The compounds can be used as host materials, charge transporting materials, charge blocking materials and emitters in an organic electroluminescent device. Compared to existing materials, the novel compounds can effectively modulate the charge transporting properties in the above materials and give OLEDs better performance.

According to an embodiment of the present invention, a compound having Formula 1 is disclosed:

Formula 1

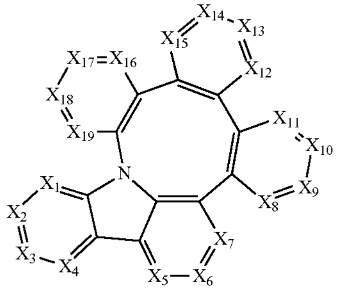

wherein $X_1$ to $X_{19}$ are each independently selected from N or CR;

Wherein R are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 50 carbon atoms, a substituted or unsubstituted heteroaryl group having 3 to 50 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring.

According to another embodiment, an electroluminescent device is disclosed, which comprises:

an anode, a cathode, and an organic layer, disposed between the anode and the cathode, comprising a compound of Formula 1:

Formula 1

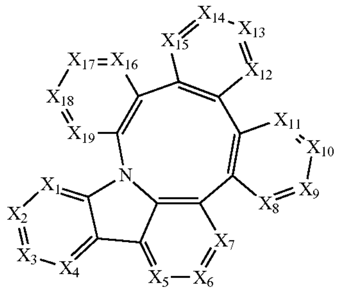

wherein $X_1$ to $X_{19}$ are each independently selected from N or CR;

Wherein R are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 50 carbon atoms, a substituted or unsubstituted heteroaryl group having 3 to 50 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring.

According to yet another embodiment, a formulation comprising a compound of Formula 1 is also disclosed.

The novel 9 membered ring carbazole compounds disclosed in the present invention can be used as host materials, charge transporting materials, charge blocking materials or emitters in an electroluminescent device. Compared to existing materials, the novel compounds can effectively modulate the charge transporting properties in the above materials and give OLEDs better performance.

DETAILED DESCRIPTION

Figure 1:
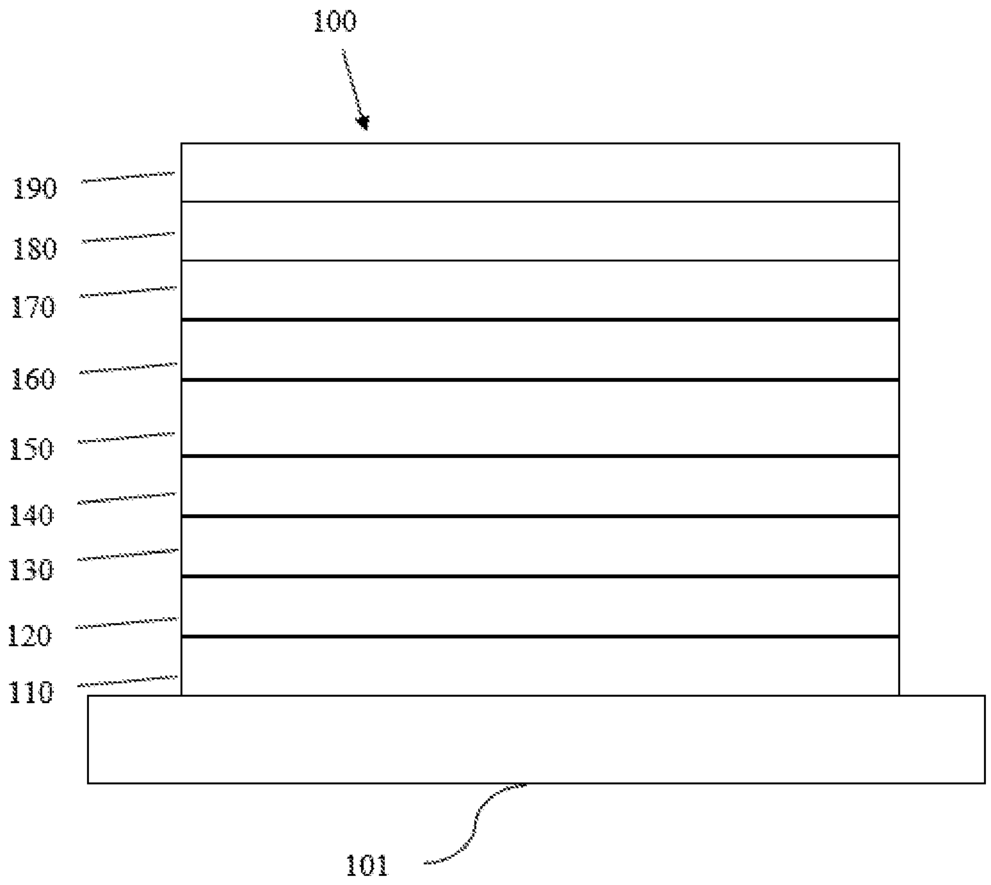
FIG. 1 schematically shows an organic light emitting device that can incorporate the compound or the formulation disclosed herein.

OLEDs can be fabricated on various types of substrates such as glass, plastic, and metal foil. FIG. 1 schematically shows the organic light emitting device 100 without limitation. The figures are not necessarily drawn to scale. Some of the layer in the figure can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, which are incorporated by reference in its entirety.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F4-TCNQ at a molar ratio of 50:1, as disclosed in U.S. Patent Application Publication No. 2003/0230980, which is incorporated by reference in its entirety. Examples of host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

The layered structure described above is provided by way of non-limiting example. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have a two layers of different emitting materials to achieve desired emission spectrum.

In one embodiment, an OLED may be described as having an "organic layer" disposed between a cathode and an anode. This organic layer may comprise a single layer or multiple layers.

Figure 2:
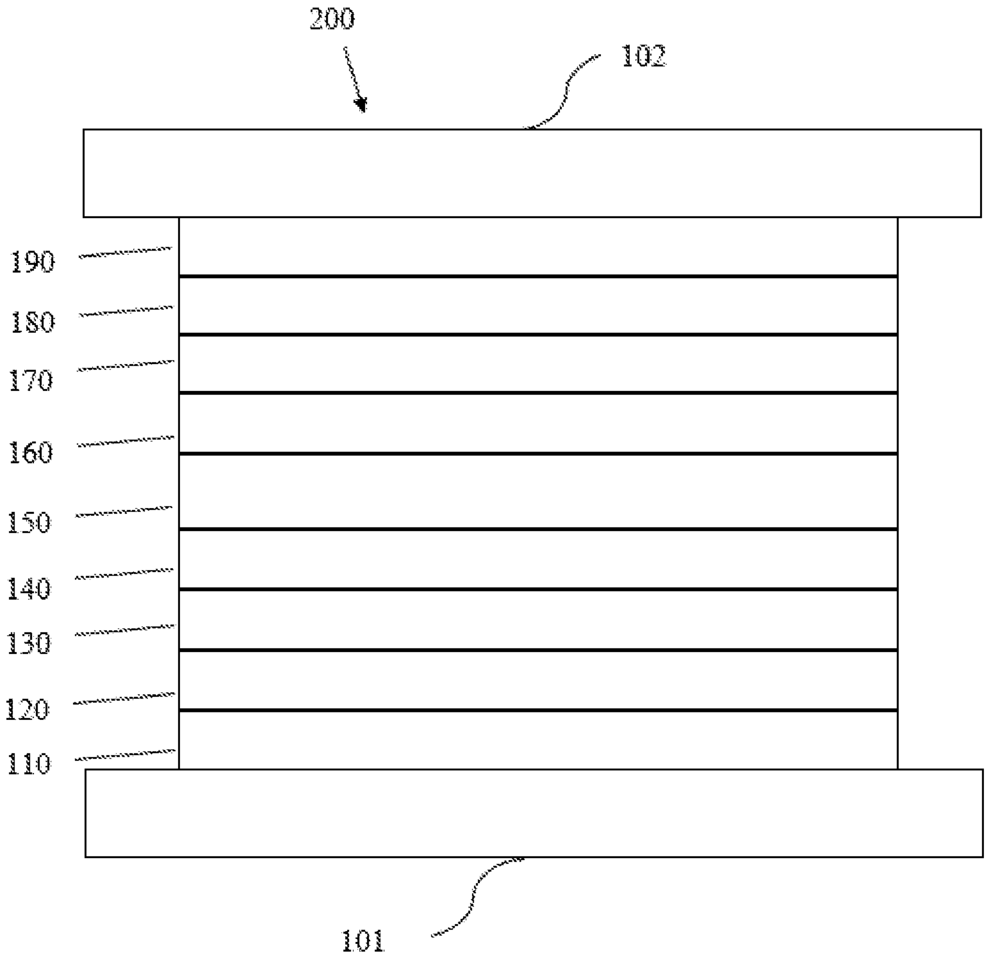
FIG. 2 schematically shows another organic light emitting device that can incorporate the compound or the formulation disclosed herein.
Figure 3:
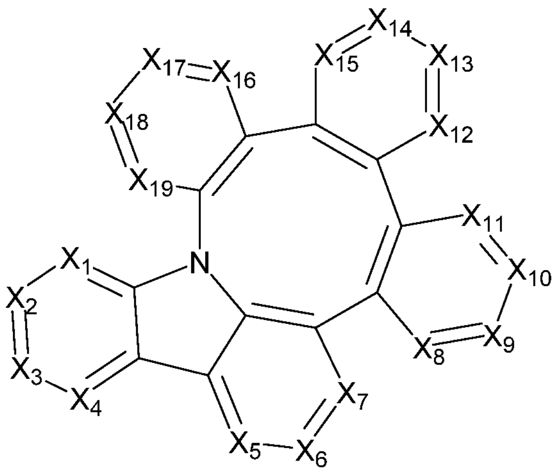
FIG. 3 shows the Formula 1 of the compound disclosed herein.

An OLED can be encapsulated by a barrier layer to protect it from harmful species from the environment such as moisture and oxygen. FIG. 2 schematically shows the organic light emitting device 200 without limitation. FIG. 2 differs from FIG. 1 in that the organic light emitting device 200 include a barrier layer 102, which is above the cathode 190. Any material that can provide the barrier function can be used as the barrier layer such as glass and organic-inorganic hybrid layers. The barrier layer should be placed directly or indirectly outside of the OLED device. Multilayer thin film encapsulation was described in U.S. Pat. No. 7,968,146, which is herein incorporated by reference in its entirety.

Devices fabricated in accordance with embodiments of the invention can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic rings.

Definition of Terms of Substituents halogen or halide—as used herein includes fluorine, chlorine, bromine, and iodine.

Alkyl—contemplates both straight and branched chain alkyl groups. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group. Additionally, the alkyl group may be optionally substituted. The carbons in the alkyl chain can be replaced by other hetero atoms. Of the above, preferred are methyl group, ethyl group, propyl group, isopropyl group, n-butyl group, s-butyl group, isobutyl group, t-butyl group, n-pentyl group, and neopentyl group.

Cycloalkyl—as used herein contemplates cyclic alkyl groups. Preferred cycloalkyl groups are those containing 4 to 10 ring carbon atoms and includes cyclobutyl, cyclopentyl, cyclohexyl, 4-methylcyclohexyl, 4,4-dimethylcyclohexyl, 1-adamantyl, 2-adamantyl, 1-norbornyl, 2-norbornyl and the like. Additionally, the cycloalkyl group may be optionally substituted. The carbons in the ring can be replaced by other hetero atoms.

Alkenyl—as used herein contemplates both straight and branched chain alkene groups. Preferred alkenyl groups are those containing two to fifteen carbon atoms. Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl 1-butenyl group, and 3-phenyl-1-butenyl group. Additionally, the alkenyl group may be optionally substituted.

Alkynyl—as used herein contemplates both straight and branched chain alkyne groups. Preferred alkynyl groups are those containing two to fifteen carbon atoms. Additionally, the alkynyl group may be optionally substituted.

Aryl or aromatic group—as used herein contemplates noncondensed and condensed systems. Preferred aryl groups are those containing six to sixty carbon atoms, preferably six to fifty carbon atoms, more preferably six to thirty carbon atoms, more preferably six to twenty carbon atoms, more preferably six to twelve carbon atoms. Examples of the aryl group include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl group may be optionally substituted. Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl) phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quarterphenyl group.

Heterocyclic group or heterocycle—as used herein contemplates aromatic and non-aromatic cyclic groups. Heteroaromatic also means heteroaryl. Preferred non-aromatic heterocyclic groups are those containing 3 to 7 ring atoms which includes at least one hetero atom such as nitrogen, oxygen, and sulfur. The heterocyclic group can also be an aromatic heterocyclic group having at least one heteroatom selected from nitrogen atom, oxygen atom, sulfur atom, and selenium atom.

Heteroaryl—as used herein contemplates noncondensed and condensed hetero-aromatic groups that may include from one to five heteroatoms. Preferred heteroaryl groups are those containing three to fifty carbon atoms, preferably three to thirty carbon atoms, more preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—it is represented by —O-Alkyl. Examples and preferred examples thereof are the same as those described above. Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Aryloxy—it is represented by —O-Aryl or —O-heteroaryl. Examples and preferred examples thereof are the same as those described above. Examples of the aryloxy group having 6 to 40 carbon atoms include phenoxy group and biphenyloxy group.

Arylalkyl—as used herein contemplates an alkyl group that has an aryl substituent. Additionally, the arylalkyl group may be optionally substituted. Examples of the arylalkyl group include benzyl group, 1-phenylethyl group, 2-phenylethyl group, 1-phenylisopropyl group, 2-phenylisopropyl group, phenyl-t-butyl group, alpha-naphthylmethyl group, 1-alpha-naphthylethyl group, 2-alpha-naphthylethyl group, 1-alpha-naphthylisopropyl group, 2-alpha-naphthylisopropyl group, beta-naphthylmethyl group, 1-beta-naphthylethyl group, 2-beta-naphthylethyl group, 1-beta-naphthylisopropyl group, 2-beta-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro2-phenylisopropyl group. Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The term “aza” in azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline, dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, arylalkyl, alkoxy, aryloxy, amino, cyclic amino, silyl, alkenyl, cycloalkenyl, heteroalkenyl, alkynyl, aryl, heteroaryl, an acyl group, a carbonyl group, a carboxylic acid group, an ether group, an ester group, a nitrile group, an isonitrile group, a sulfanyl group, a sulfinyl group, a sulfonyl group, a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in this disclosure, the hydrogen atoms can be partially or fully replaced by deuterium. Other atoms such as carbon and nitrogen, can also be replaced by their other stable isotopes. The replacement by other stable isotopes in the compounds may be preferred due to its enhancements of device efficiency and stability.

In the compounds mentioned in this disclosure, multi substitutions refer to a range that includes a double substitution, up to the maximum available substitutions. When some substituent of the compound mentioned in this disclosure represent multi substitutions (including double substitution, triple substitution, tetra substitution, and etc.), it refers that the substituent can exist at multiple substitutable positions, and the substituents existing at the multiple substitutable positions can have the same structures or different structures.

In the compounds mentioned in this disclosure, the expression that adjacent substitutions can be optionally joined to form a ring is intended to be taken to mean that two radicals are linked to each other by a chemical bond. This is illustrated by the following scheme:

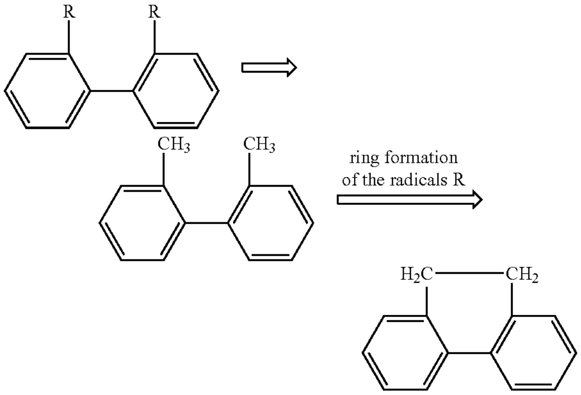

Furthermore, the expression that adjacent substitutions can be optionally joined to form a ring is also intended to be taken to mean that in the case where one of the two radicals represents hydrogen, the second radical is bonded at a position to which the hydrogen atom was bonded, with formation of a ring. This is illustrated by the following scheme:

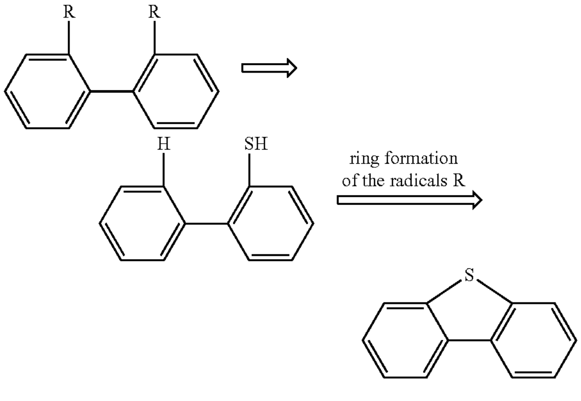

By analogy, it should also be understood that, in the case that both radicals represent hydrogen atoms, ring formation takes place by a single bond instead of the two hydrogen atoms.

Furthermore, the expression that adjacent substitutions can be optionally joined to form a ring is also intended to be taken to mean that in the case where one of the two radicals represents hydrogen, the second radical is bonded at a position to which the hydrogen atom was bonded, with formation of a fused ring. The fused ring can include a hetero atom. This is illustrated by the following scheme:

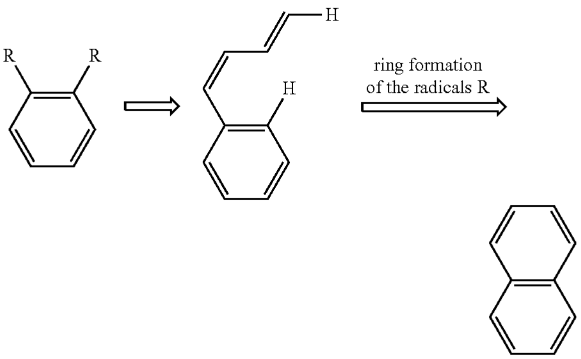

According to an embodiment of the present invention, a compound having a Formula 1 is disclosed:

Formula 1

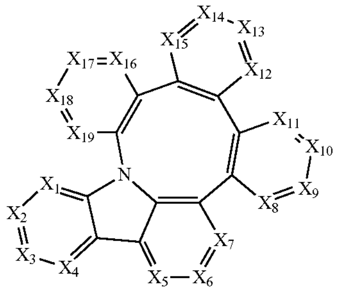

wherein $X_1$ to $X_{19}$ are each independently selected from the group consisting of CR, and N;

Wherein R are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 50 carbon atoms, a substituted or unsubstituted heteroaryl group having 3 to 50 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring.

According to one embodiment of the present invention, wherein $X_1$ to $X_{19}$ are each independent CR.

According to one embodiment of the present invention, wherein the compound has a Formula 2 structure:

Formula 2

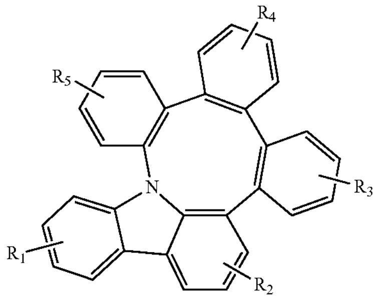

Wherein $R_1$, $R_3$, $R_4$, and $R_5$ independently represent mono, di, tri, tetra substitution, or no substitution;

$R_2$ independently represent mono, di, tri substitution, or no substitution;

$R_1$, $R_2$, $R_3$, $R_4$, and $R_5$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 50 carbon atoms, a substituted or unsubstituted heteroaryl group having 3 to 50 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring.

According to one embodiment of the present invention, wherein the compound has a structure of anyone of Formula 3-6:

Formula 3

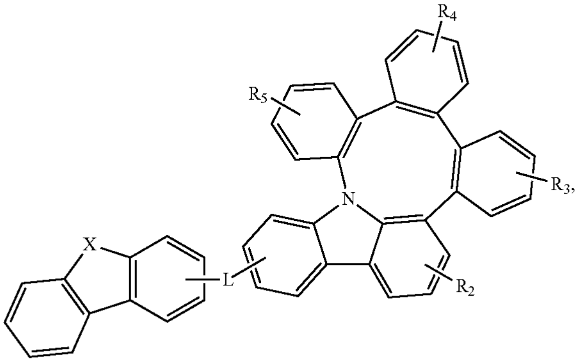

Formula 4

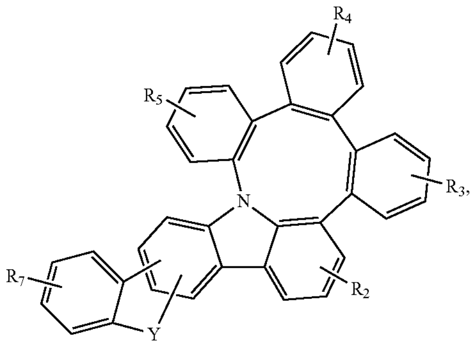

Formula 5

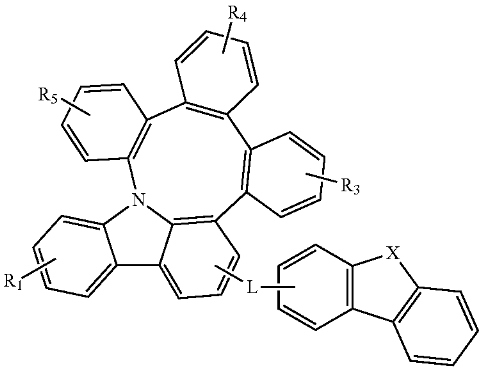

,

Formula 6

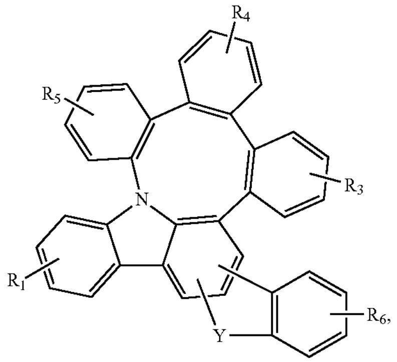

Wherein $R_1$, $R_3$, $R_4$, $R_5$, $R_6$, and $R_7$ independently represent mono, di, tri, tetra substitution, or no substitution;

$R_2$ independently represent mono, di, tri substitution, or no substitution;

X, and Y are each independently selected from the group consisting of O, S, Se, NR', CR''R''' and SiR''''R''''';

R', R'', R''', R'''', R''''', $R_1$, $R_2$, $R_3$, $R_4$, $R_5$, $R_6$, and $R_7$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 50 carbon atoms, a substituted or unsubstituted heteroaryl group having 3 to 50 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring;

L is selected from the group consisting of:

Single bond

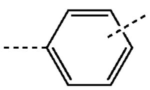,
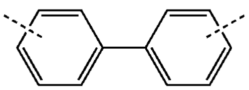,
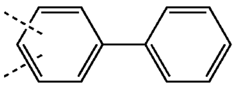,
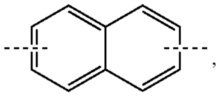,
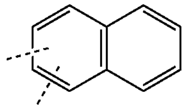,
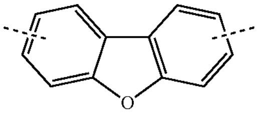,
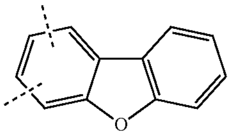,
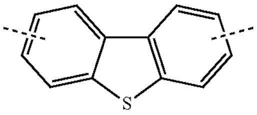,
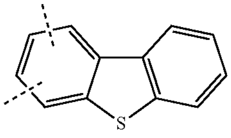,
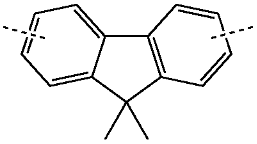,
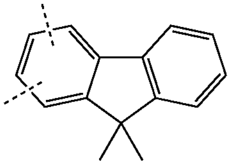,
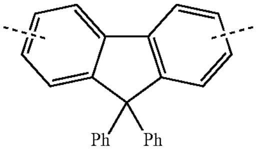,
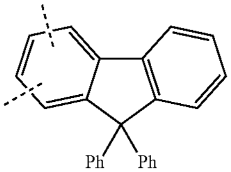,
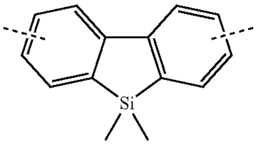, -continued

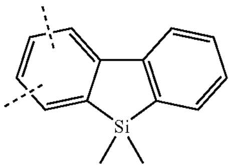,
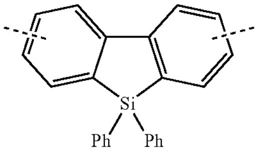,
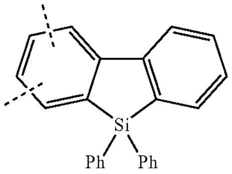,
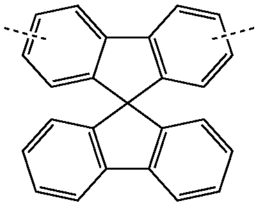,
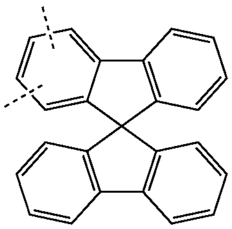,
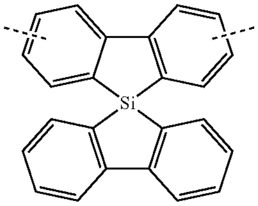,
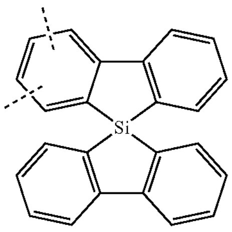,
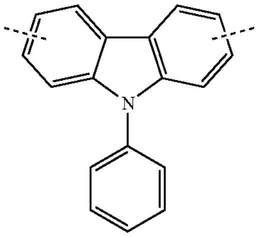,
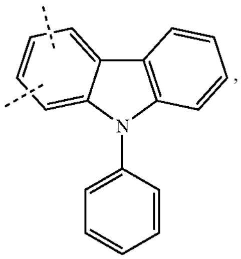,
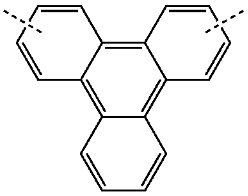,
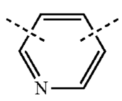,
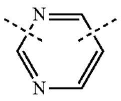,
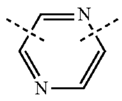,
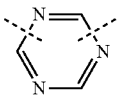,
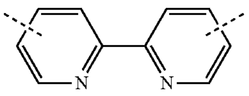,
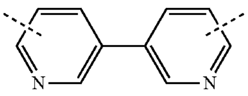,
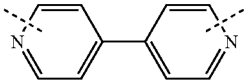.

According to one embodiment of the present invention, wherein the compound has a structure of anyone of Formula 7-9:

Formula 7

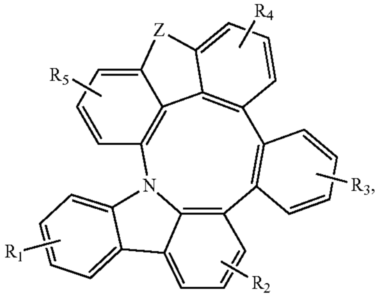

Formula 8

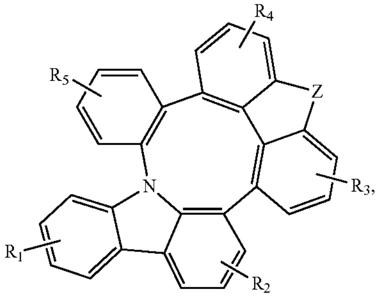

Formula 9

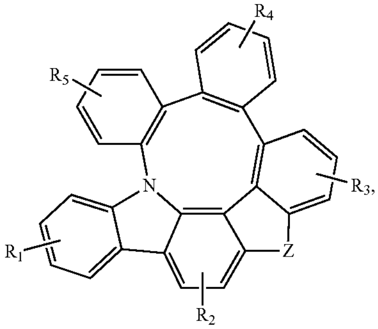

Wherein $R_1$, $R_2$, $R_3$, $R_4$, and $R_5$ independently represent mono, multi substitution, or no substitution; said multi substitution refer to a range that includes di substitution, up to the maximum available substitutions of the formula;

Z are each independently selected from the group consisting of O, S, Se, NR', CR''R''' and SiR''''R''''';

R', R'', R''', R'''', R''''', $R_1$, $R_2$, $R_3$, $R_4$, and $R_5$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 50 carbon atoms, a substituted or unsubstituted heteroaryl group having 3 to 50 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring;

In this embodiment, with the different positions of Z, the maximum available substitutions for the substituents of the ring attached to Z are changed. Taking the Formula 9 in this embodiment as an example, the ring where $R_2$ is located and the ring where $R_3$ is located are connected through Z. In this case, $R_2$ may represent mono, di substitution, or no substitution, and $R_3$ may represent mono, di, tri substitution, or no substitution. Formulas 7 and 8 are analogously.

According to one embodiment of the present invention, wherein $R_1$, and $R_2$ in Formula 2, Formula 7, Formula 8, and Formula 9 are each independently selected from the group consisting of:

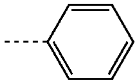
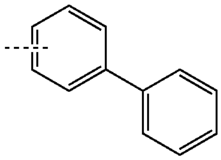
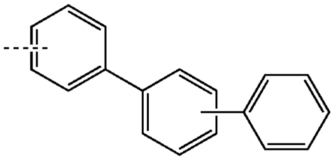
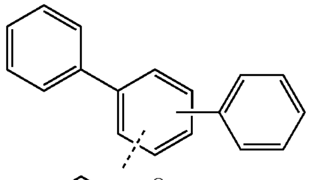
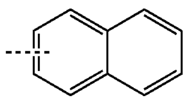
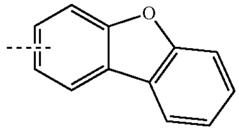
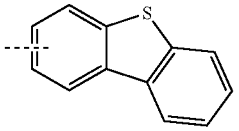
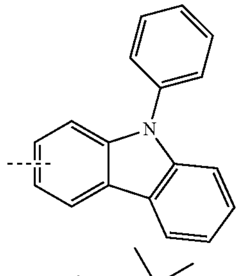
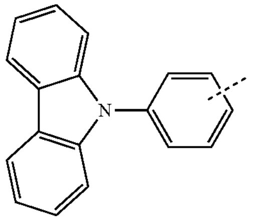
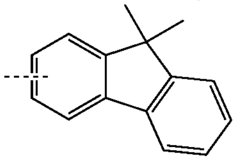
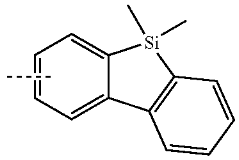
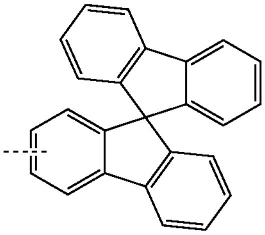
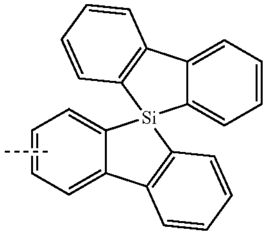

-continued
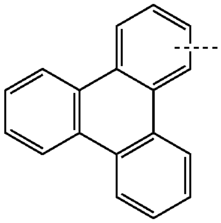
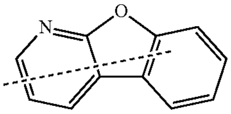
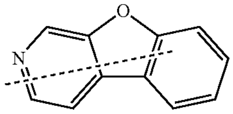
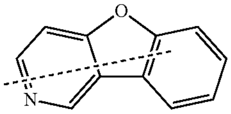
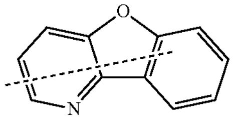
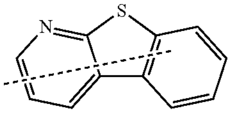
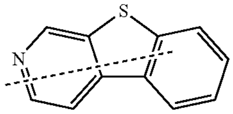
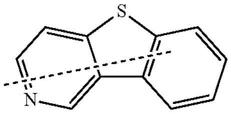
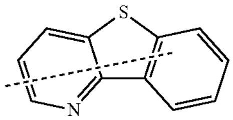
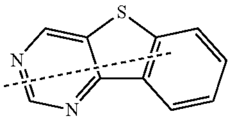
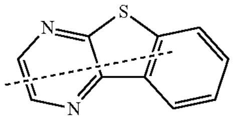
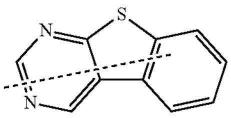
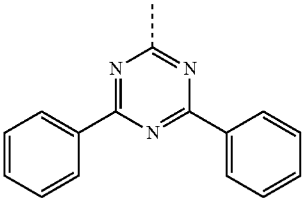
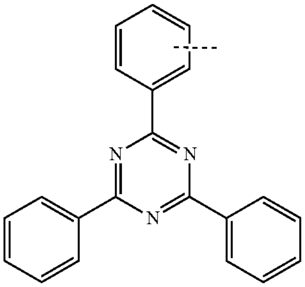
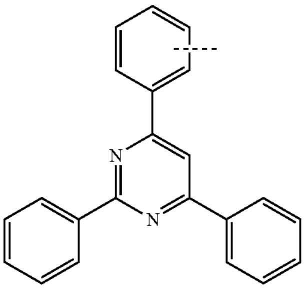
-continued
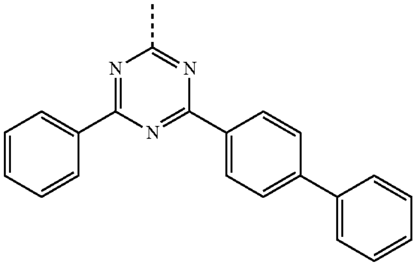
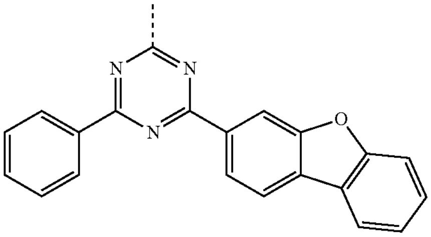
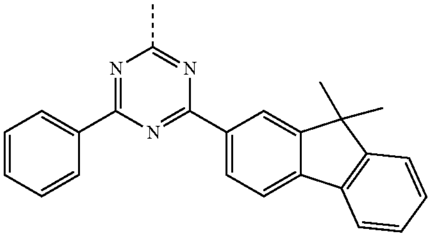
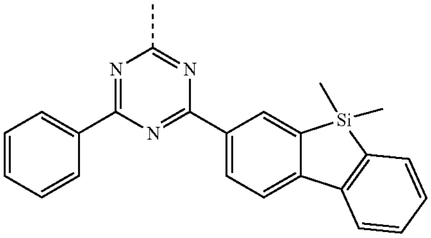
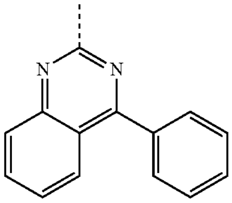
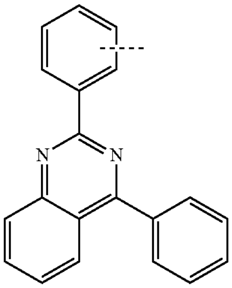
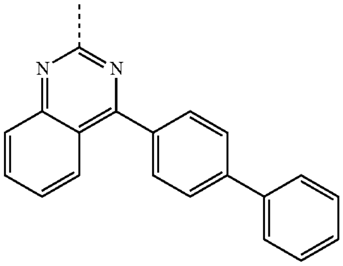
.
According to one embodiment of the present invention, wherein $R_1$, $R_2$, $R_6$, and $R_7$ in Formula 3-6 are each independently selected from the group consisting of:

-continued
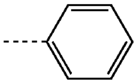
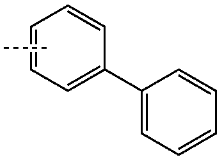
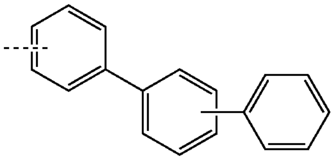
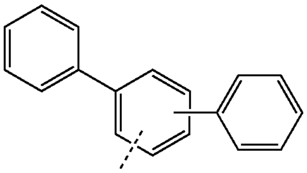
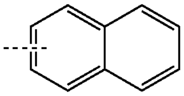
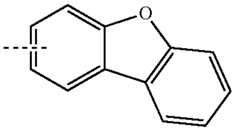
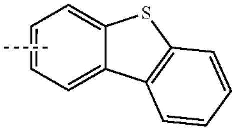
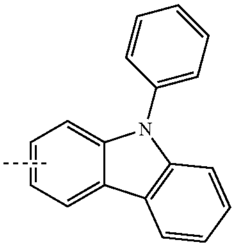
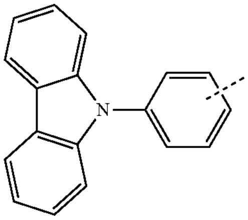
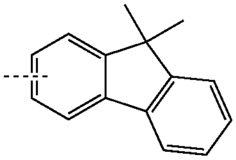
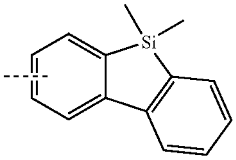
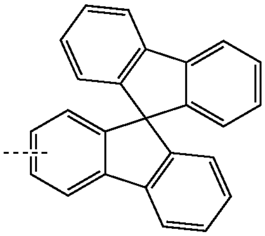
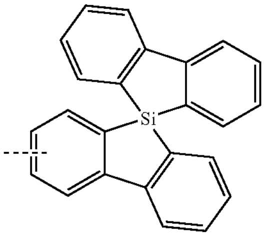
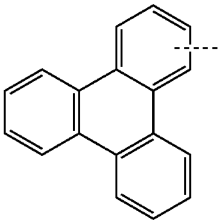
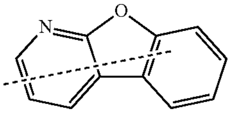
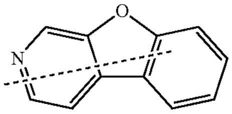
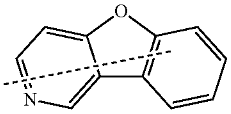
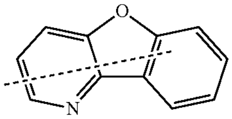
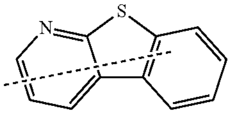
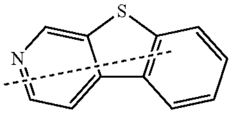
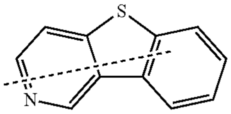
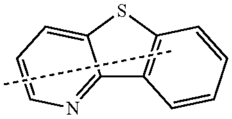
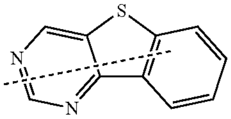
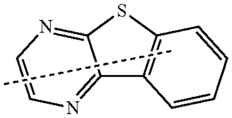
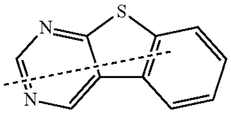
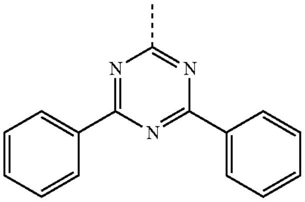
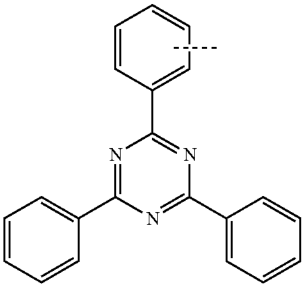
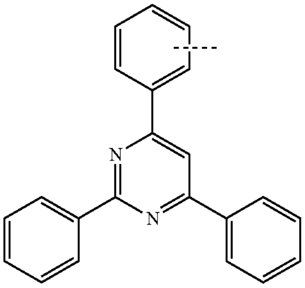
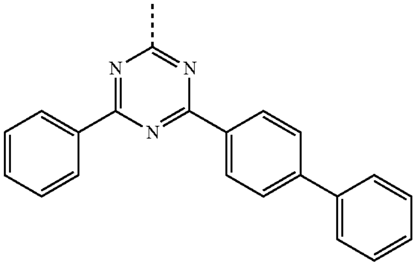
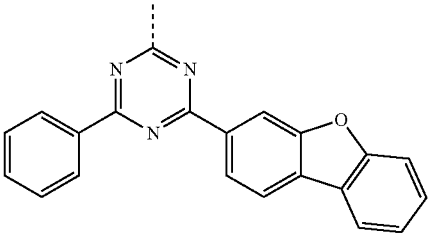

-continued
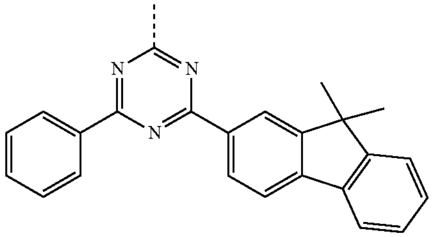
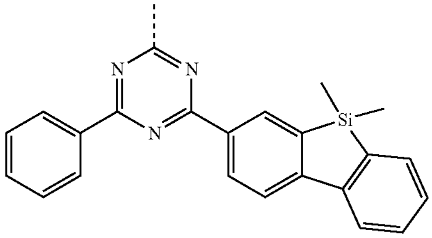
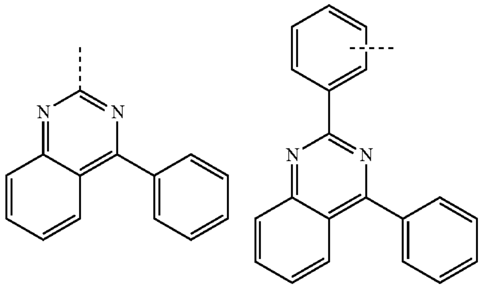
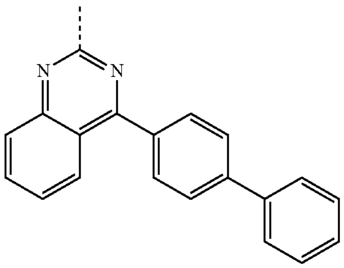
.
According to one embodiment of the present invention, wherein the compound is selected from the group consisting of:
Compound 1
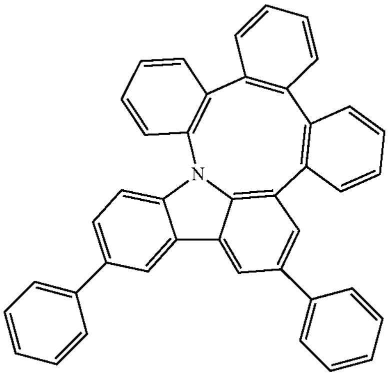
,
-continued
Compound 2
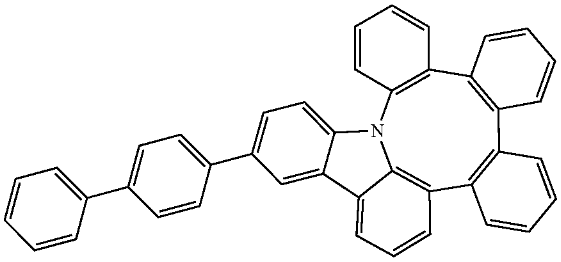
,
Compound 3
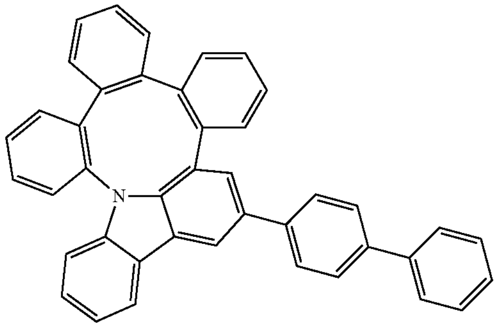
,
Compound 4
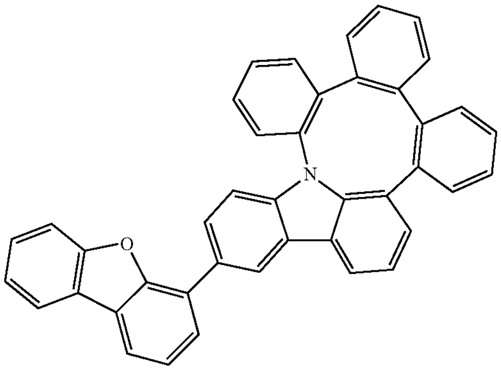
,
Compound 5
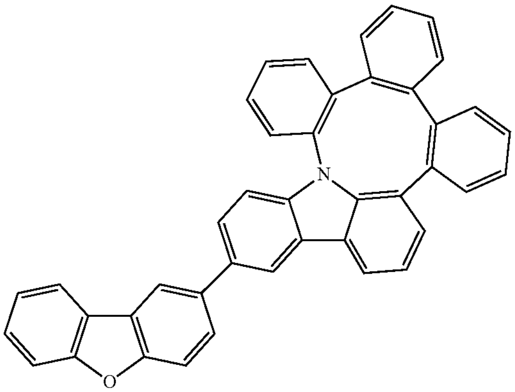
, -continued
Compound 6
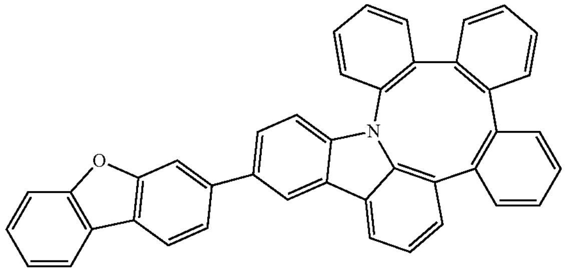
,
Compound 7
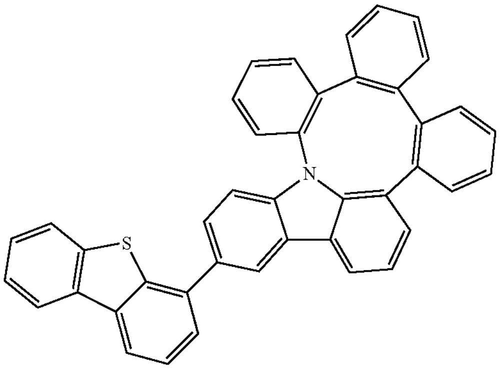
,
Compound 8
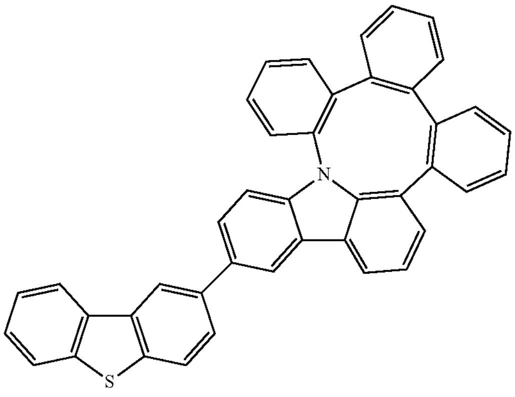
,
Compound 9
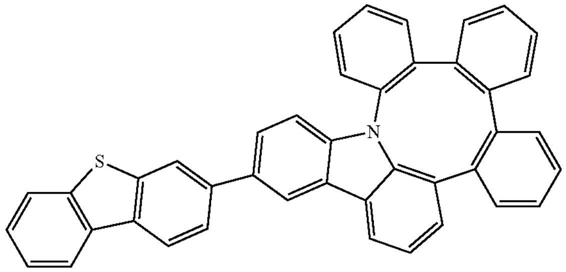
,
-continued
Compound 10
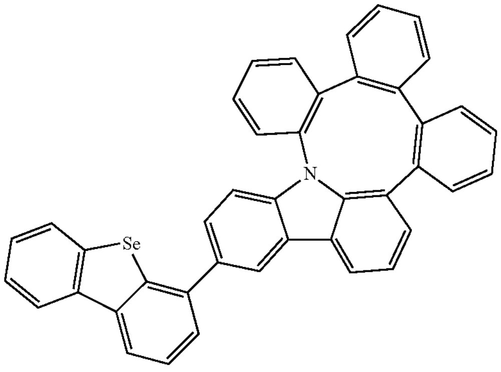
,
Compound 11
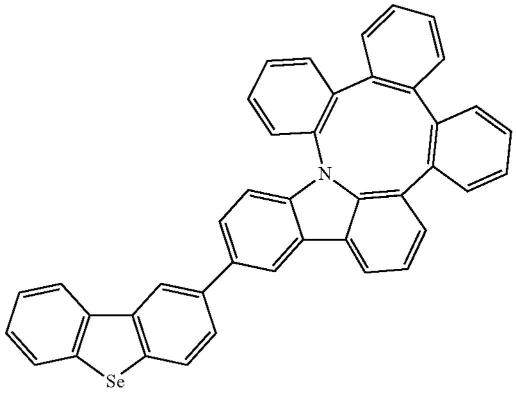
,
Compound 12
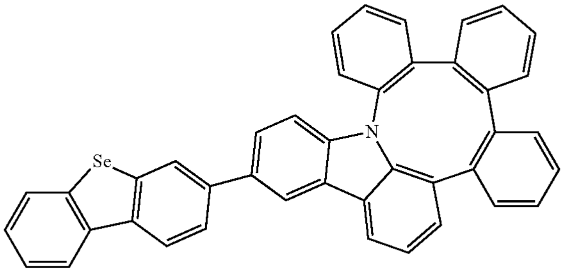
,
Compound 13
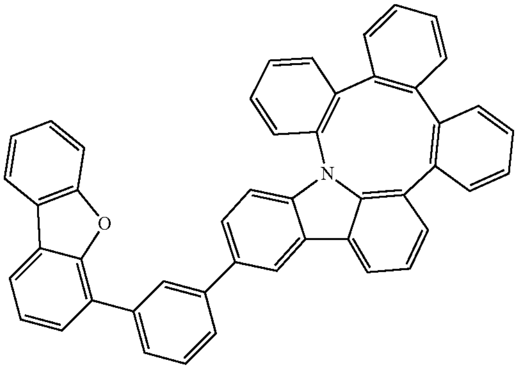
, -continued
Compound 14
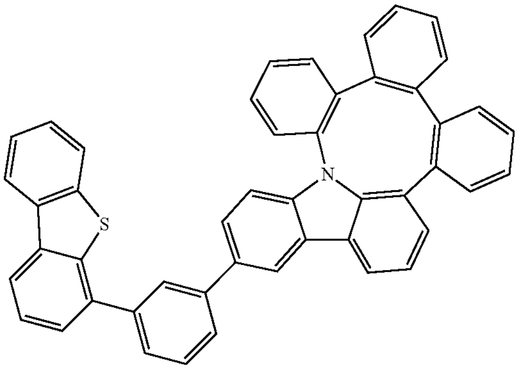
,
Compound 15
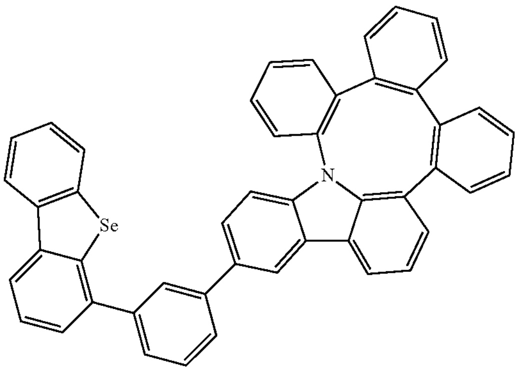
,
Compound 16
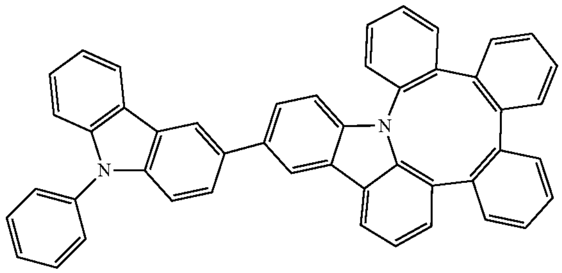
,
Compound 17
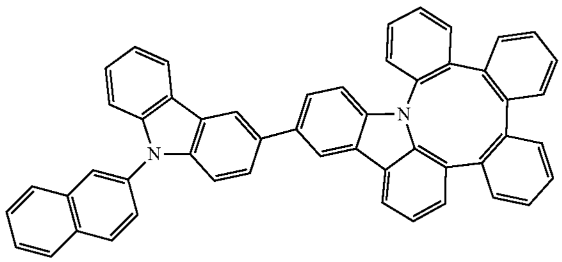
,
-continued
Compound 18
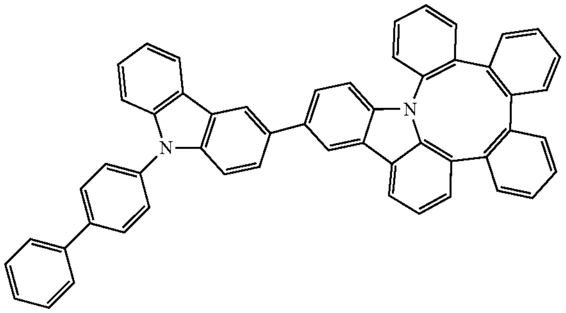
,
Compound 19
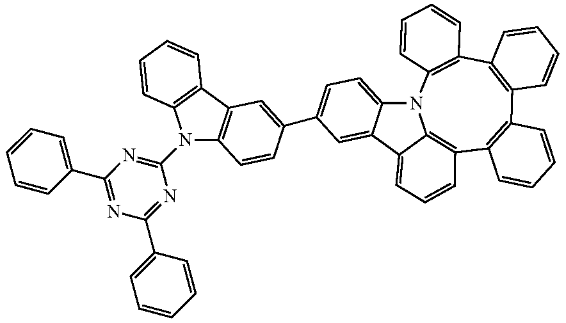
,
Compound 20
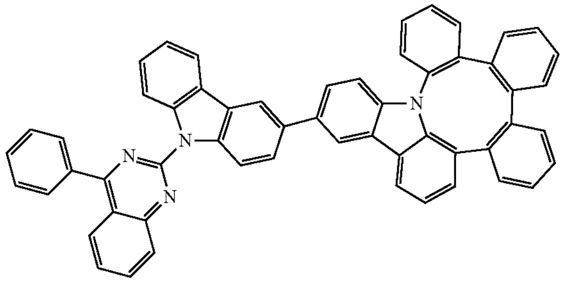
,
Compound 21
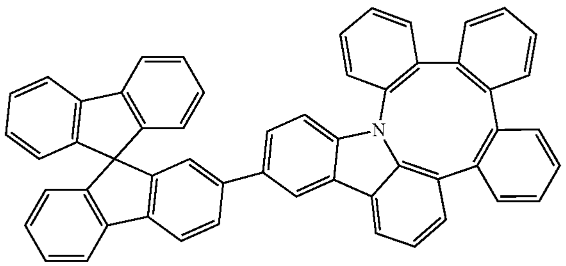
,
Compound 22
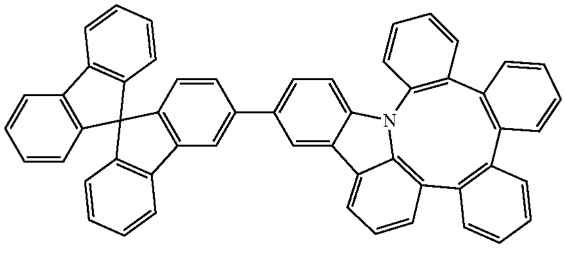
, -continued
Compound 23
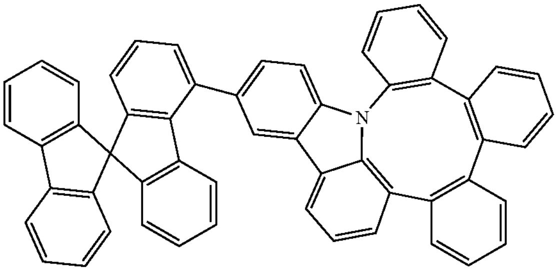
,
Compound 24
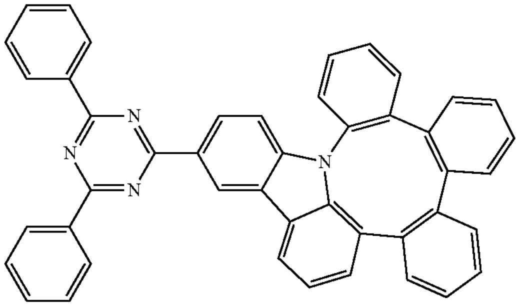
,
Compound 25
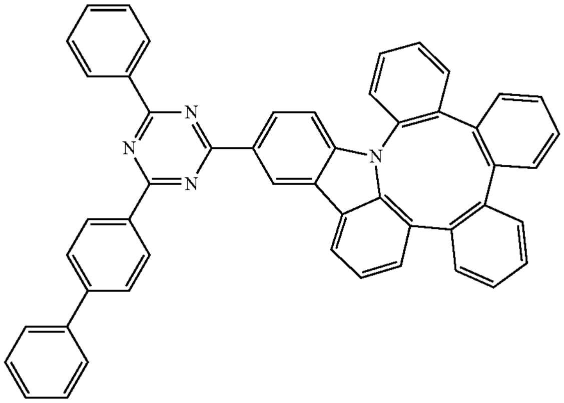
,
Compound 26
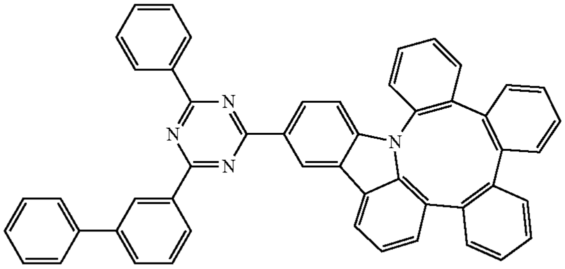
,
-continued
Compound 27
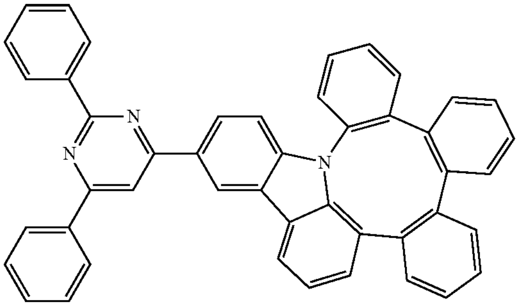
,
Compound 28
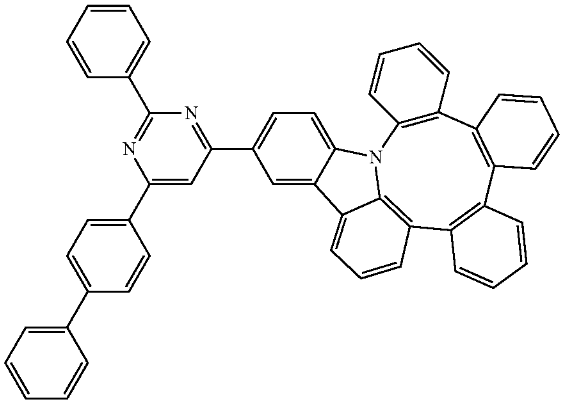
,
Compound 29
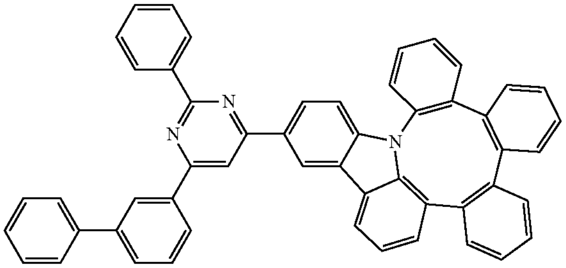
,
Compound 30
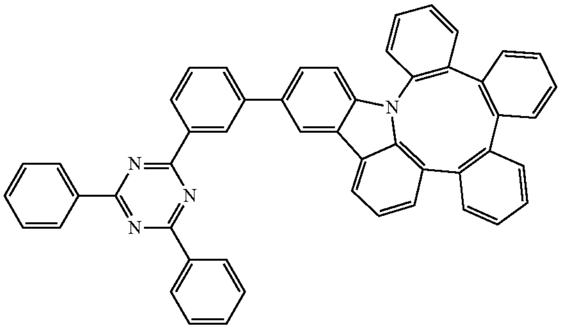
, -continued
Compound 31
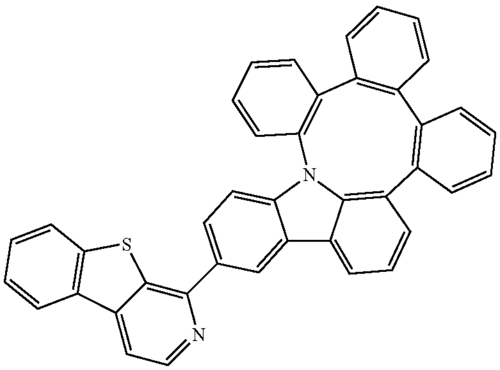
,
Compound 32
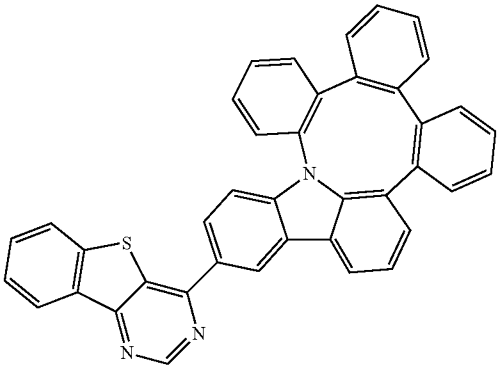
,
Compound 33
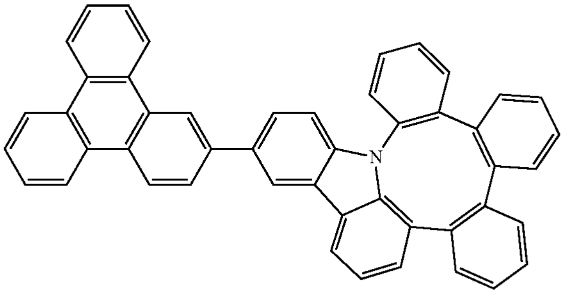
,
Compound 34
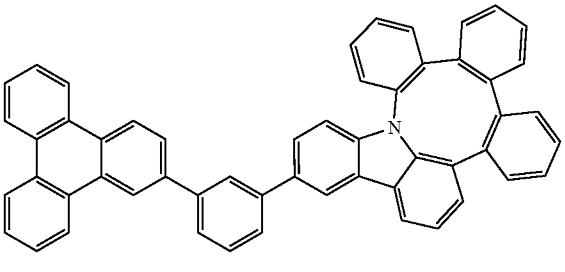
,
-continued
Compound 35
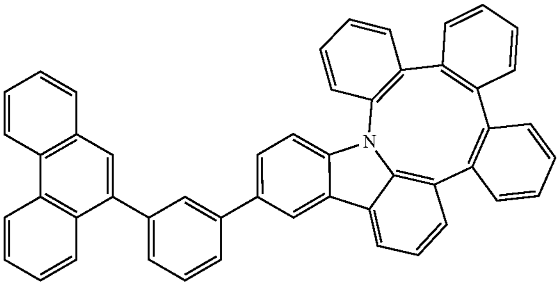
,
Compound 36
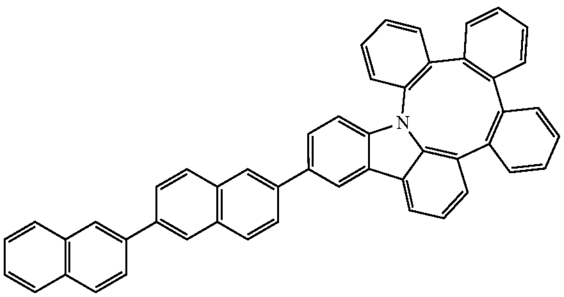
,
Compound 37
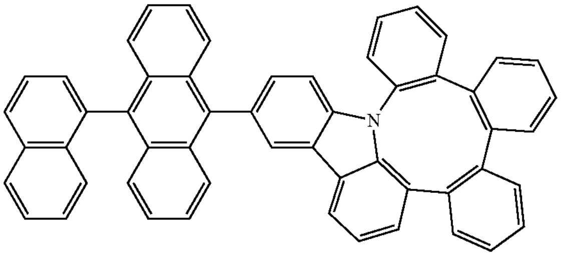
,
Compound 38
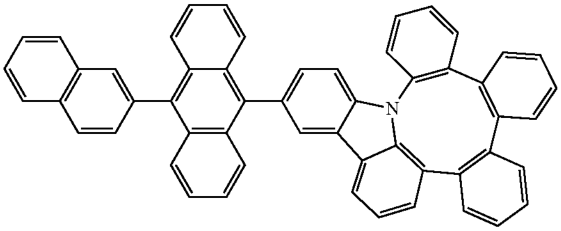
,
Compound 39
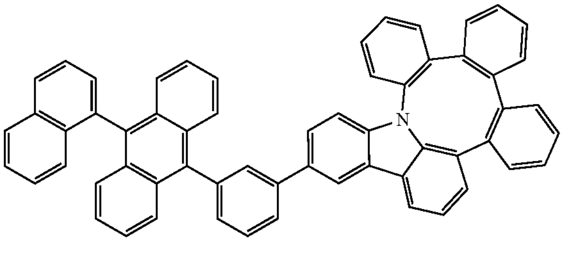
, -continued
Compound 40
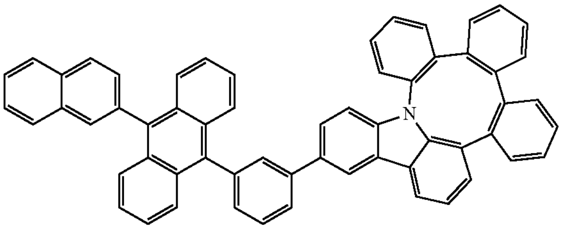
,
Compound 41
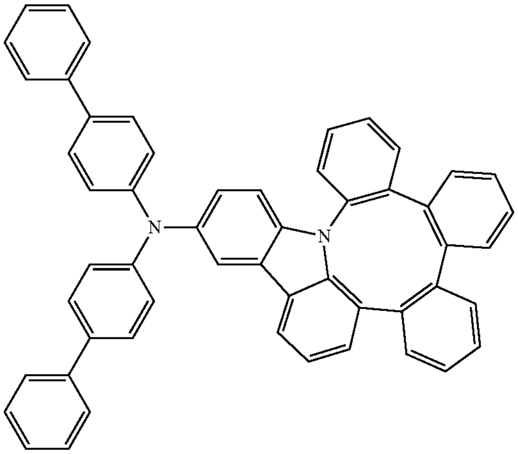
,
Compound 42
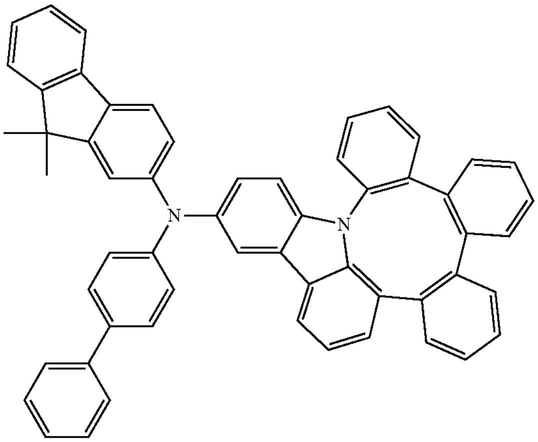
,
Compound 43
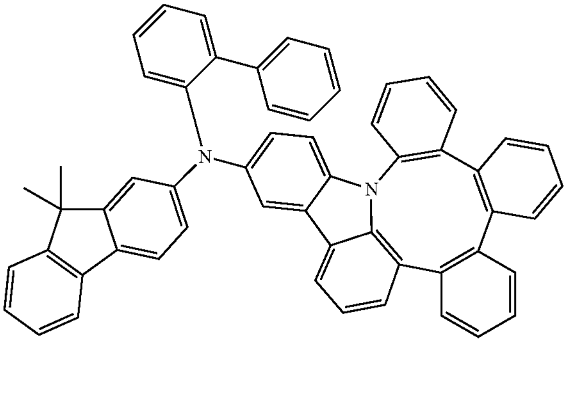
,
-continued
Compound 44
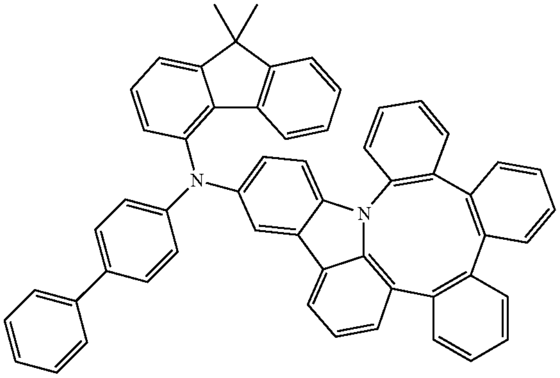
,
Compound 45
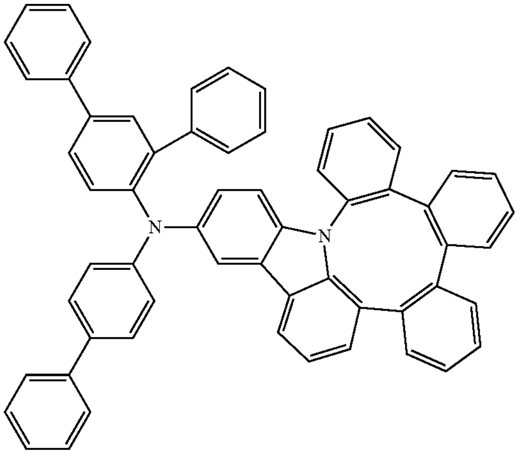
,
Compound 46
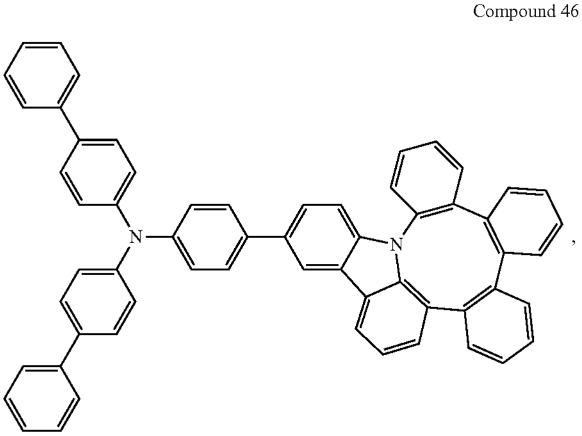
, -continued
Compound 47
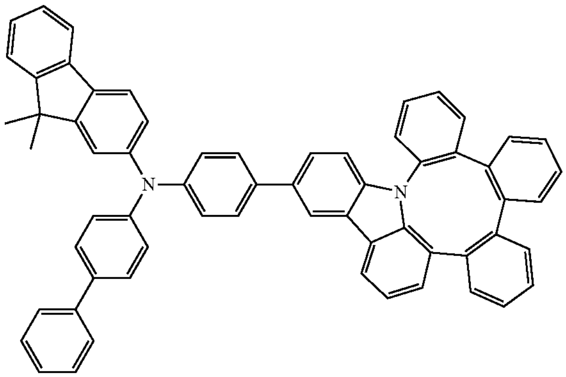
,
Compound 48
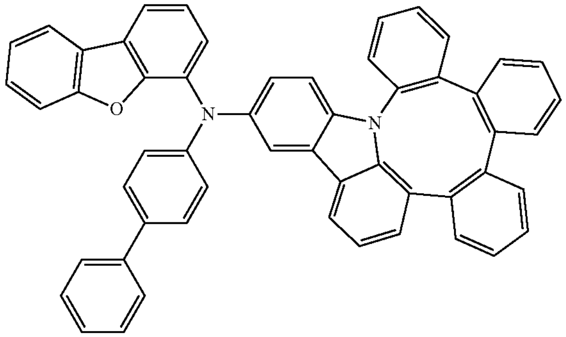
,
Compound 49
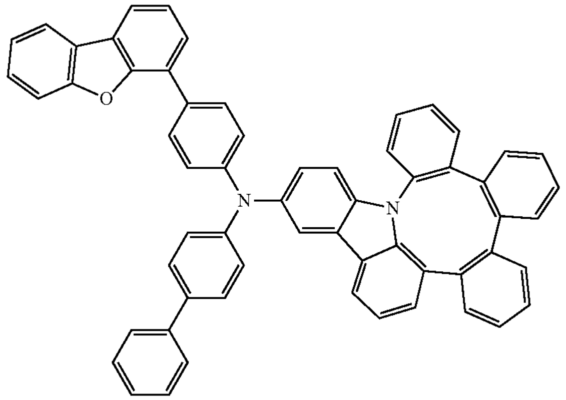
,
Compound 50
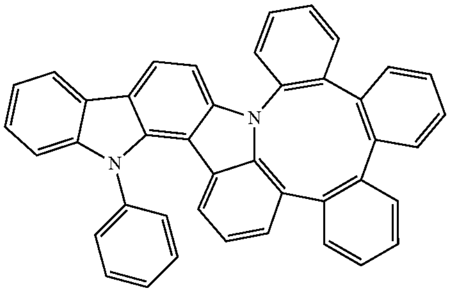
,
-continued
Compound 51
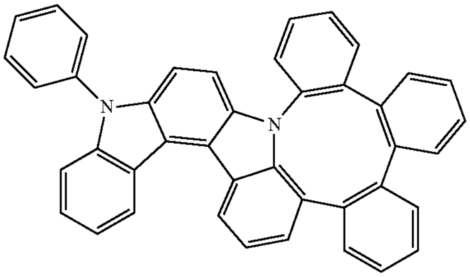
,
Compound 52
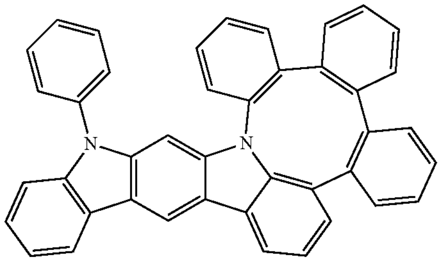
,
Compound 53
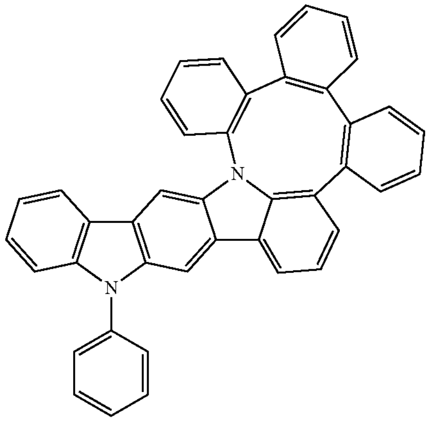
,
Compound 54
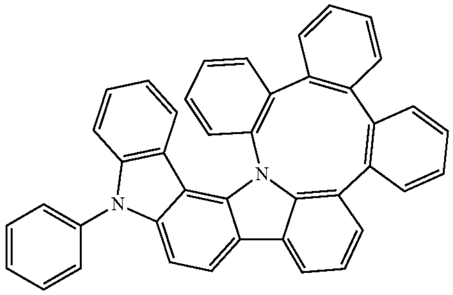
, -continued
Compound 55
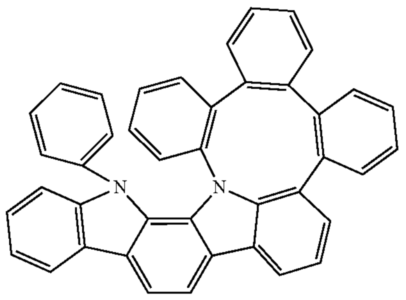
,
Compound 56
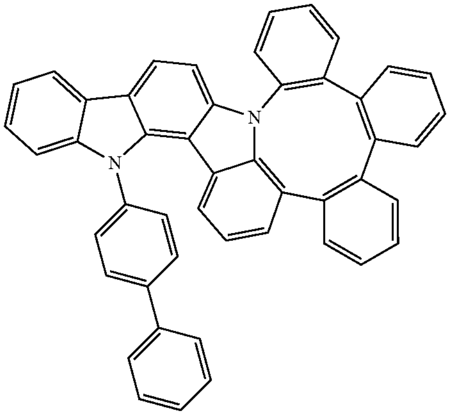
,
Compound 57
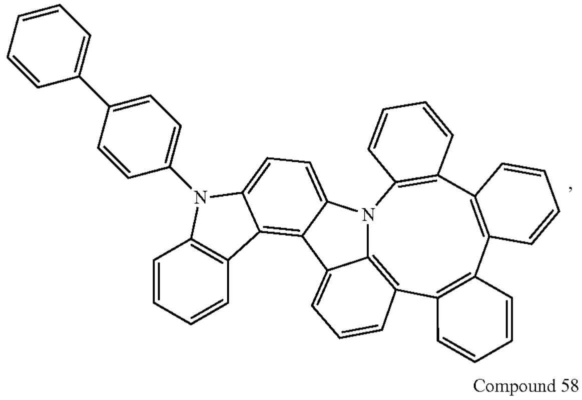
,
Compound 58
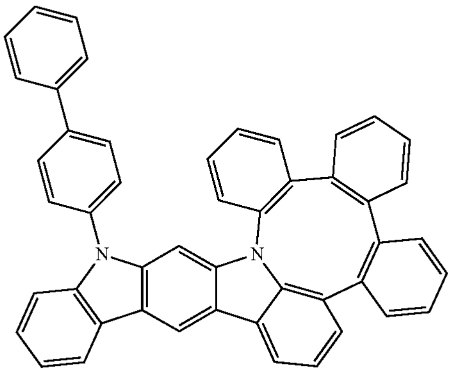
,
-continued
Compound 59
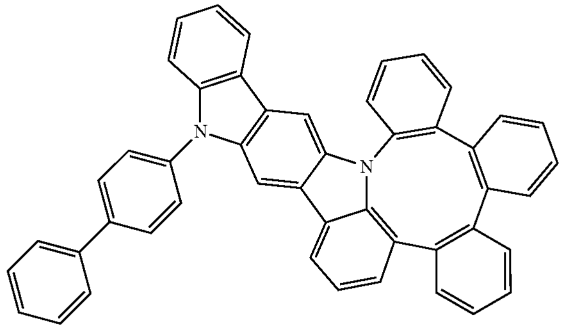
,
Compound 60
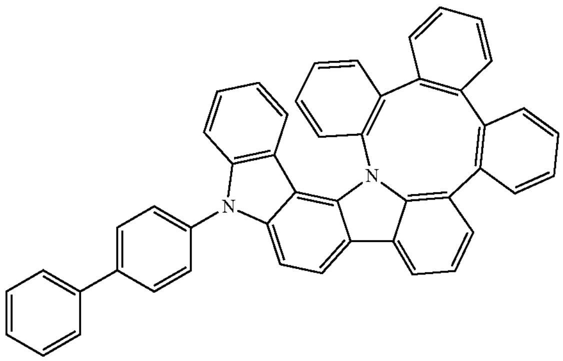
,
Compound 61
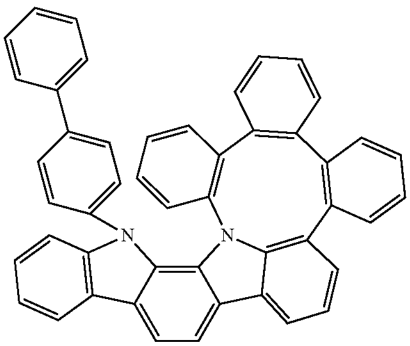
,
Compound 62
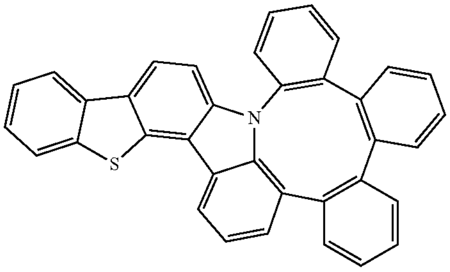
, -continued
Compound 63
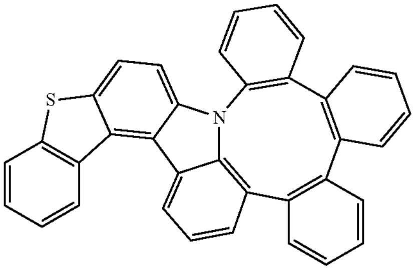
,
Compound 64
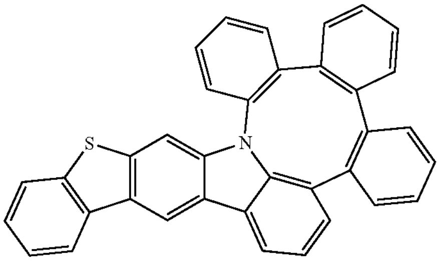
,
Compound 65
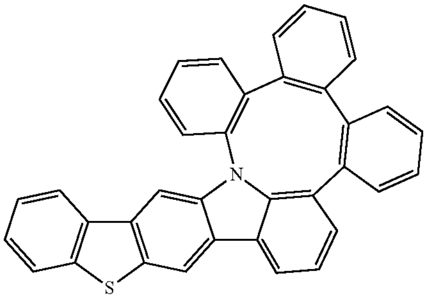
,
Compound 66
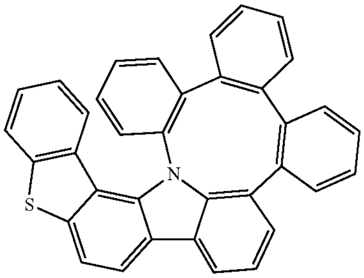
,
Compound 67
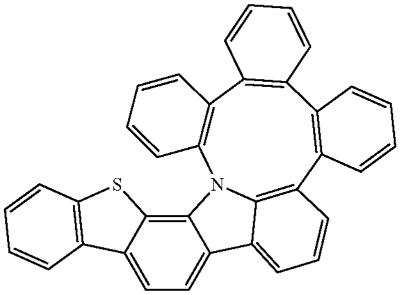
,
-continued
Compound 68
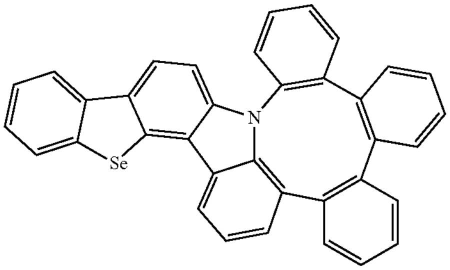
,
Compound 69
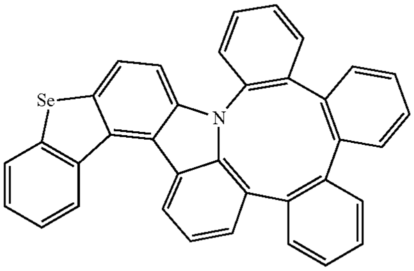
,
Compound 70
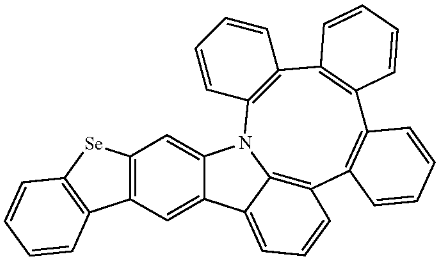
,
Compound 71
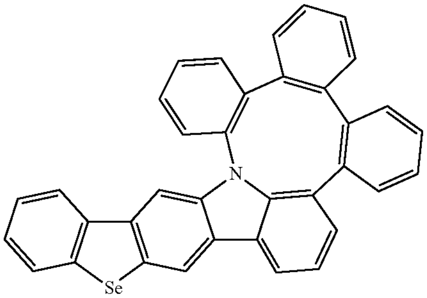
,
Compound 72
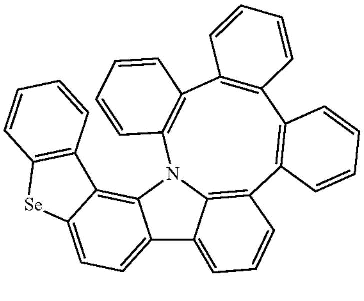
, -continued
Compound 73
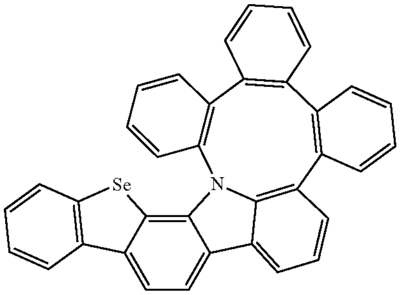
,
Compound 74
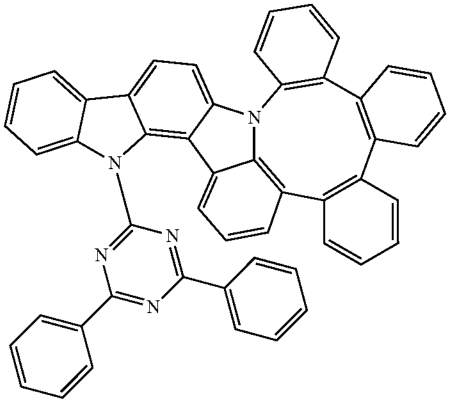
,
Compound 75
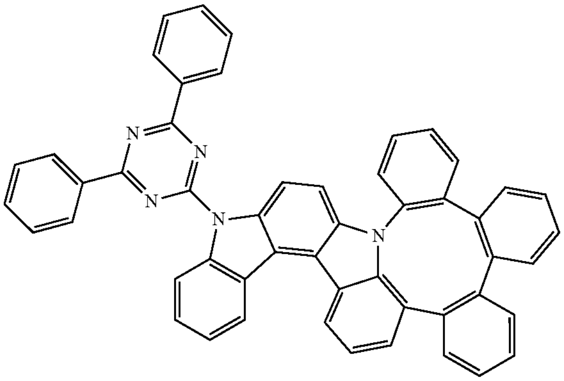
,
Compound 76
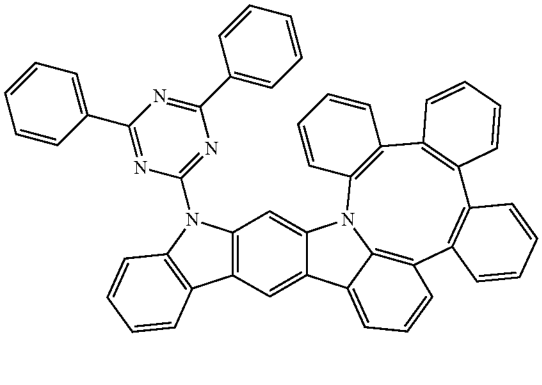
,
-continued
Compound 77
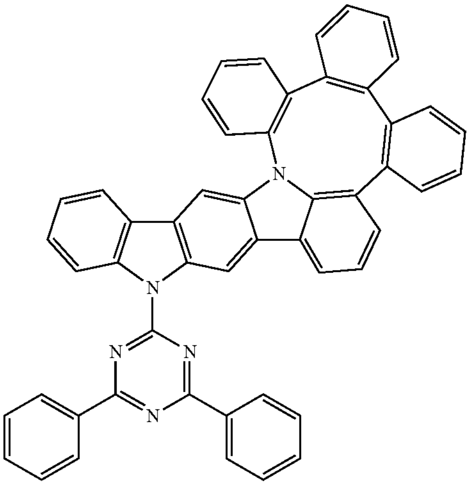
,
Compound 78
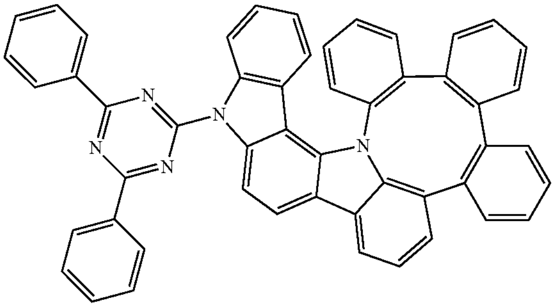
,
Compound 79
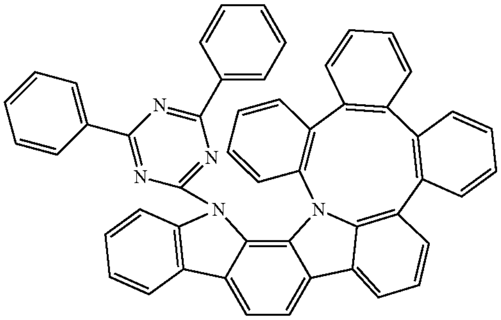
,
Compound 80
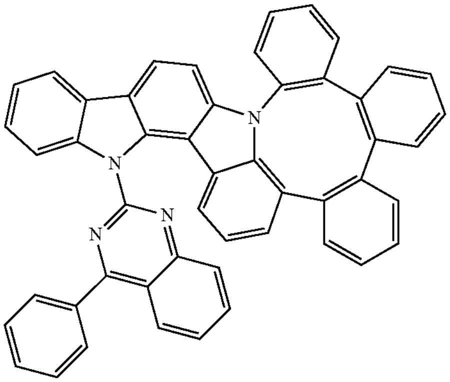
, -continued
Compound 81
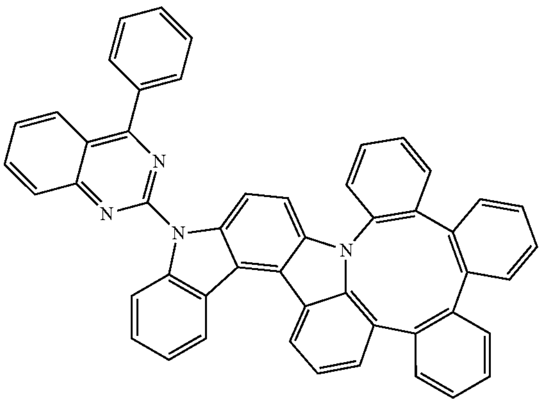
,
Compound 82
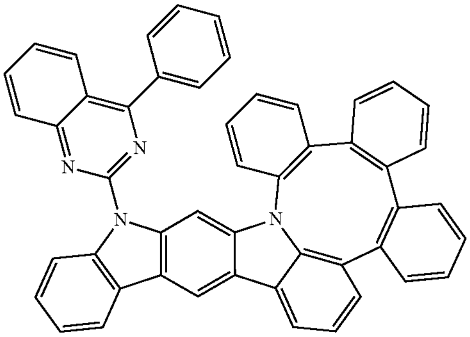
,
Compound 83
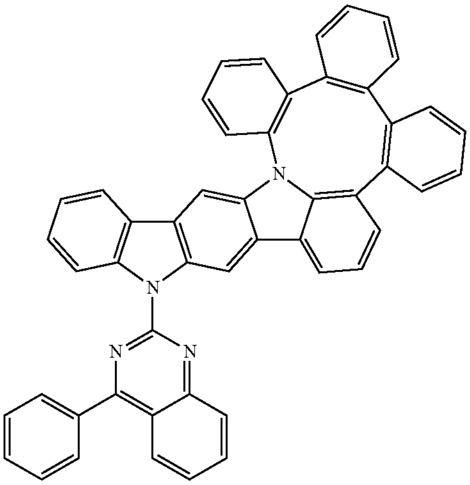
,
Compound 84
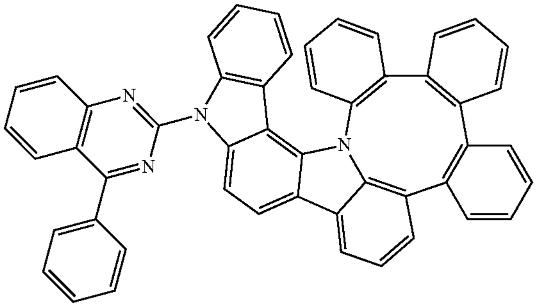
,
Compound 85
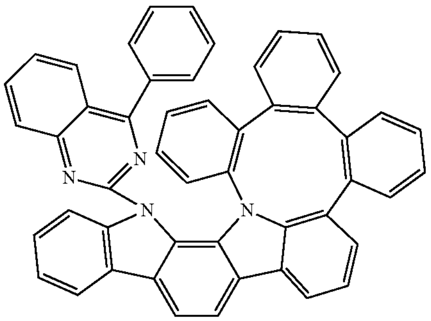
,
Compound 86
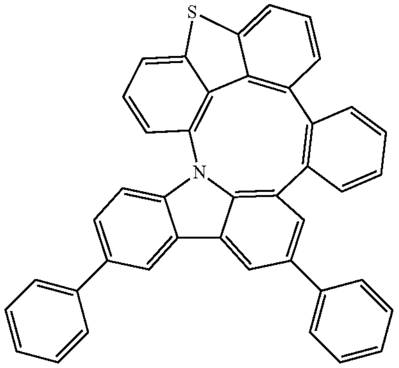
,
Compound 87
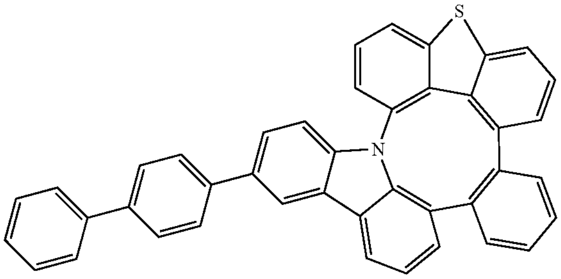
,
Compound 88
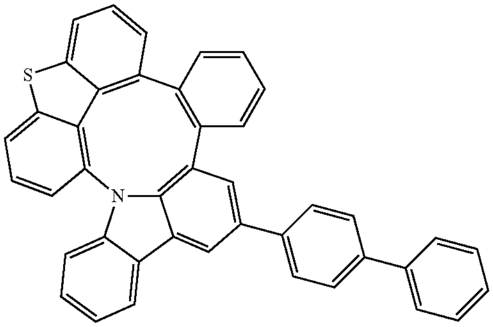
, -continued
Compound 89
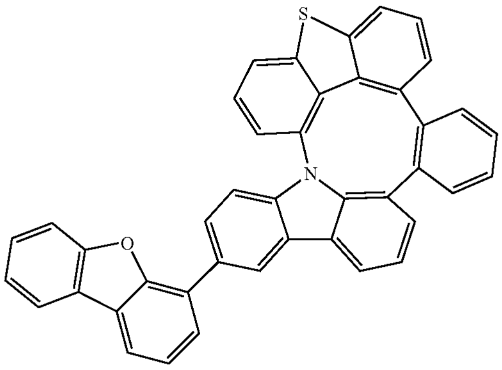
,
Compound 90
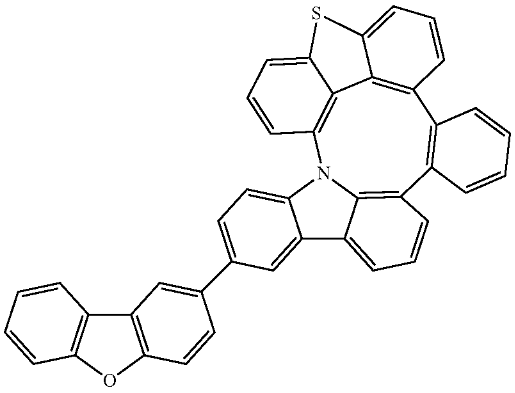
,
Compound 91
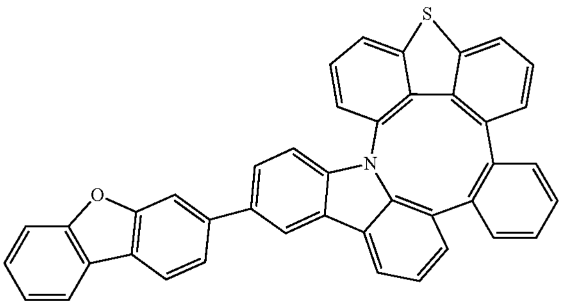
,
Compound 92
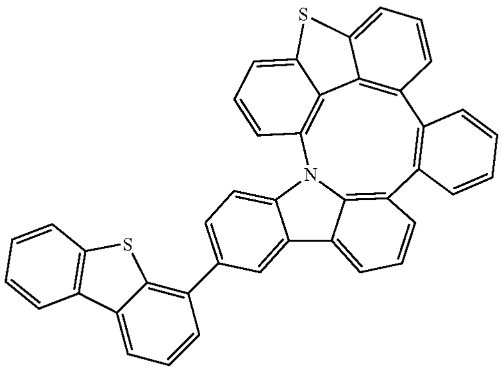
,
-continued
Compound 93
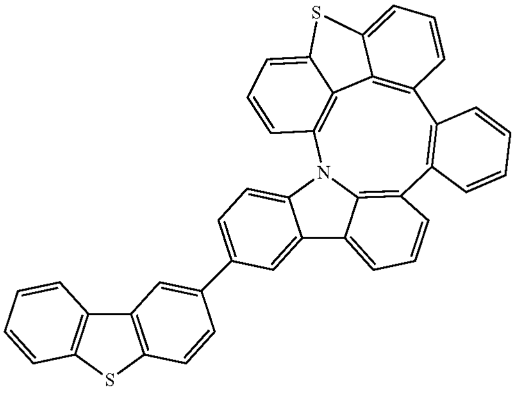
,
Compound 94
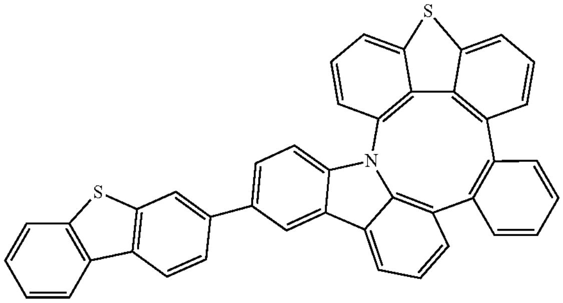
,
Compound 95
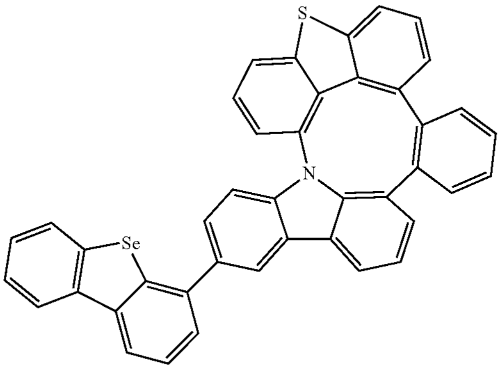
,
Compound 96
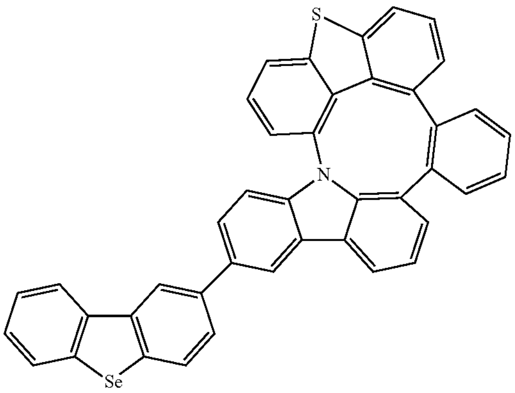
, -continued
Compound 97
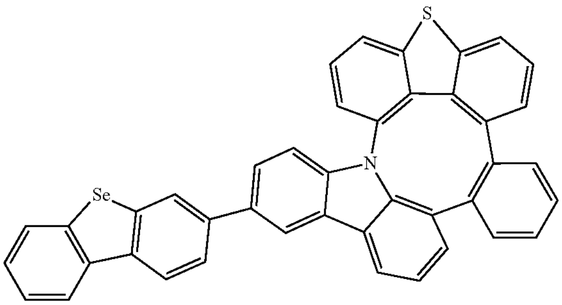
,
Compound 98
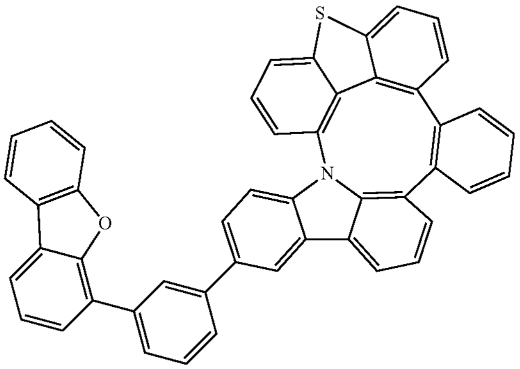
,
Compound 99
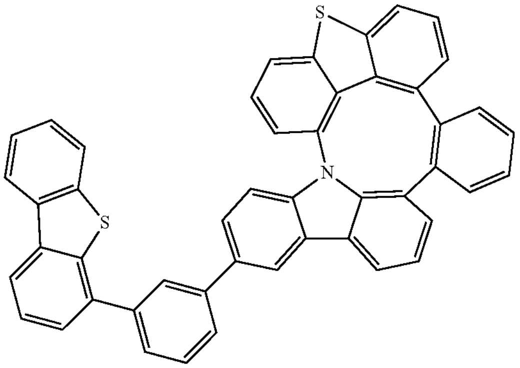
,
Compound 100
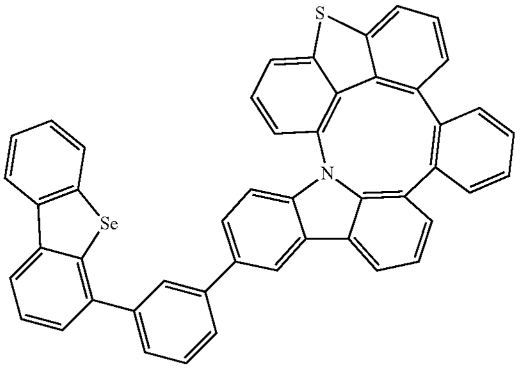
,
-continued
Compound 101
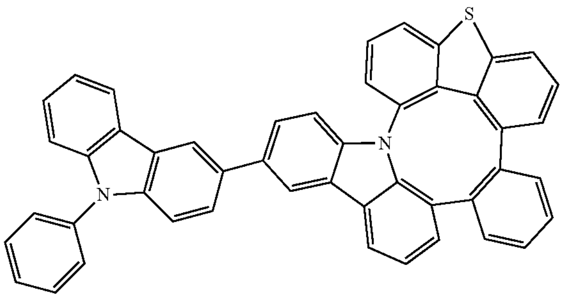
,
Compound 102
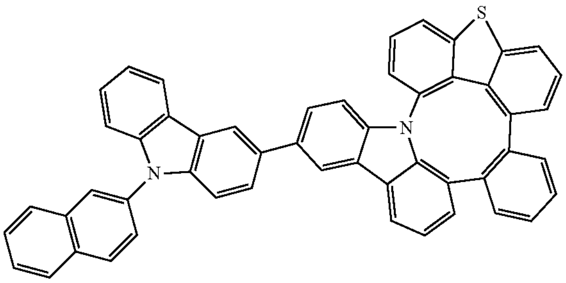
,
Compound 103
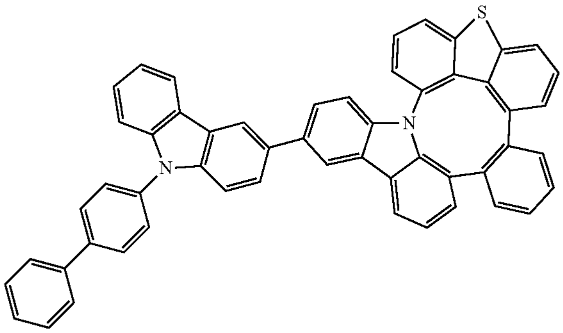
,
Compound 104
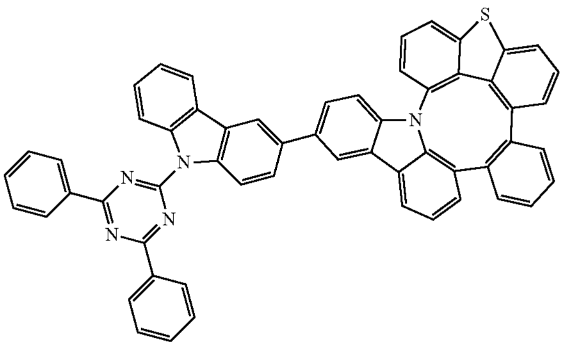
, -continued
Compound 105
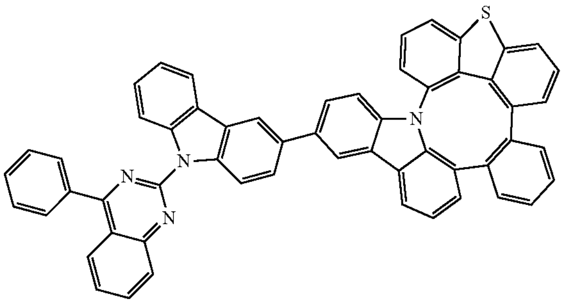
,
Compound 106
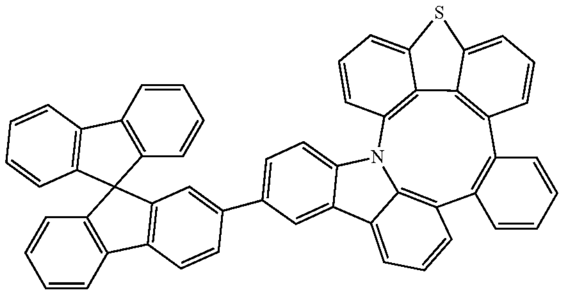
,
Compound 107
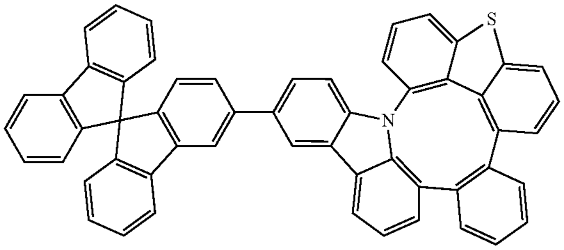
,
Compound 108
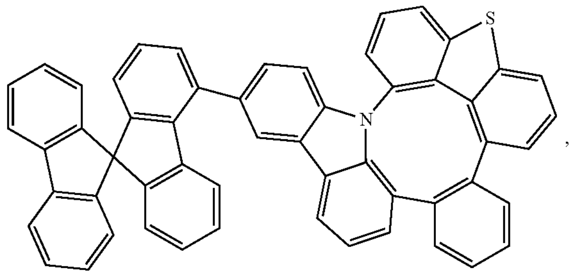
,
Compound 109
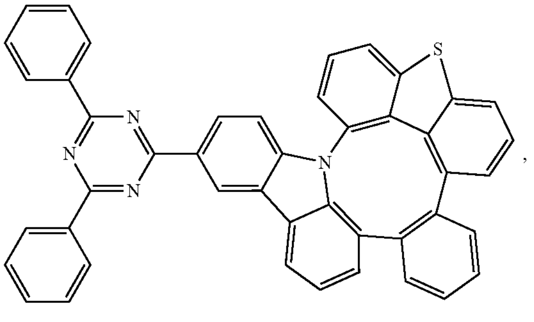
,
-continued
Compound 110
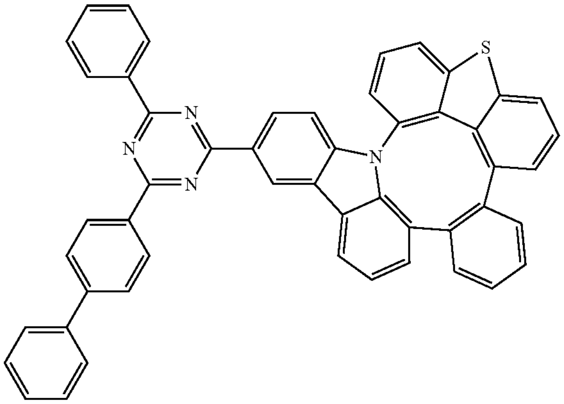
,
Compound 111
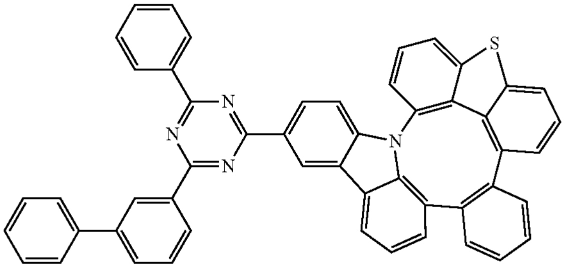
,
Compound 112
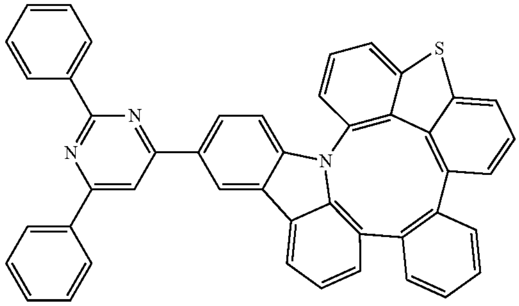
,
Compound 113
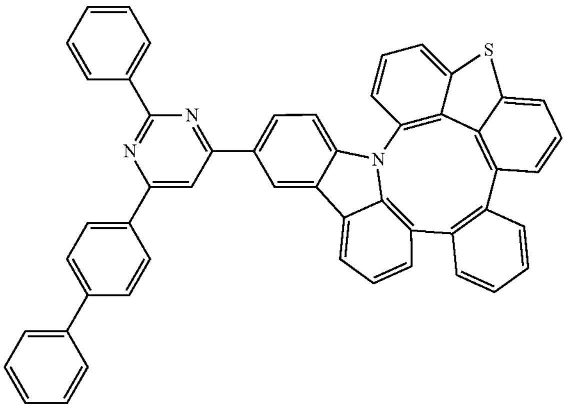
, -continued
Compound 114
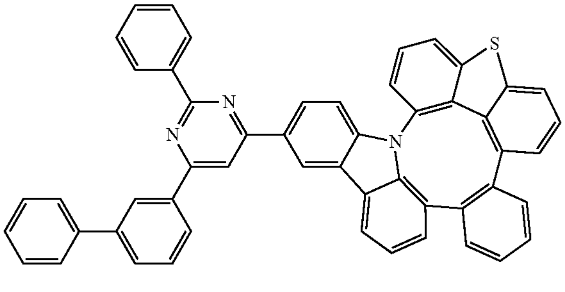
,
Compound 115
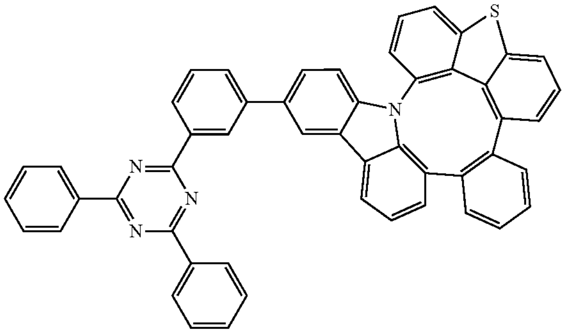
,
Compound 116
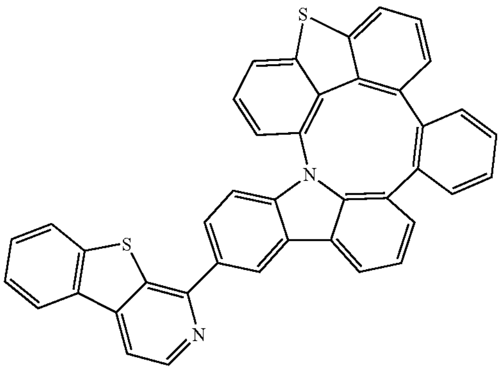
,
Compound 117
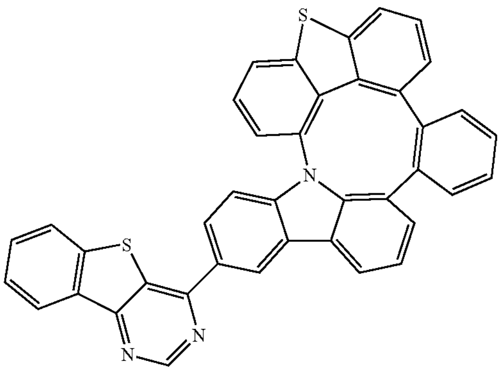
,
-continued
Compound 118
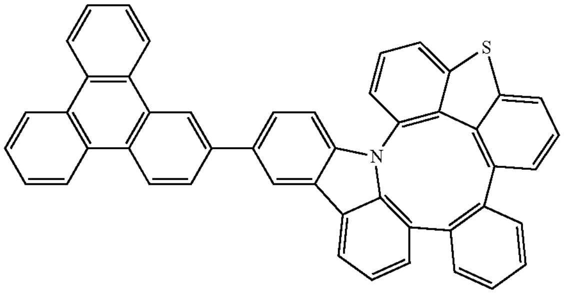
,
Compound 119
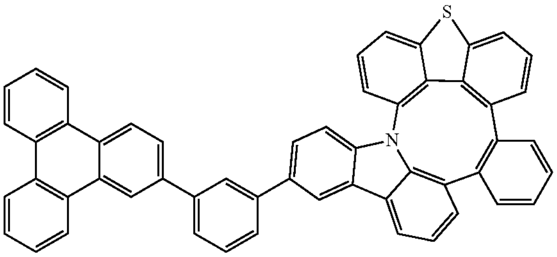
,
Compound 120
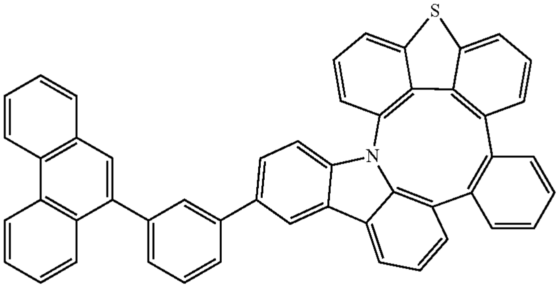
,
Compound 121
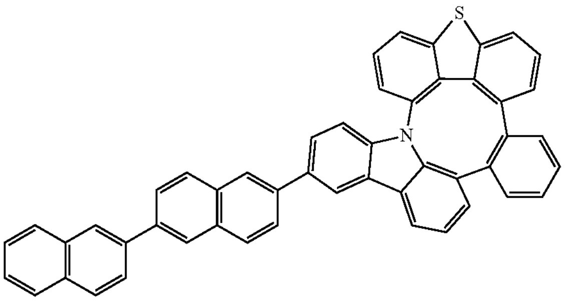
,
Compound 122
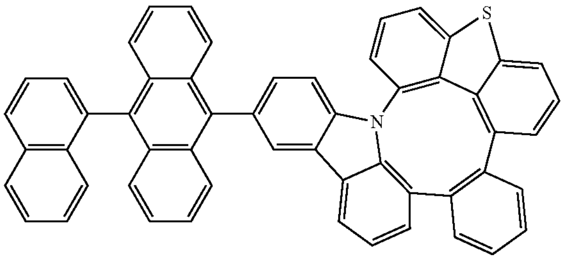
, -continued
Compound 123
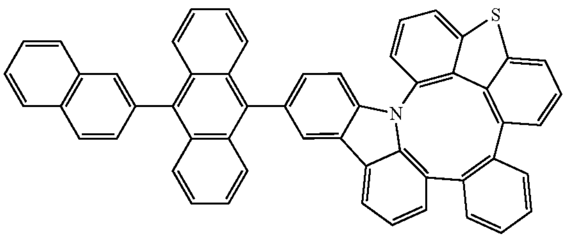,
Compound 124
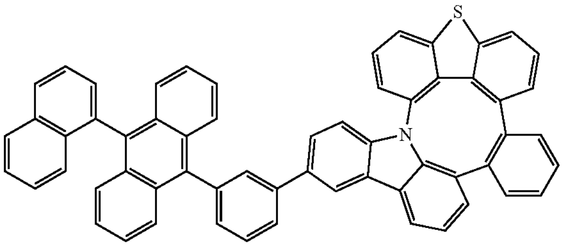,
Compound 125
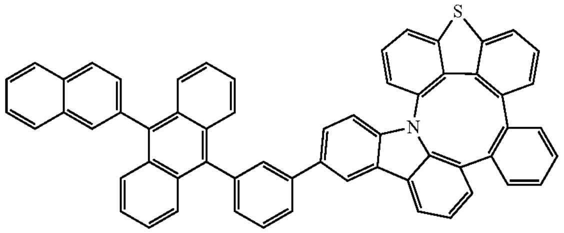,
Compound 126
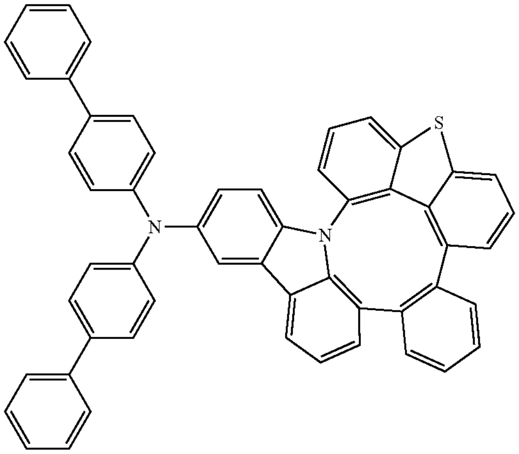,
-continued
Compound 127
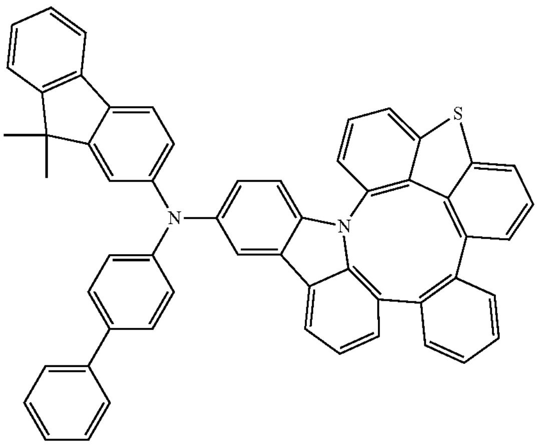,
Compound 128
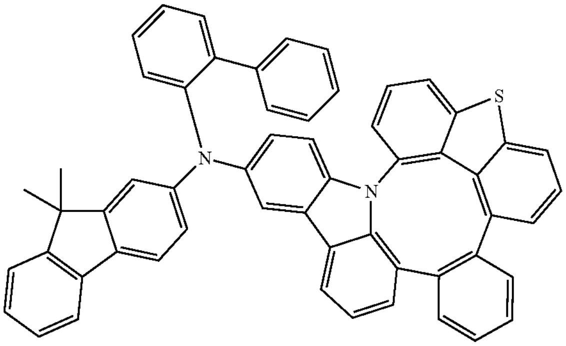,
Compound 129
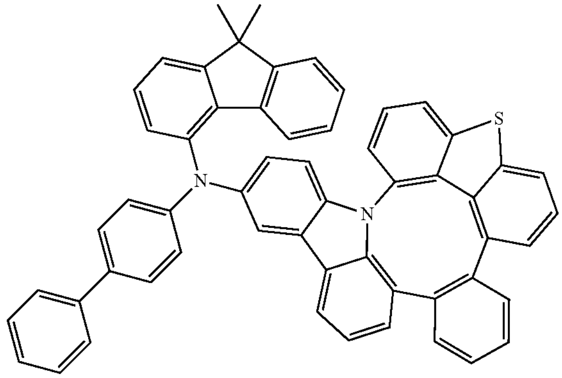, -continued
Compound 130
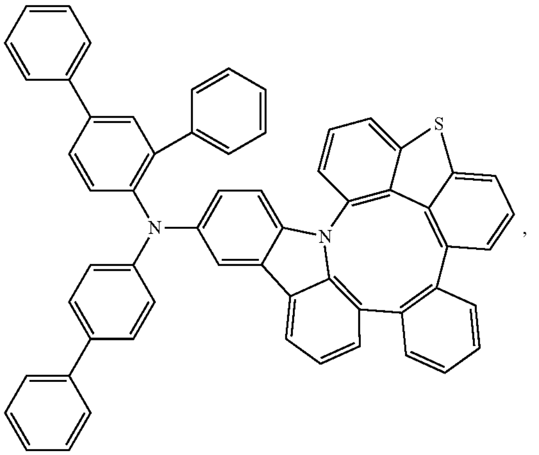
Compound 131
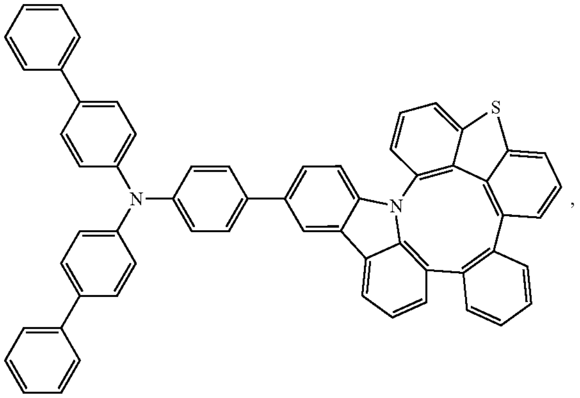
Compound 132
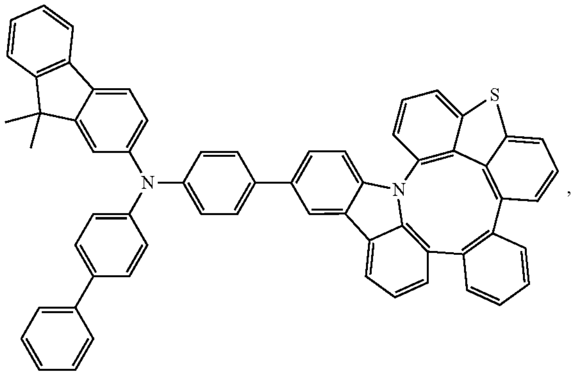
Compound 133
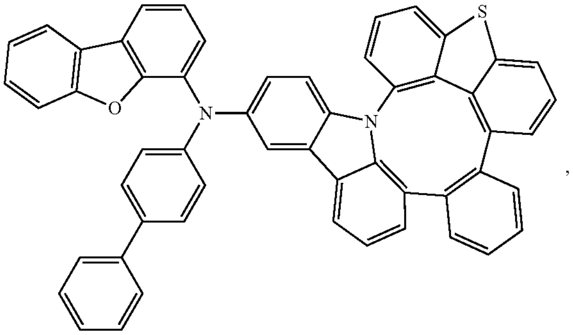
-continued
Compound 134
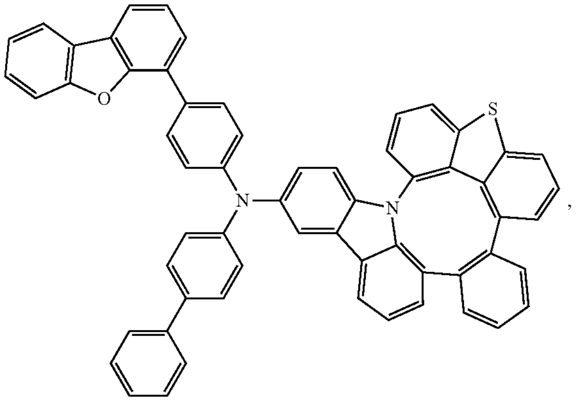
Compound 135
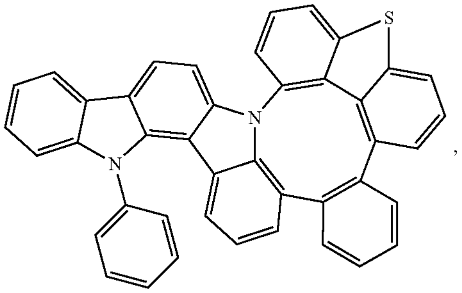
Compound 136
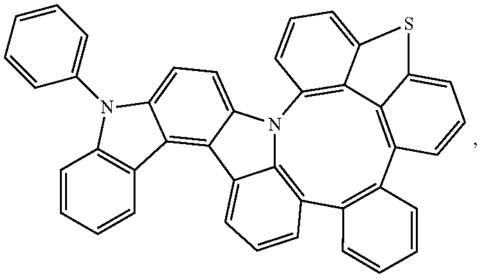
Compound 137
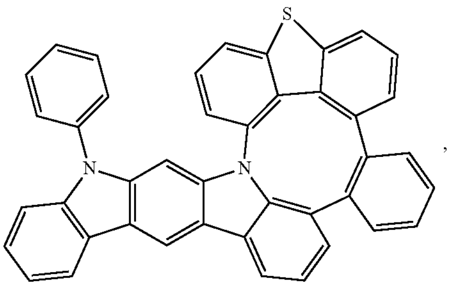

-continued
Compound 138
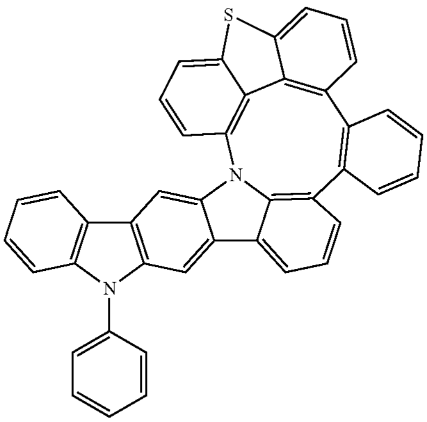
,
Compound 139
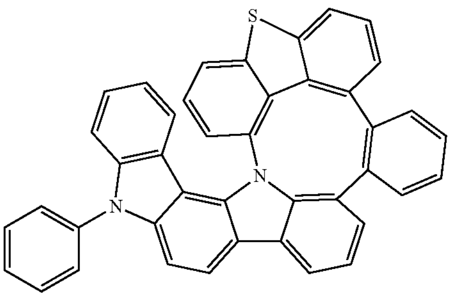
,
Compound 140
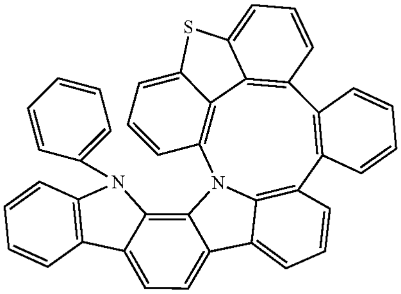
,
Compound 141
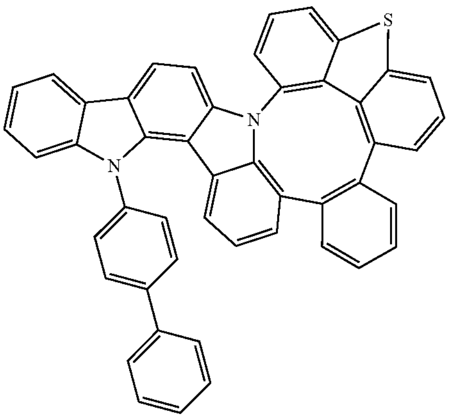
,
-continued
Compound 142
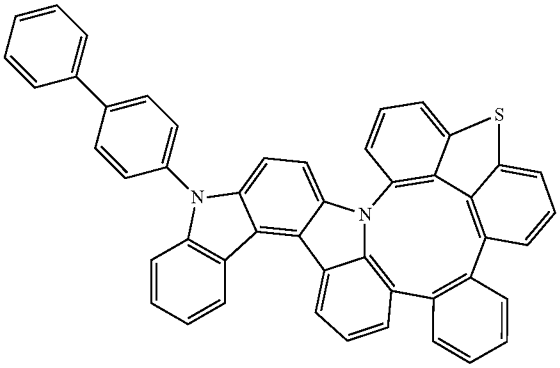
,
Compound 143
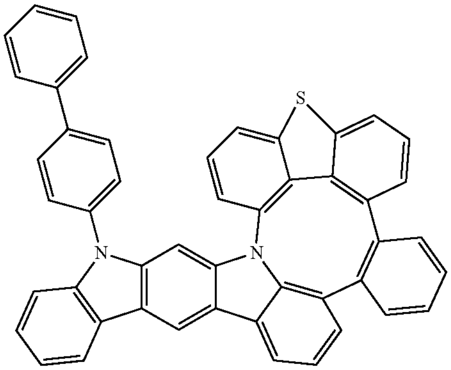
,
Compound 144
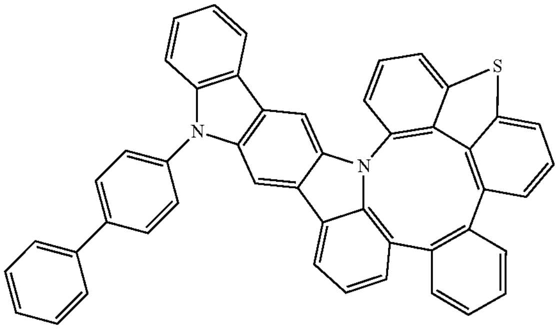
,
Compound 145
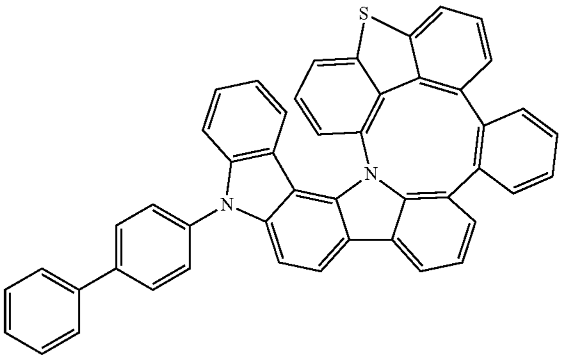
, -continued
Compound 146
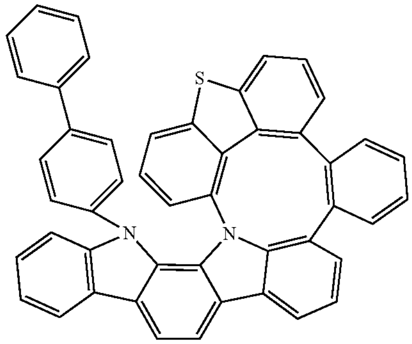
,
Compound 147
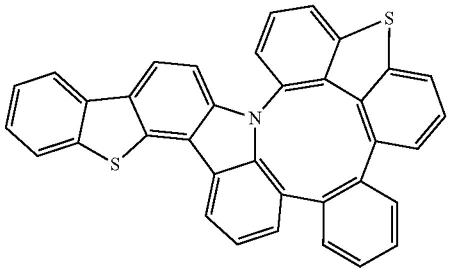
,
Compound 148
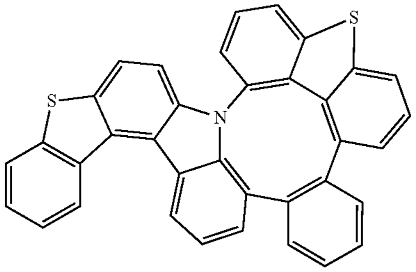
,
Compound 149
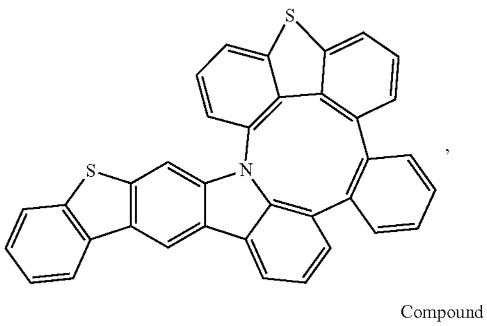
,
Compound 150
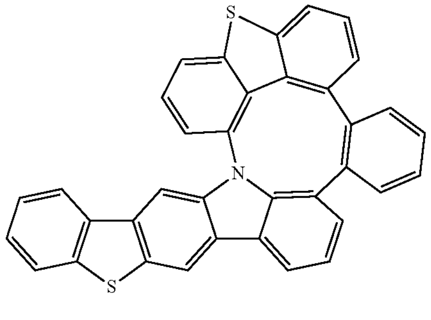
,
-continued
Compound 151
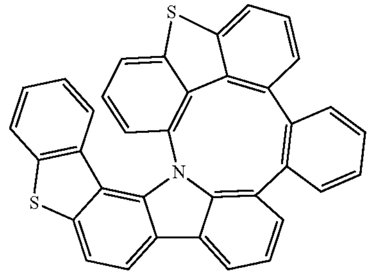
,
Compound 152
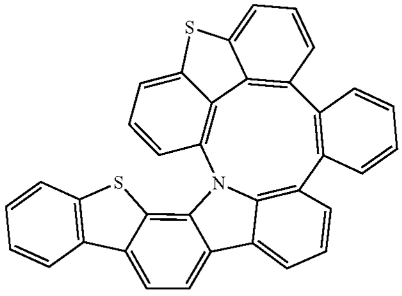
,
Compound 153
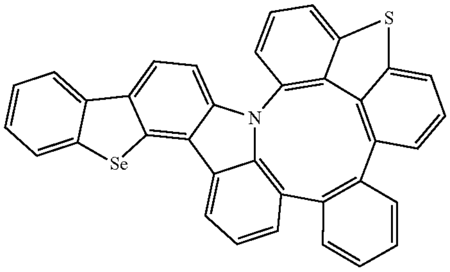
,
Compound 154
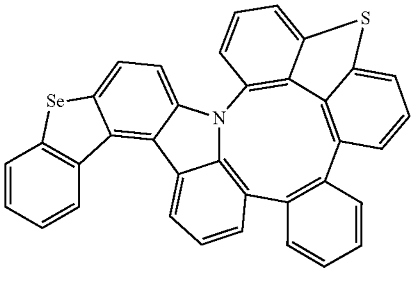
,
Compound 155
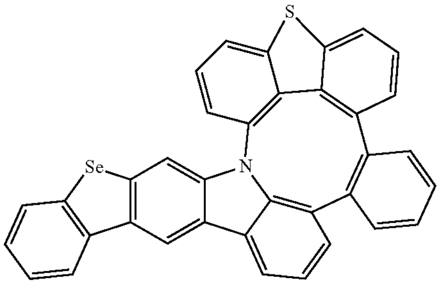
, -continued
Compound 156
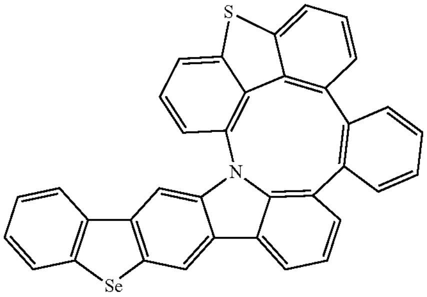
,
Compound 157
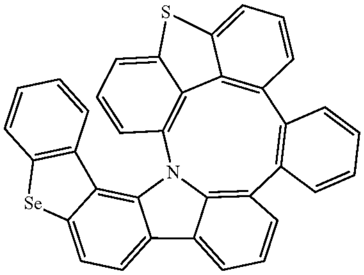
,
Compound 158
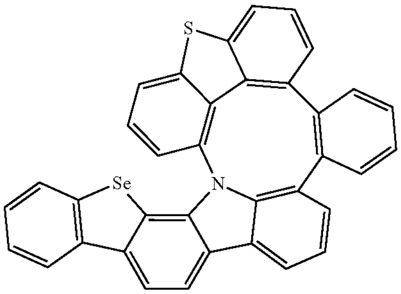
,
Compound 159
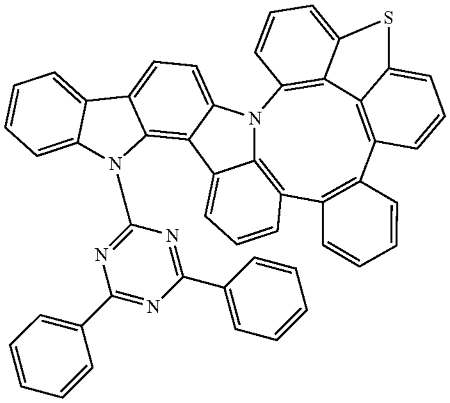
,
-continued
Compound 160
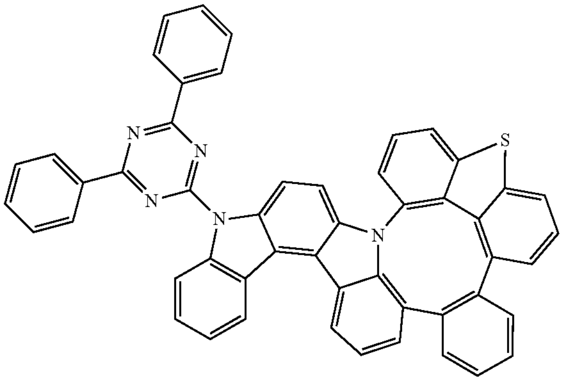
,
Compound 161
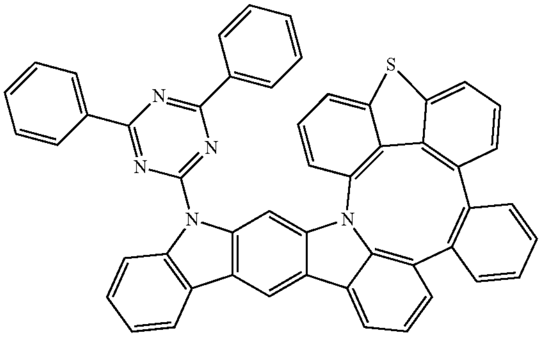
,
Compound 162
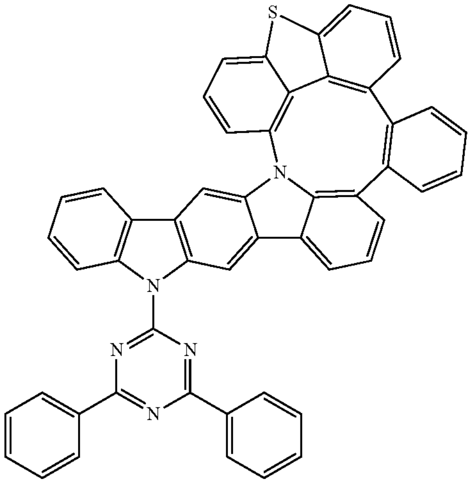
,
Compound 163
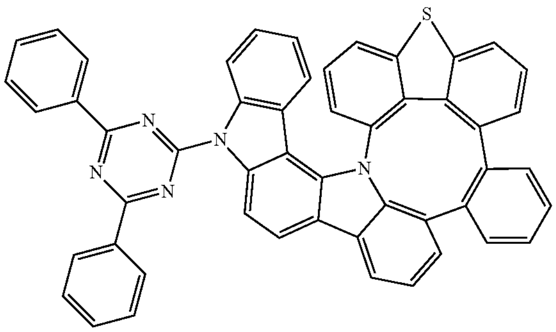
, -continued
Compound 164
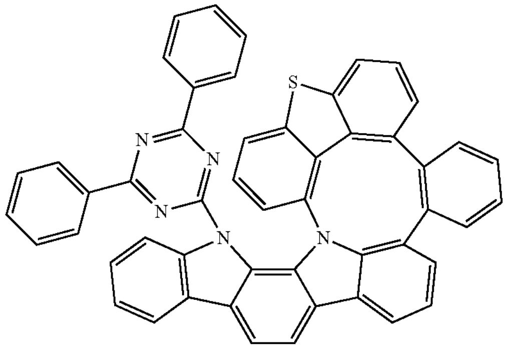
,
Compound 165
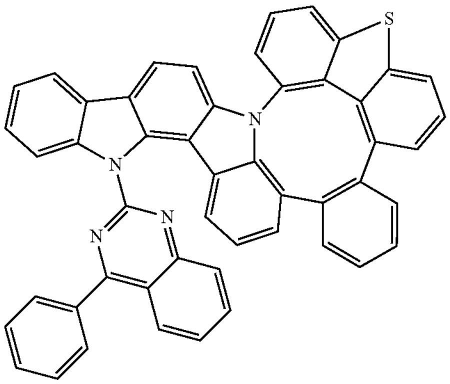
,
Compound 166
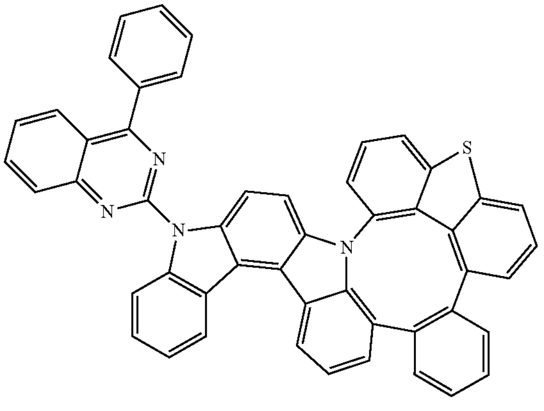
,
Compound 167
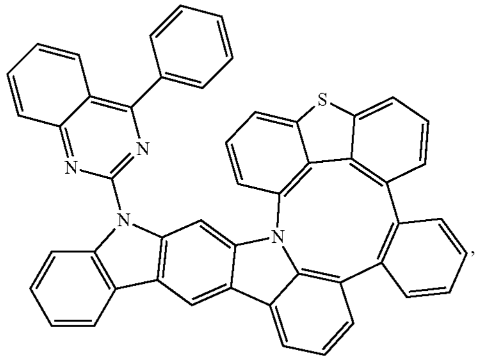
,
Compound 168
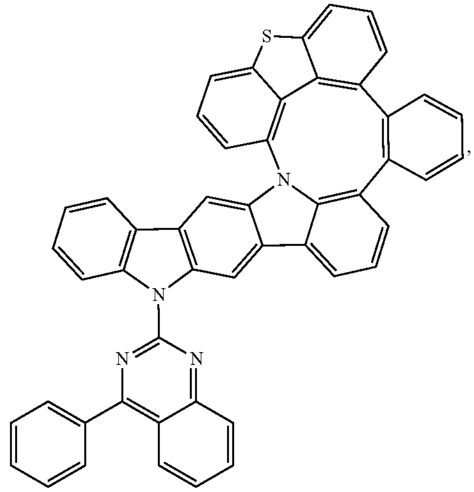
,
Compound 169
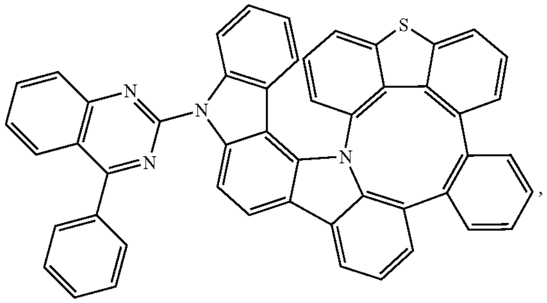
,
Compound 170
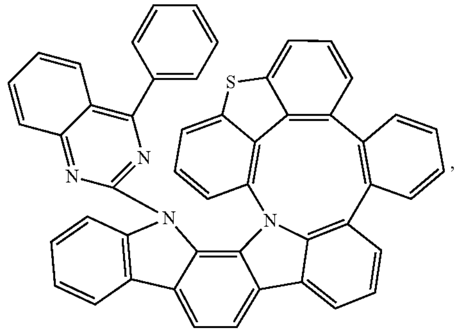
, -continued
Compound 171
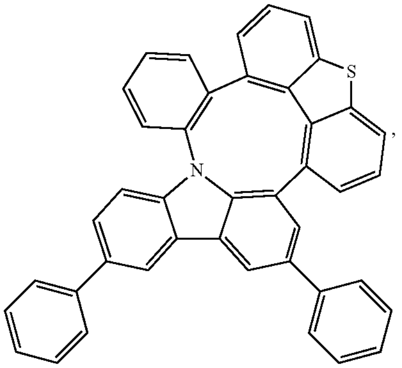
Compound 172
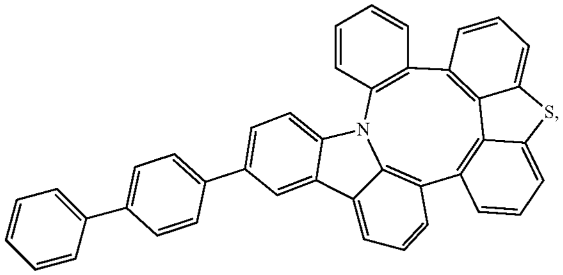
Compound 173
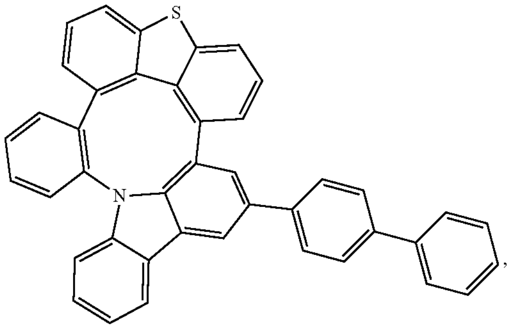
Compound 174
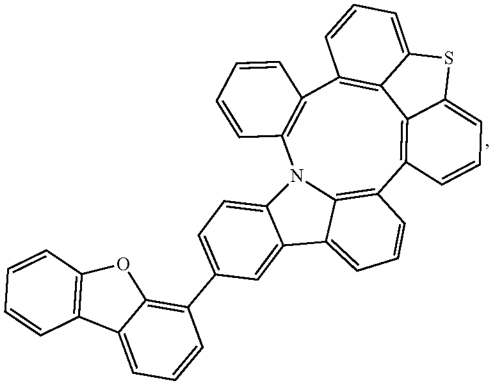
-continued
Compound 175
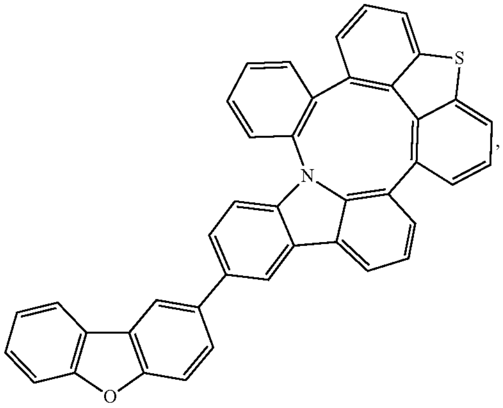
Compound 176
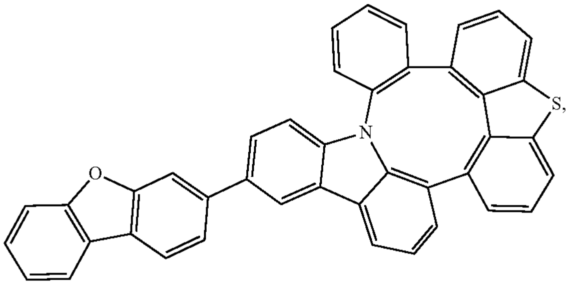
Compound 177
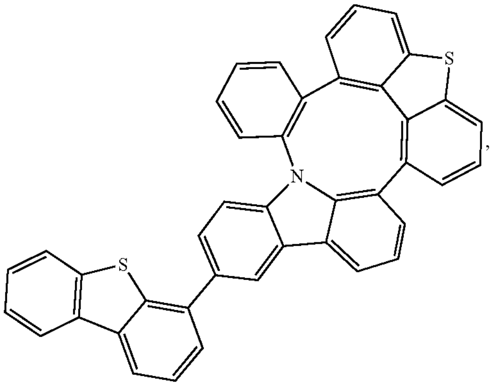
Compound 178
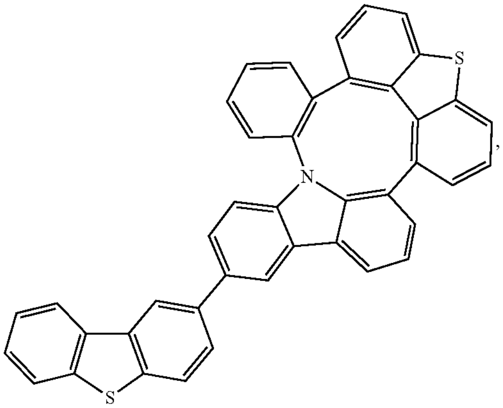

Compound 179
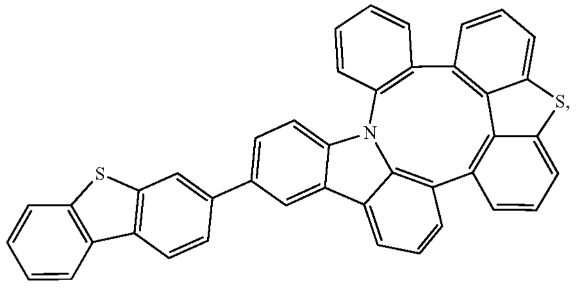
Compound 180
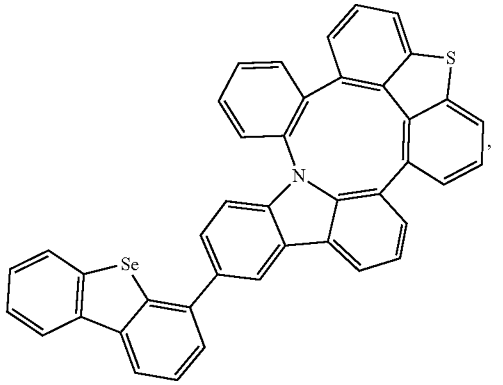
Compound 181
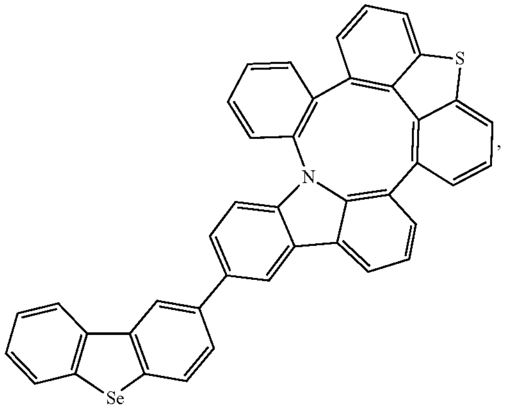
Compound 182
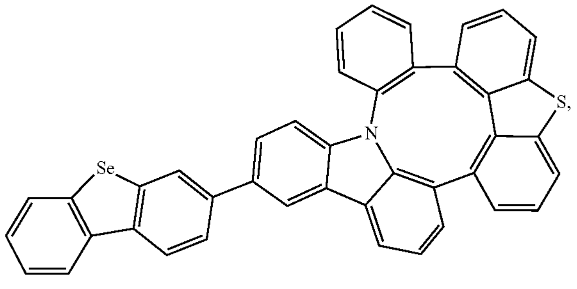
Compound 183
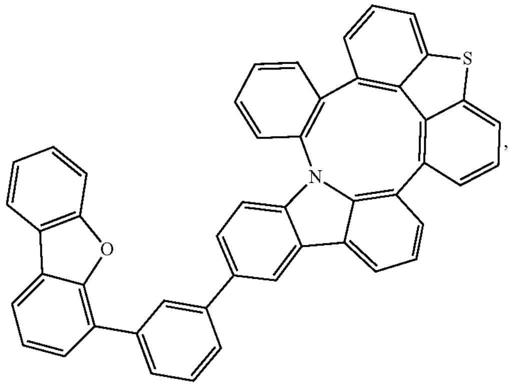
Compound 184
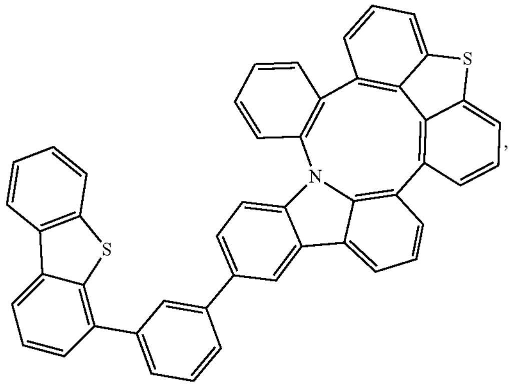
Compound 185
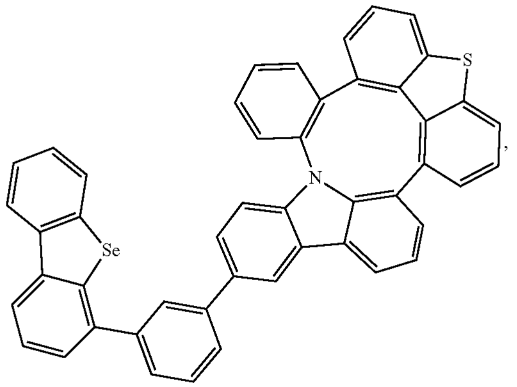
Compound 186
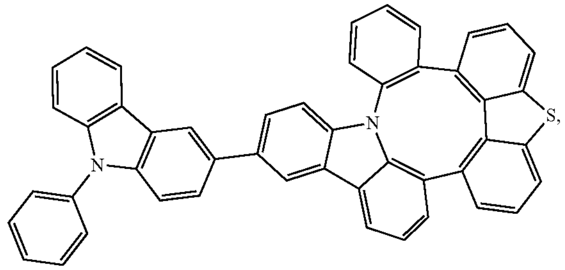

-continued
Compound 187
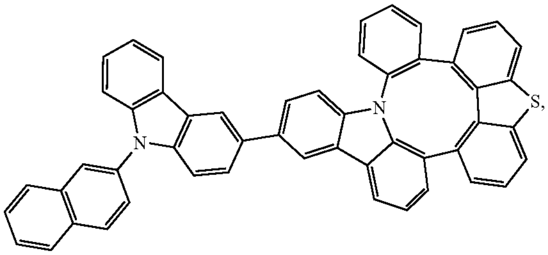
Compound 188
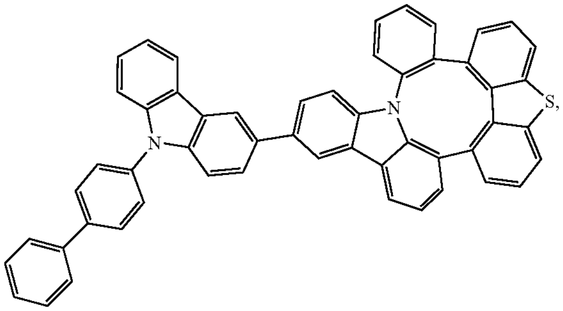
Compound 189
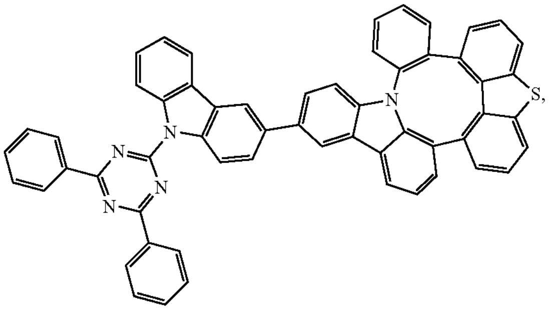
Compound 190
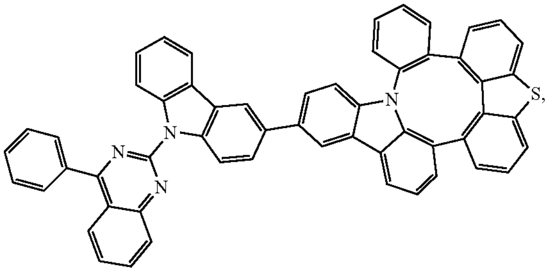
Compound 191
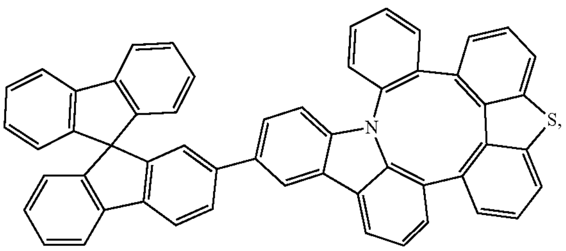
-continued
Compound 192
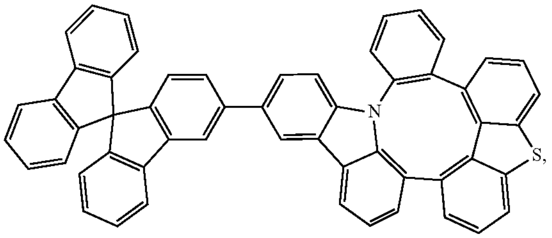
Compound 193
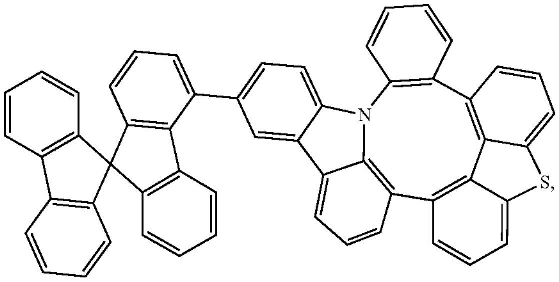
Compound 194
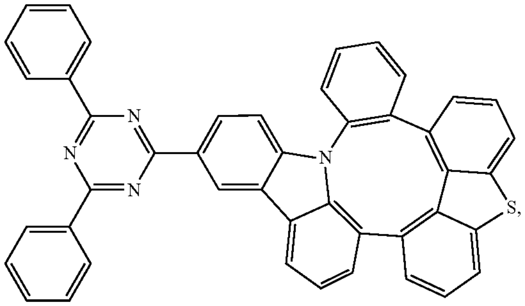
Compound 195
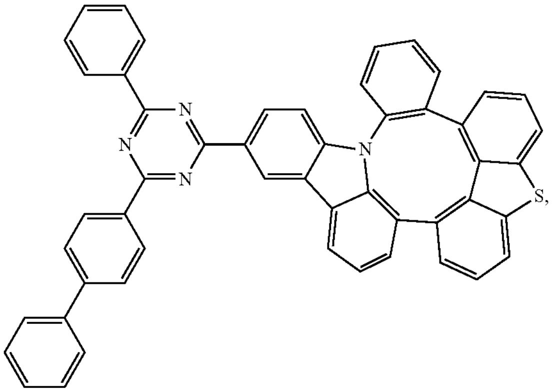
Compound 196
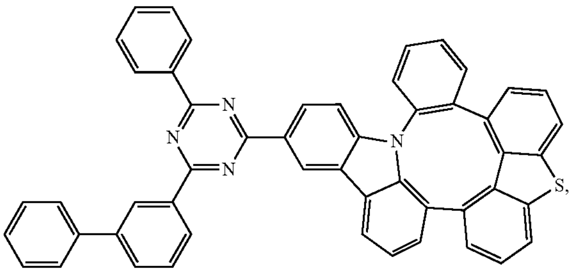

-continued
Compound 197
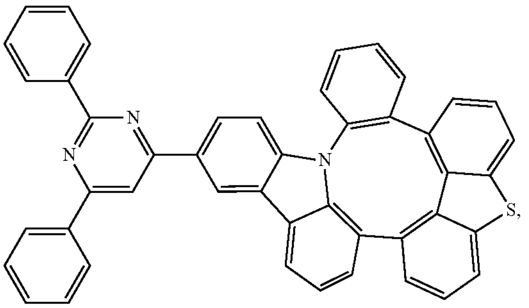
Compound 198
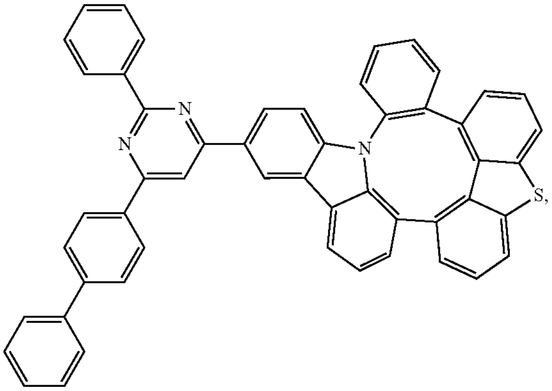
Compound 199
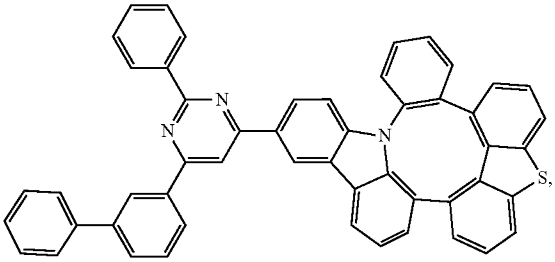
Compound 200
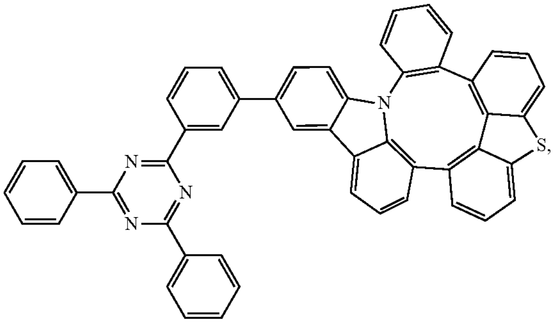
-continued
Compound 201
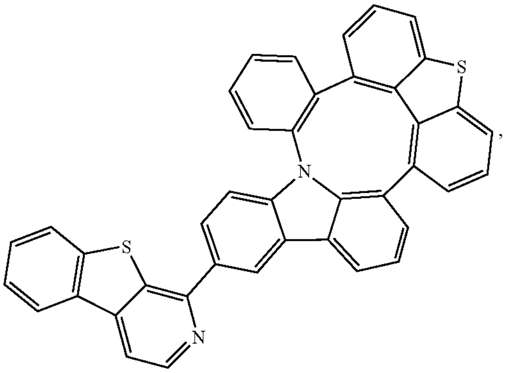
Compound 202
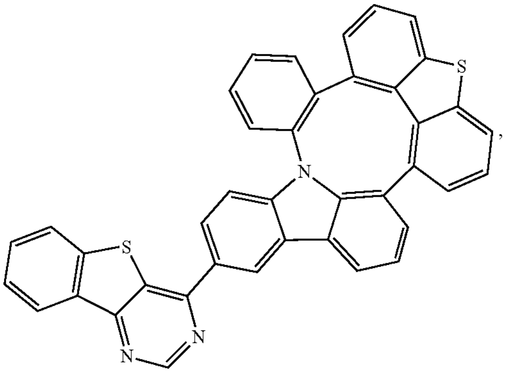
Compound 203
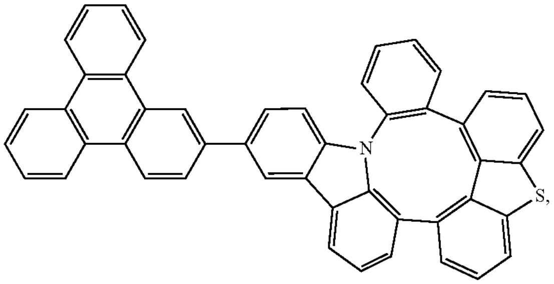
Compound 204
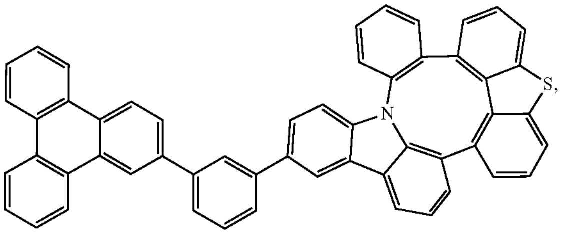
Compound 205
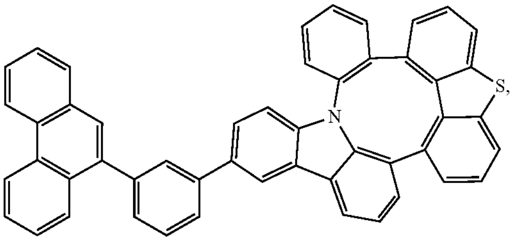

-continued
Compound 206
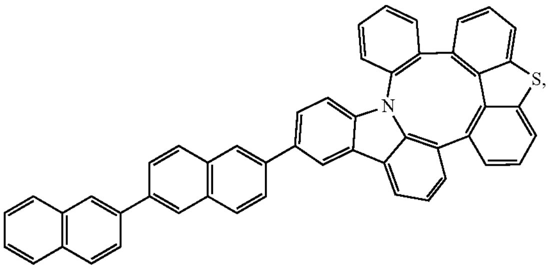
Compound 207
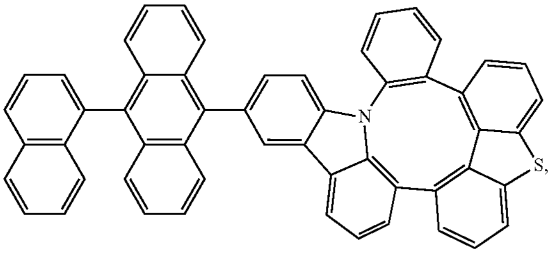
Compound 208
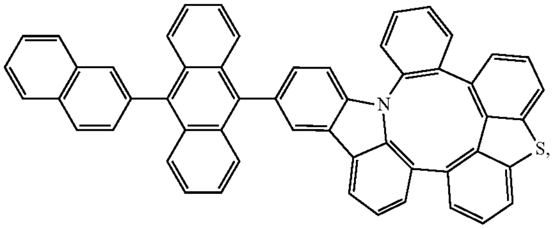
Compound 209
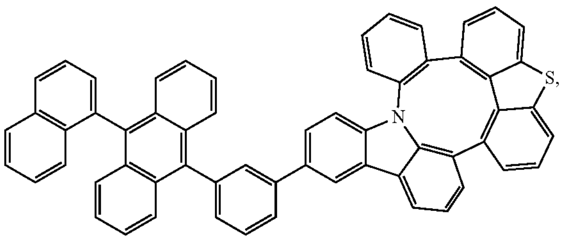
Compound 210
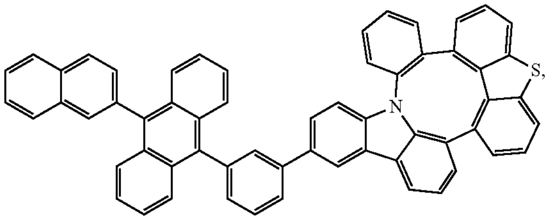
-continued
Compound 211
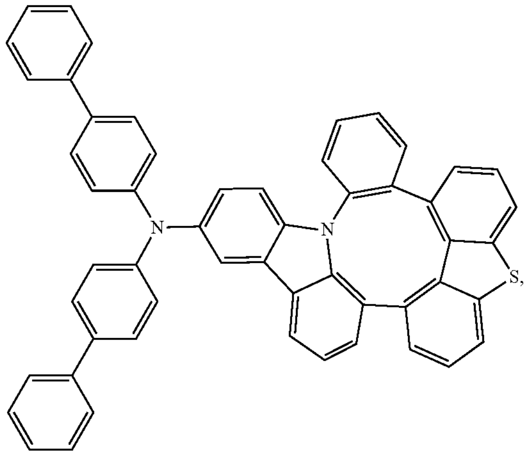
Compound 212
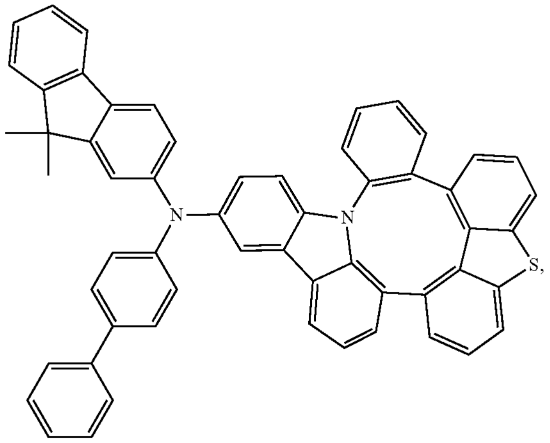
Compound 213
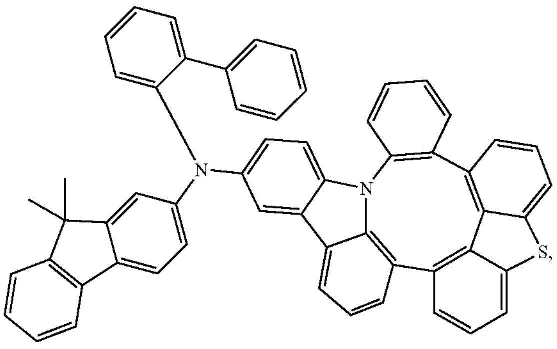

-continued
Compound 214
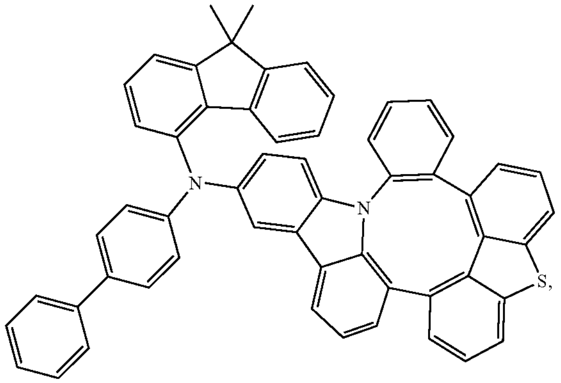
Compound 215
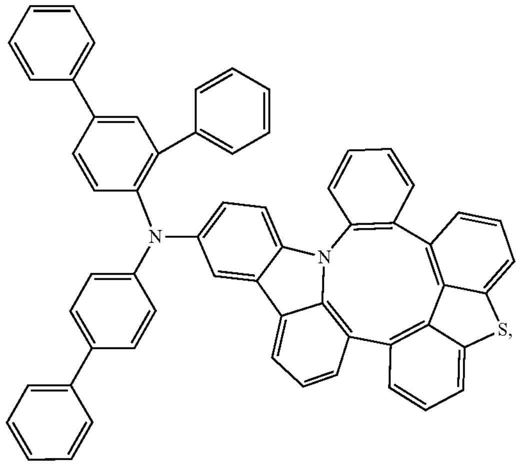
Compound 216
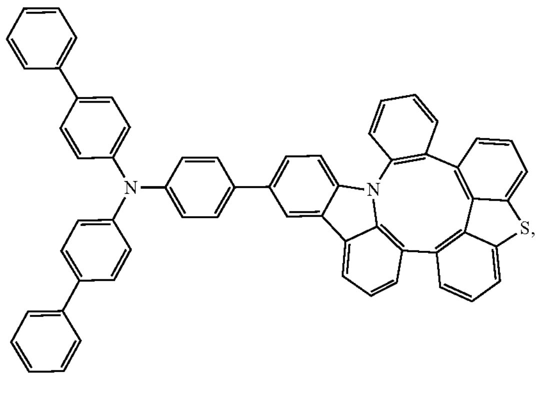
-continued
Compound 217
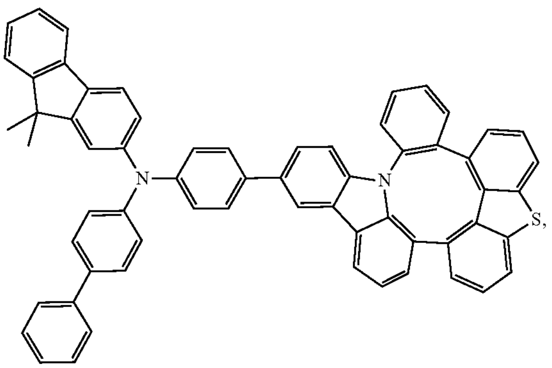
Compound 218
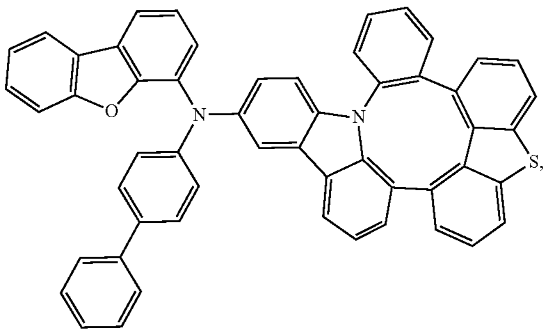
Compound 219
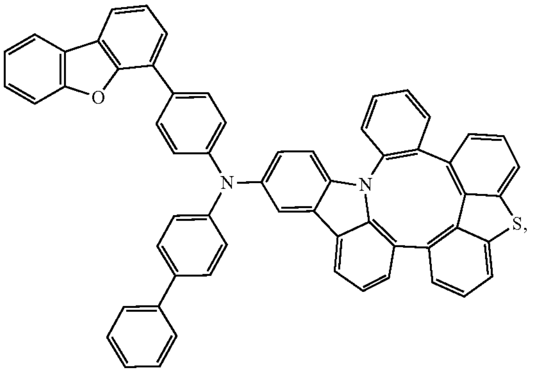
Compound 220
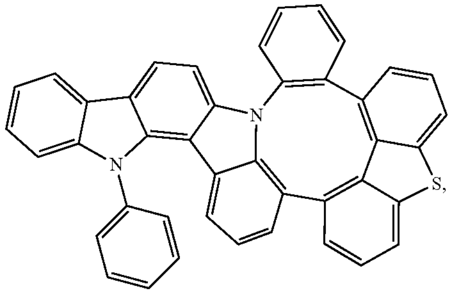

-continued
Compound 221
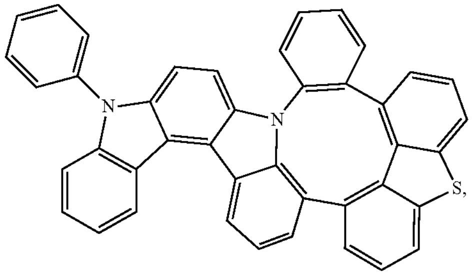
Compound 222
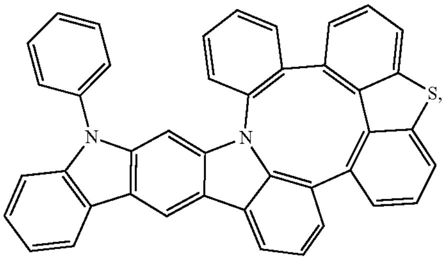
Compound 223
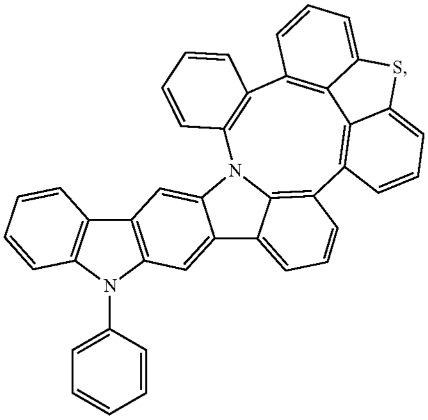
Compound 224
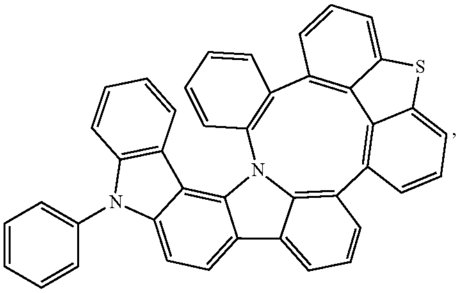
-continued
Compon 225
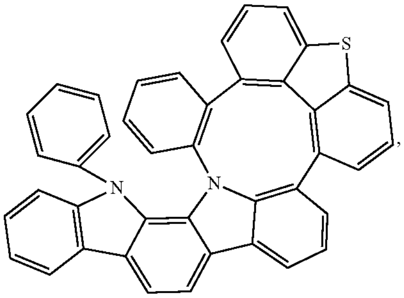
Compound 226
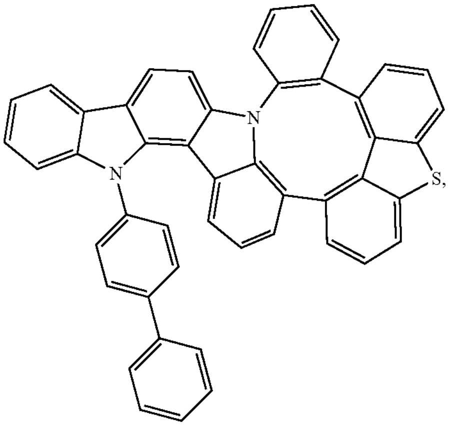
Compound 227
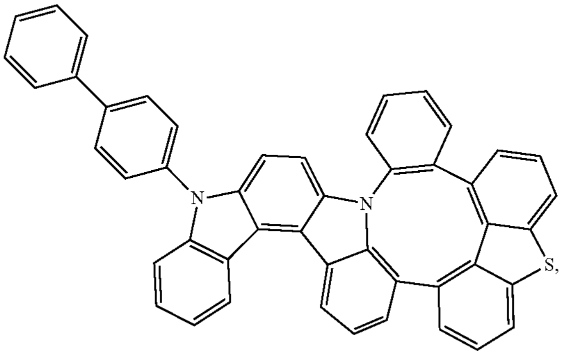
Compound 228
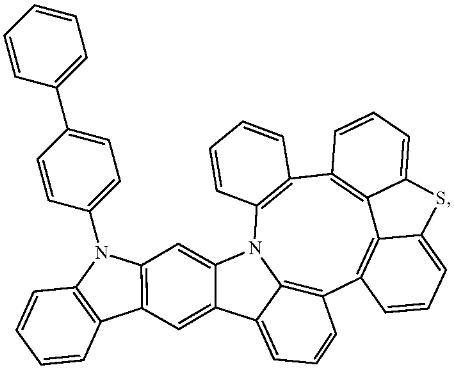

-continued
Compound 229
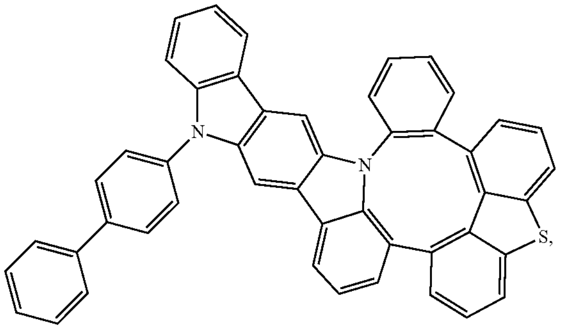
Compound 230
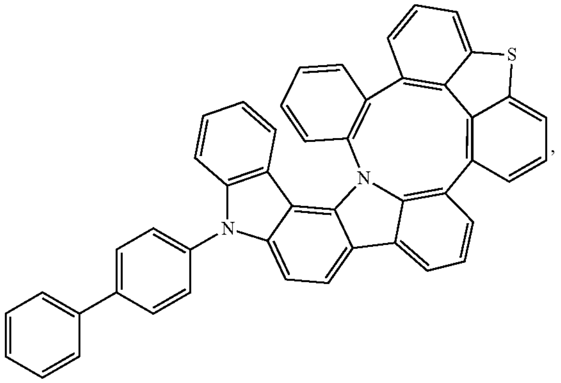
Compound 231
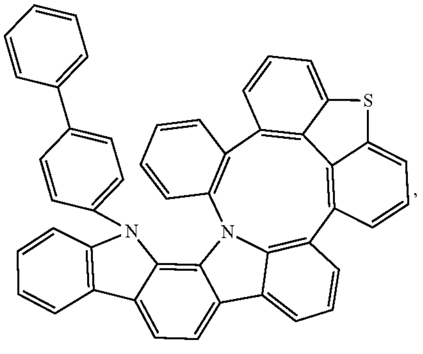
Compound 232
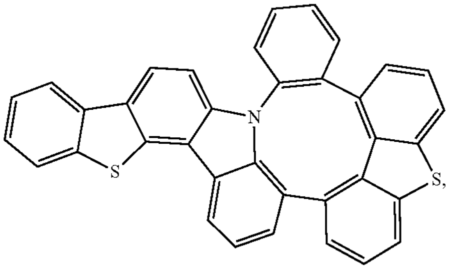
-continued
Compound 233
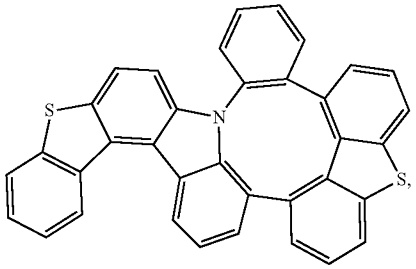
Compound 234
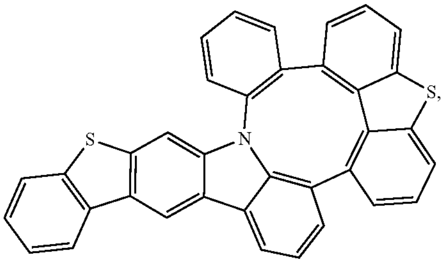
Compound 235
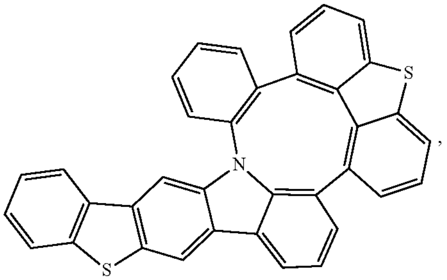
Compound 236
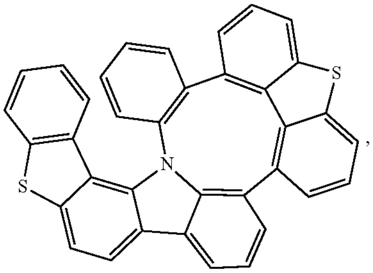
Compound 237
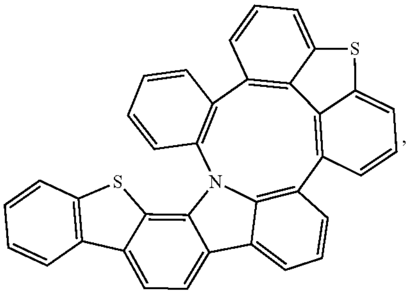

-continued
Compound 238
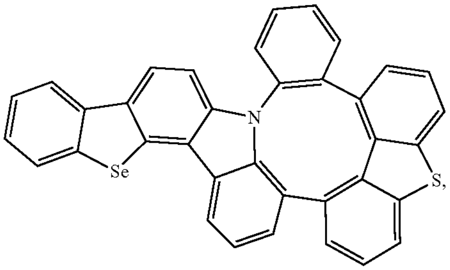
Compound 239
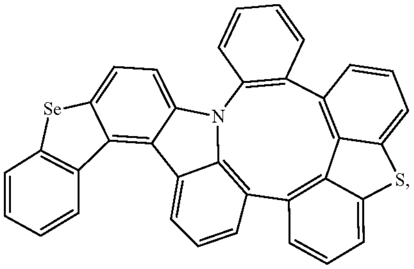
Compound 240
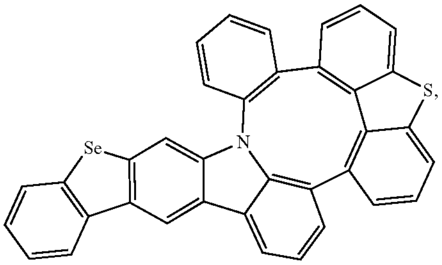
Compound 241
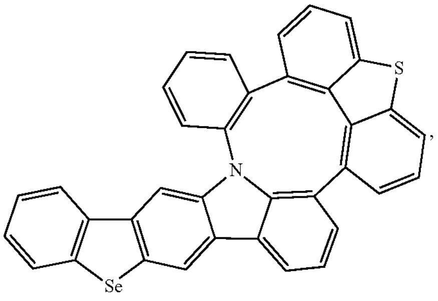
Compound 242
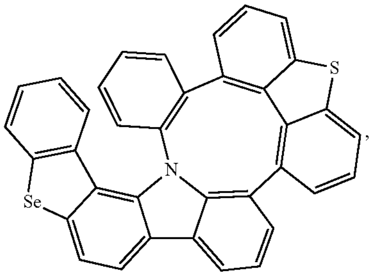
-continued
Compound 243
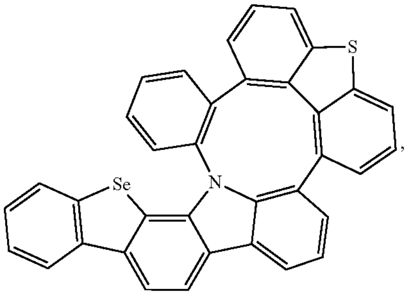
Compound 244
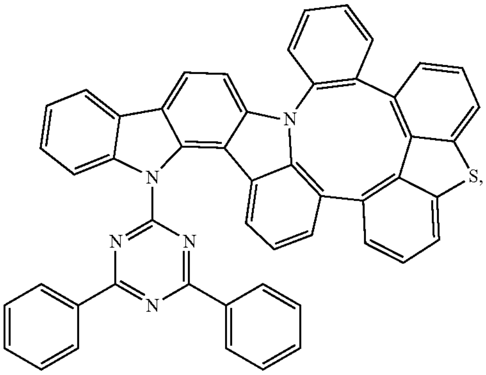
Compound 245
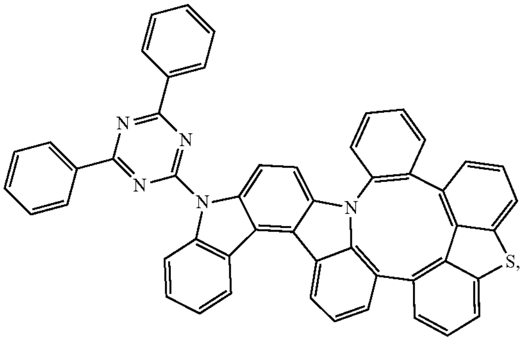
Compound 246
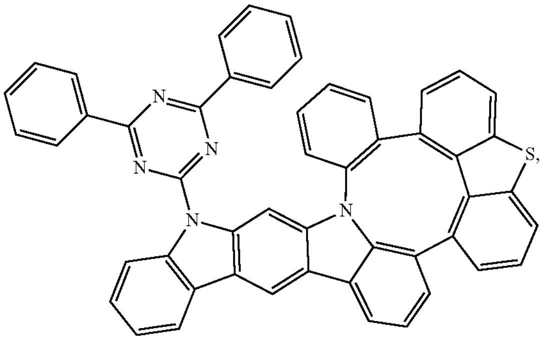

-continued
Compound 247
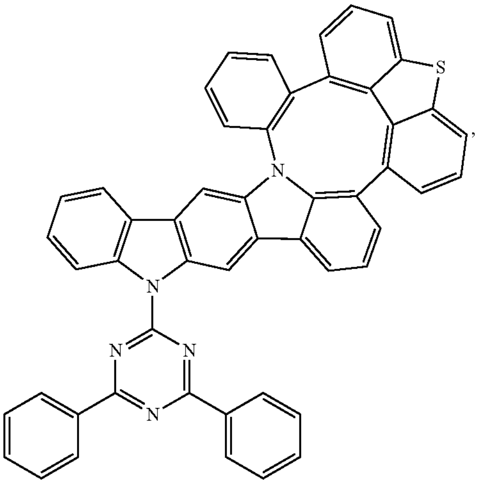
Compound 248
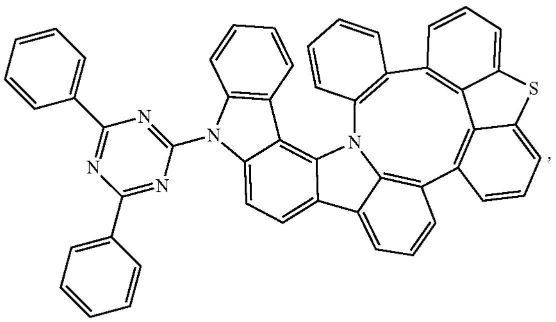
Compound 249
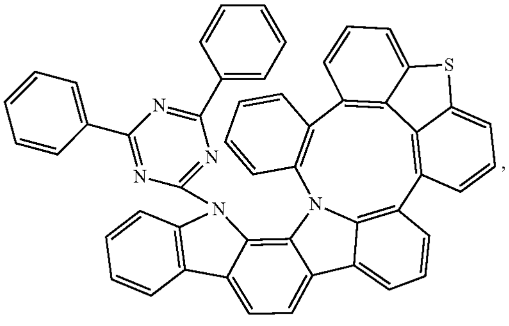
Compound 250
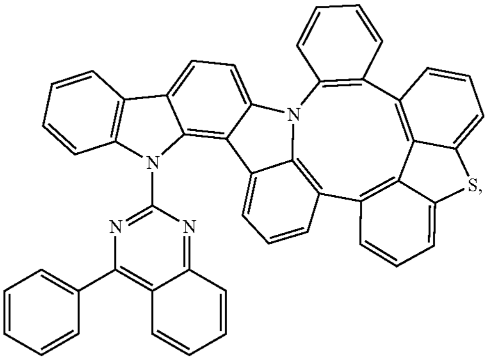
-continued
Compound 251
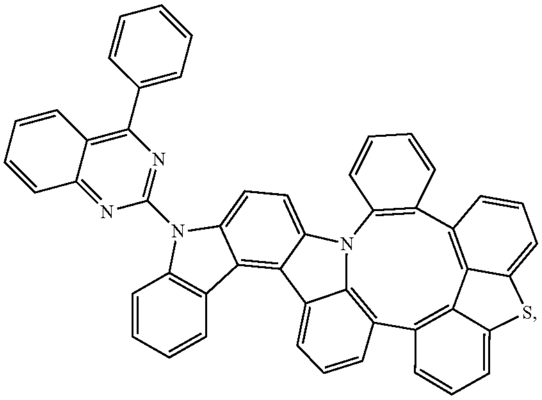
Compound 252
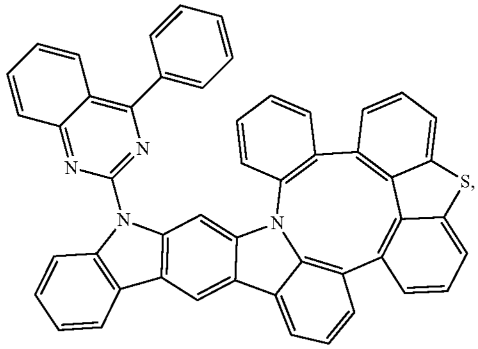
Compound 253
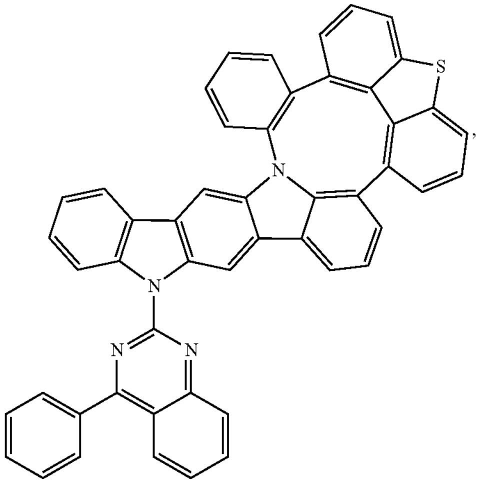
Compound 254
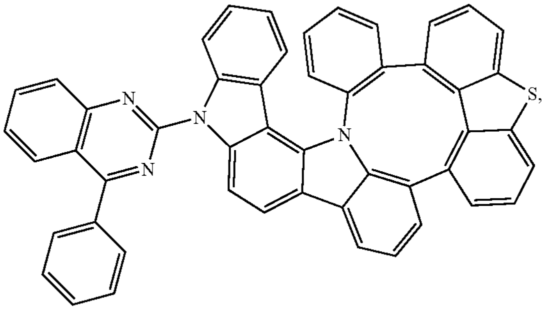

-continued
Compound 255
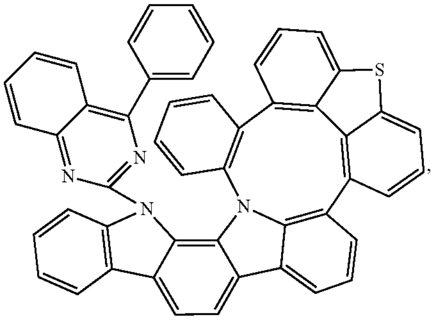
,
Compound 256
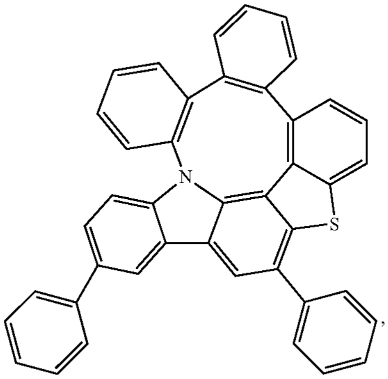
,
Compound 257
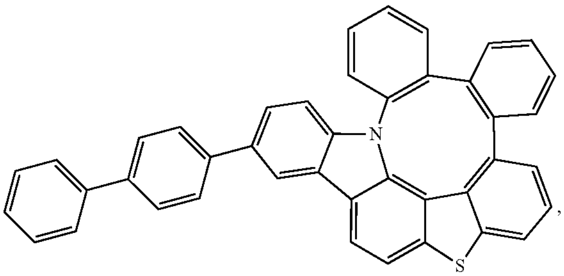
,
Compound 258
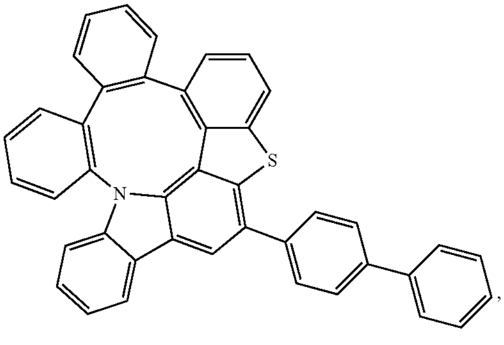
,
-continued
Compound 259
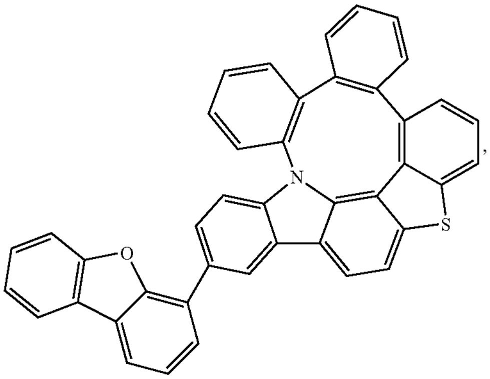
,
Compound 260
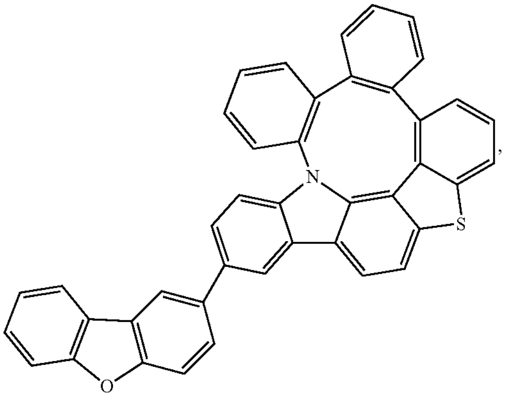
,
Compound 261
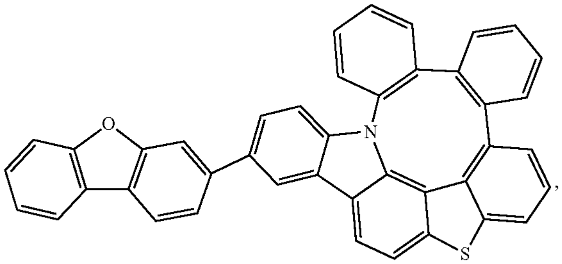
,
Compound 262
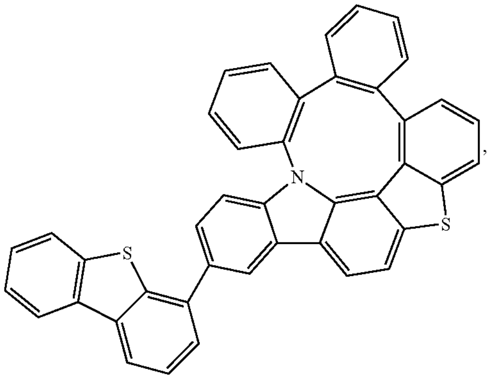
, -continued
Compound 263
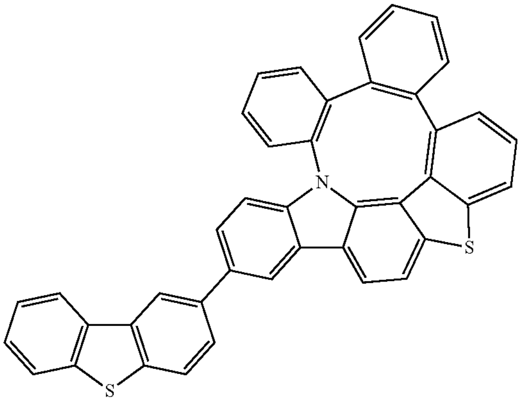
,
Compound 264
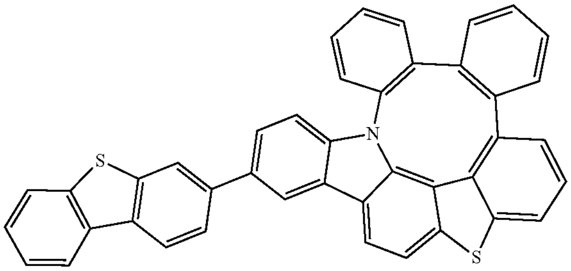
,
Compound 265
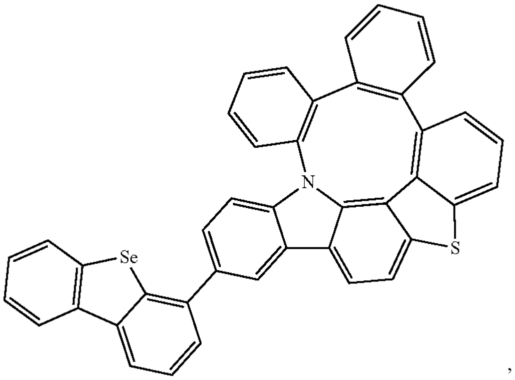
,
Compound 266
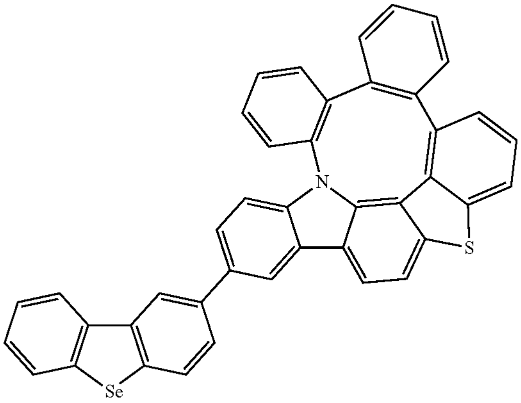
,
Compound 267
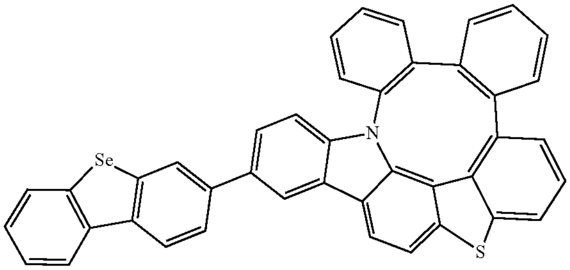
,
Compound 268
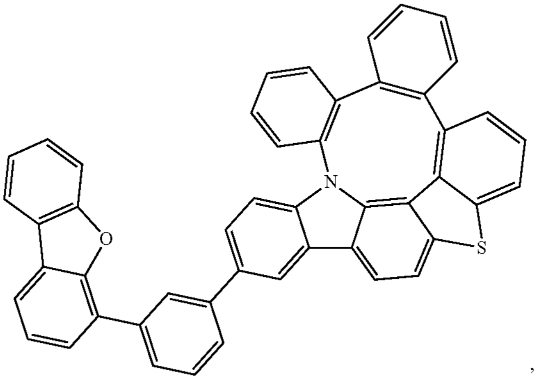
,
Compound 269
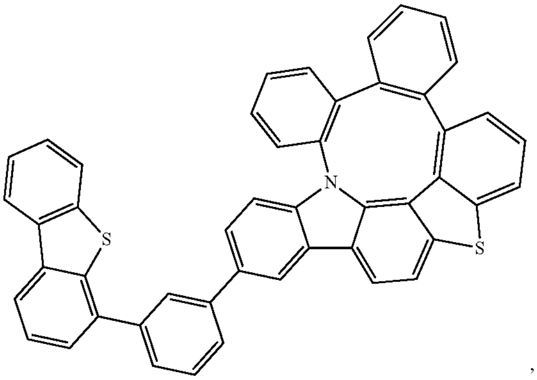
,
Compound 270
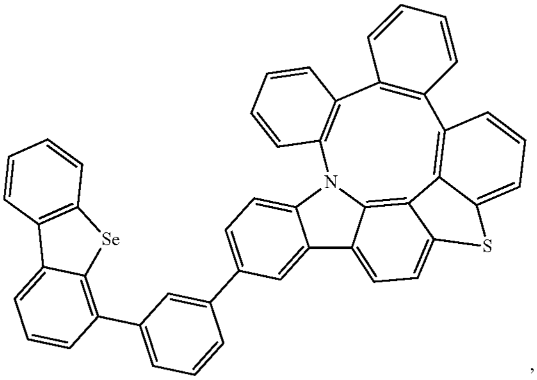
, -continued
Compound 271
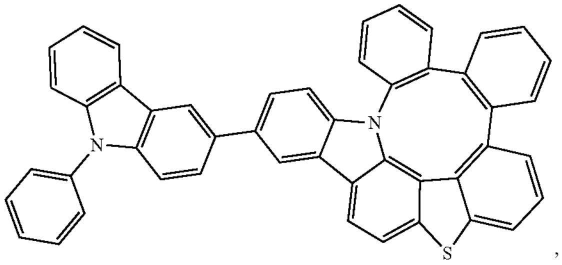
,
Compound 272
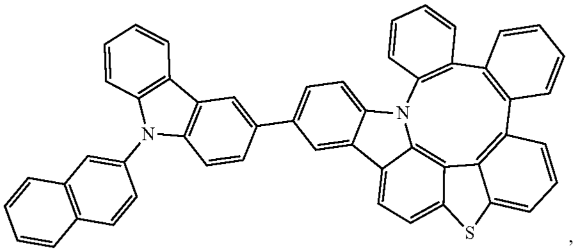
,
Compound 273
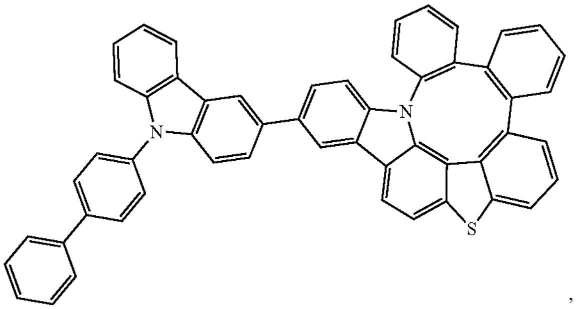
,
Compound 274
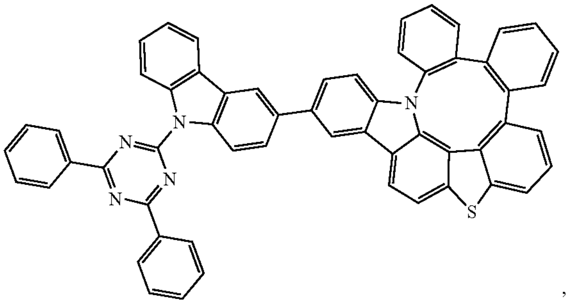
,
Compound 275
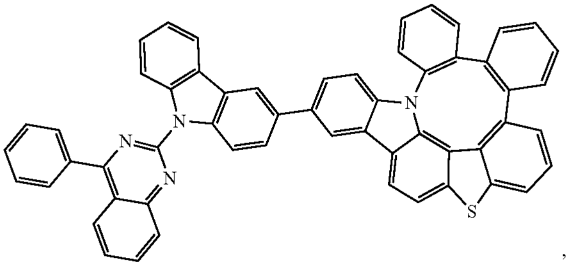
,
-continued
Compound 276
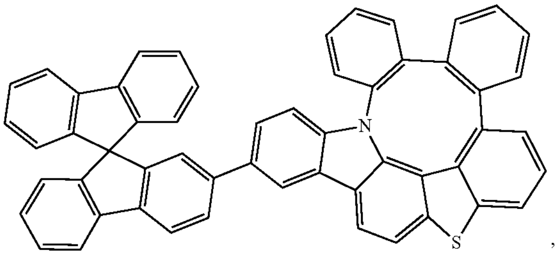
,
Compound 277
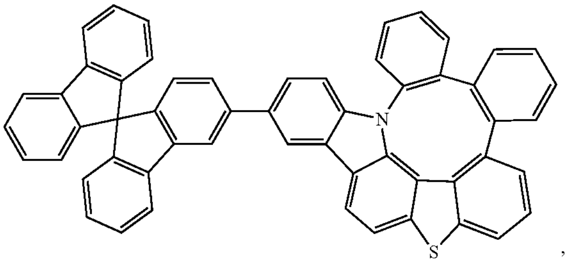
,
Compound 278
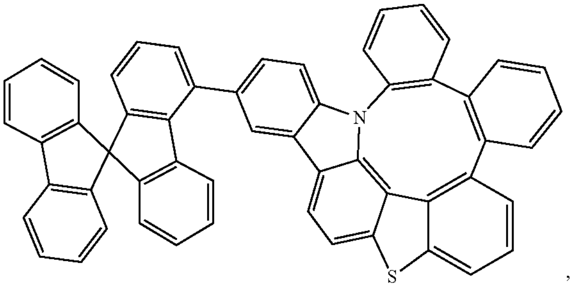
,
Compound 279
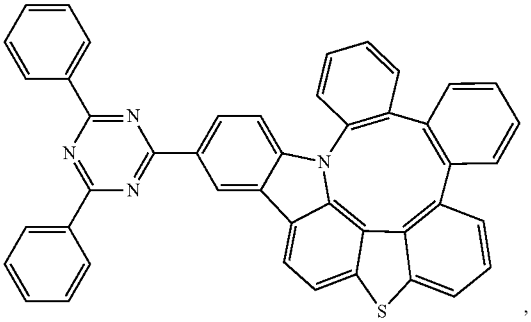
,
Compound 280
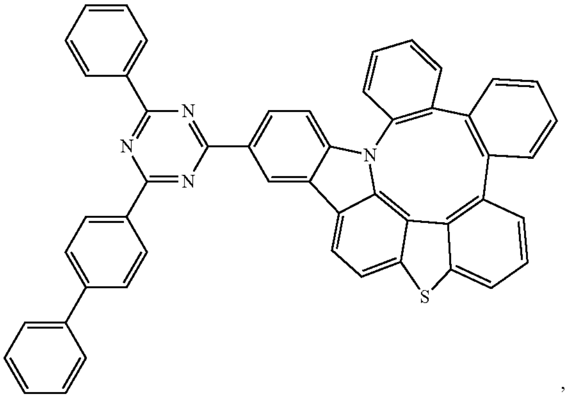
, -continued
Compound 281
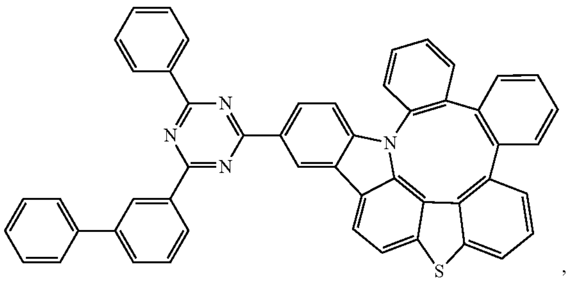
,
Compound 282
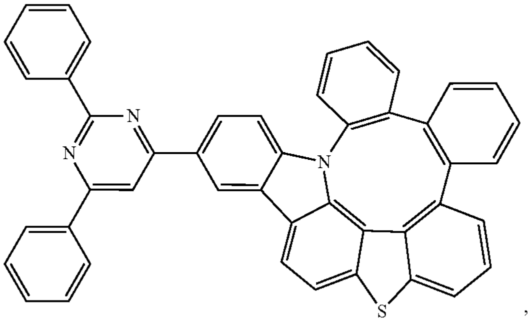
,
Compound 283
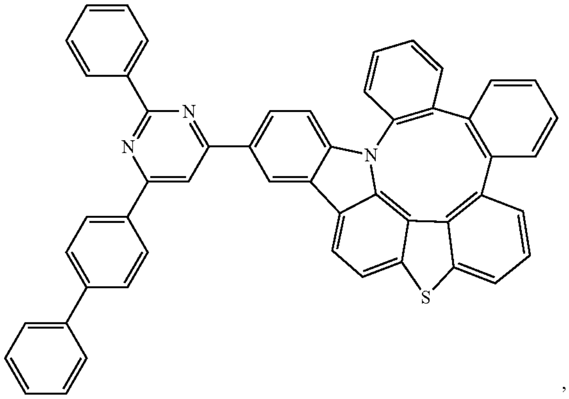
,
Compound 284
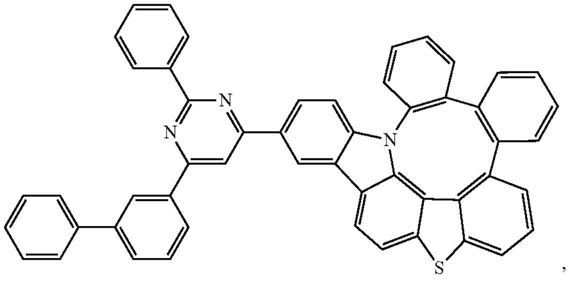
,
-continued
Compound 285
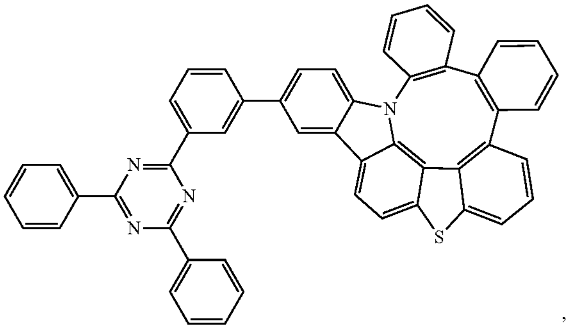
,
Compound 286
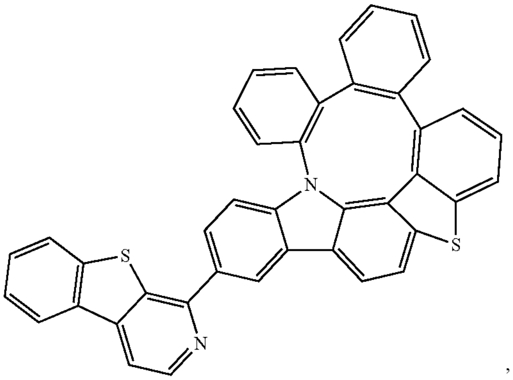
,
Compound 287
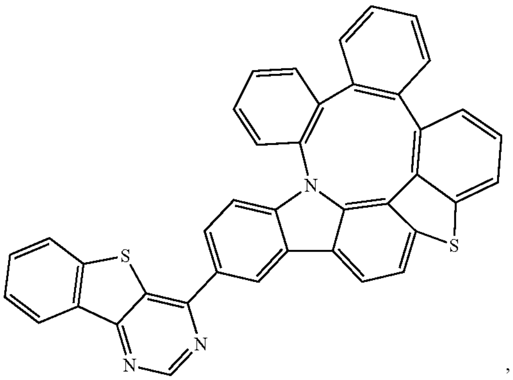
,
Compound 288
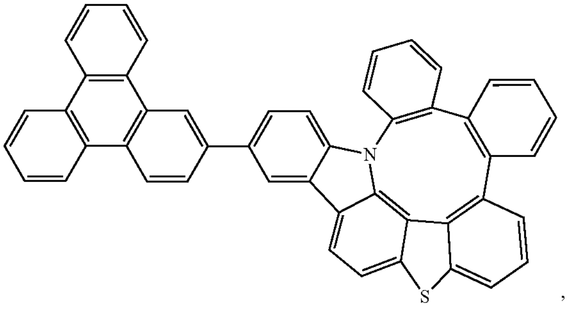
, -continued
Compound 289
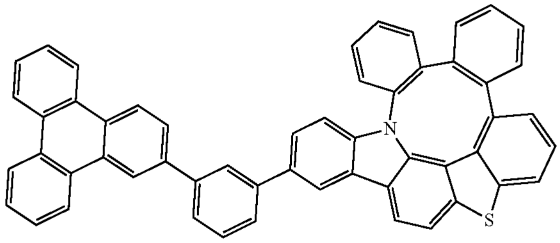
,
Compound 290
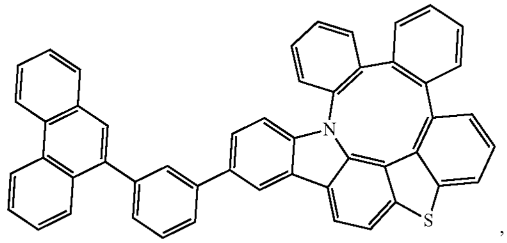
,
Compound 291
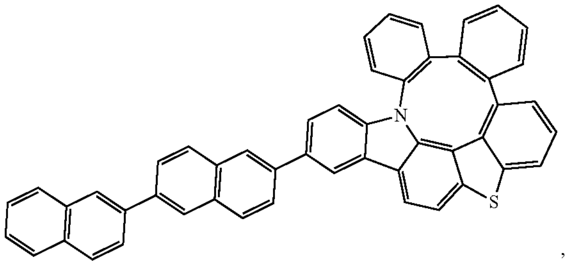
,
Compound 292
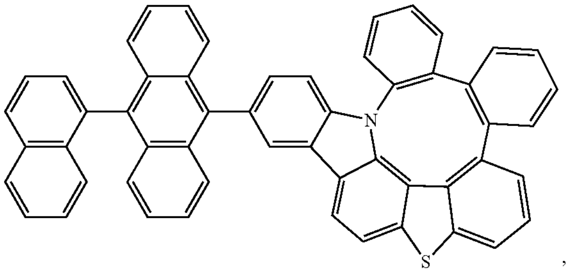
,
Compound 293
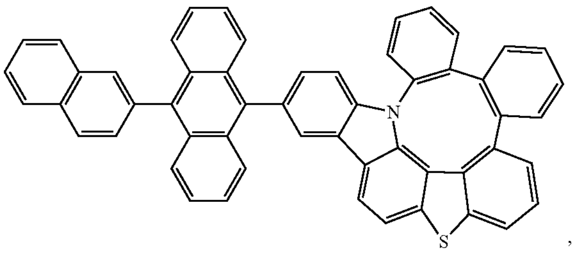
,
-continued
Compound 294
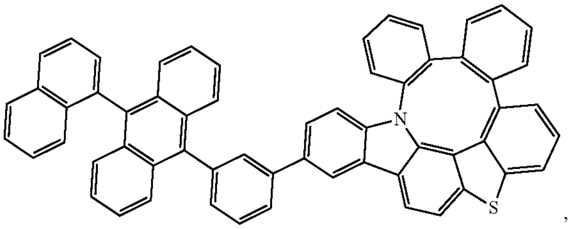
,
Compound 295
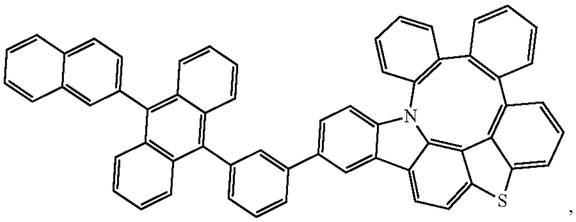
,
Compound 296
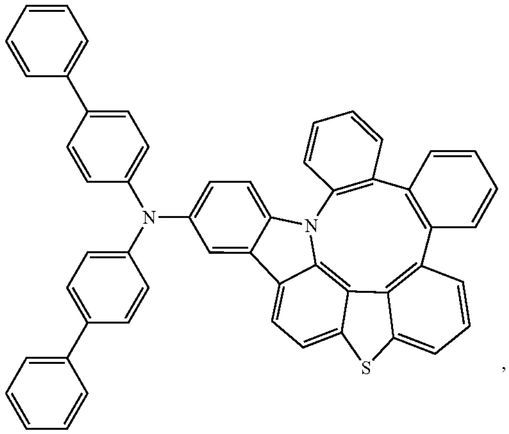
,
Compound 297
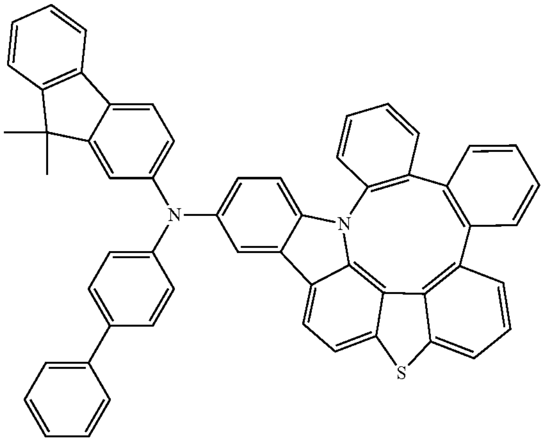
, -continued
Compound 298
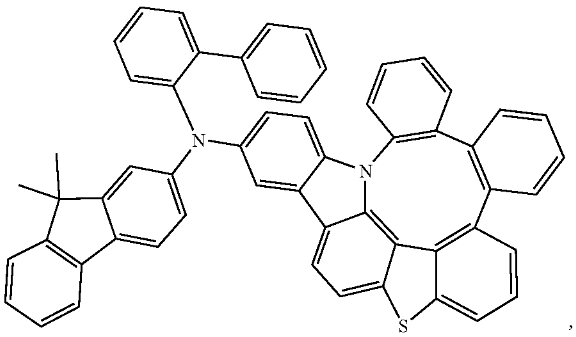
,
Compound 299
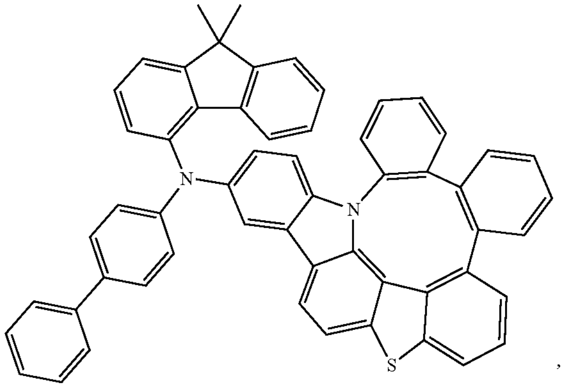
,
Compound 300
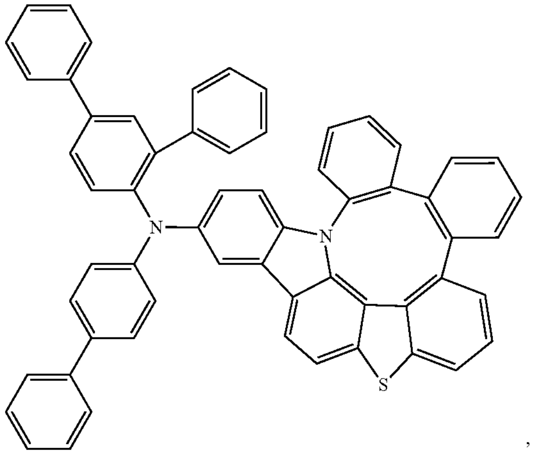
,
Compound 301
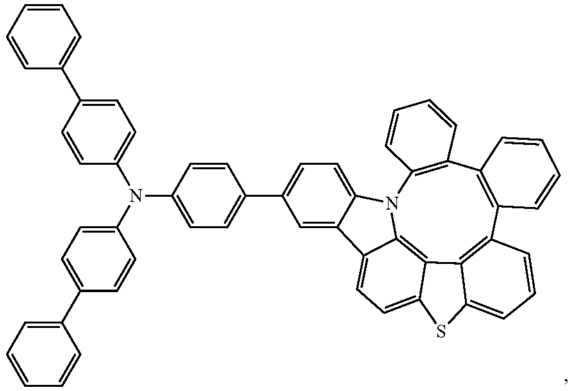
,
-continued
Compound 302
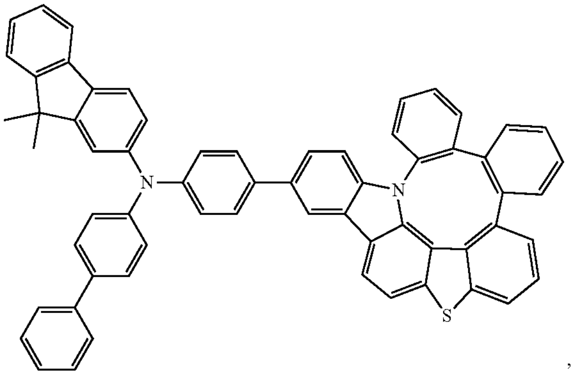
,
Compound 303
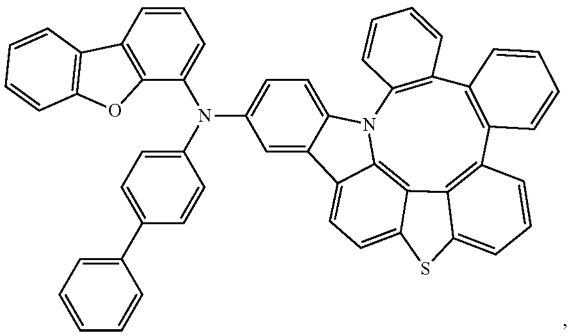
,
Compound 304
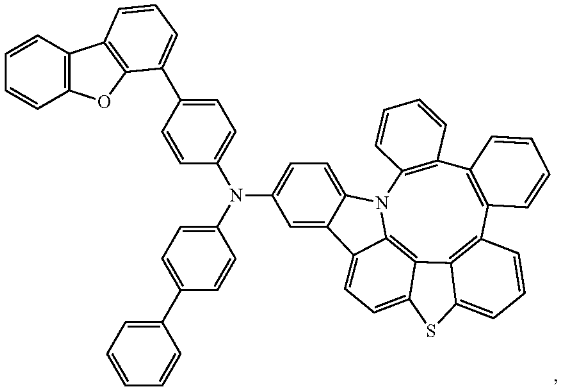
,
Compound 305
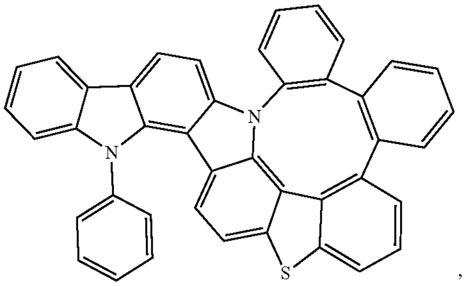
, -continued
Compound 306
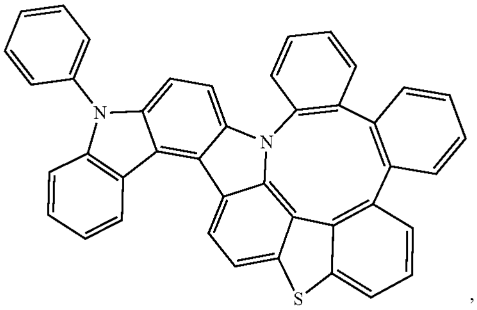
,
Compound 307
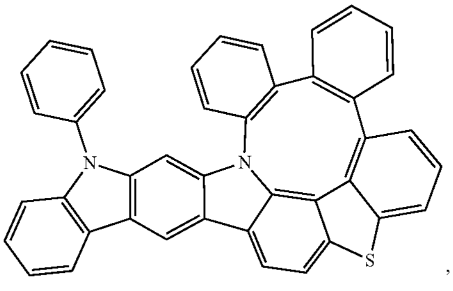
,
Compound 308
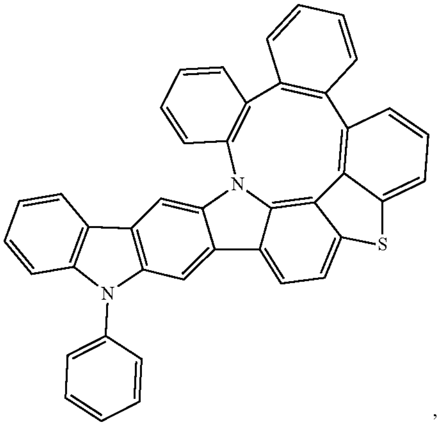
,
Compound 309
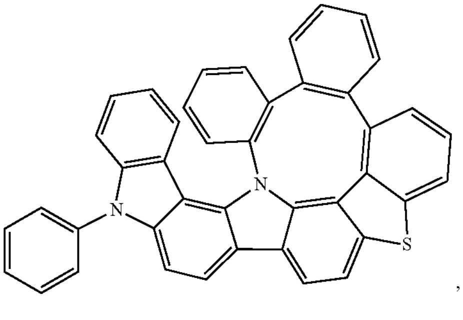
,
Compound 310
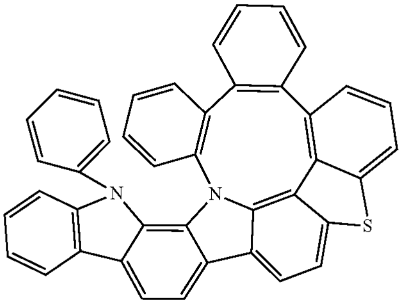
,
Compound 311
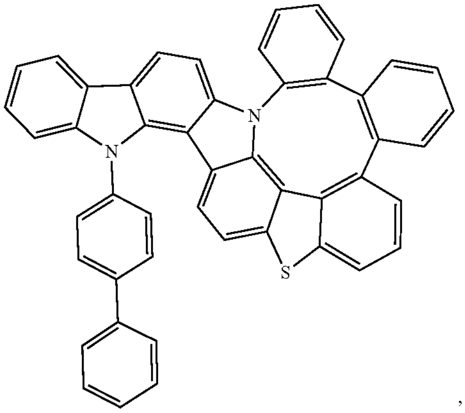
,
Compound 312
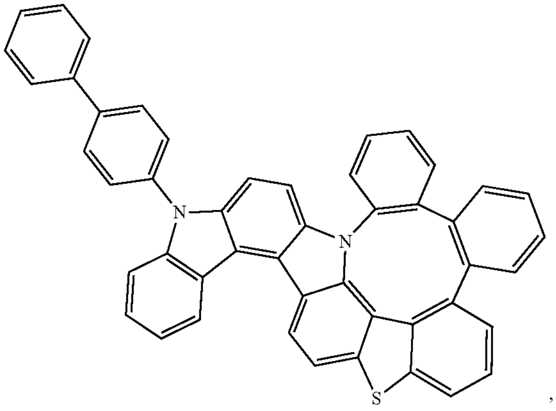
,
Compound 313
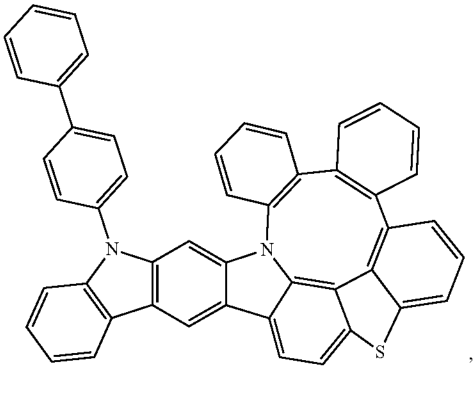
, -continued
Compound 314
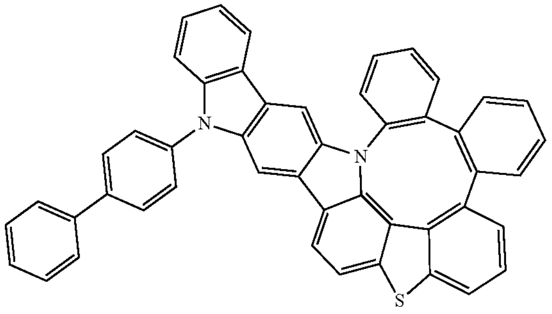
,
Compound 315
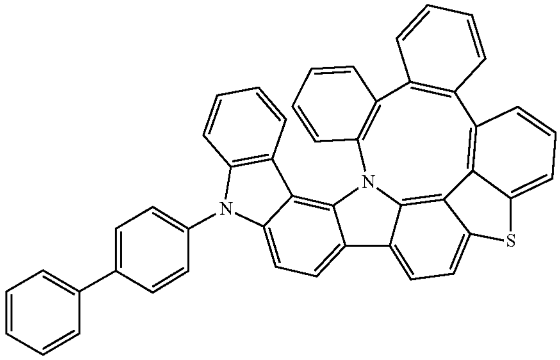
,
Compound 316
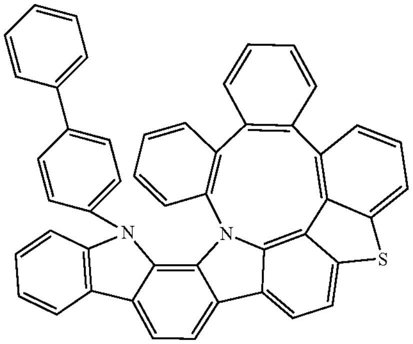
,
Compound 317
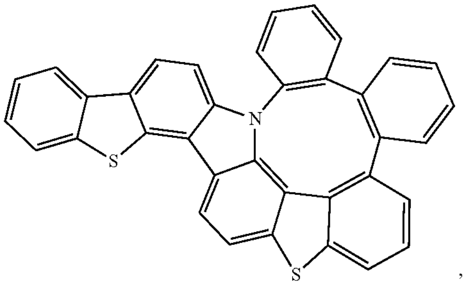
,
-continued
Compound 318
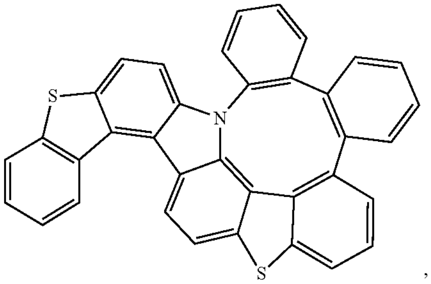
,
Compound 319
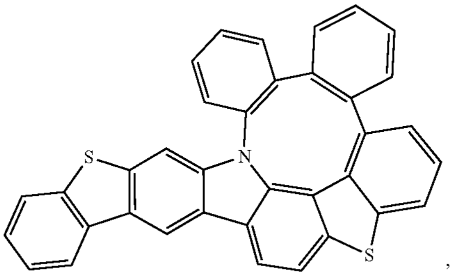
,
Compound 320
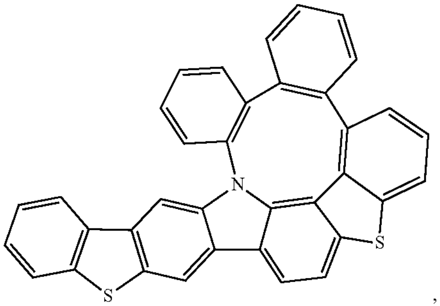
,
Compound 321
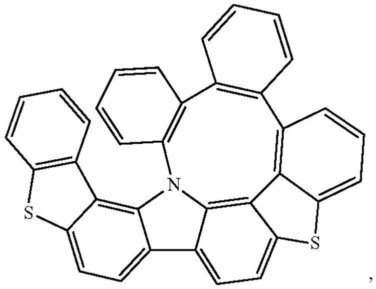
,
Compound 322
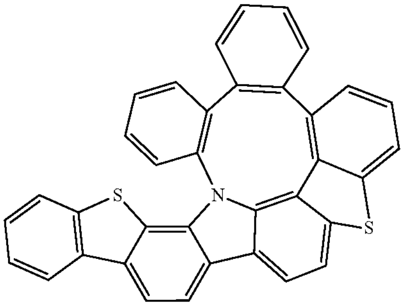
, -continued
Compound 323
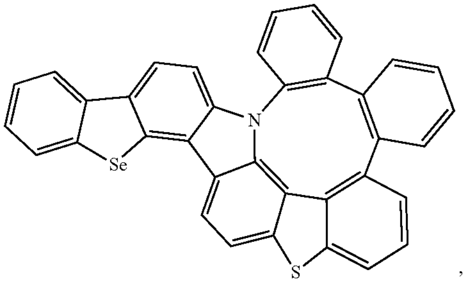
,
Compound 324
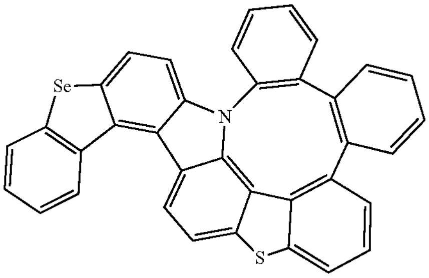
,
Compound 325
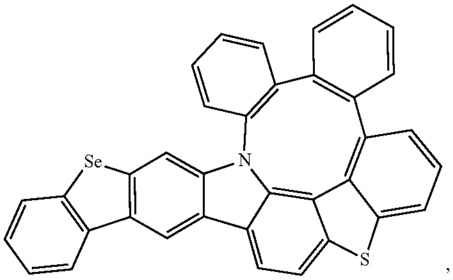
,
Compound 326
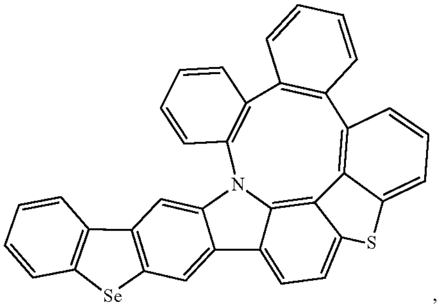
,
Compound 327
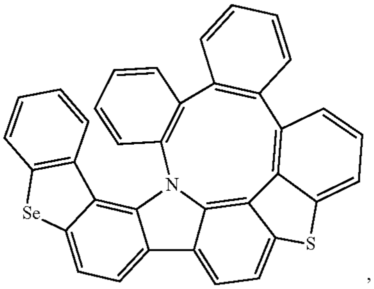
,
-continued
Compound 328
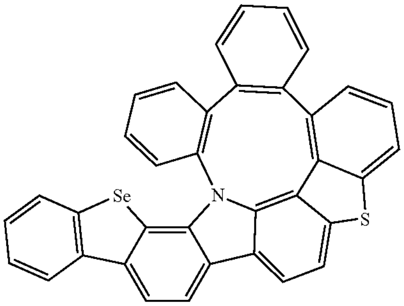
,
Compound 329
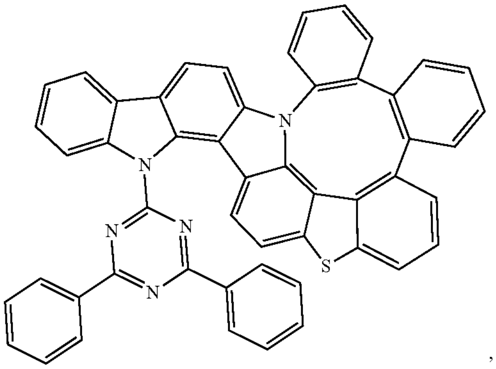
,
Compound 330
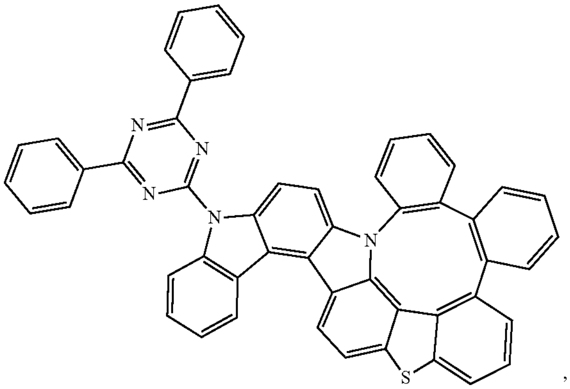
,
Compound 331
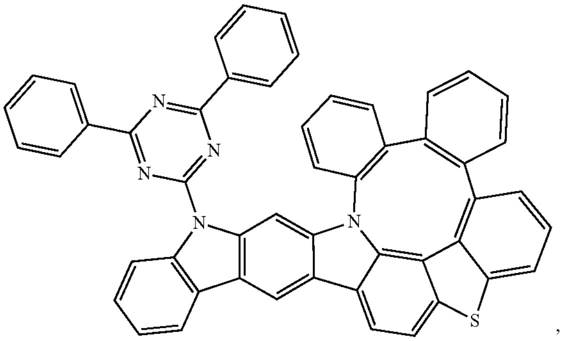
, -continued
Compound 332
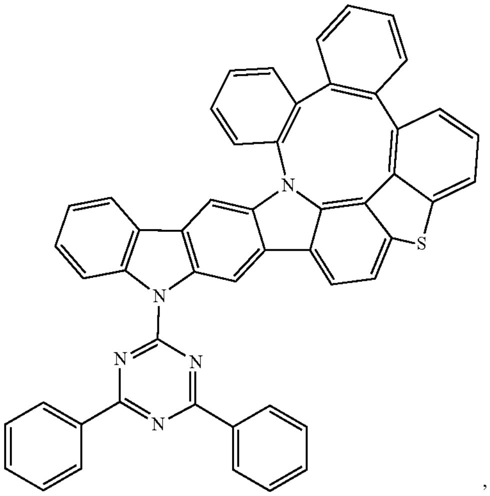
,
Compound 333
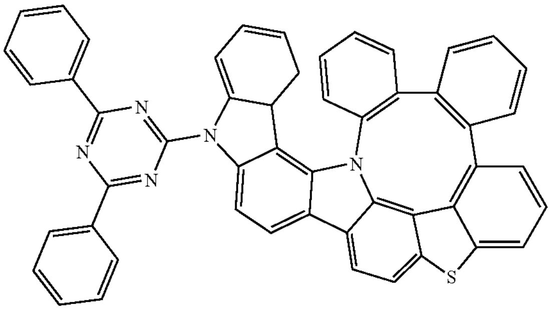
,
Compound 334
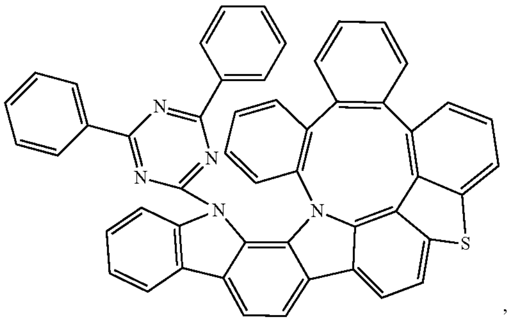
,
Compound 335
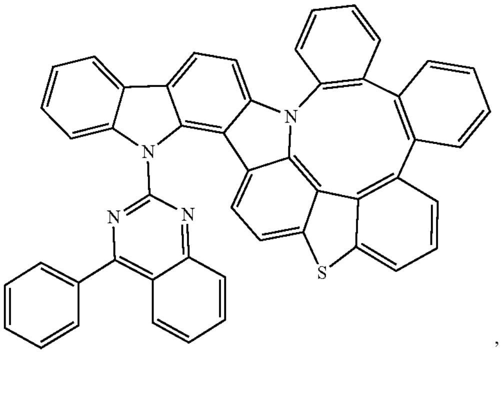
,
-continued
Compound 336
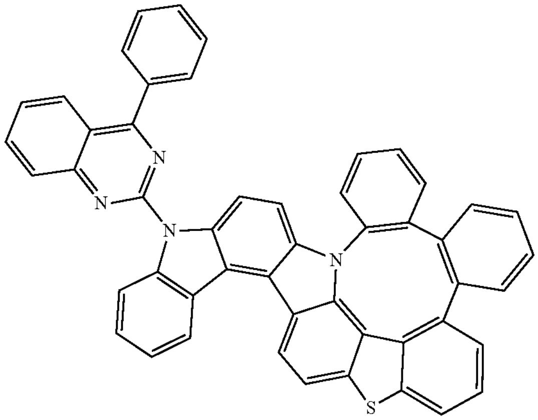
,
Compound 337
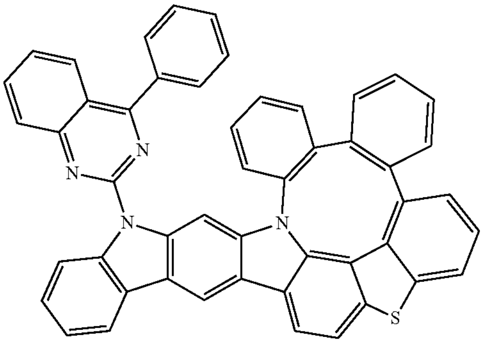
,
Compound 338
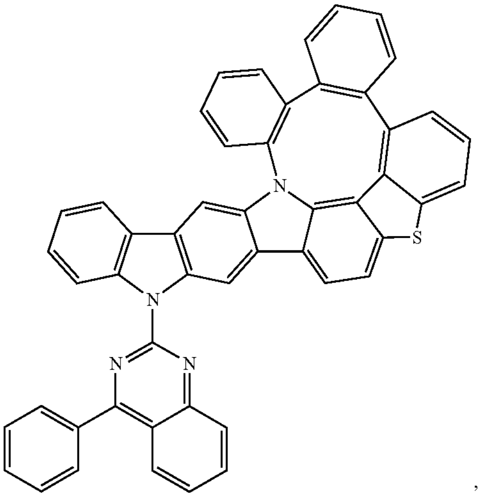
,
Compound 339
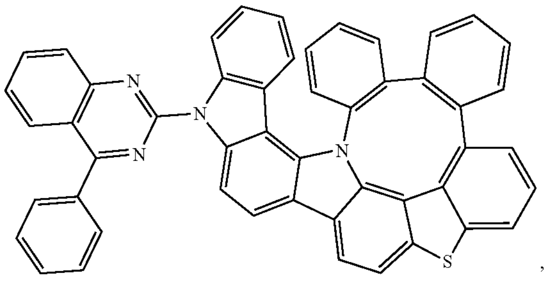
, -continued
Compound 340
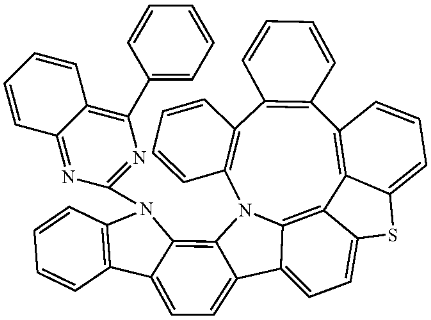
,
Compound 341
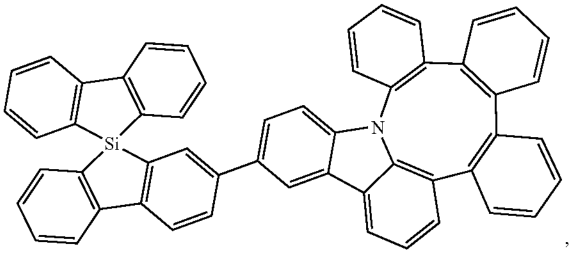
,
Compound 342
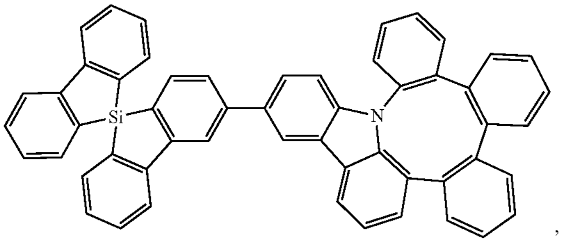
,
Compound 343
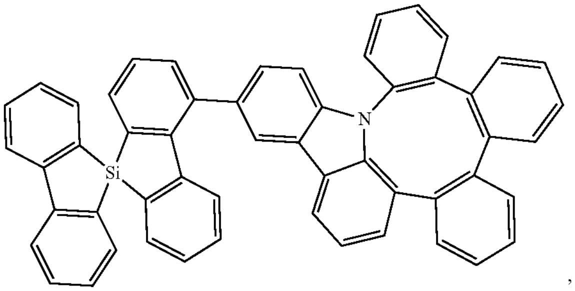
,
-continued
Compound 344
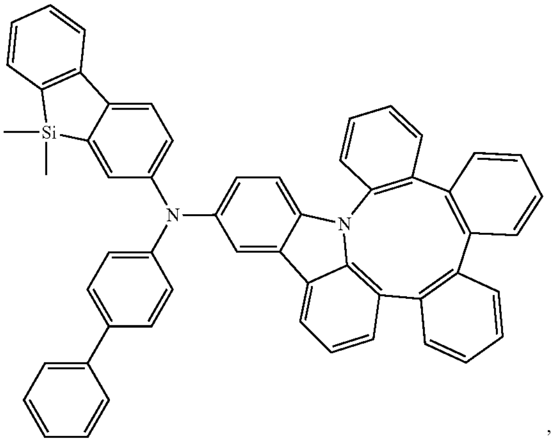
,
Compound 345
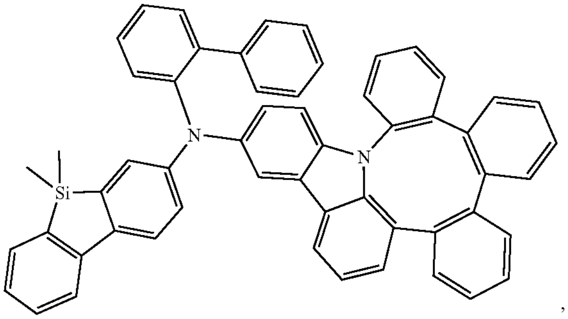
,
Compound 346
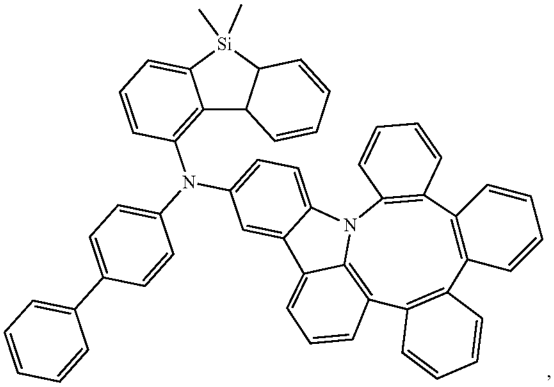
,
Compound 347
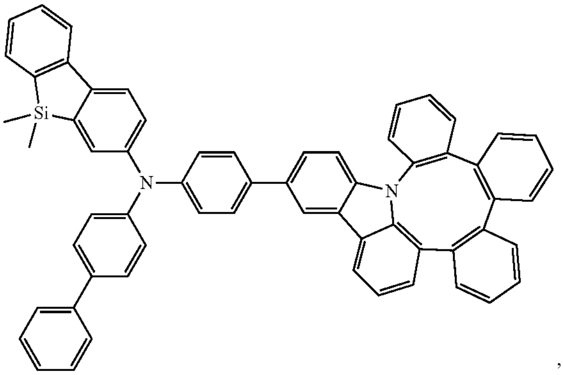
, -continued
Compound 348
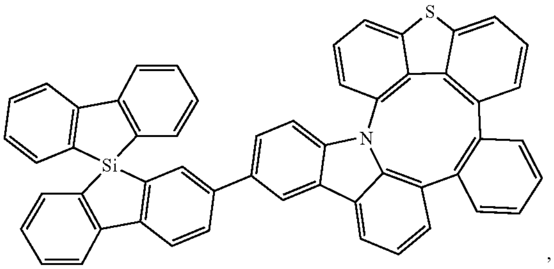
,
Compound 349
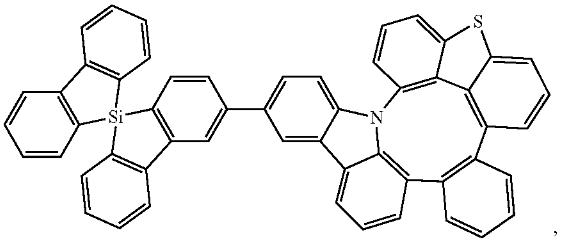
,
Compound 350
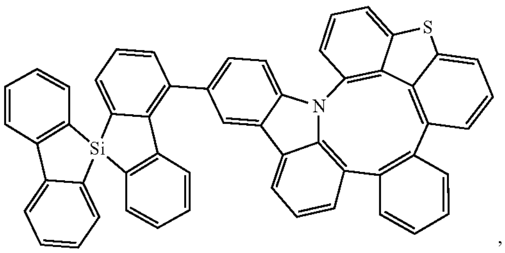
,
Compound 351
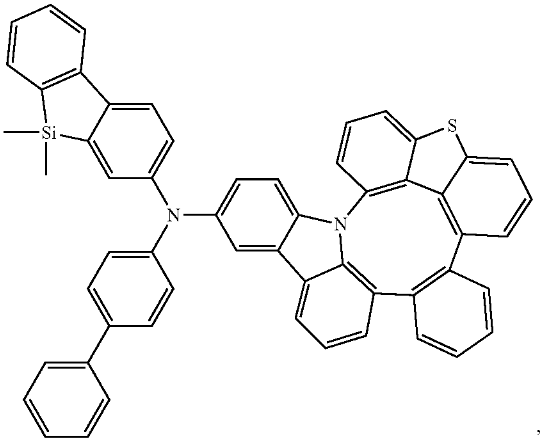
,
-continued
Compound 352
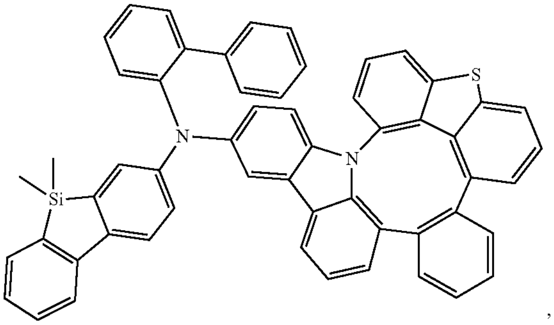
,
Compound 353
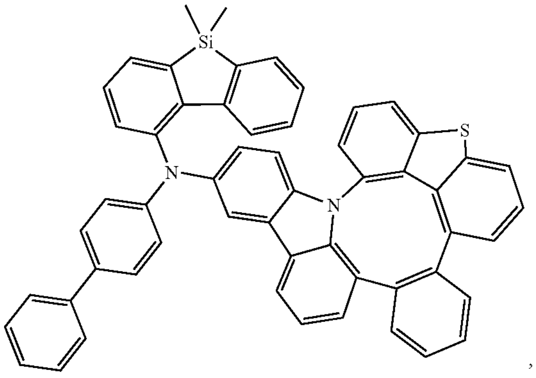
,
Compound 354
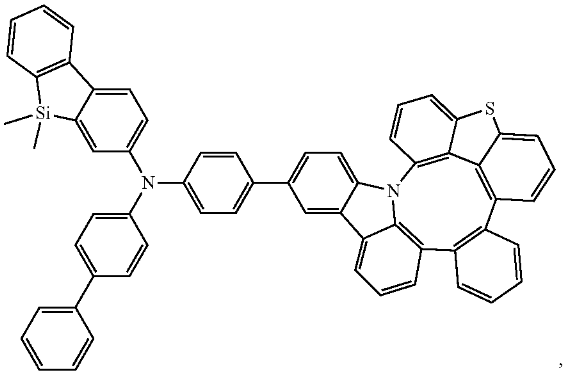
,
Compound 355
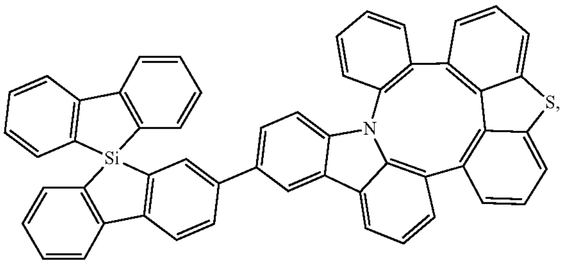
, -continued
Compound 356
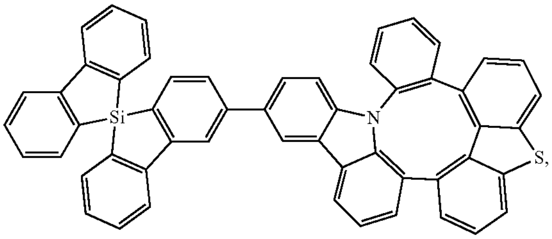
S,
Compound 357
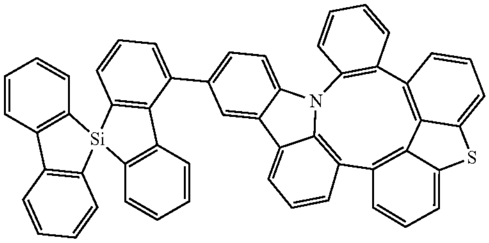
,
Compound 358
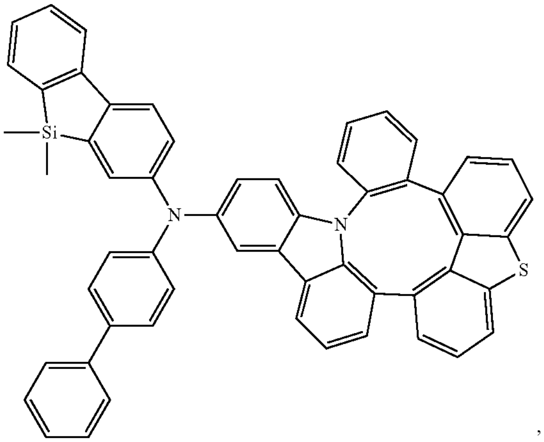
,
Compound 359
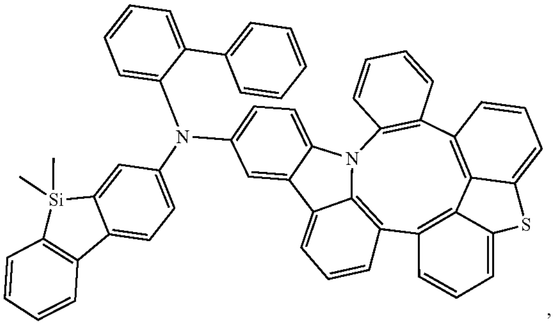
,
-continued
Compound 360
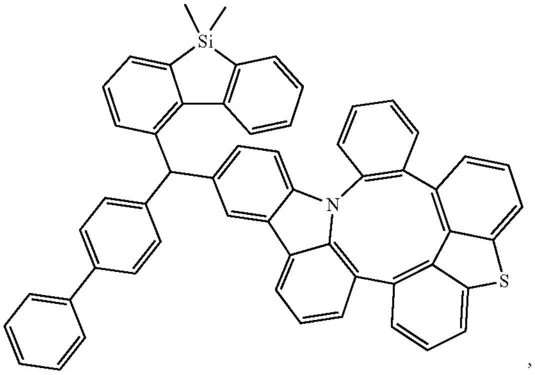
,
Compound 361
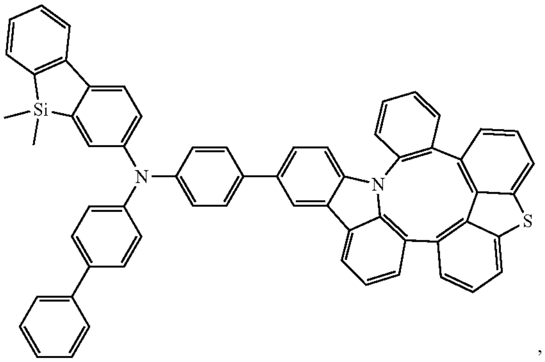
,
Compound 362
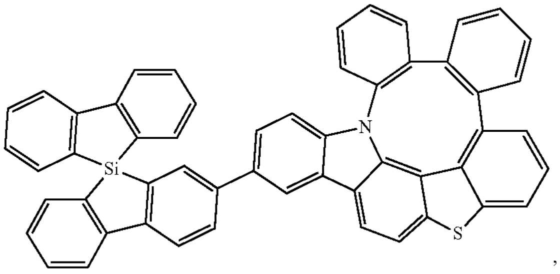
,
Compound 363
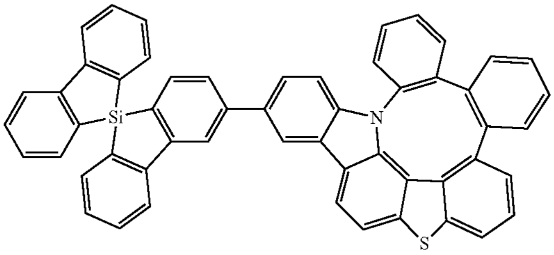
, -continued Compound 364

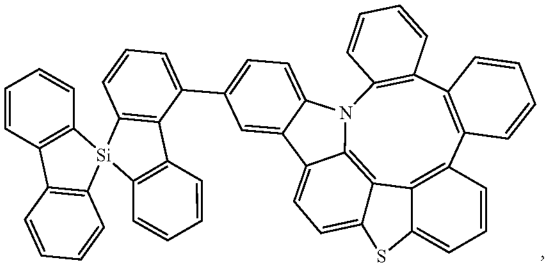

,

Compound 365

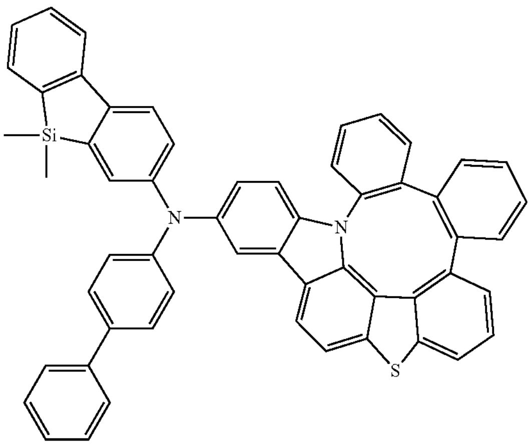

,

Compound 366

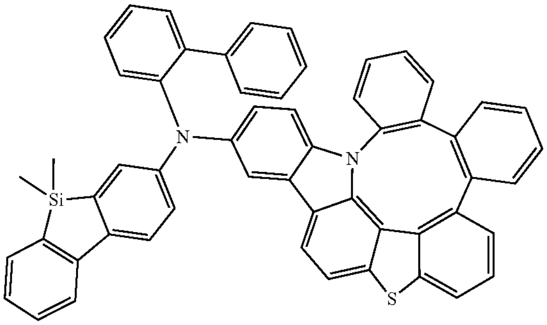

,

Compound 367

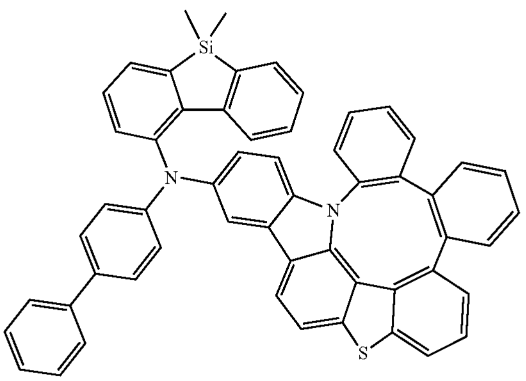

,

-continued

Compound 368

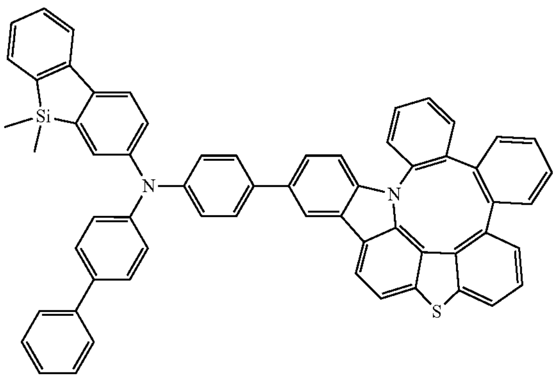

.

According to another embodiment, an electroluminescent device is disclosed. The electroluminescent device comprises:

an anode, a cathode, and an organic layer, disposed between the anode and the cathode, comprising a compound of Formula 1:

Formula 1

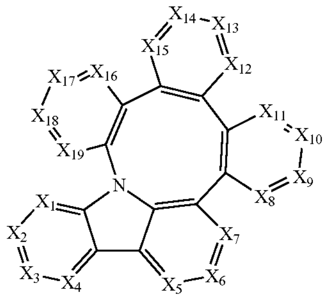

Wherein $X_1$ to $X_{19}$ are each independently selected from the group consisting of CR, and N;

Wherein R are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 50 carbon atoms, a substituted or unsubstituted heteroaryl group having 3 to 50 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring.

According to one embodiment of the present invention, wherein the organic layer is a charge transporting layer.

According to one embodiment of the present invention, wherein the organic layer is a charge blocking layer.

According to one embodiment of the present invention, wherein the organic layer is an emissive layer and the compound is a host.

According to one embodiment of the present invention, wherein the organic layer further comprises a phosphorescent emitter.

According to one embodiment of the present invention, wherein the organic layer further comprises a phosphorescent emitter and the phosphorescent emitter is a metal complex having at least one ligand comprising the any following structures:

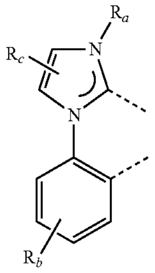 , 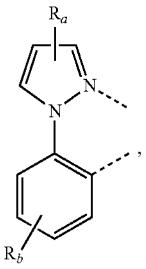 , 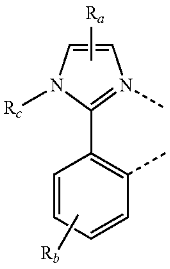 ,

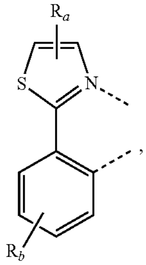 , 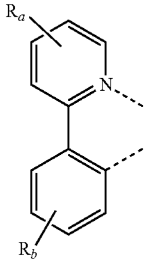 , 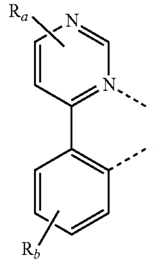 ,

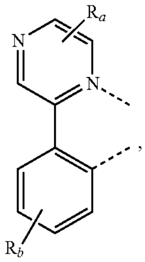 , 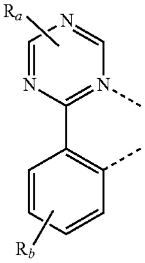 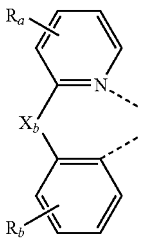

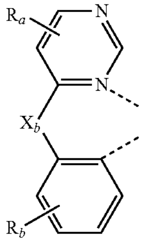 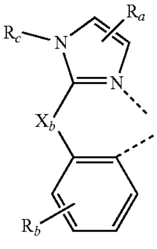 ,

Wherein $R_a$, $R_b$, and $R_c$ can represent mono, di, tri, or tetra substitution or no substitution;

$X_b$ is independently selected from the group consisting of O, S, Se, $NR_{N1}$, and $CR_{C1}R_{C2}$;

$R_a$, $R_b$, $R_c$, $R_{N1}$, $R_{C1}$ and $R_{C2}$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 50 carbon atoms, a substituted or unsubstituted heteroaryl group having 3 to 50 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring.

According to one embodiment of the present invention, wherein the organic layer is the emissive layer and the compound of Formula 1 is the thermally delayed fluorescent dopant.

According to yet another embodiment, a formulation comprising a compound having Formula 1 is also disclosed. The specific structures of the compounds are described in any of the above embodiments.

Combination with Other Materials

The materials described herein as useful for a particular layer in an organic light emitting device may be used in combination with a wide variety of other materials present in the device. The combinations of these materials are described in more detail in U.S. Pat. App. No. 20160359122 at paragraphs 0132-0161, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, host materials disclosed herein may be used in combination with a wide variety of emissive dopants, hosts, transport layers, blocking layers, injection layers, electrodes and other layers that may be present. The combination of these materials is described in detail in paragraphs 0080-0101 of U.S. Pat. App. No. 20150349273, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

It is understood that the various embodiments described herein are by way of example only, and are not intended to limit the scope of the invention. The present invention as claimed may therefore include variations from the particular examples and preferred embodiments described herein, as will be apparent to one of skill in the art. Many of the materials and structures described herein may be substituted with other materials and structures without deviating from the spirit of the invention. It is understood that various theories as to why the invention works are not intended to be limiting.

What is claimed is:

1. A compound comprising Formula 1:

Formula 1

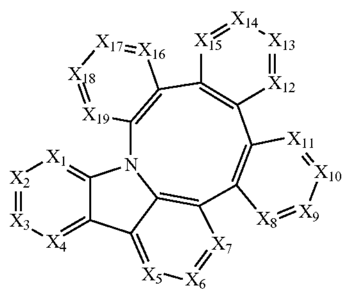

wherein $X_1$ to $X_{19}$ are each independently selected from CR, or N;

R are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 50 carbon atoms, a substituted or unsubstituted heteroaryl group having 3 to 50 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring.

2. The compound of claim 1, wherein $X_1$ to $X_{19}$ are each independent CR.

3. The compound of claim 1, wherein the compound comprises a Formula 2 structure:

Formula 2

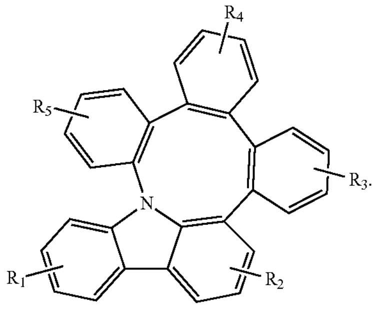

Wherein $R_1$, $R_3$, $R_4$, and $R_5$ independently represent mono, di, tri, tetra substitution, or no substitution;

$R_2$ independently represent mono, di, tri substitution, or no substitution;

$R_1$, $R_2$, $R_3$, $R_4$, and $R_5$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 50 carbon atoms, a substituted or unsubstituted heteroaryl group having 3 to 50 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring.

4. The compound of claim 1, wherein the compound comprises a structure of any one of Formula 3-6:

Formula 3

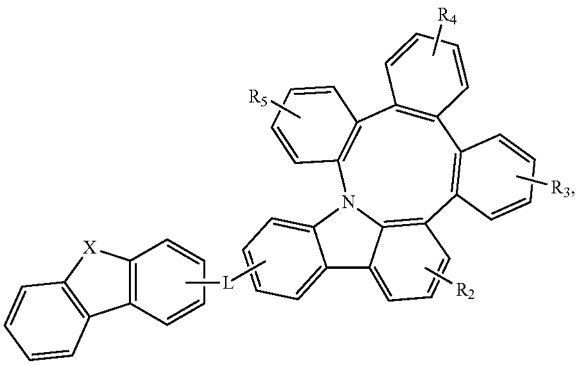

Formula 4

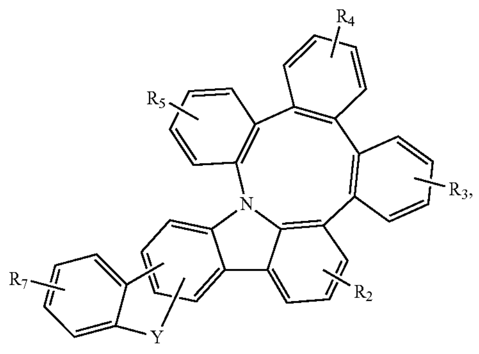

-continued

Formula 5

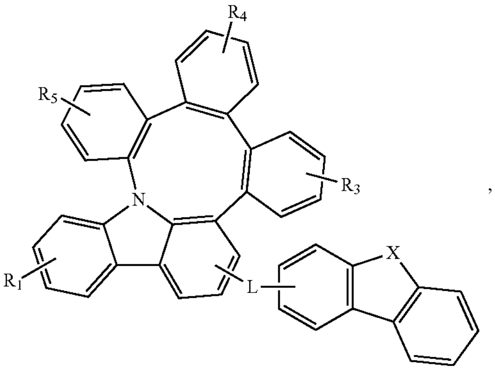

,

Formula 6

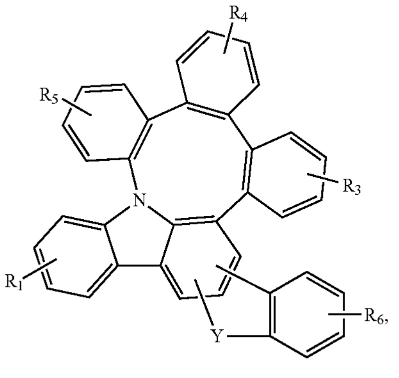

Wherein $R_1$, $R_3$, $R_4$, $R_5$, $R_6$, and $R_7$ independently represent mono, di, tri, tetra substitution, or no substitution;

$R_2$ independently represent mono, di, tri substitution, or no substitution;

X, are each independently selected from the group consisting of O, S, Se, NR', CR"R'" and SiR""R""';

Y are each independently selected from the group consisting of O, S, NR', CR"R'" and SiR""R""';

R', R", R'", R"", R""', $R_1$, $R_2$, $R_3$, $R_4$, $R_5$, $R_6$, and $R_7$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 50 carbon atoms, a substituted or unsubstituted heteroaryl group having 3 to 50 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring;

L is selected from the group consisting of:

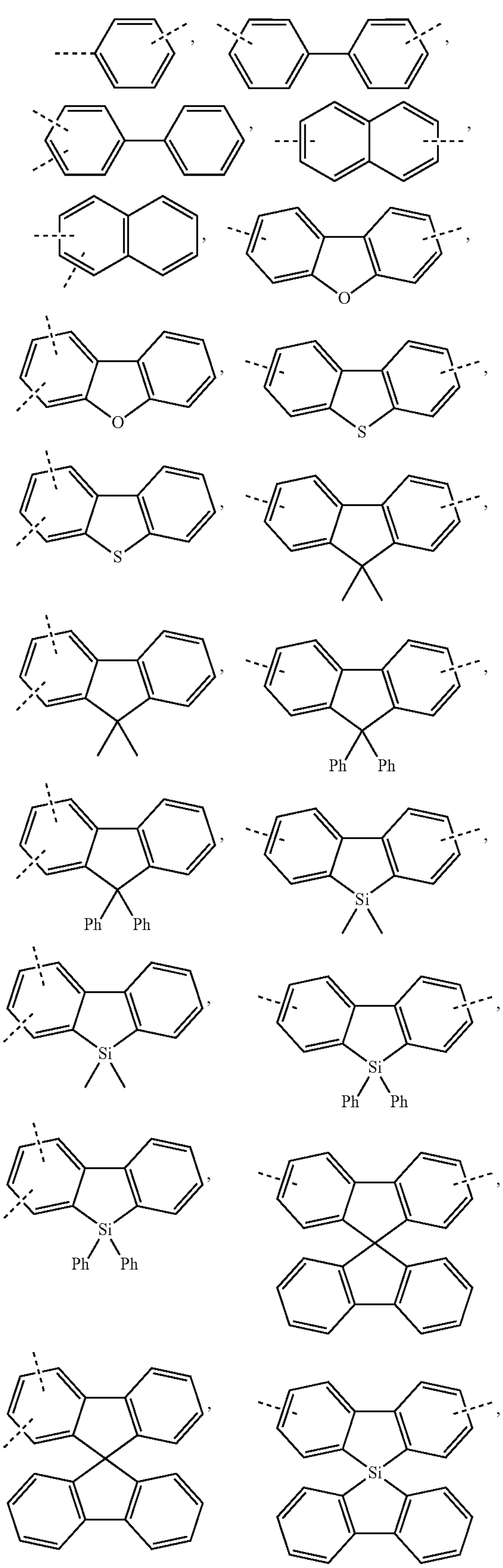

-continued

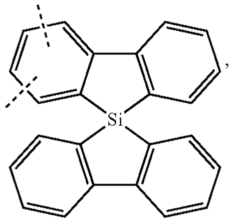

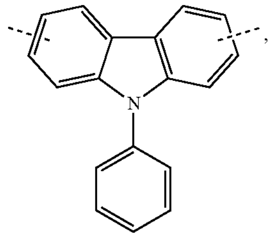

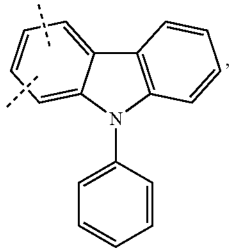

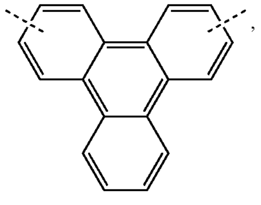

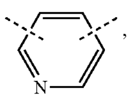

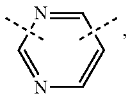

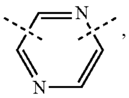

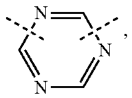

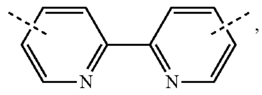

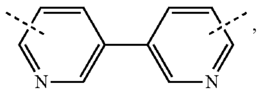

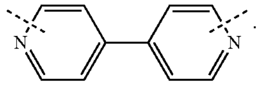

Single bond.

5. The compound of claim 1, wherein the compound comprises a structure of any one of Formula 7-9:

Formula 7

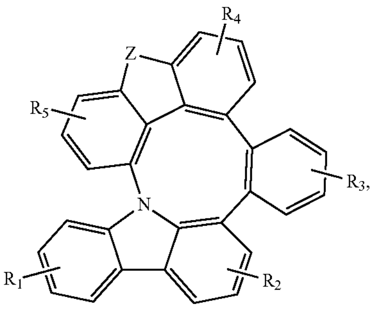

Formula 8

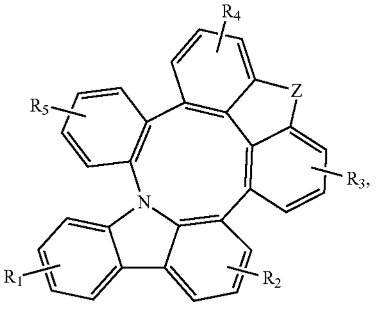

-continued

Formula 9

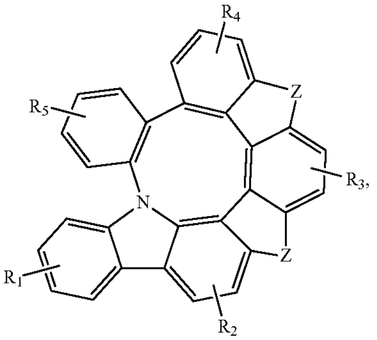

Wherein $R_1$ independently represent mono, di, tri, tetra substitution, or no substitution;

$R_2$, $R_3$, $R_4$, and $R_5$ independently represent mono, multi substitution, or no substitution; said multi substitution refer to a range that includes di substitution, up to the maximum available substitutions of the formula;

Z are each independently selected from the group consisting of O, S, NR', CR"R"' and SiR""R""';

R', R", R"', R"", R""', $R_1$, $R_2$, $R_3$, $R_4$, and $R_5$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 50 carbon atoms, a substituted or unsubstituted heteroaryl group having 3 to 50 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring.

6. The compound of claim 3, wherein $R_1$, and $R_2$ are each independently selected from the group consisting of:

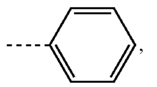

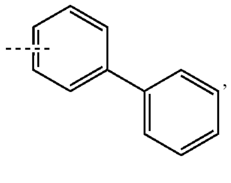

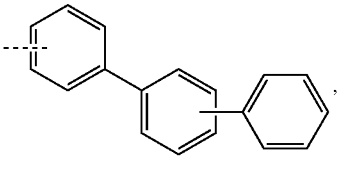

-continued
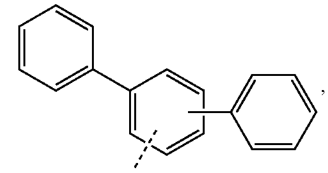,
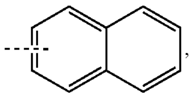,
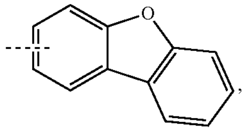,
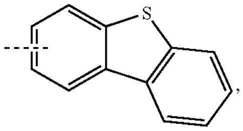,
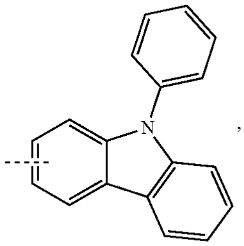,
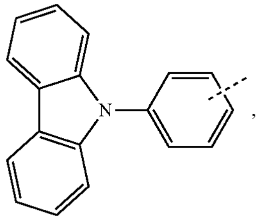,
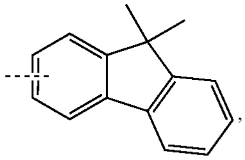,
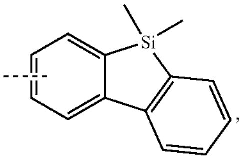,
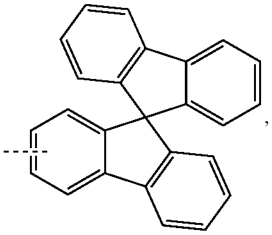,
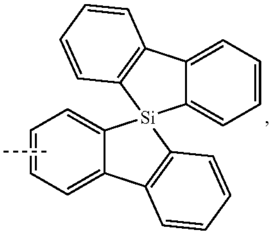,
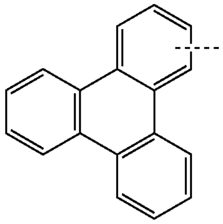,
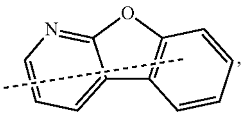,
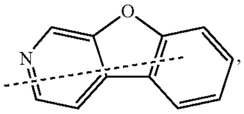,
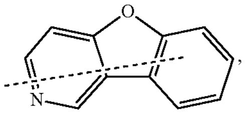,
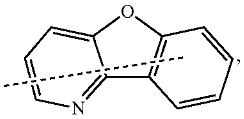,
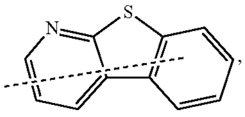,
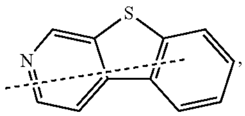,
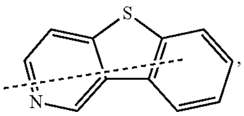,
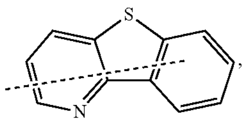,
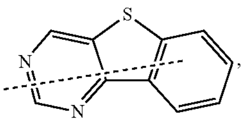,
-continued
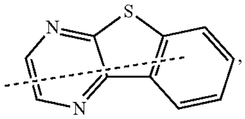,
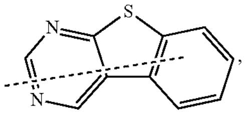,
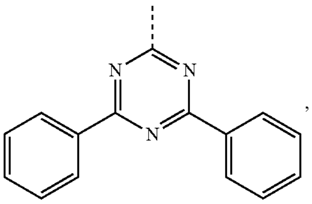,
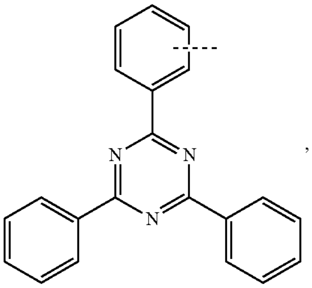,
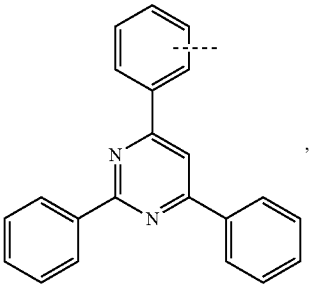,
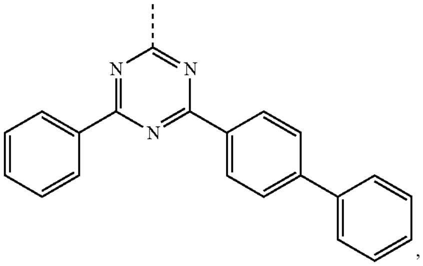,
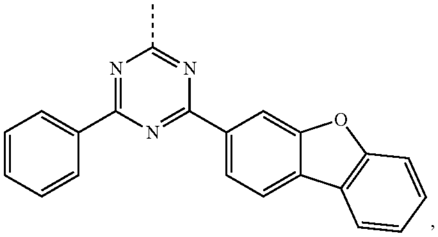,
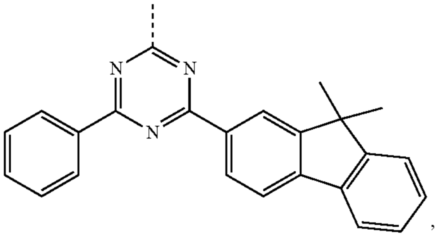, -continued
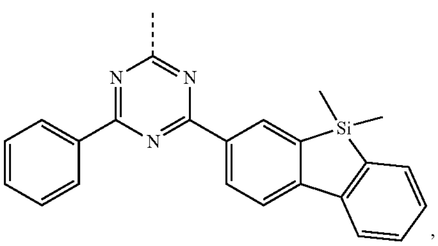,
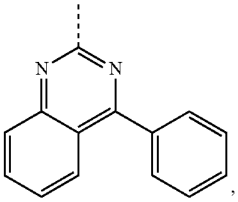, 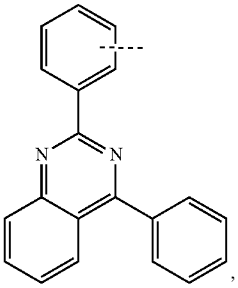,
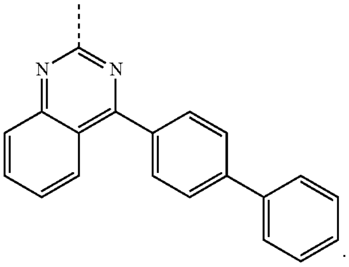.
7. The compound of claim 4, wherein $R_1$, $R_2$, $R_6$, and $R_7$ are each independently selected from the group consisting of:
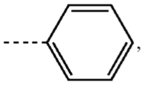, 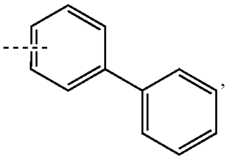,
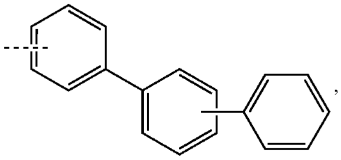,
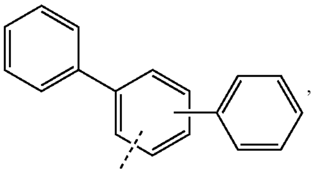, 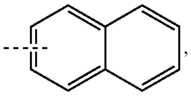,
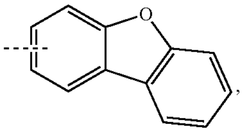, 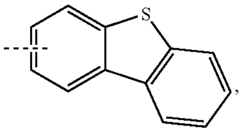,
-continued
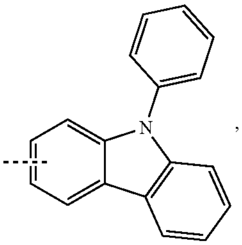, 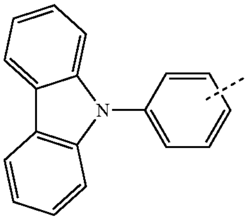,
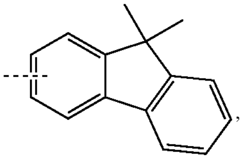, 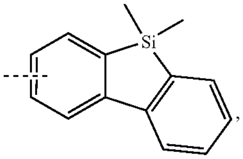,
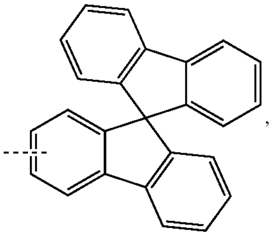, 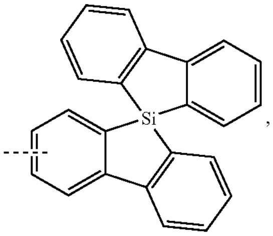,
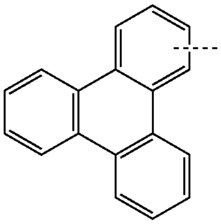, 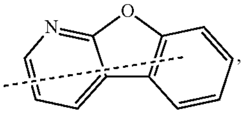,
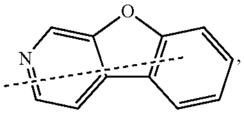, 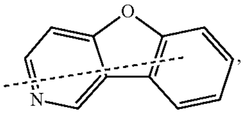,
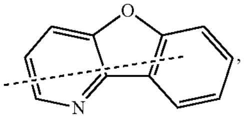, 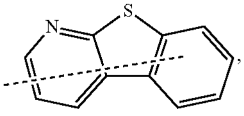,
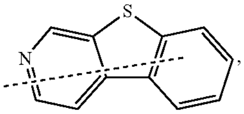, 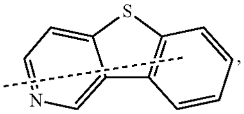,
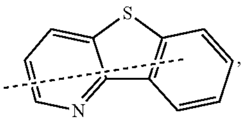, 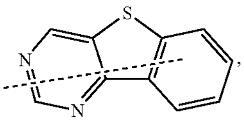,
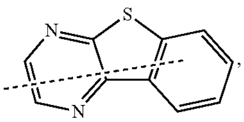, 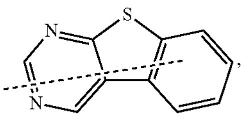,
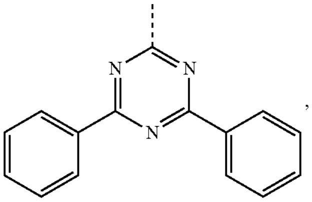, -continued
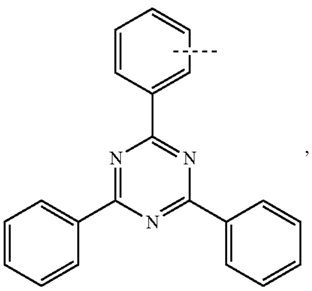
,
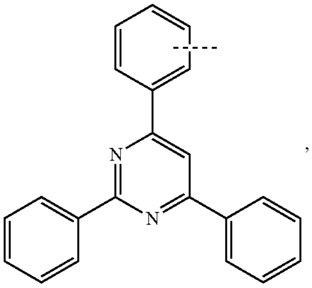
,
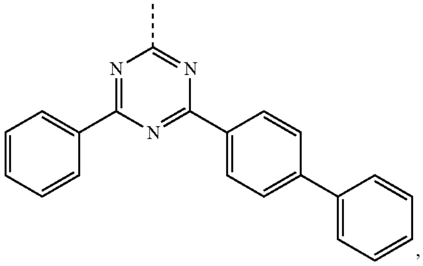
,
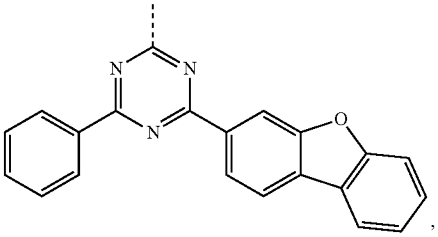
,
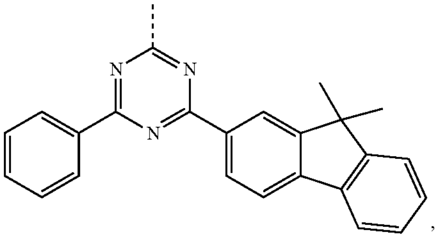
,
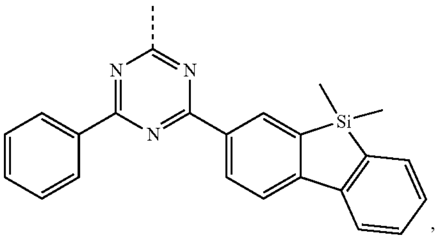
,
-continued
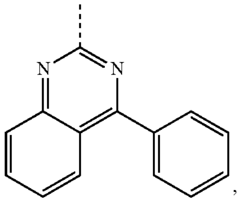
,
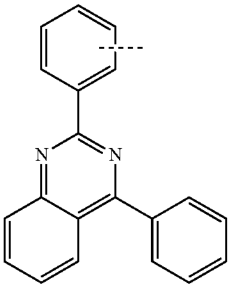
,
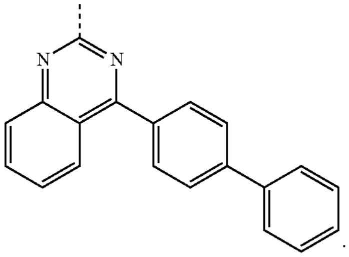
.
8. The compound of claim 5, wherein $R_1$, and $R_2$ are each independently selected from the group consisting of:
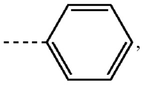
,
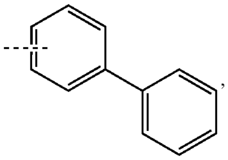
,
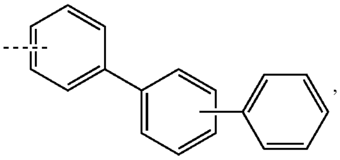
,
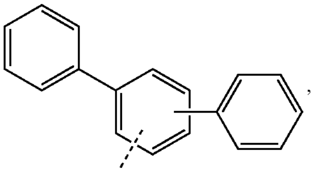
,
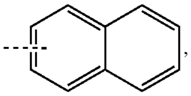
,
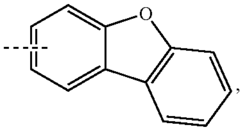
,
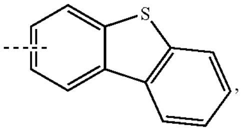
,
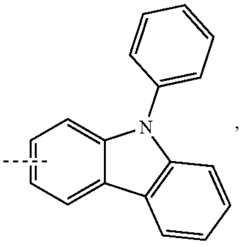
,
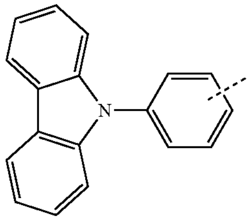
,
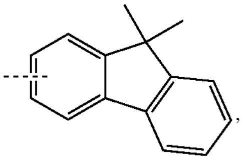
,
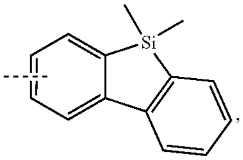
, -continued
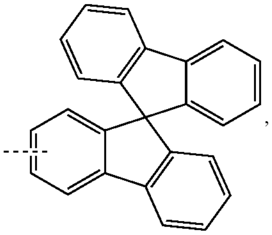,
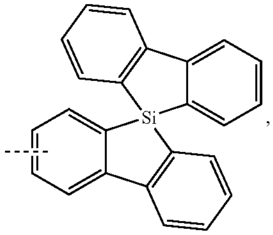,
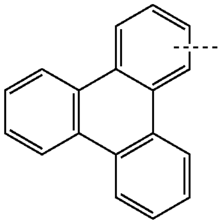,
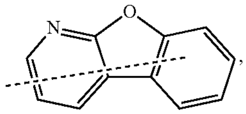,
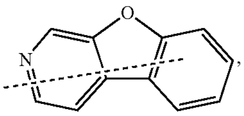,
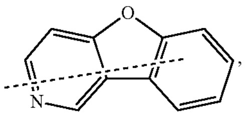,
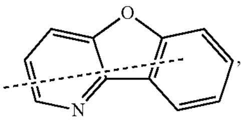,
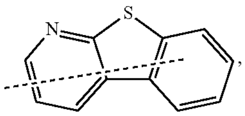,
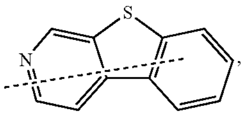,
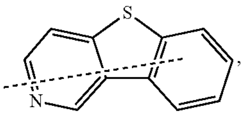,
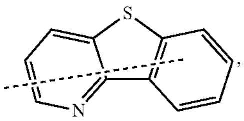,
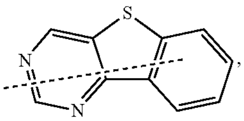,
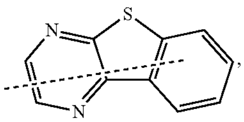,
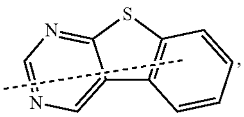,
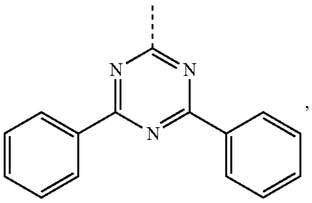,
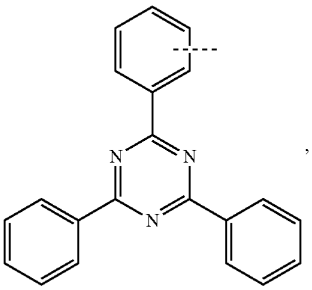,
-continued
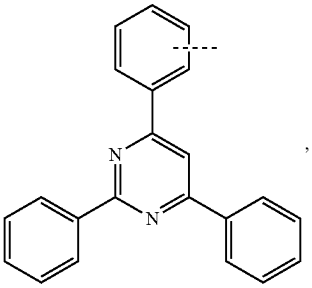,
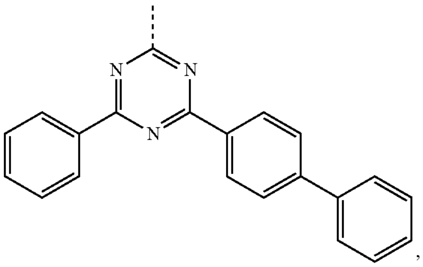,
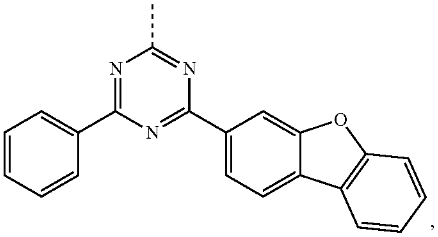,
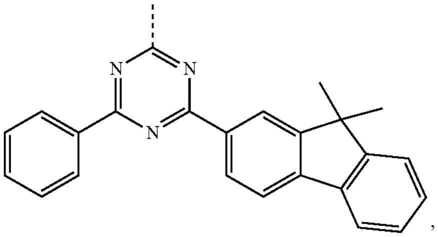,
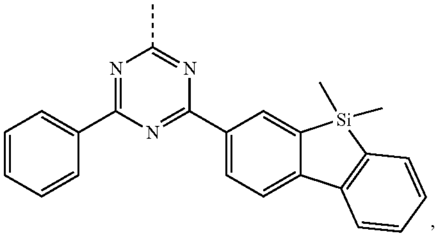,
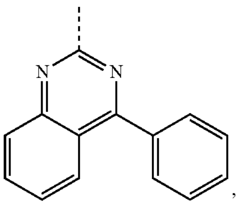,
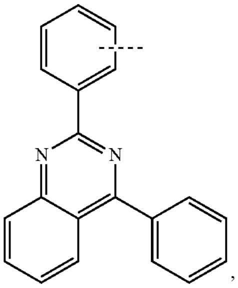, -continued
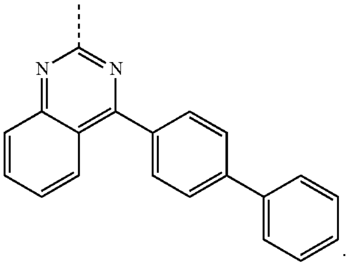
.
9. The compound of claim 1, wherein the compound is selected from the group consisting of:
Compound 1
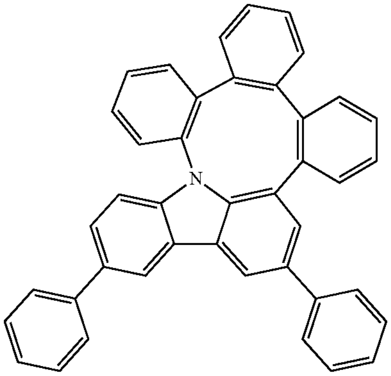
,
Compound 2
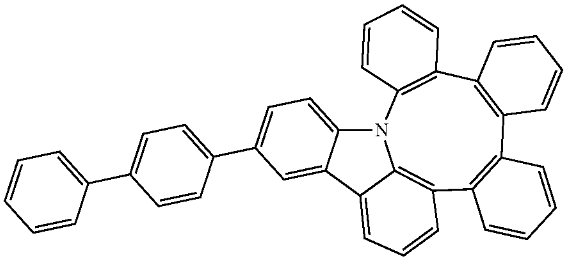
,
Compound 3
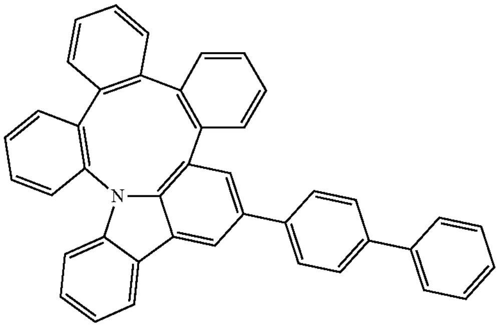
,
-continued
Compound 4
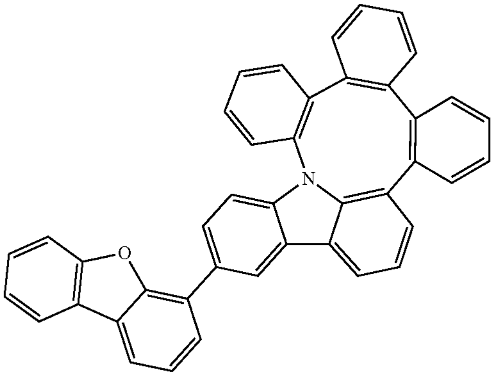
,
Compound 5
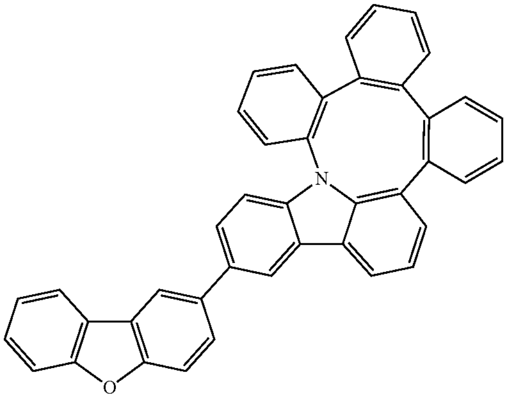
,
Compound 6
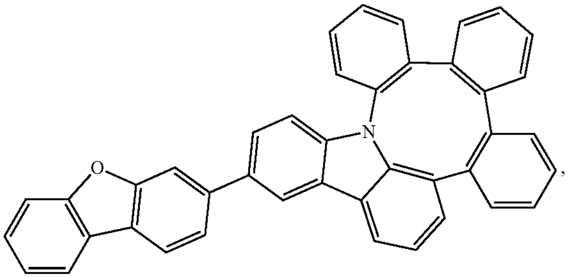
,
Compound 7
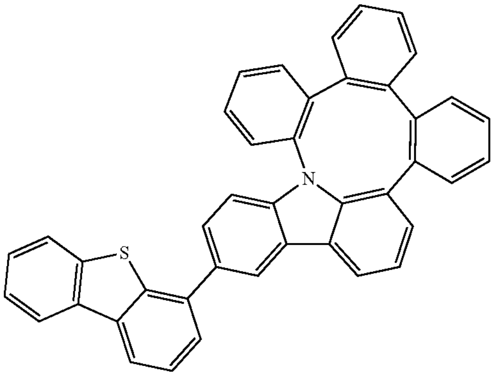
, -continued
Compound 8
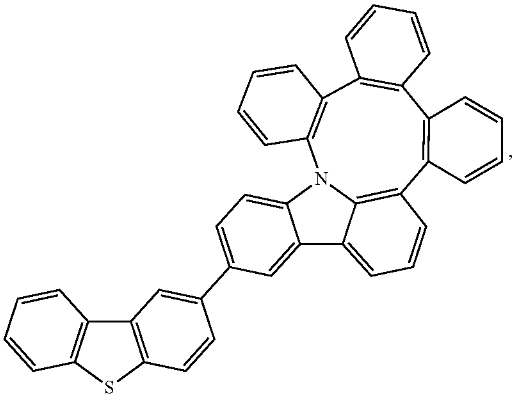
Compound 9
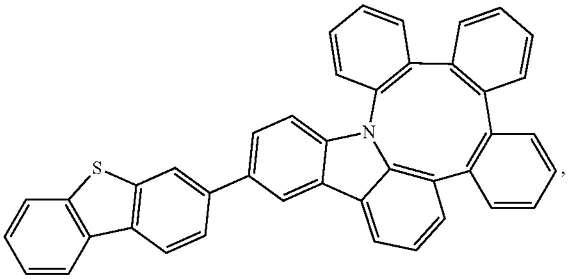
Compound 10
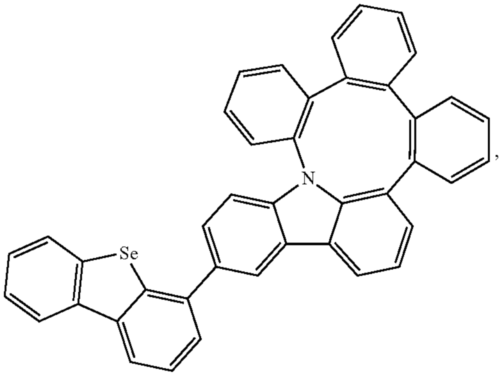
Compound 11
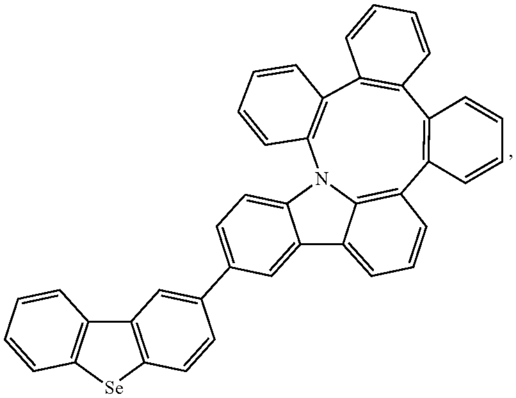
-continued
Compound 12
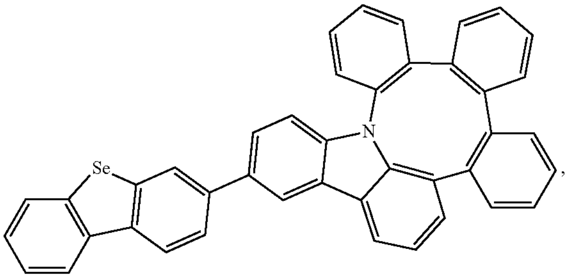
Compound 13
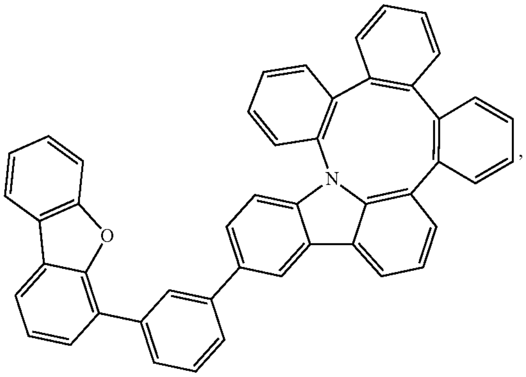
Compound 14
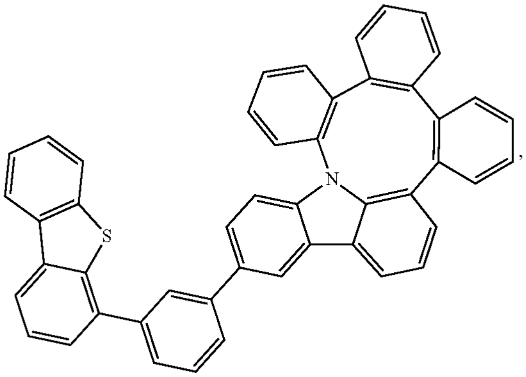
Compound 15
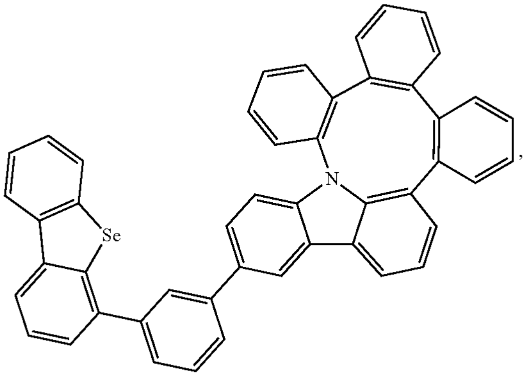

-continued
Compound 16
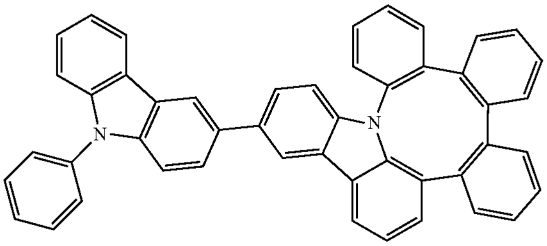
,
Compound 17
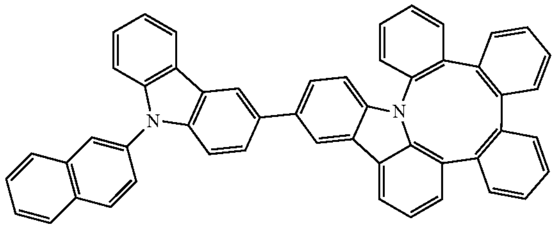
,
Compound 18
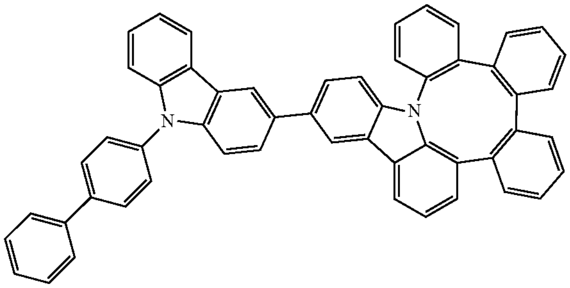
,
Compound 19
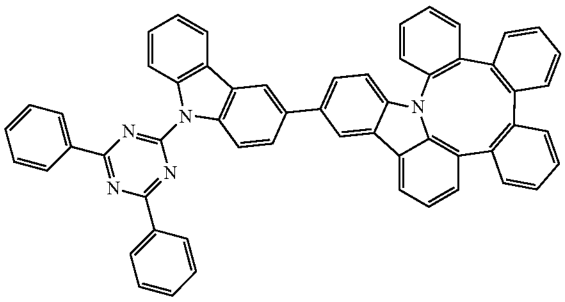
,
Compound 20
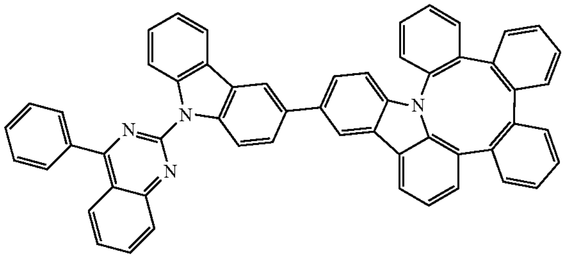
,
-continued
Compound 21
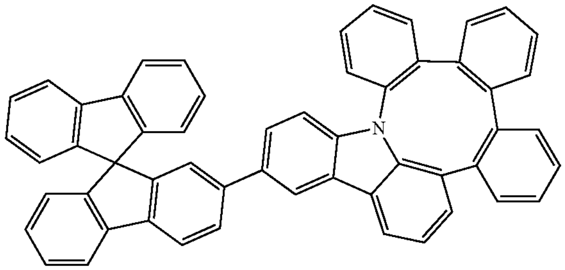
,
Compound 22
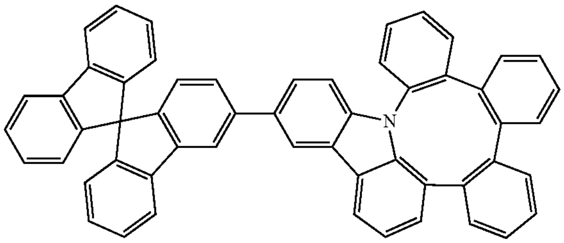
,
Compound 23
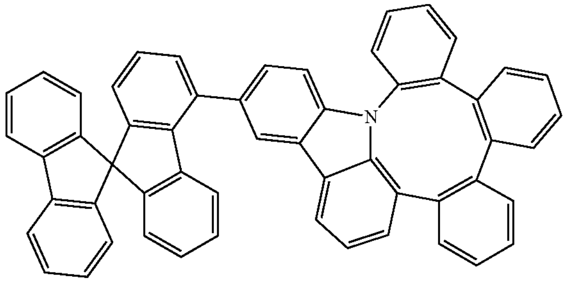
,
Compound 24
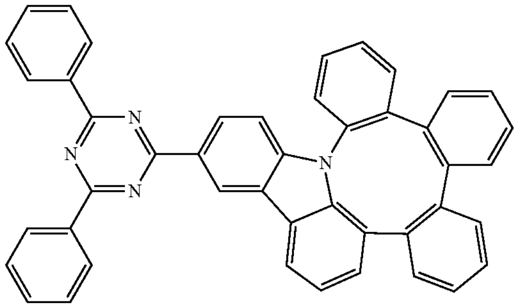
,
Compound 25
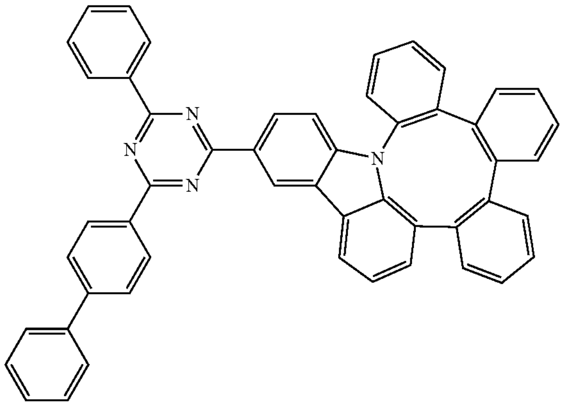
, -continued
Compound 26
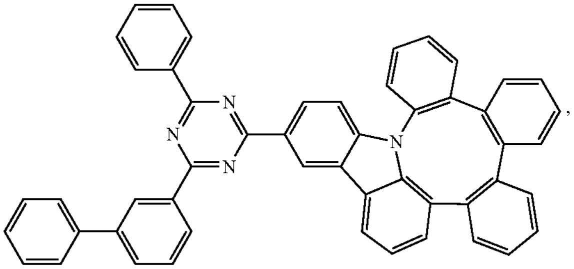
Compound 27
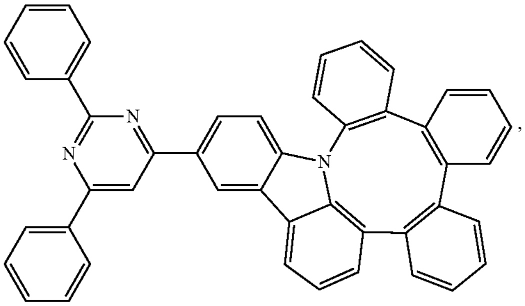
Compound 28
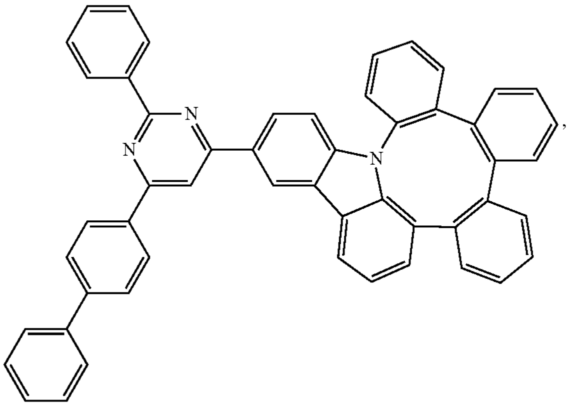
Compound 29
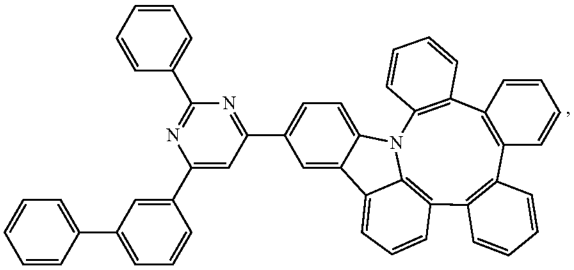
-continued
Compound 30
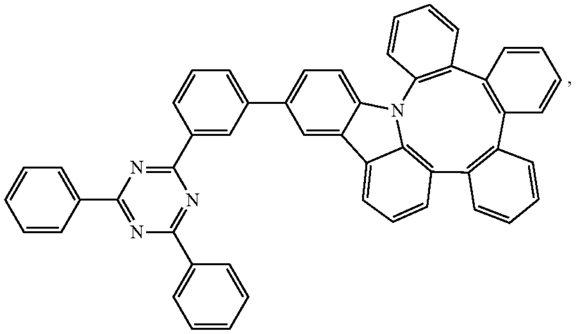
Compound 31
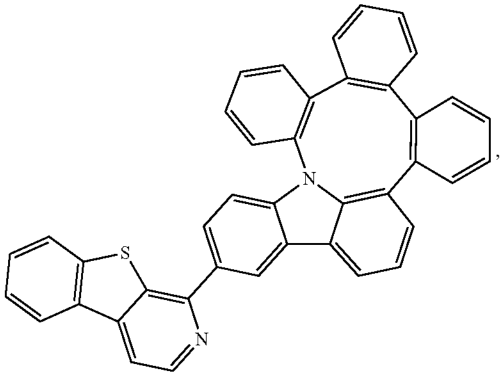
Compound 32
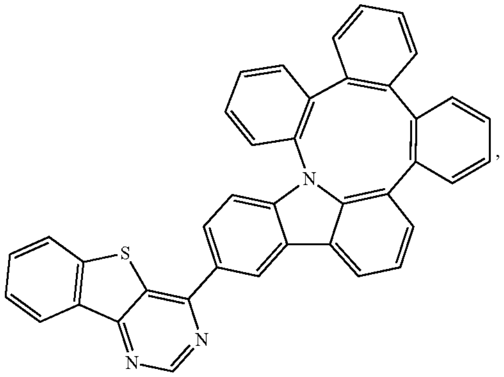
Compound 33
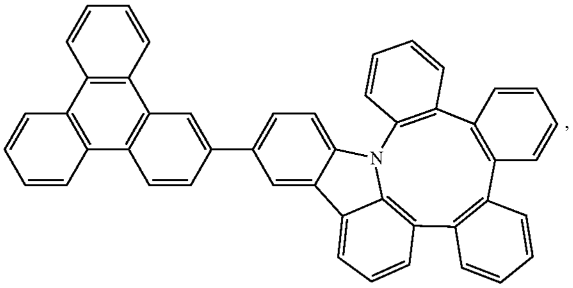

-continued
Compound 34
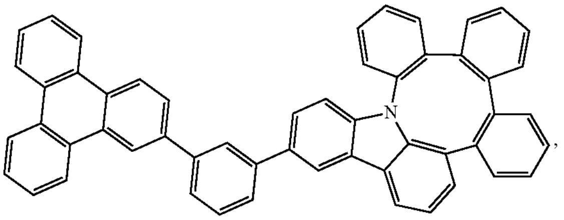
Compound 35
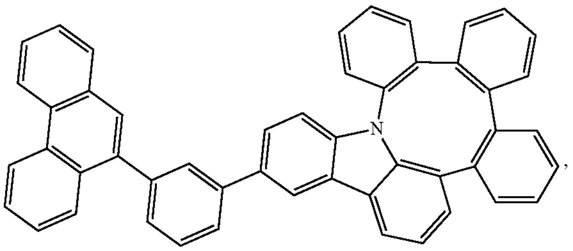
Compound 36
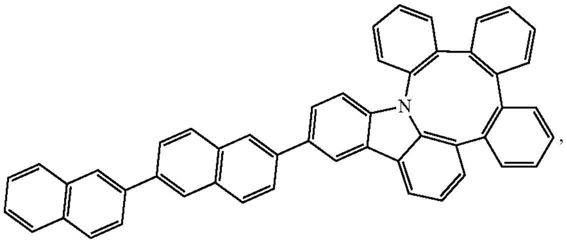
Compound 37
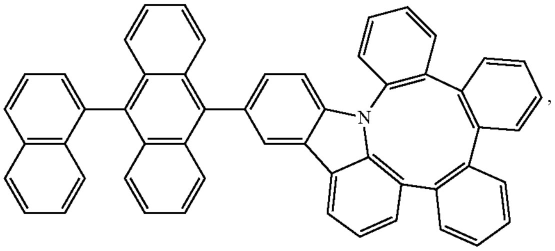
Compound 38
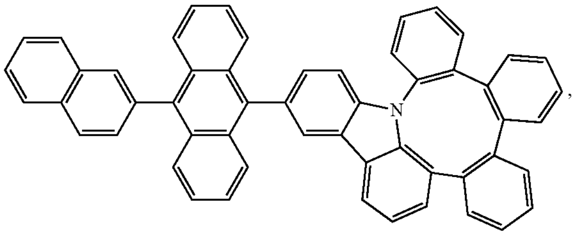
Compound 39
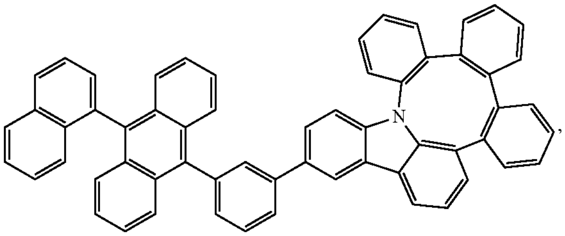
-continued
Compound 40
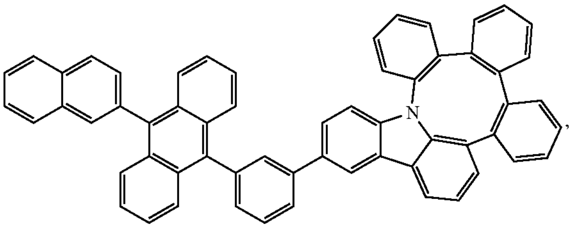
Compound 41
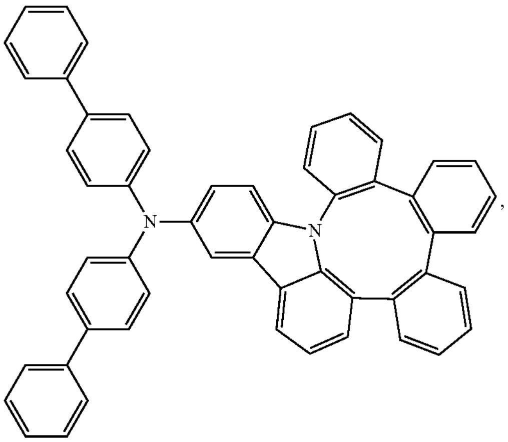
Compound 42
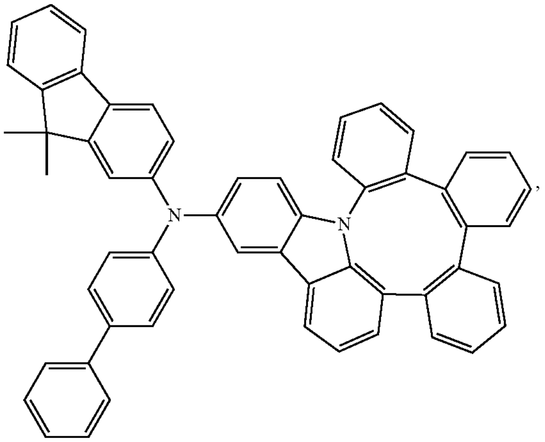
Compound 43
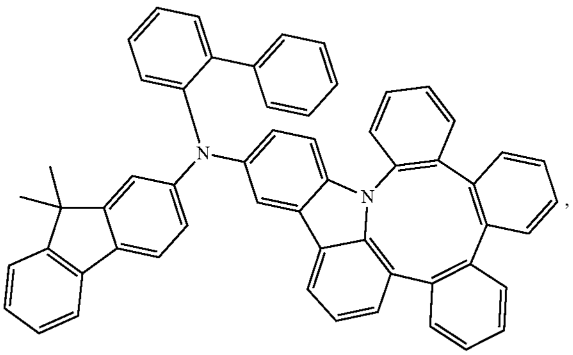

-continued
Compound 44
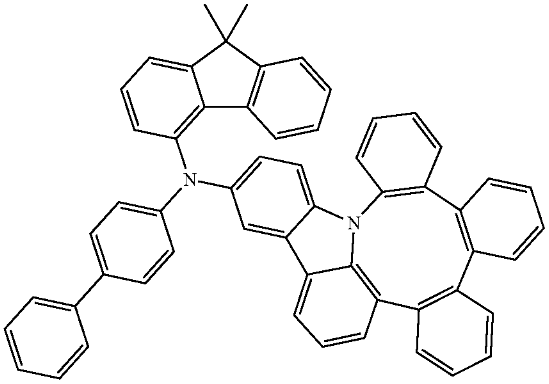
,
Compound 45
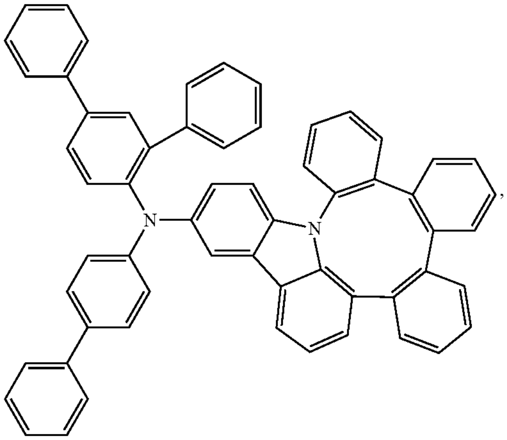
,
Compound 46
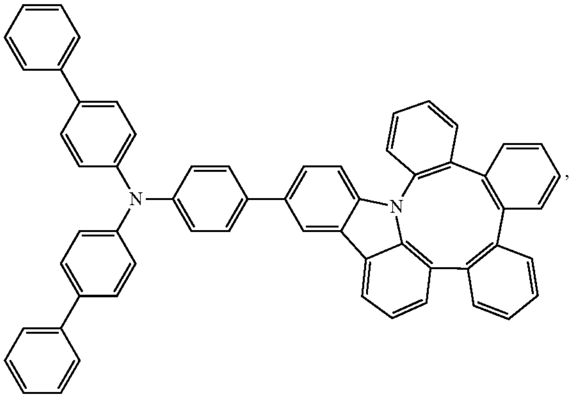
,
-continued
Compound 47
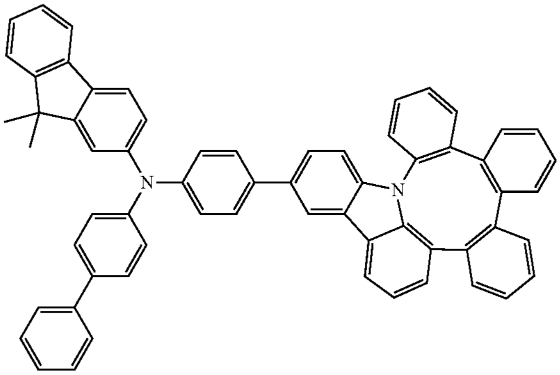
,
Compound 48
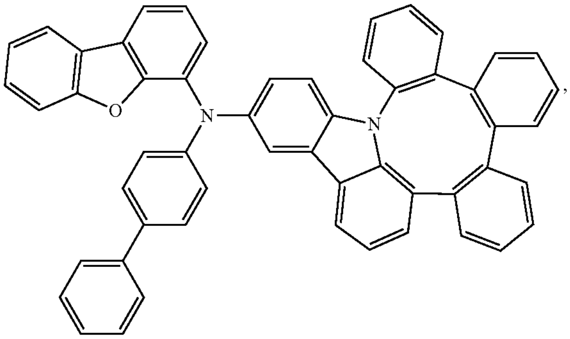
,
Compound 49
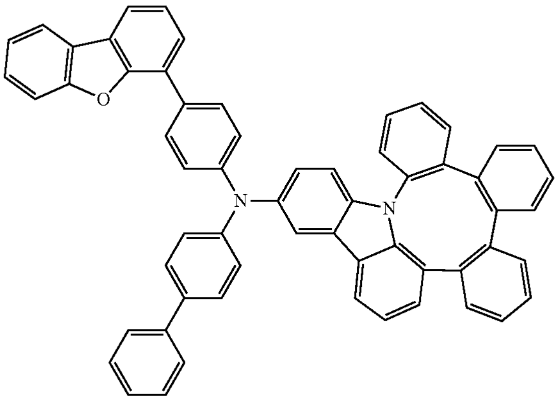
,
Compound 50
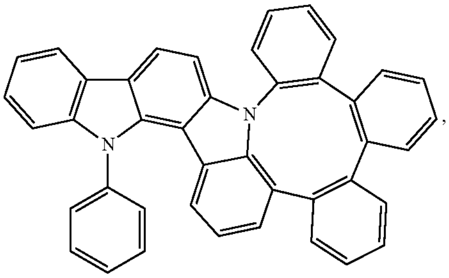
, -continued
Compound 51
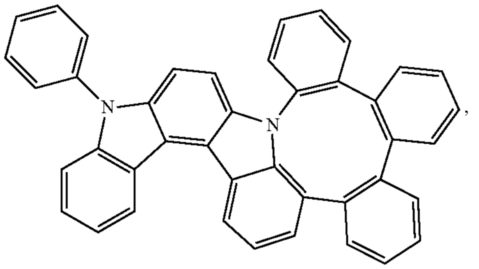
Compound 52
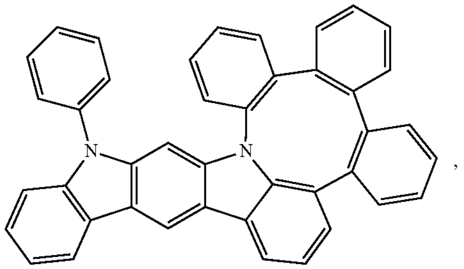
Compound 53
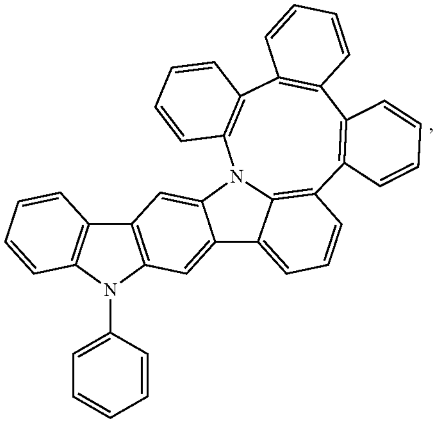
Compound 54
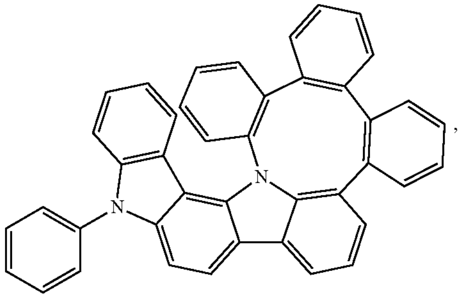
Compound 55
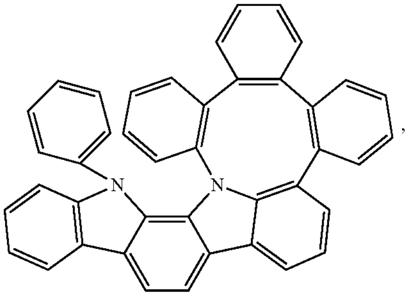
-continued
Compound 56
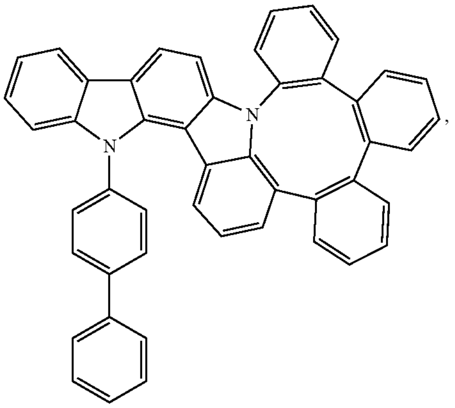
Compound 57
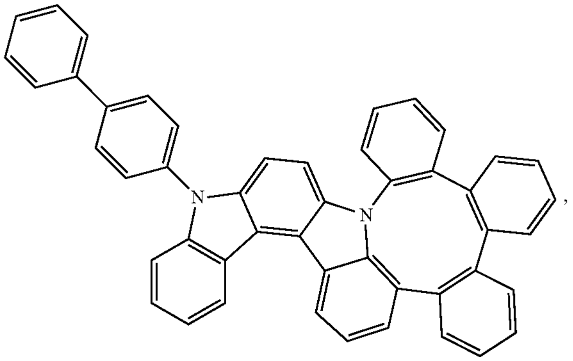
Compound 58
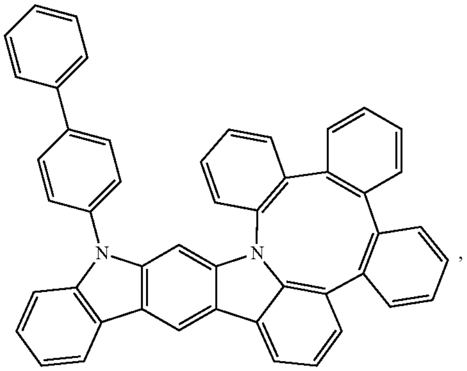
Compound 59
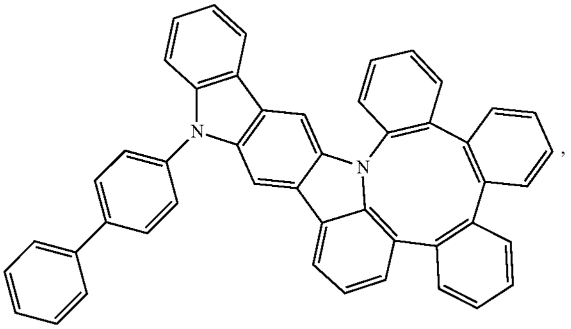

-continued
Compound 60
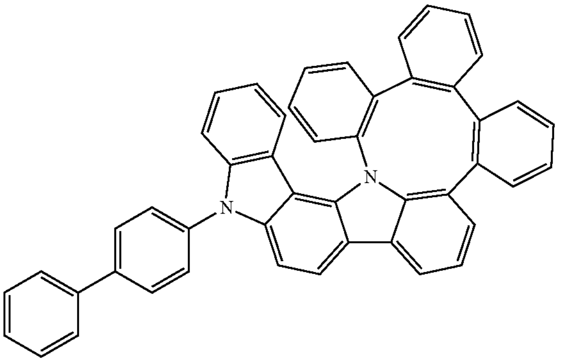
,
Compound 61
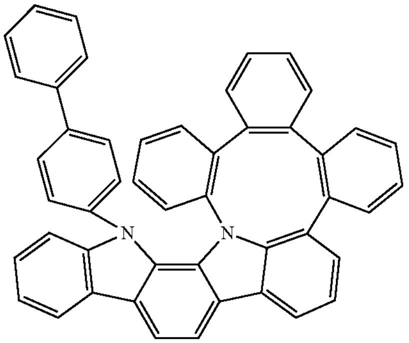
,
Compound 62
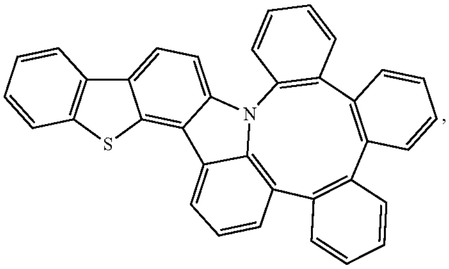
,
Compound 63
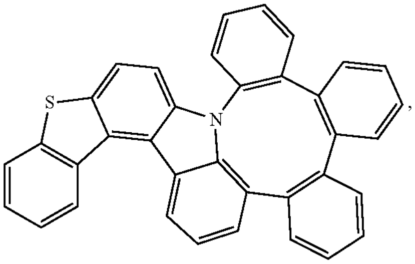
,
Compound 64
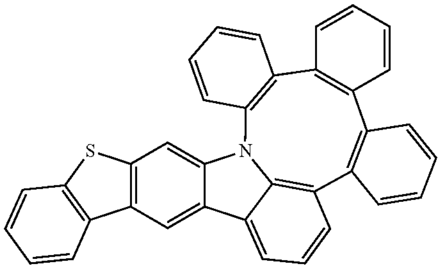
,
-continued
Compound 65
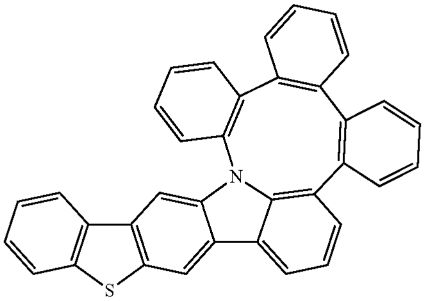
,
Compound 66
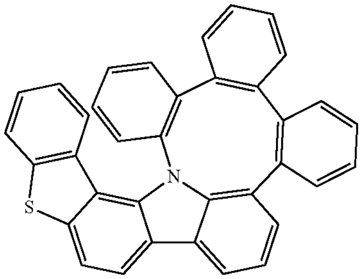
,
Compound 67
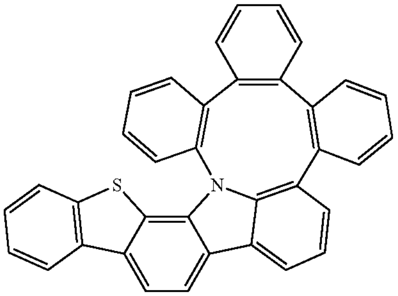
,
Compound 68
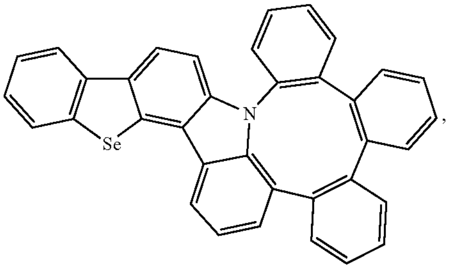
,
Compound 69
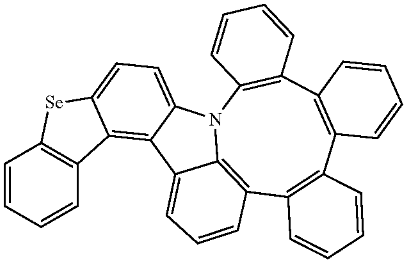
, -continued
Compound 70
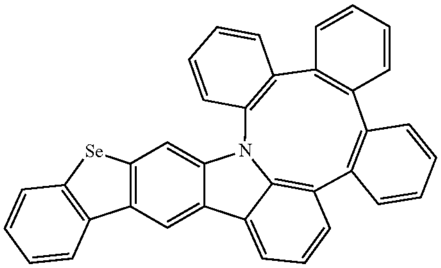
,
Compound 71
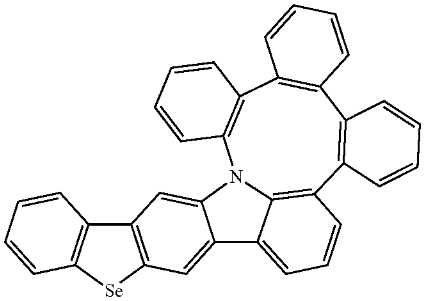
,
Compound 72
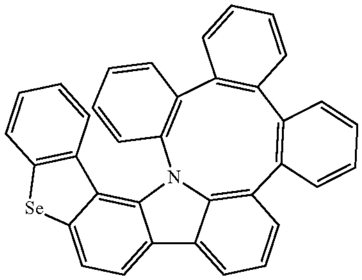
,
Compound 73
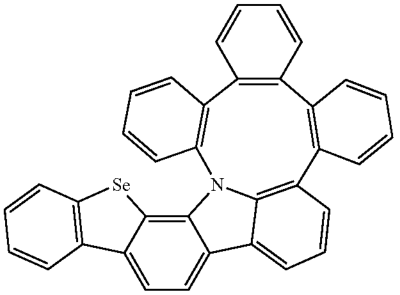
,
Compound 74
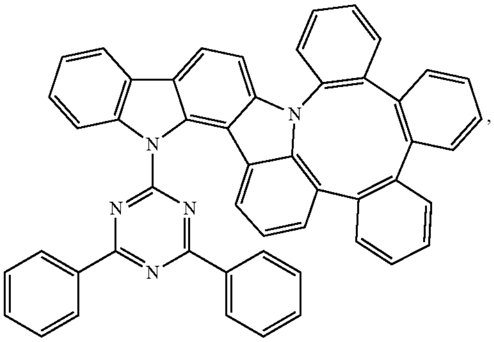
,
-continued
Compound 75
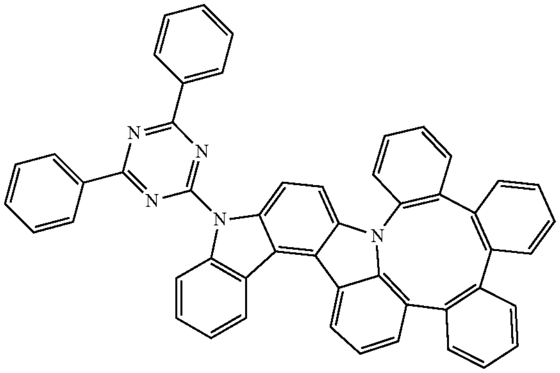
,
Compound 76
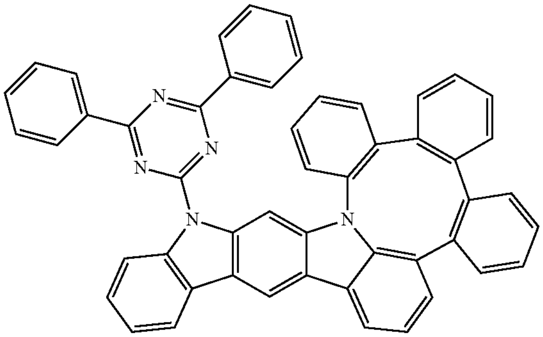
,
Compound 77
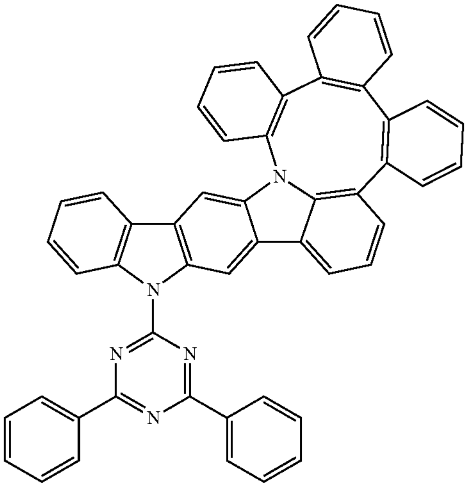
, -continued
Compound 78
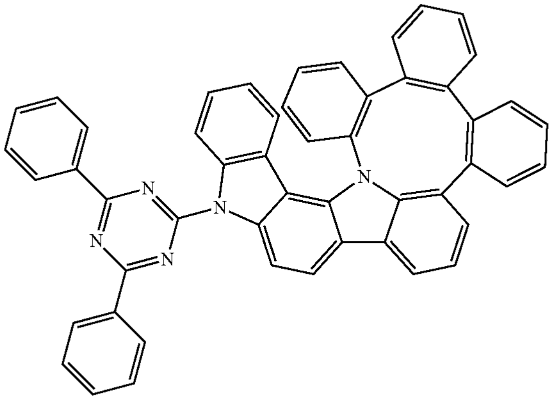
,
Compound 79
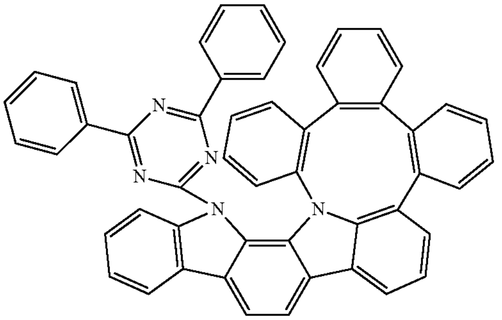
,
Compound 80
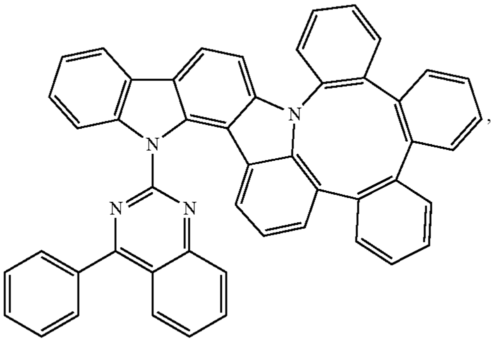
,
Compound 81
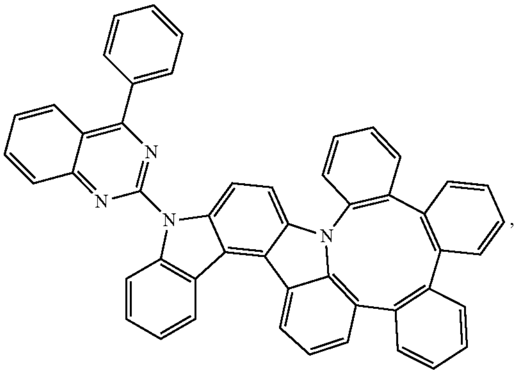
,
Compound 82
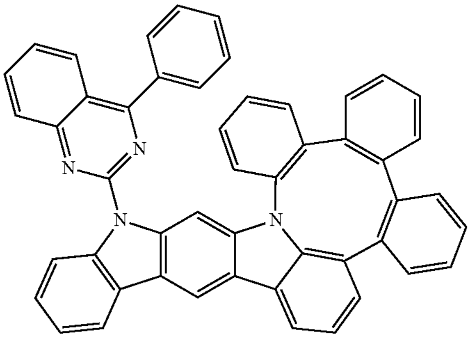
,
Compound 83
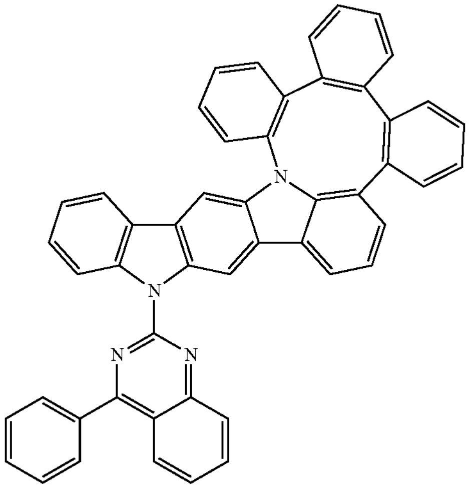
,
Compound 84
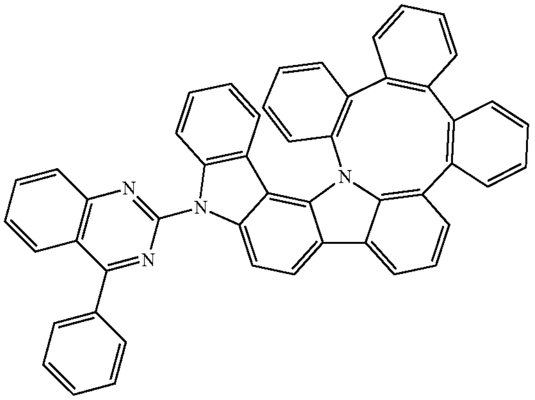
,
Compound 85
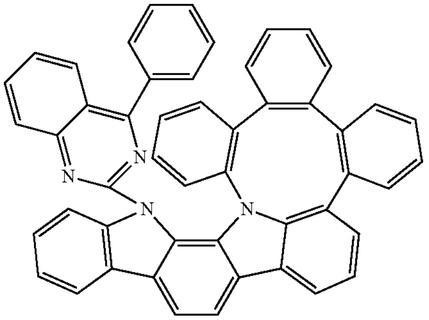
, -continued
Compound 86
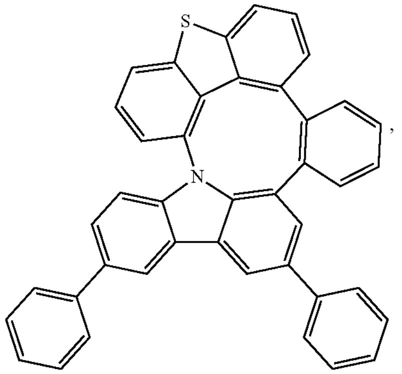
Compound 87
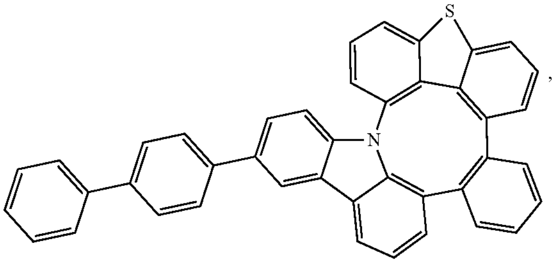
Compound 88
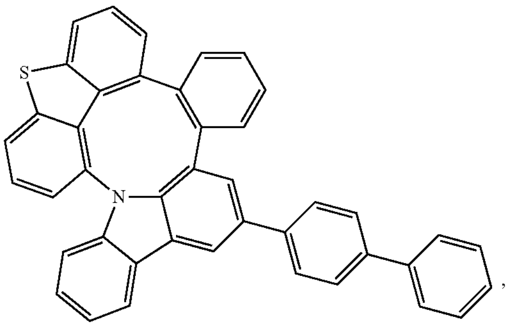
Compound 89
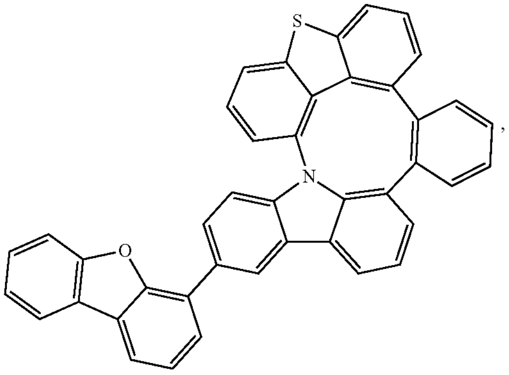
-continued
Compound 90
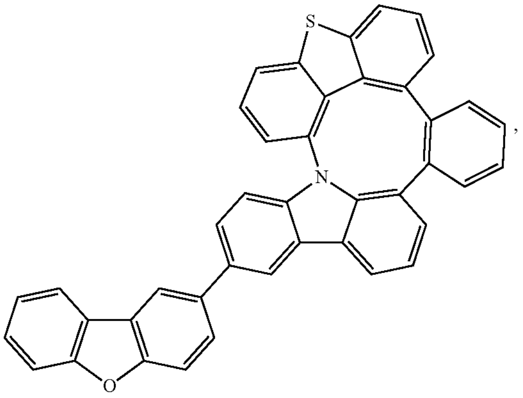
Compound 91
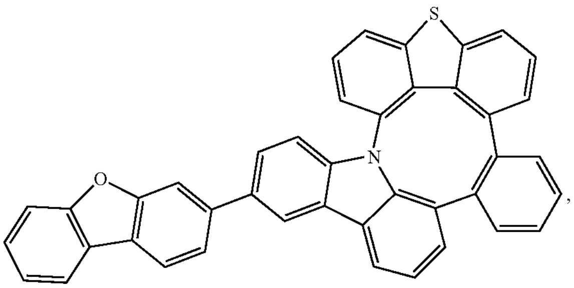
Compound 92
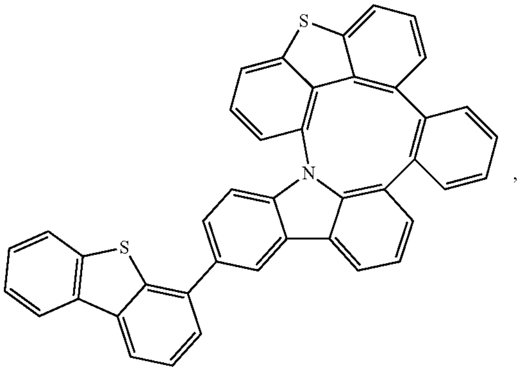
Compound 93
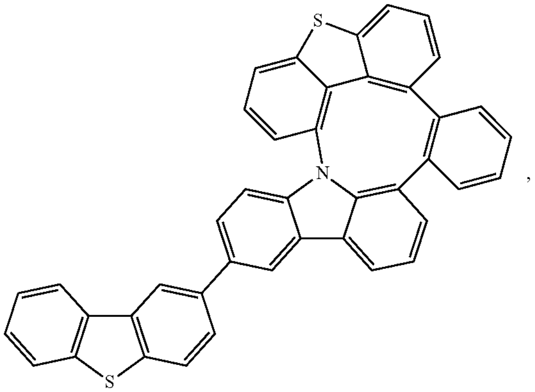

-continued
Compound 94
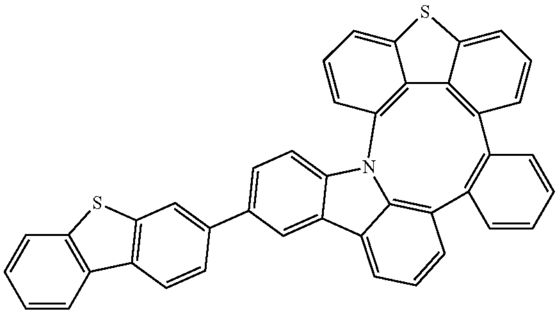
,
Compound 95
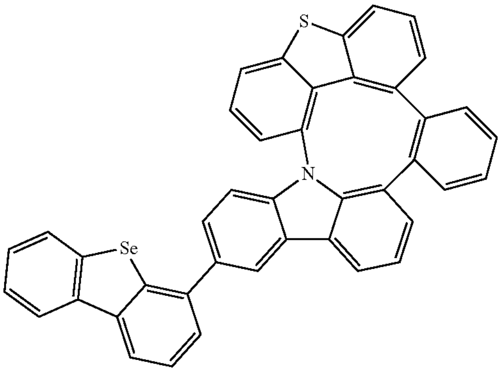
,
Compound 96
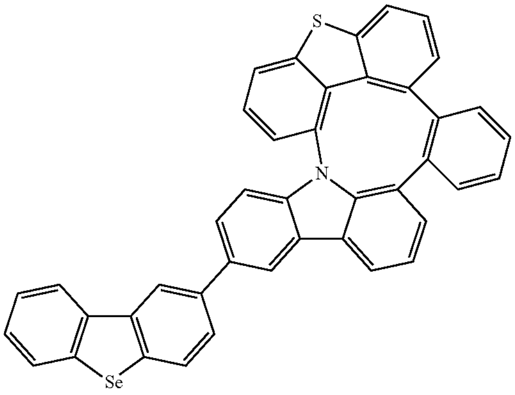
,
Compound 97
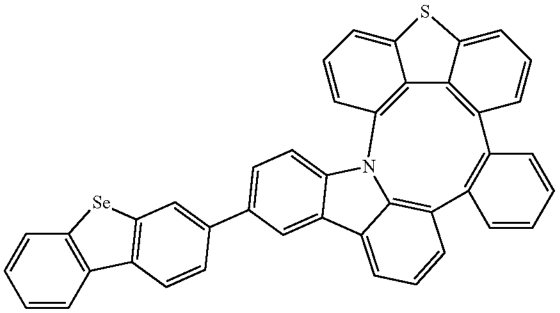
,
-continued
Compound 98
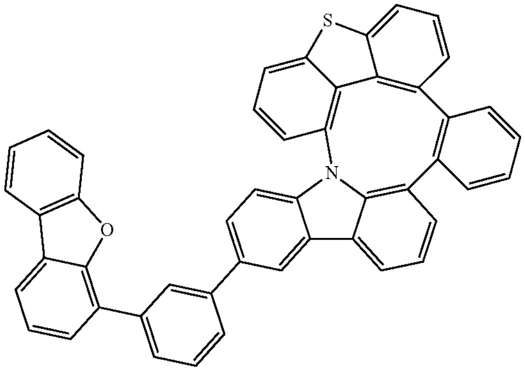
,
Compound 99
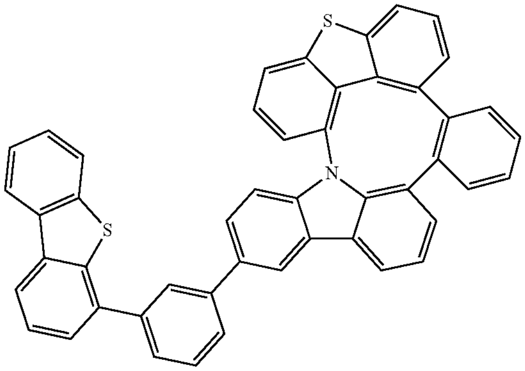
,
Compound 100
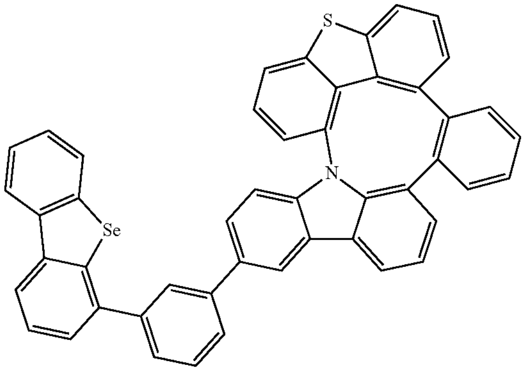
,
Compound 101
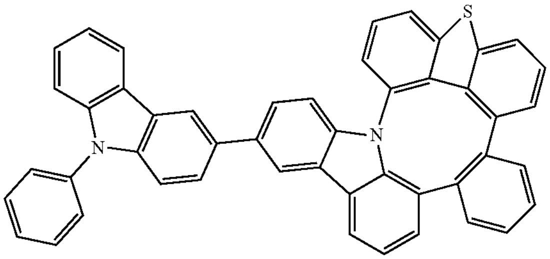
, -continued
Compound 102
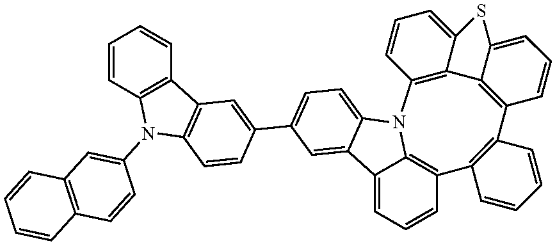
,
Compound 103
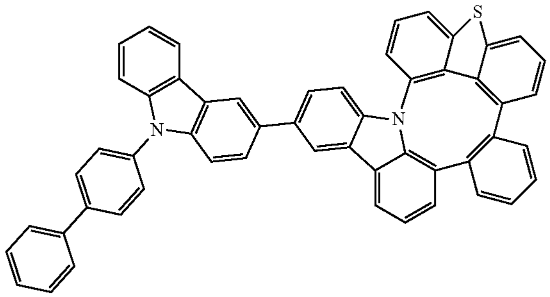
,
Compound 104
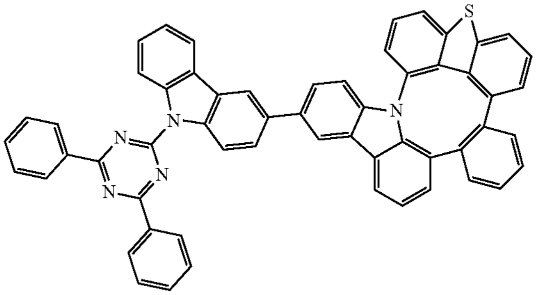
,
Compound 105
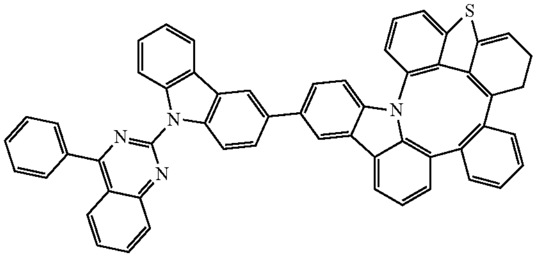
,
Compound 106
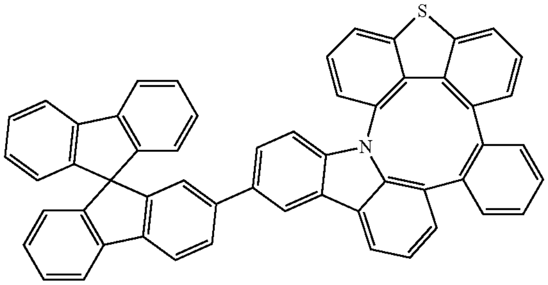
,
-continued
Compound 107
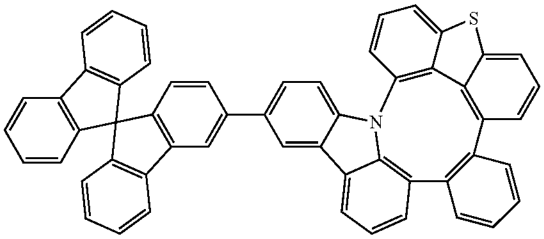
,
Compound 108
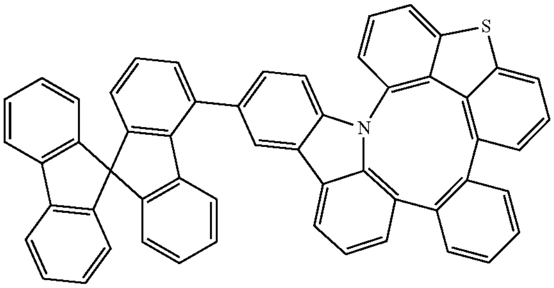
,
Compound 109
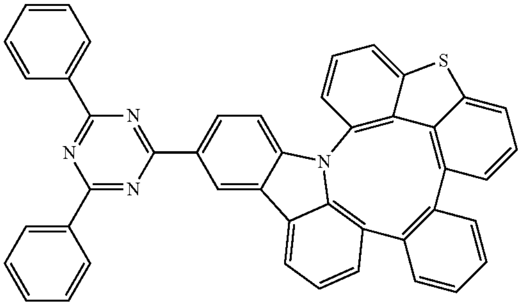
,
Compound 110
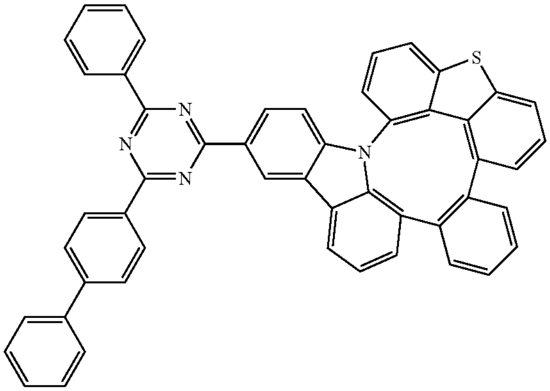
,
Compound 111
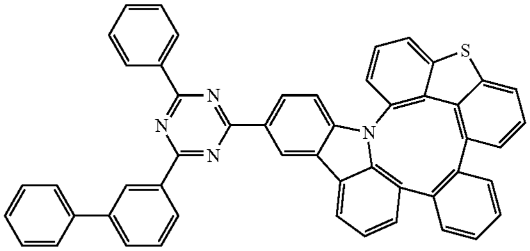
, -continued
Compound 112
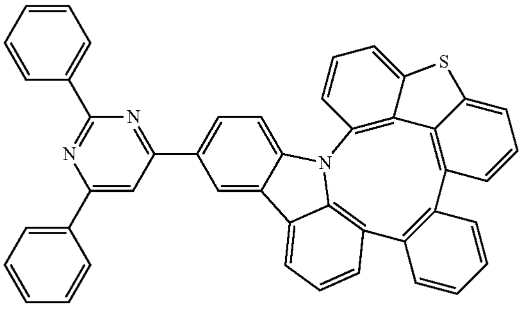
,
Compound 113
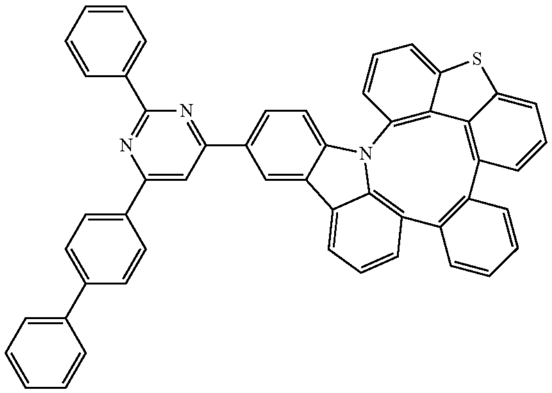
,
Compound 114
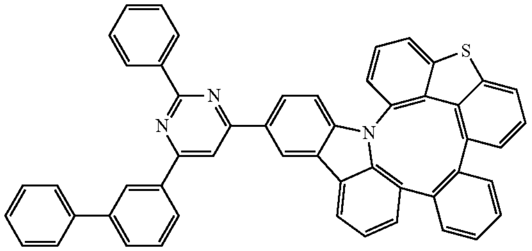
,
Compound 115
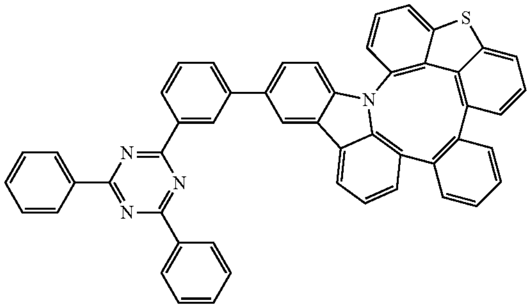
,
-continued
Compound 116
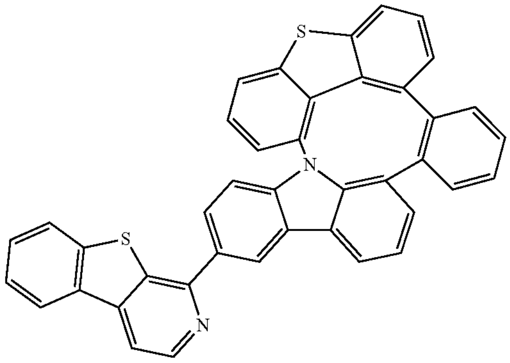
,
Compound 117
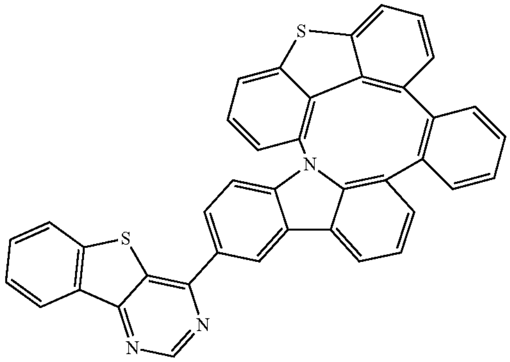
,
Compound 118
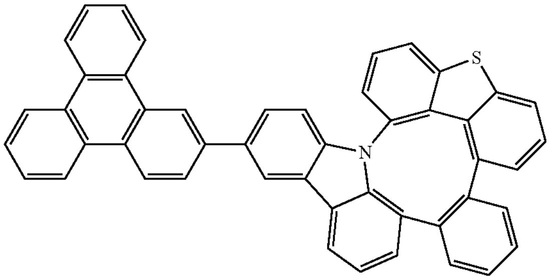
,
Compound 119
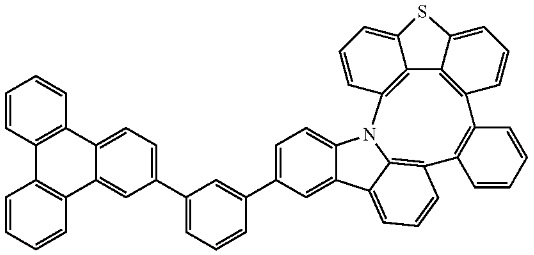
, Compound 120
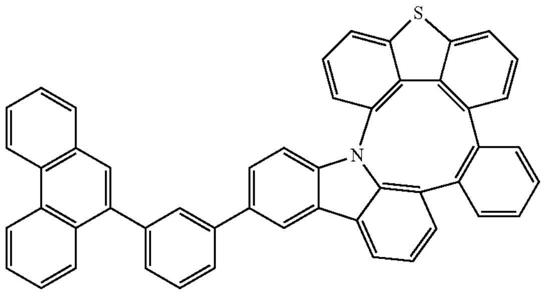
,
Compound 121
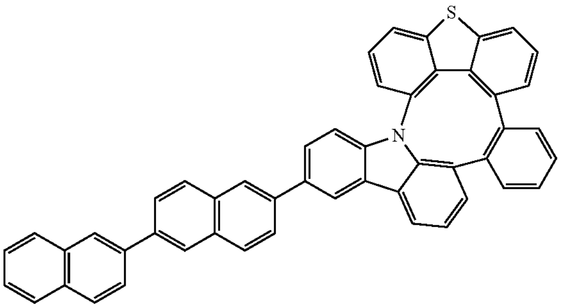
,
Compound 122
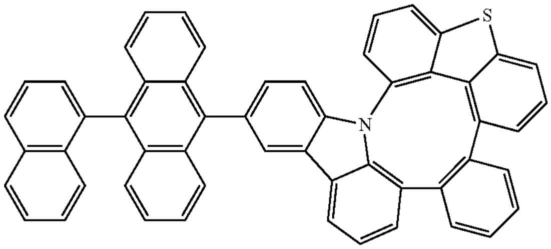
,
Compound 123
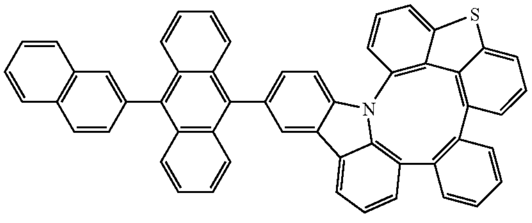
,
Compound 124
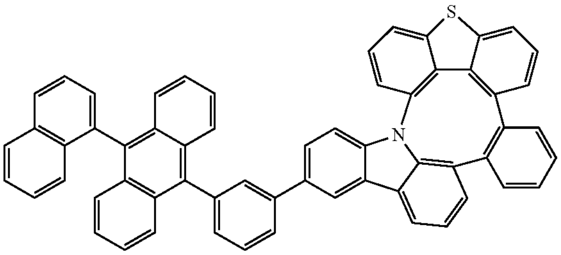
,
Compound 125
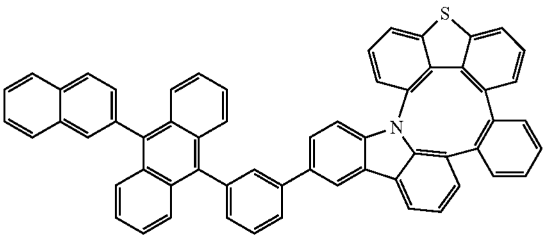
,
Compound 126
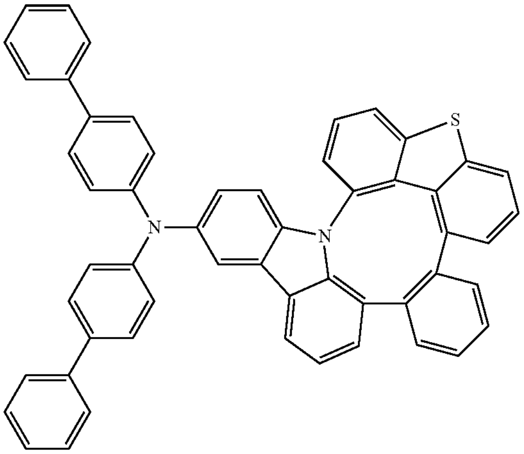
,
Compound 127
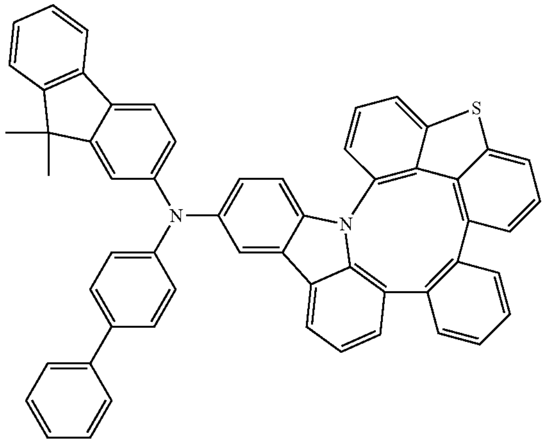
,
Compound 128
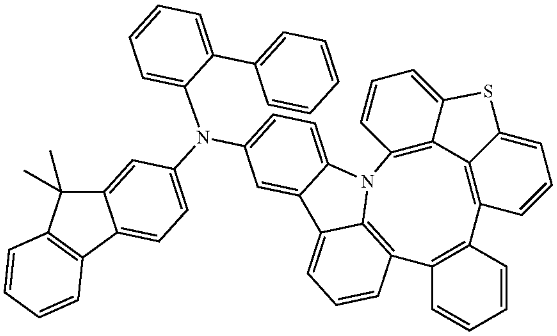
, -continued
Compound 129
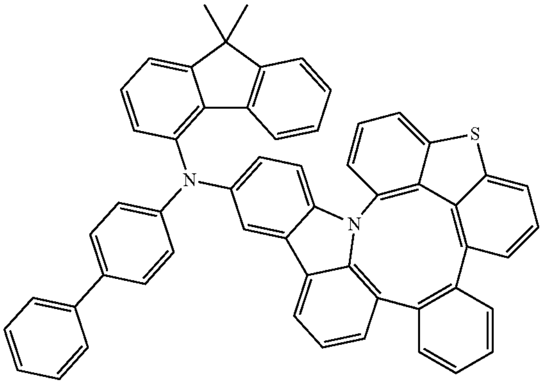
,
Compound 130
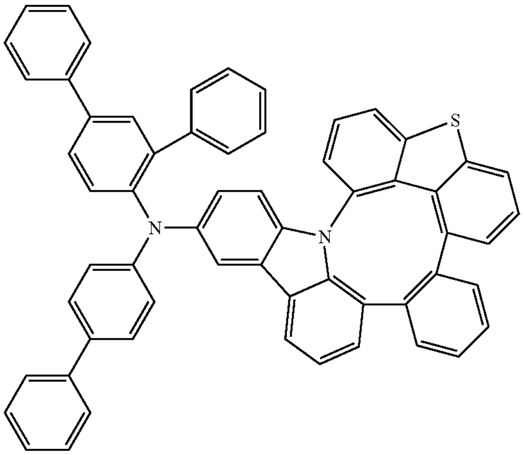
,
Compound 131
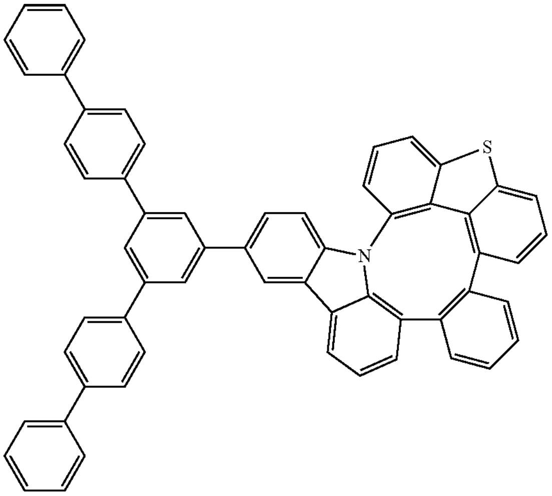
,
-continued
Compound 132
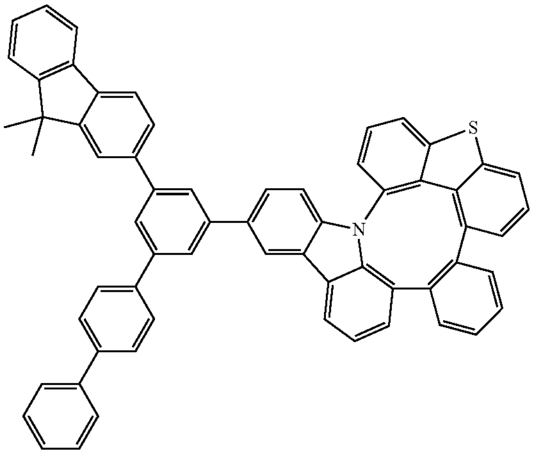
,
Compound 133
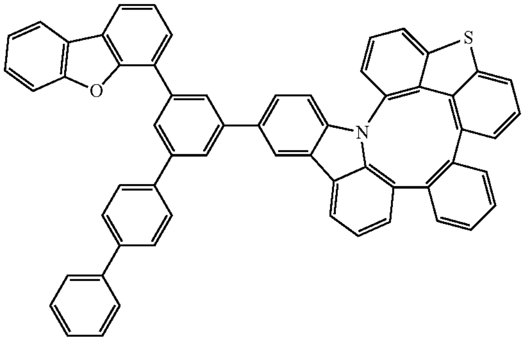
,
Compound 134
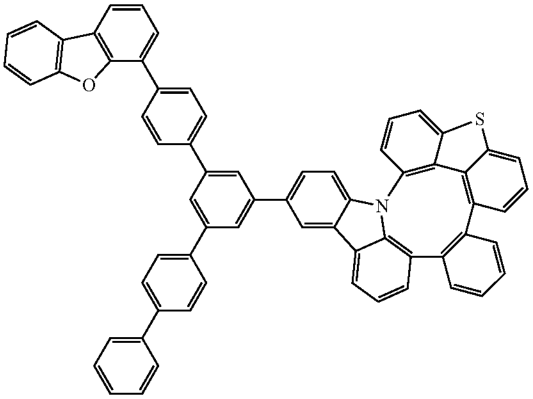
,
Compound 135
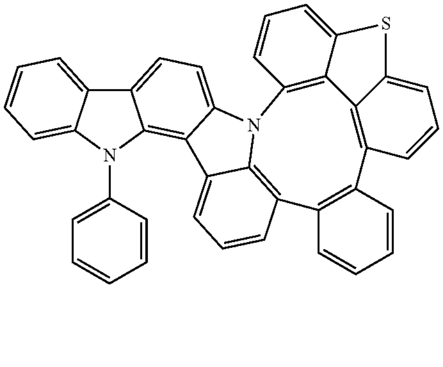
, -continued
Compound 136
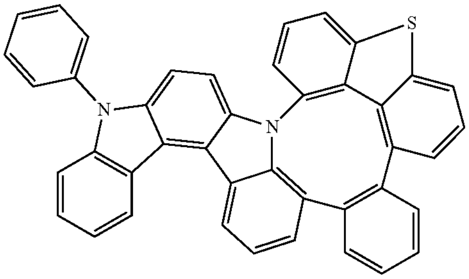
,
Compound 137
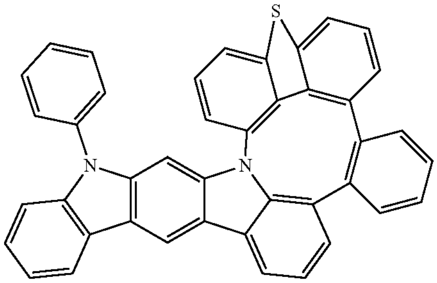
,
Compound 138
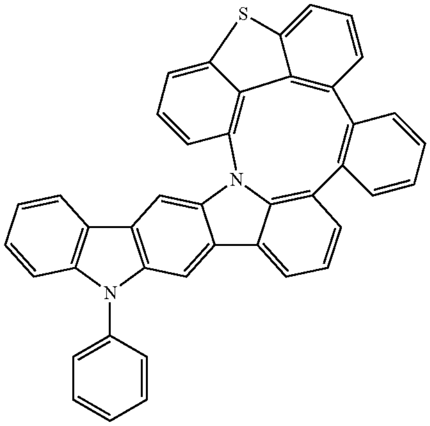
,
Compound 139
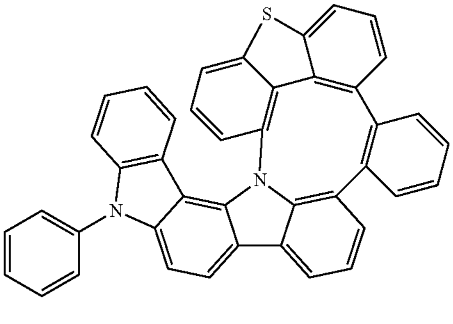
,
-continued
Compound 140
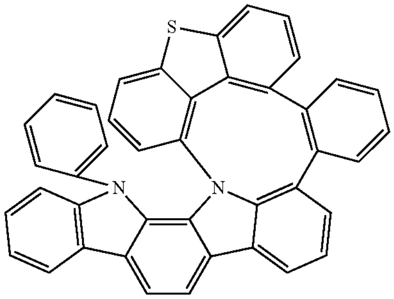
,
Compound 141
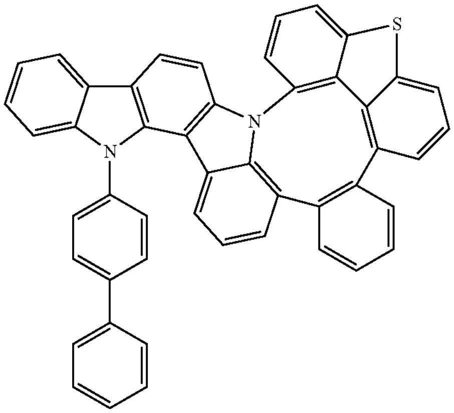
,
Compound 142
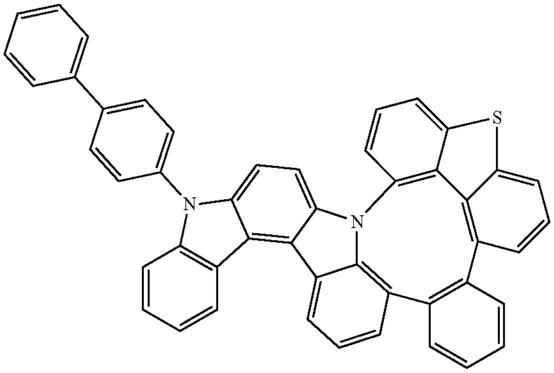
,
Compound 143
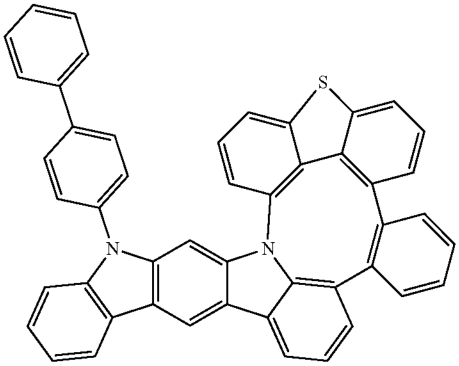
, -continued
Compound 144
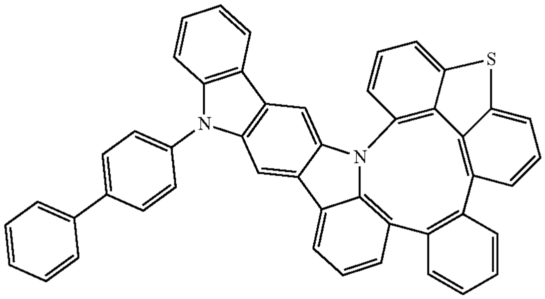
,
Compound 145
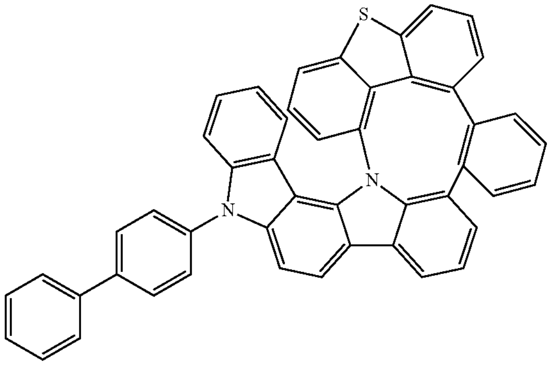
,
Compound 146
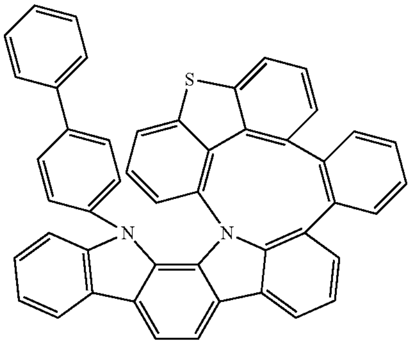
,
Compound 147
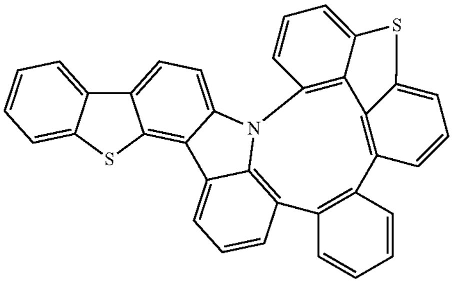
,
Compound 148
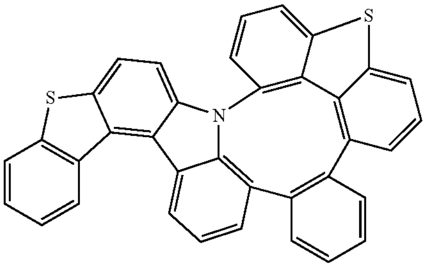
,
-continued
Compound 149
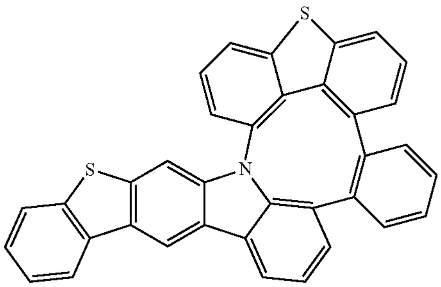
,
Compound 150
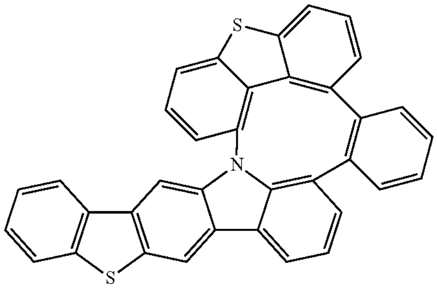
,
Compound 151
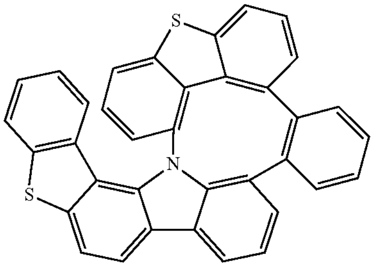
,
Compound 152
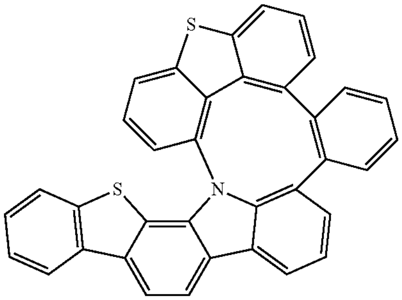
,
Compound 153
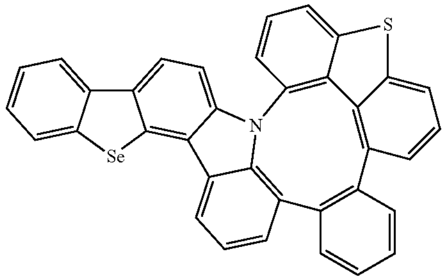
, -continued
Compound 154
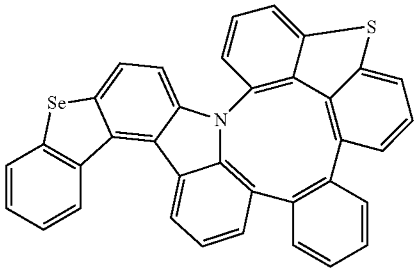
,
Compound 155
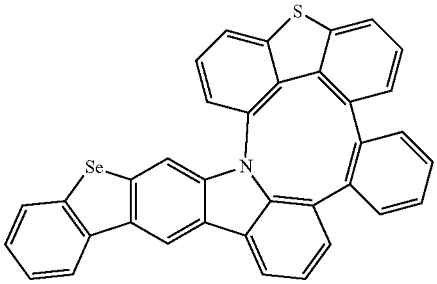
,
Compound 156
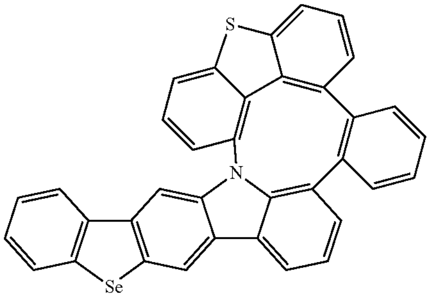
,
Compound 157
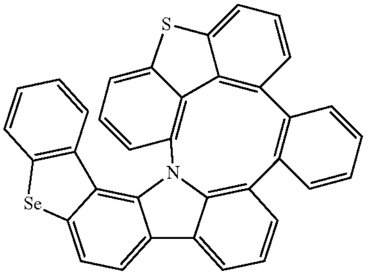
,
Compound 158
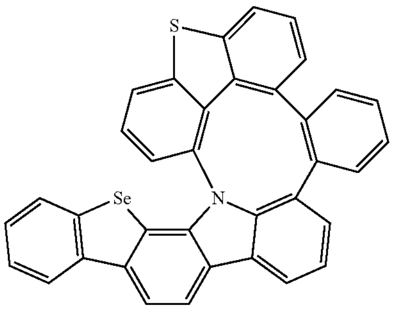
,
-continued
Compound 159
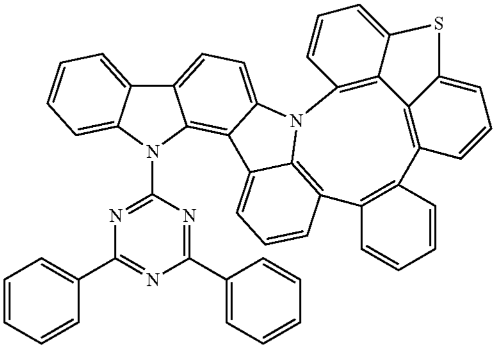
,
Compound 160
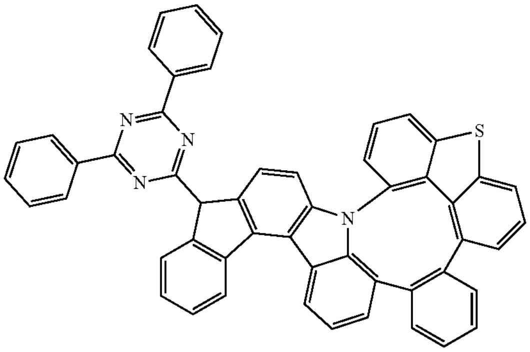
,
Compound 161
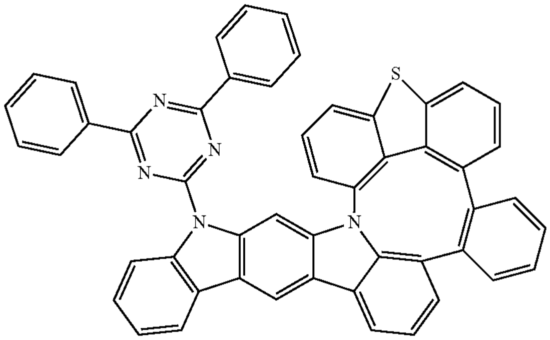
,
Compound 162
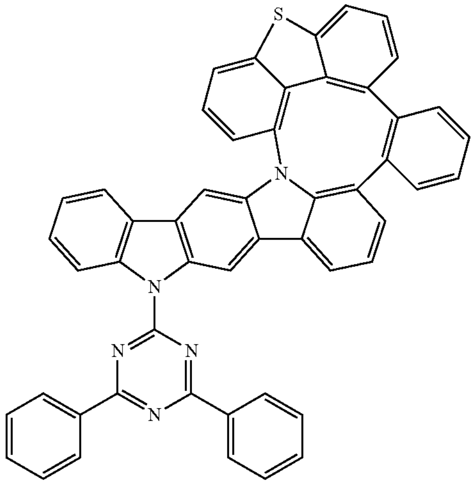
, Compound 163
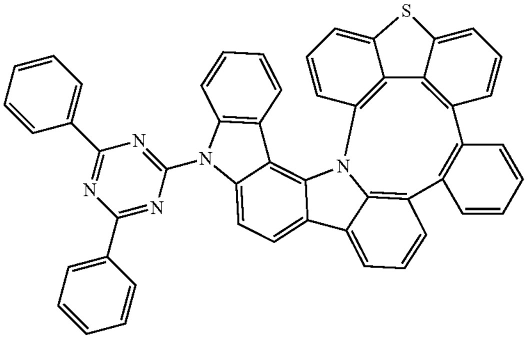
,
Compound 164
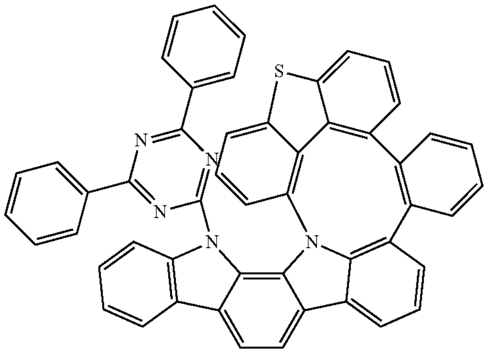
,
Compound 165
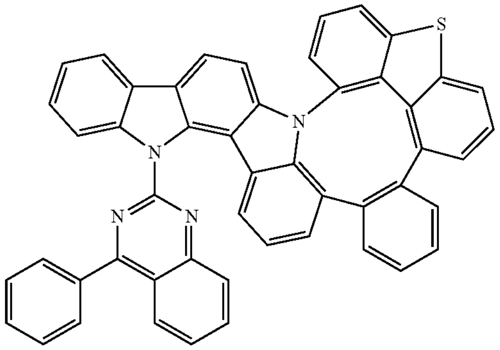
,
Compound 166
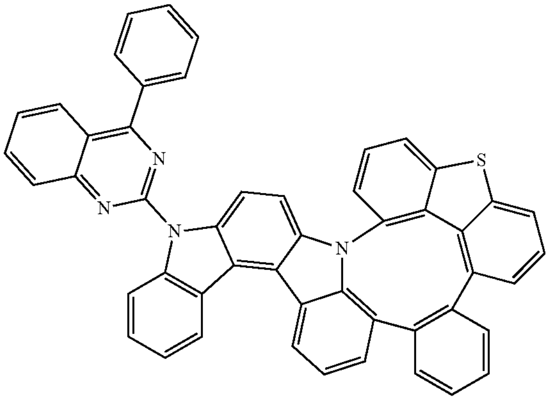
,
Compound 167
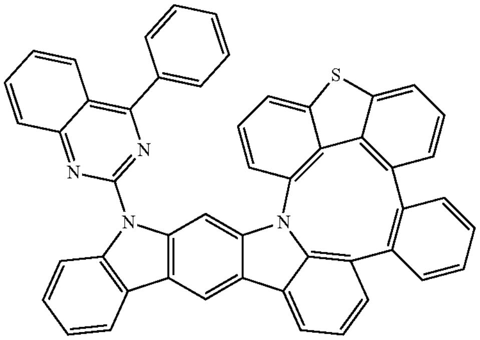
,
Compound 168
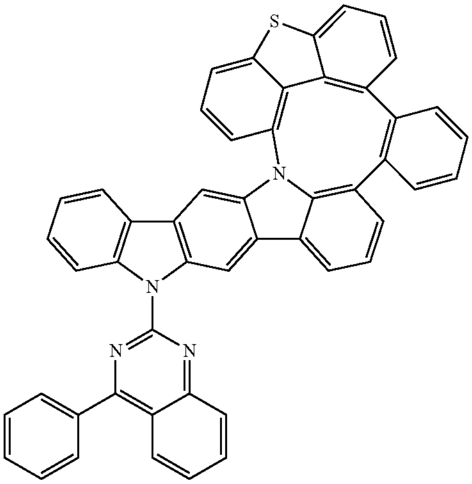
,
Compound 169
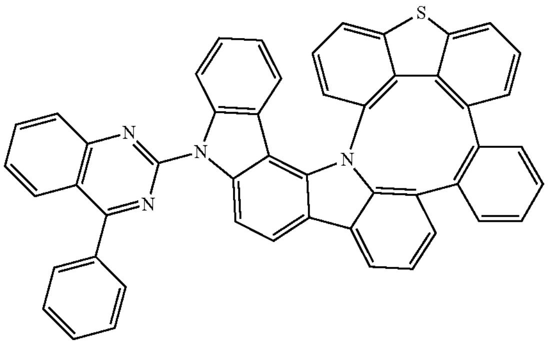
,
Compound 170
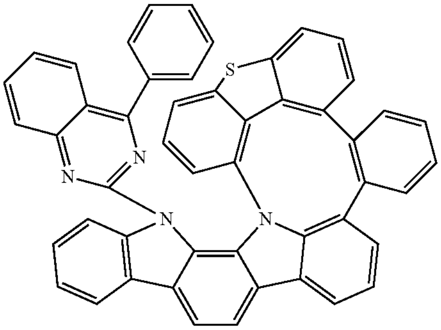
, -continued
Compound 171
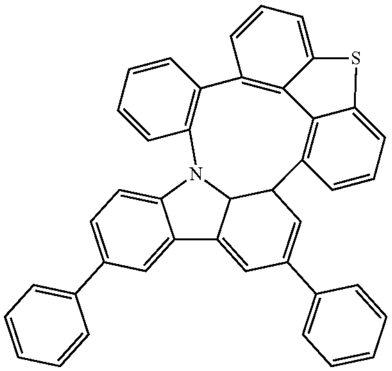
,
Compound 172
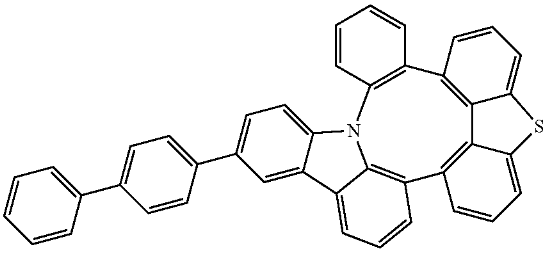
,
Compound 173
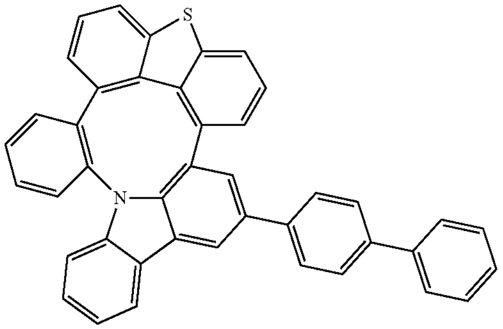
,
Compound 174
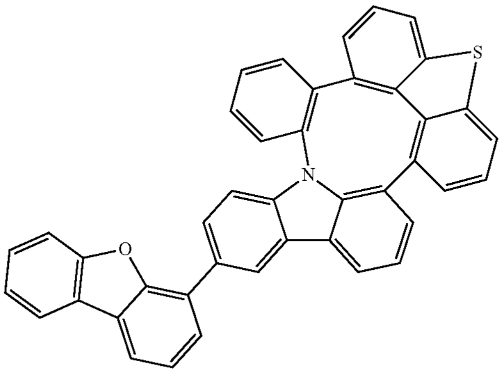
,
Compound 175
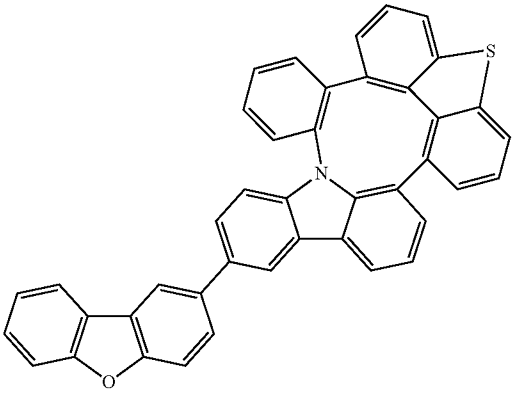
,
Compound 176
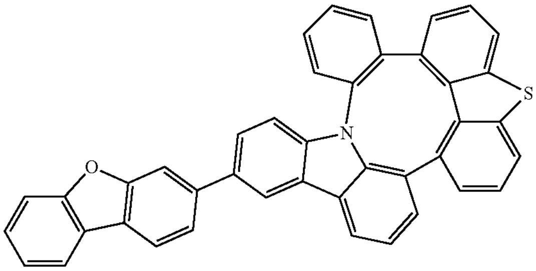
,
Compound 177
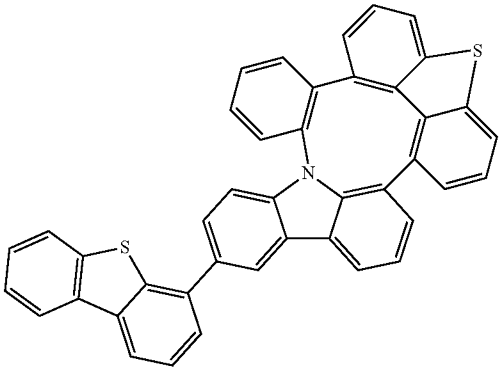
,
Compound 178
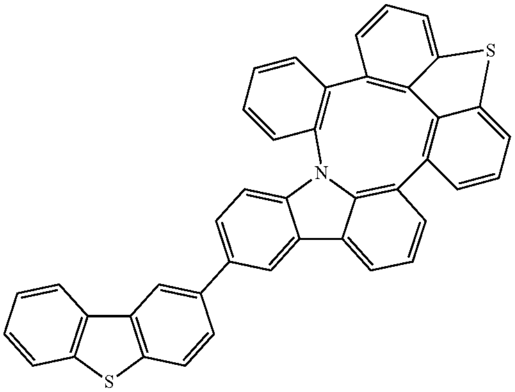
, -continued
Compound 179
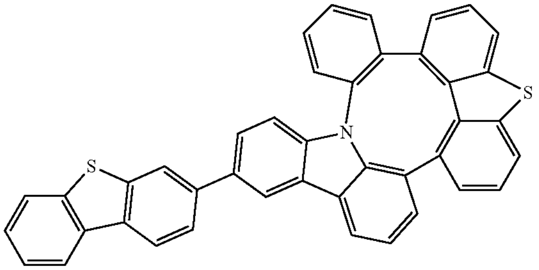
,
Compound 180
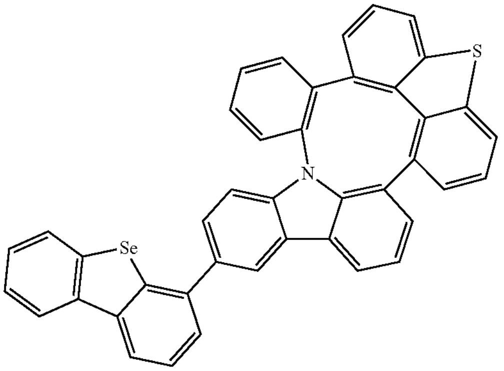
,
Compound 181
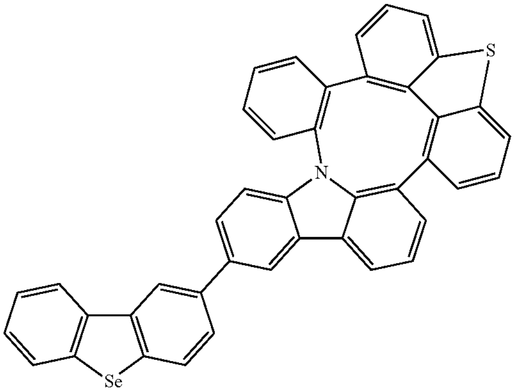
,
Compound 182
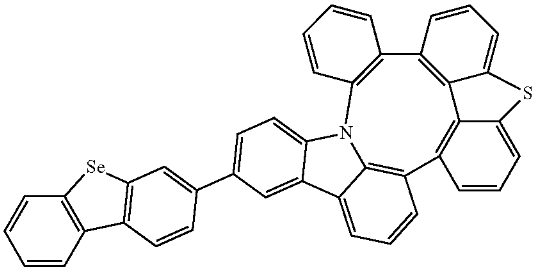
,
-continued
Compound 183
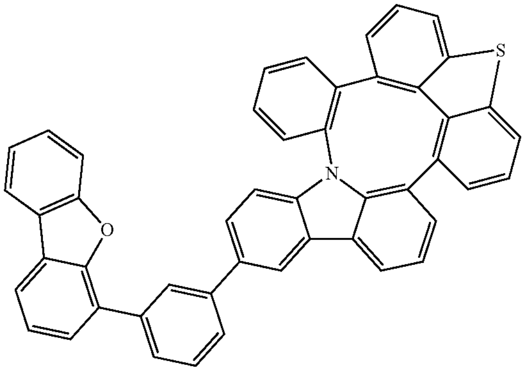
,
Compound 184
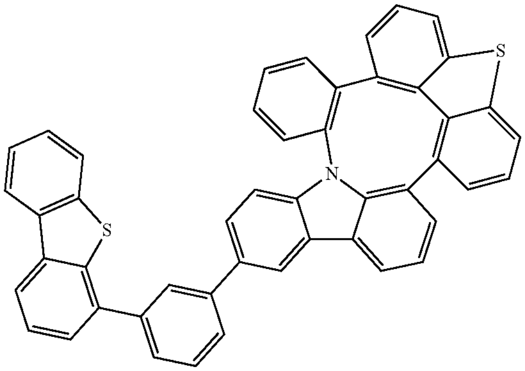
,
Compound 185
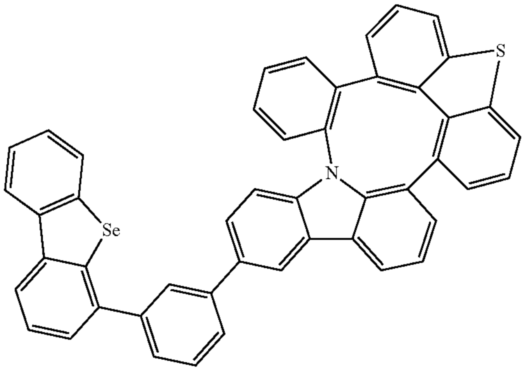
,
Compound 186
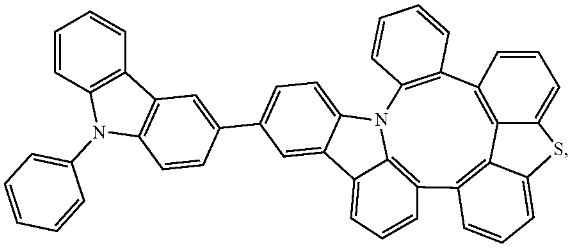

-continued
Compound 187
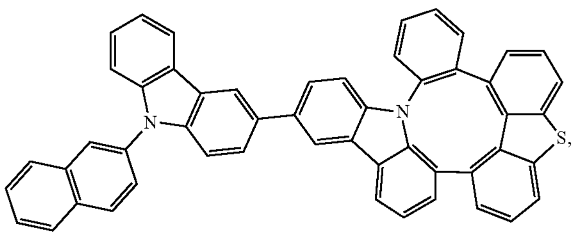
Compound 188
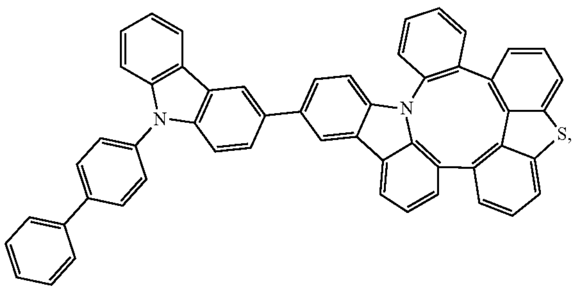
Compound 189
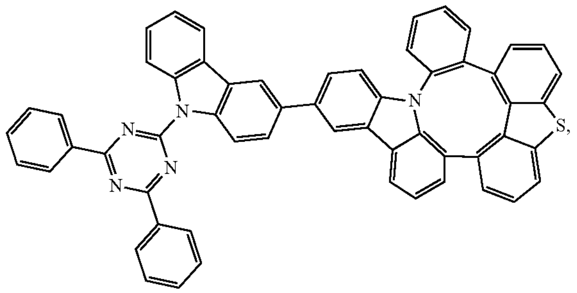
Compound 190
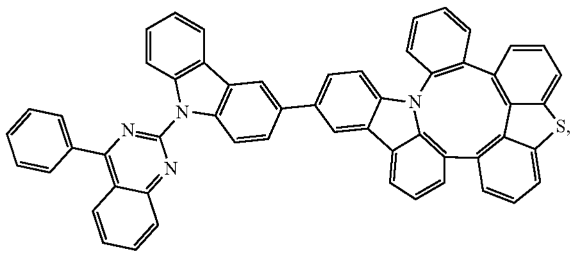
Compound 191
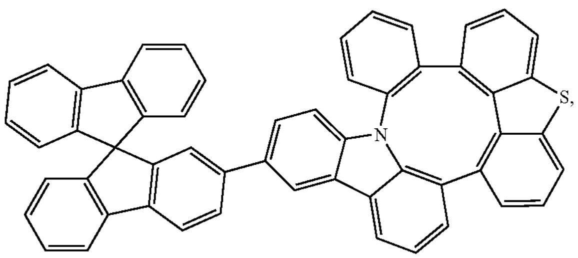
-continued
Compound 192
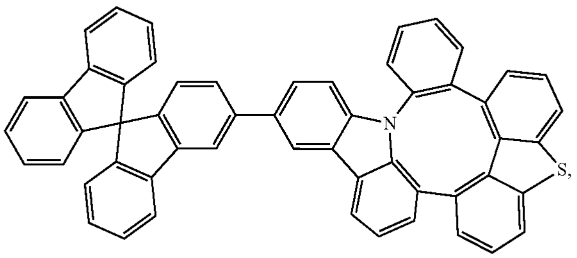
Compound 193
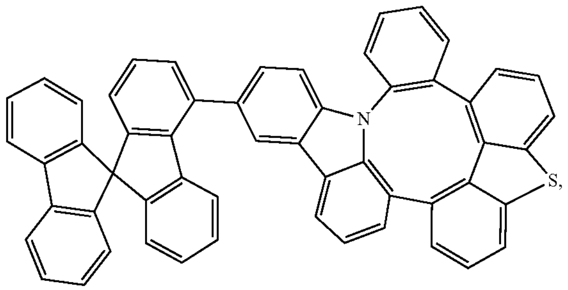
Compound 194
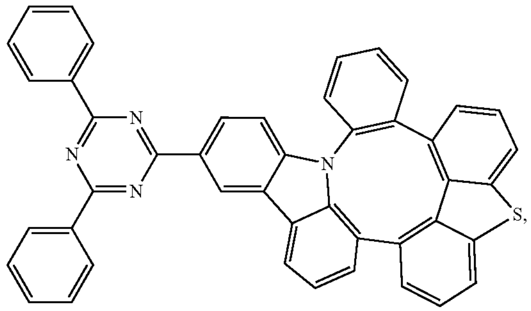
Compound 195
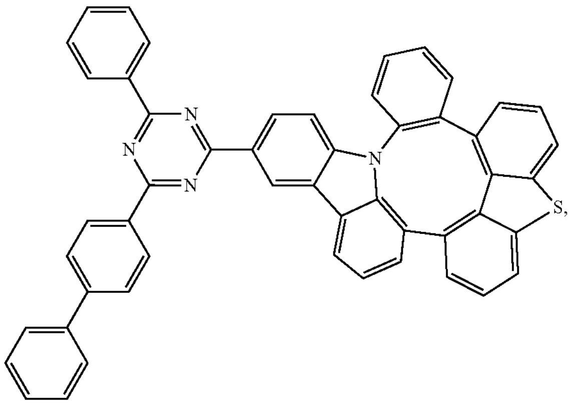
Compound 196
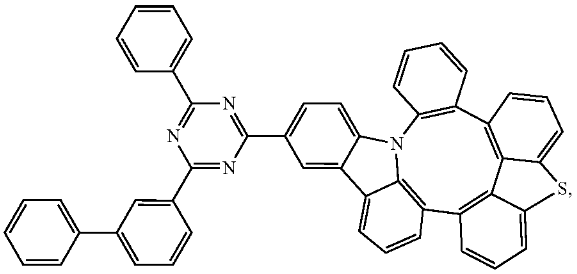

-continued
Compound 197
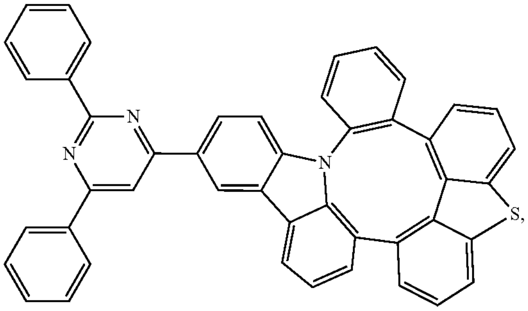
Compound 198
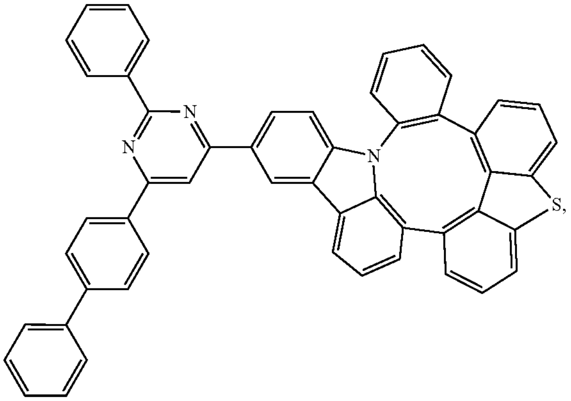
Compound 199
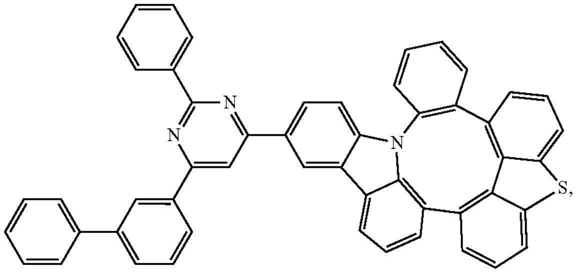
Compound 200
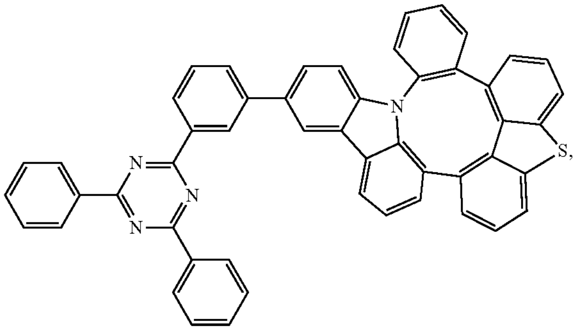
-continued
Compound 201
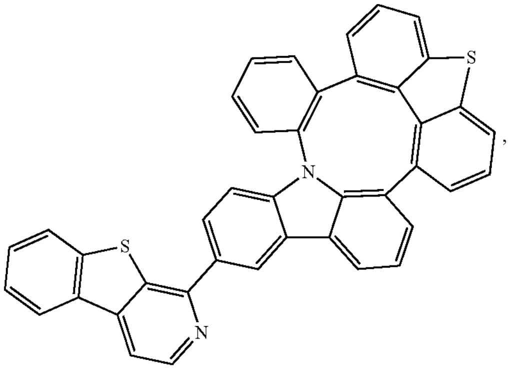
Compound 202
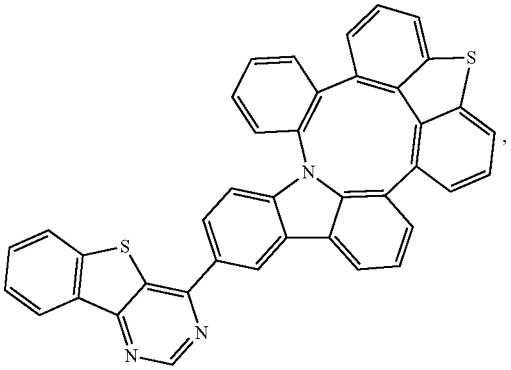
Compound 203
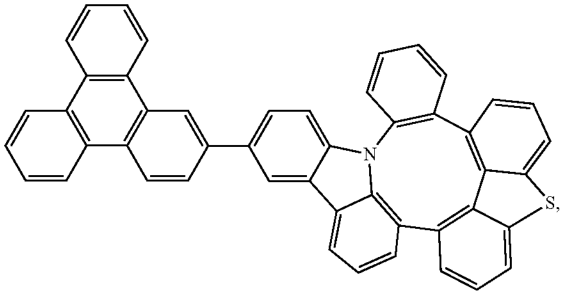
Compound 204
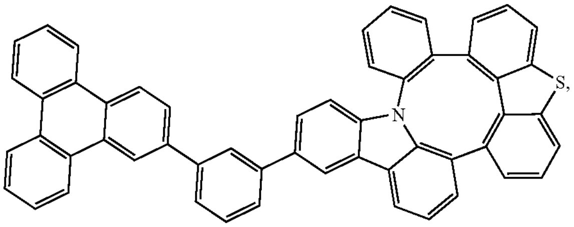
Compound 205
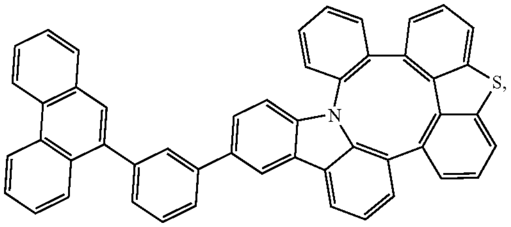

-continued
Compound 206
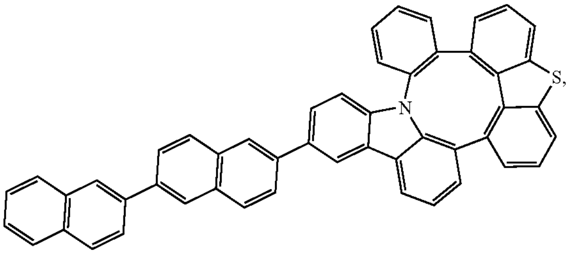
Compound 207
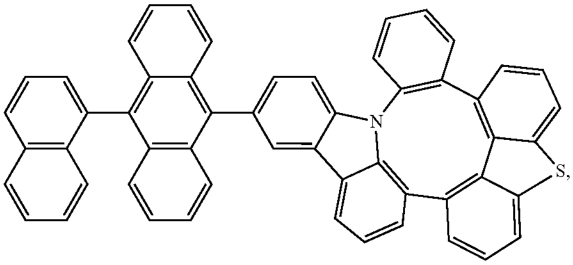
Compound 208
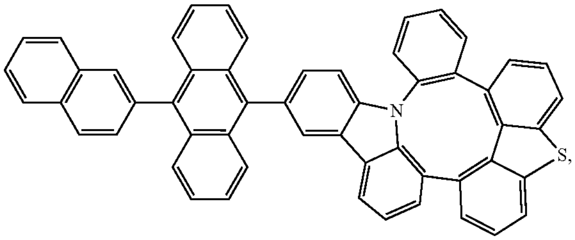
Compound 209
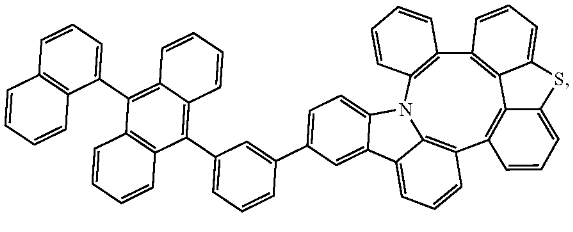
Compound 210
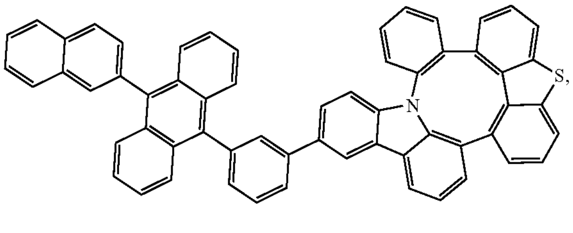
-continued
Compound 211
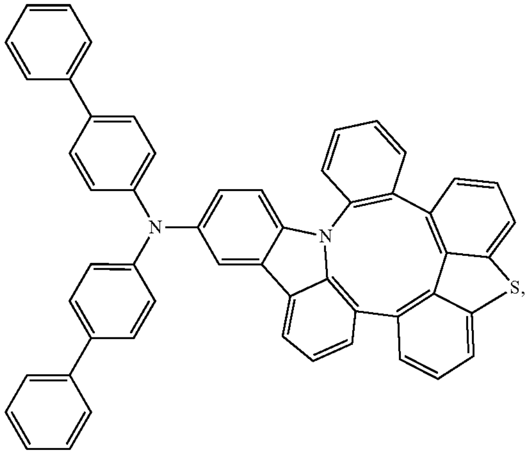
Compound 212
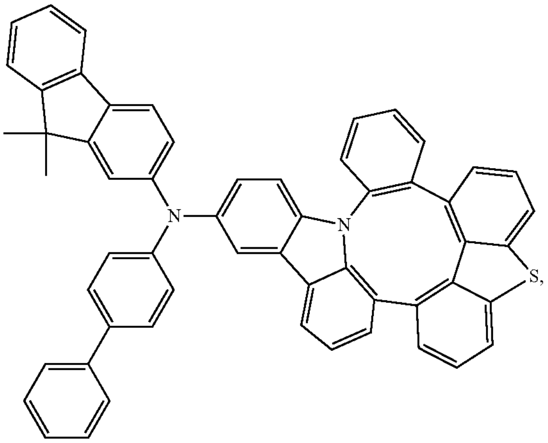
Compound 213
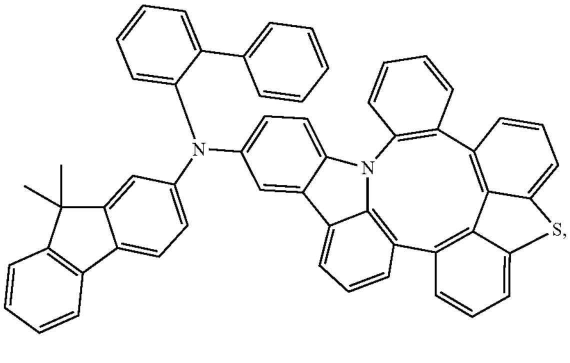

-continued
Compound 214
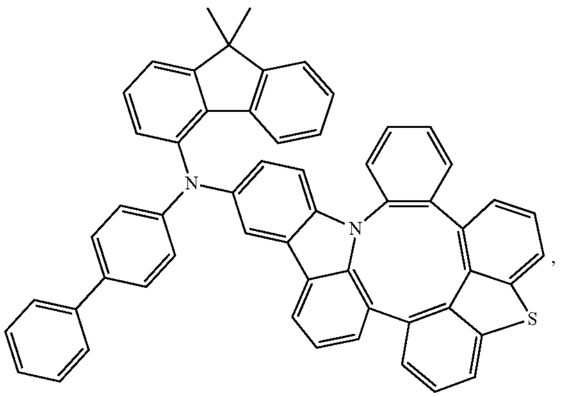
Compound 215
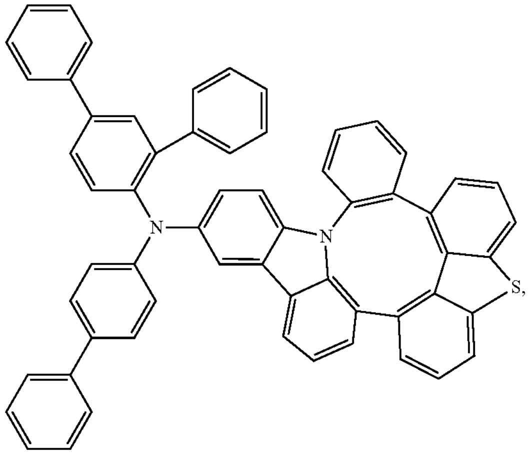
Compound 216
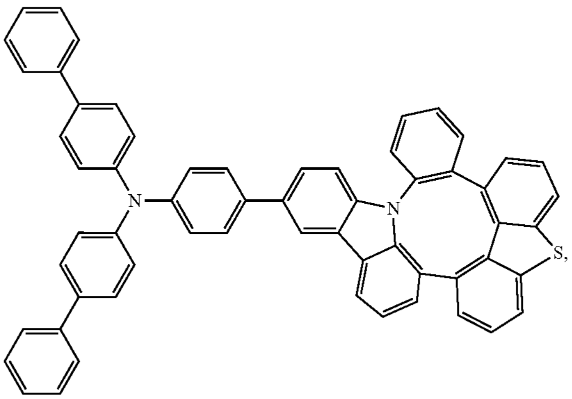
-continued
Compound 217
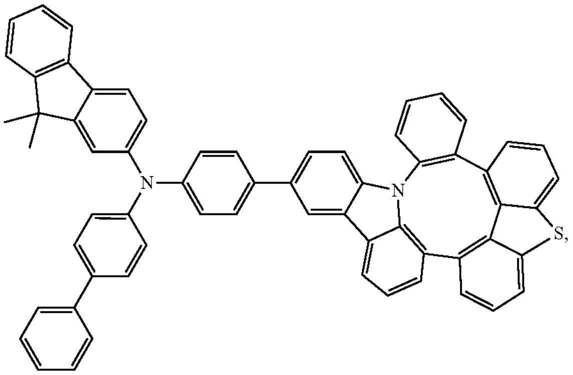
Compound 218
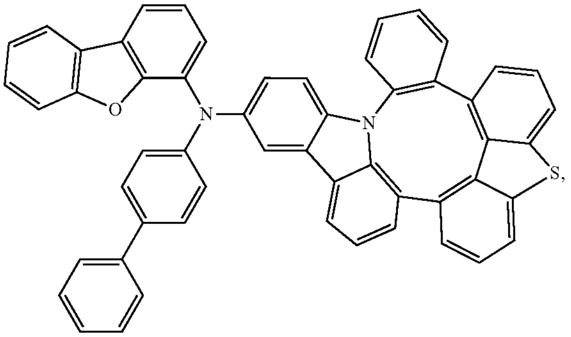
Compound 219
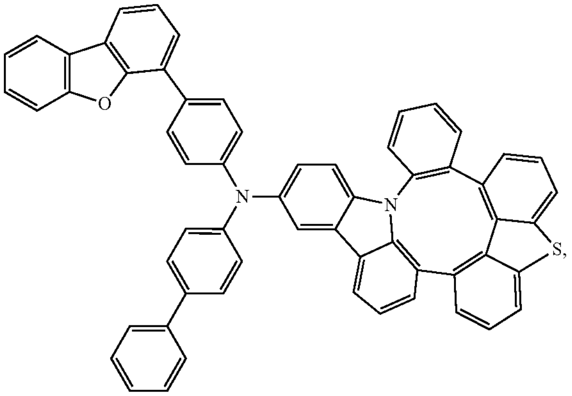
Compound 220
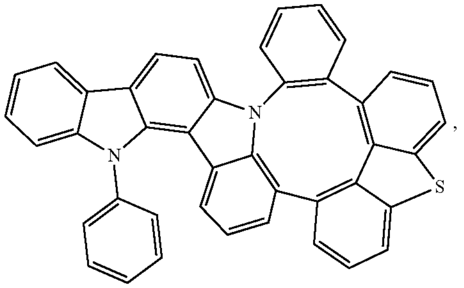

-continued
Compound 221
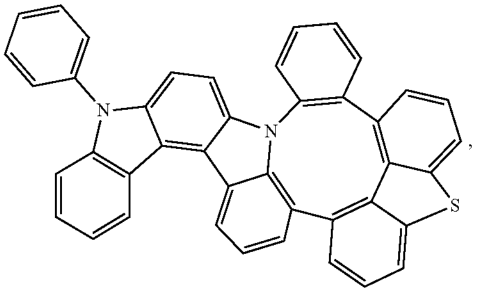
Compound 222
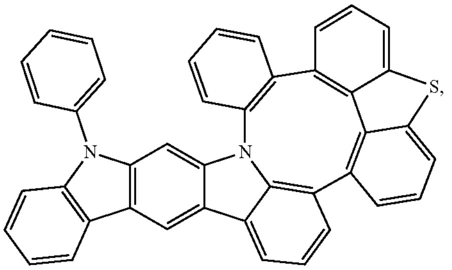
Compound 223
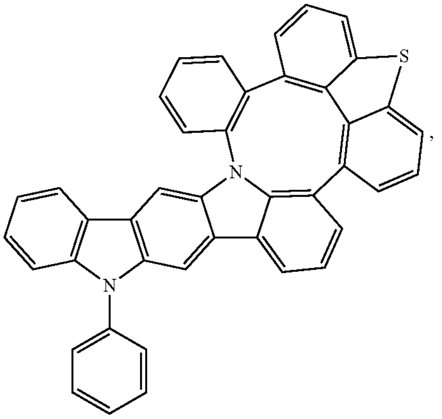
Compound 224
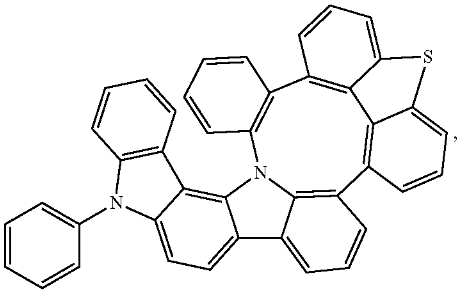
-continued
Compound 225
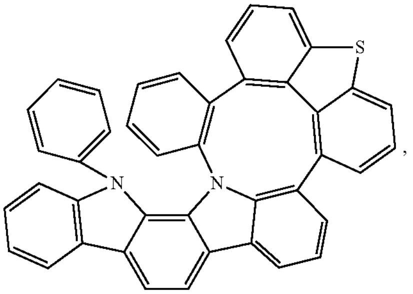
Compound 226
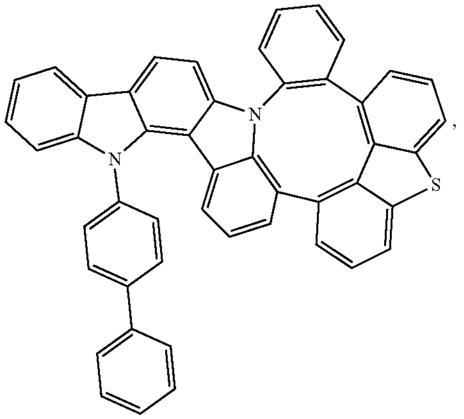
Compound 227
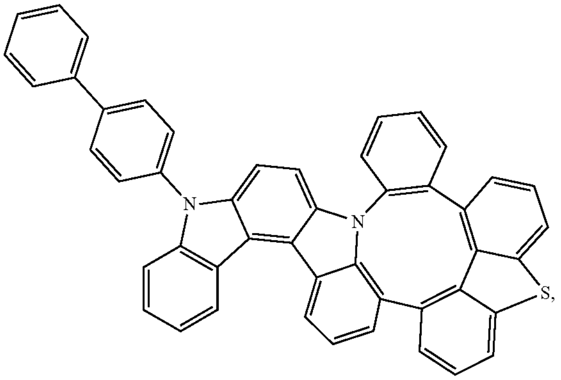
Compound 228
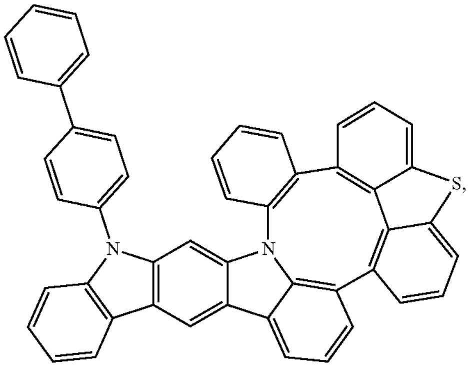

-continued
Compound 229
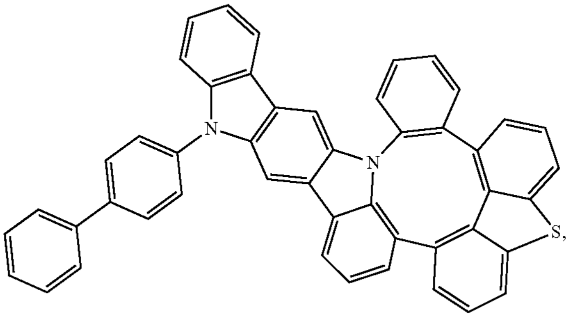
Compound 230
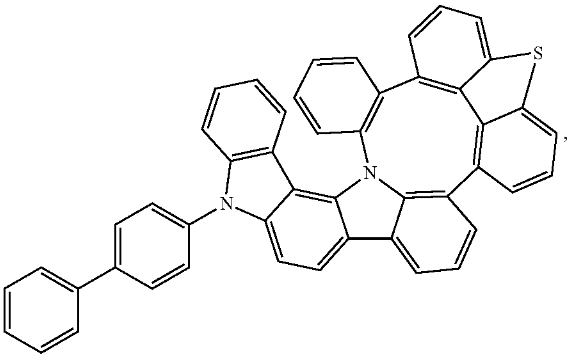
Compound 231
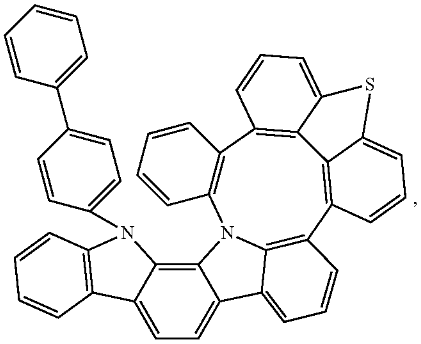
Compound 232
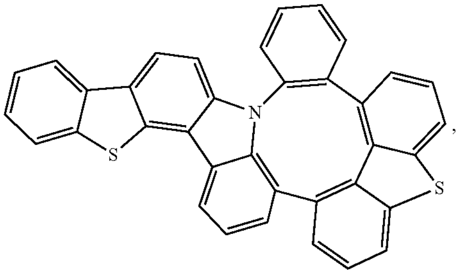
Compound 233
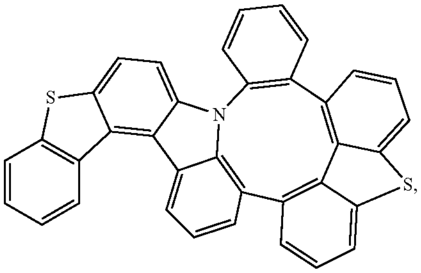
-continued
Compound 234
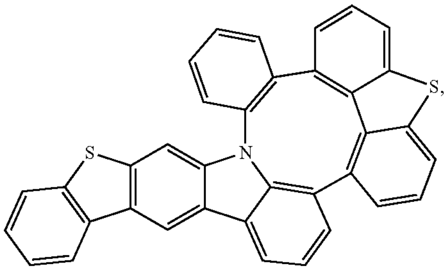
Compound 235
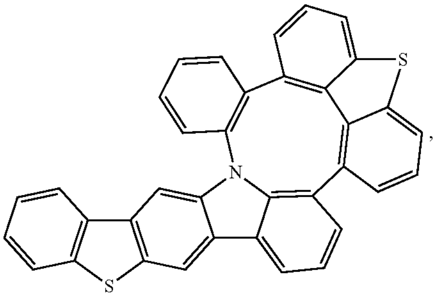
Compound 236
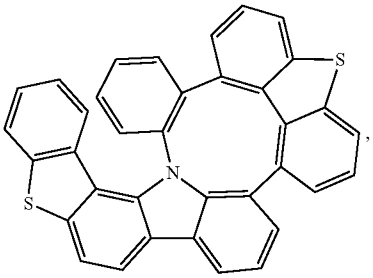
Compound 237
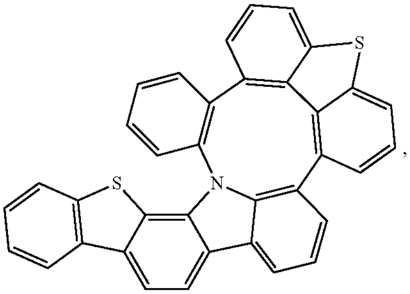
Compound 238
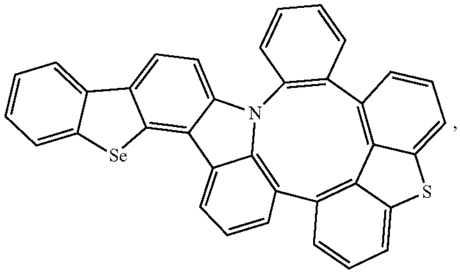

-continued
Compound 239
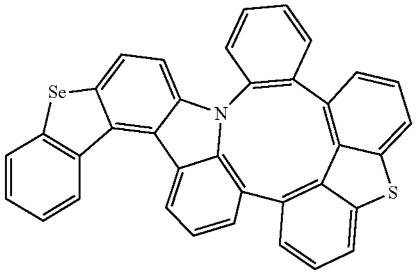
,
Compound 240
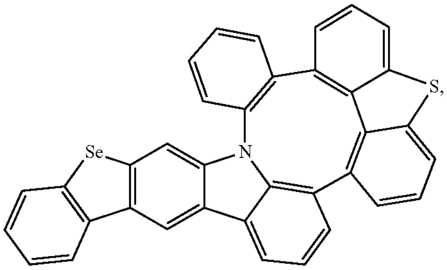
,
Compound 241
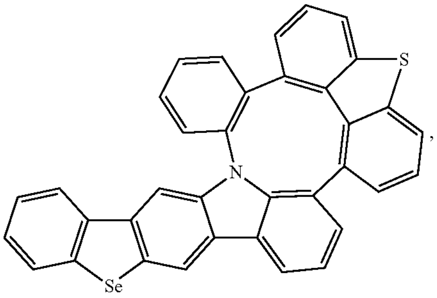
,
Compound 242
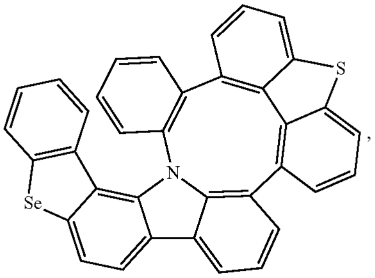
,
Compound 243
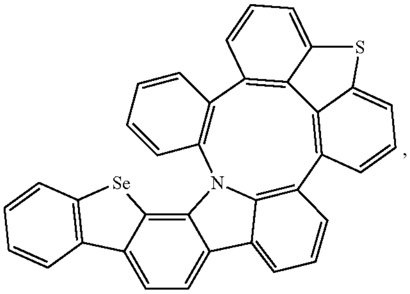
,
-continued
Compound 244
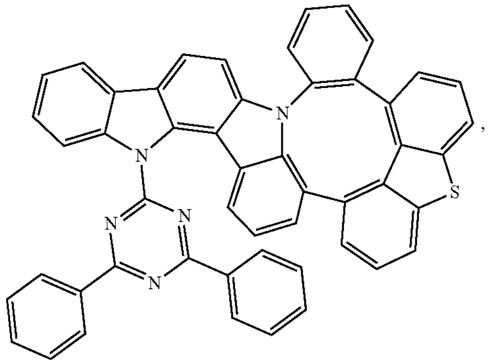
,
Compound 245
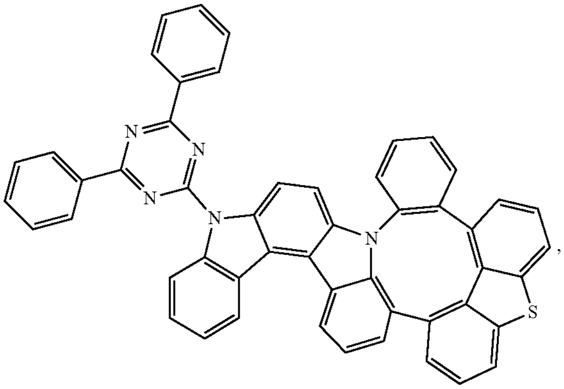
,
Compound 246
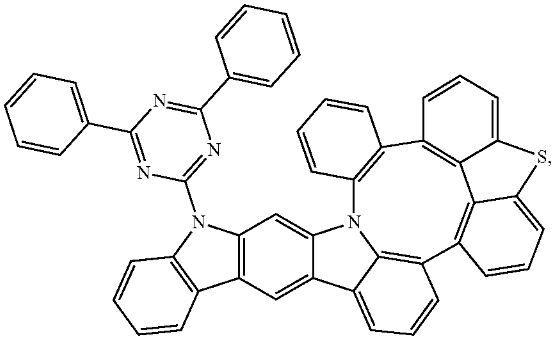
, -continued
Compound 247
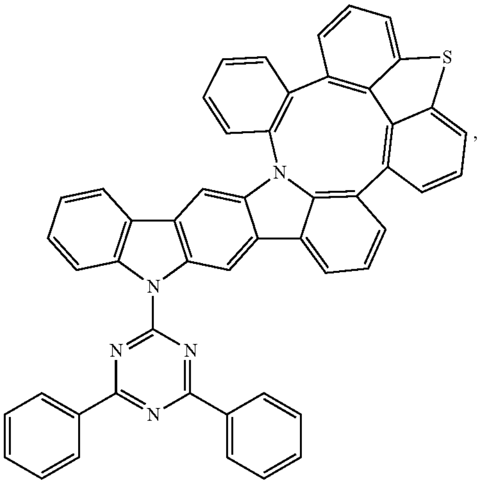
Compound 248
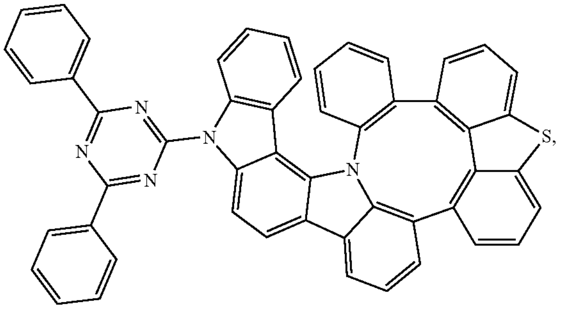
Compound 249
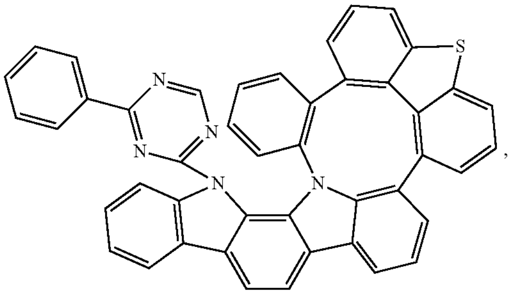
Compound 250
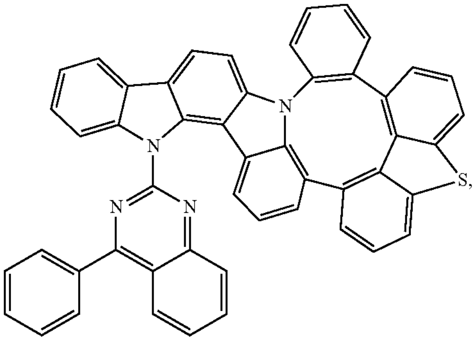
-continued
Compound 251
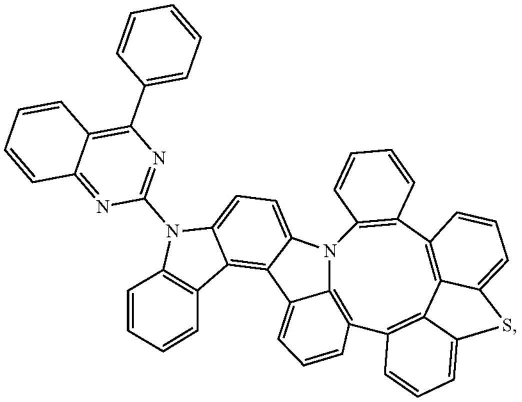
Compound 252
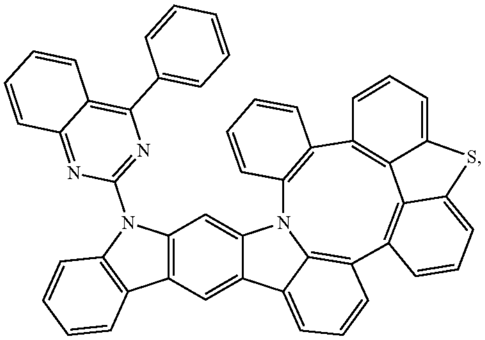
Compound 253
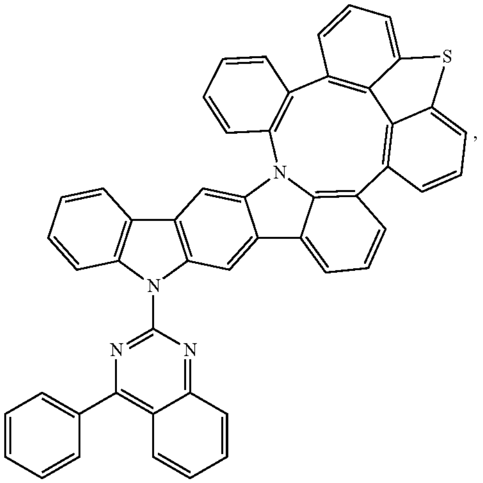
Compound 254
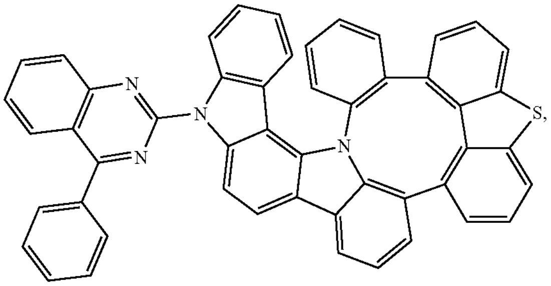

-continued
Compound 255
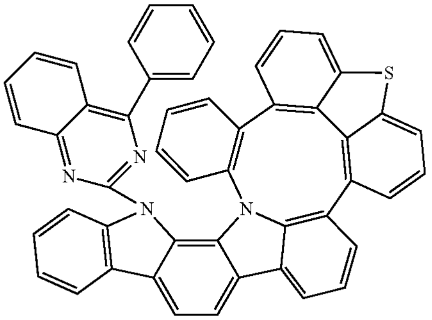
,
Compound 256
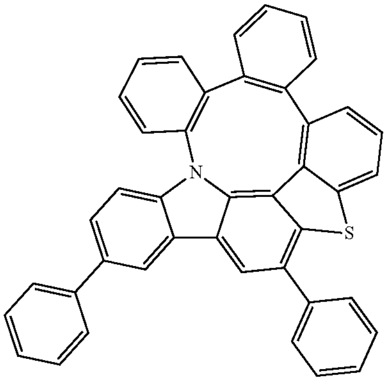
,
Compound 257
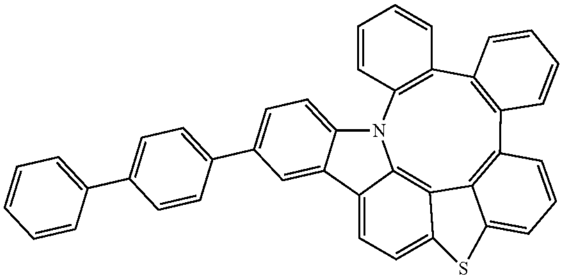
,
Compound 258
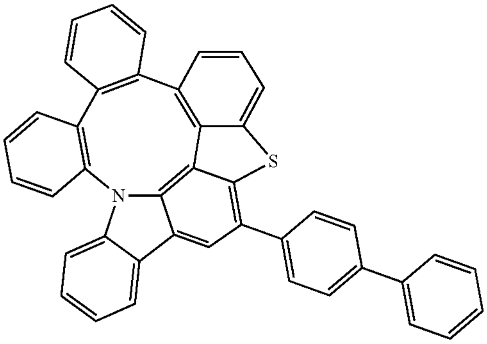
,
-continued
Compound 259
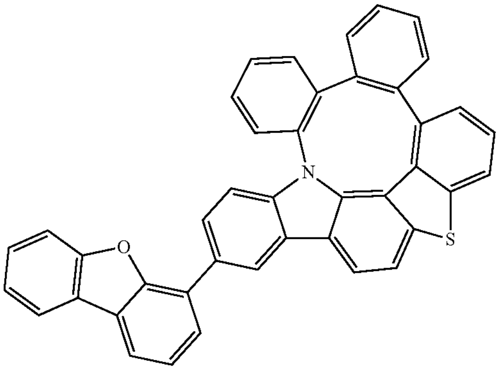
,
Compound 260
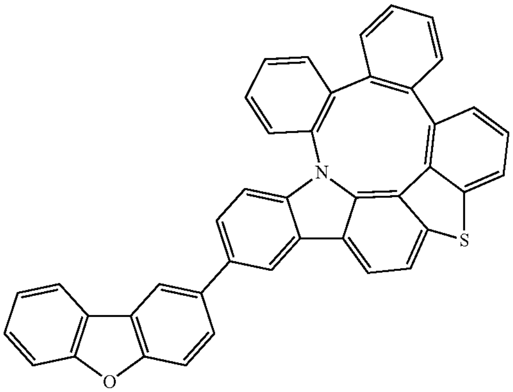
,
Compound 261
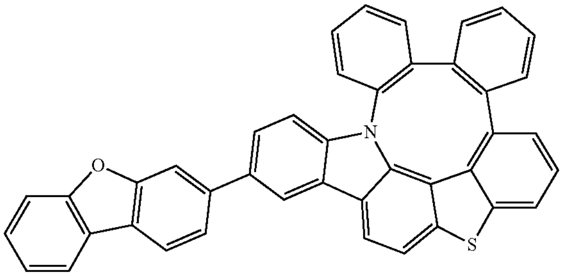
,
Compound 262
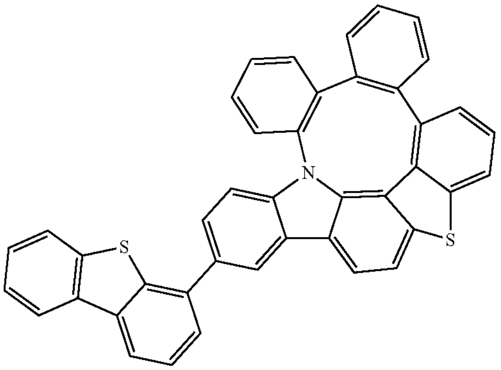
, -continued
Compound 263
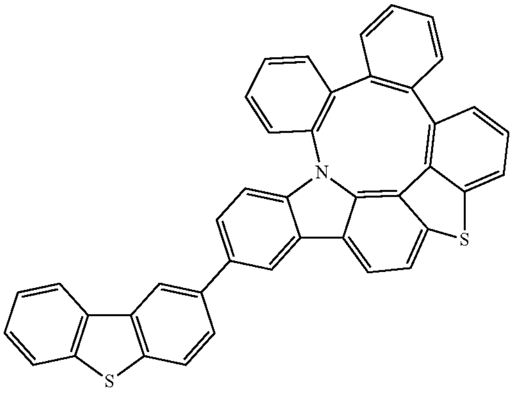
,
Compound 264
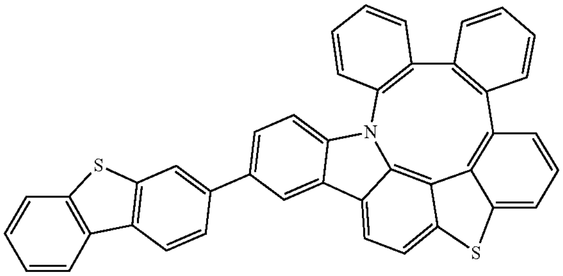
,
Compound 265
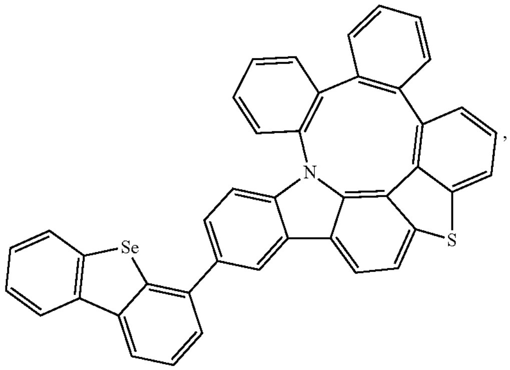
,
Compound 266
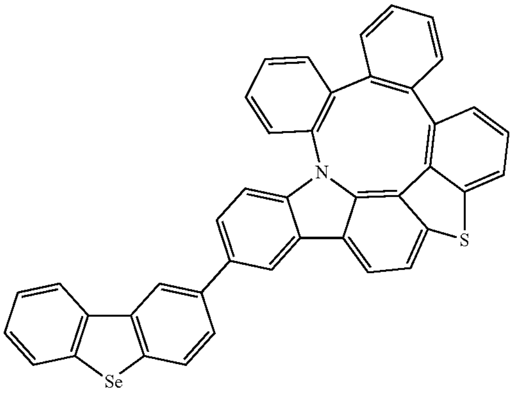
,
-continued
Compound 267
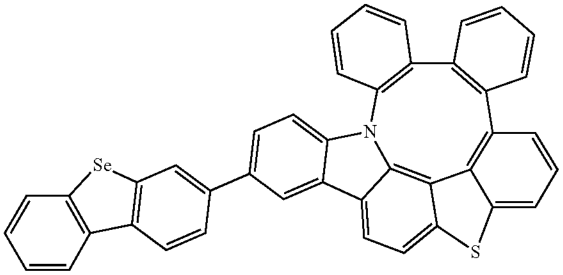
,
Compound 268
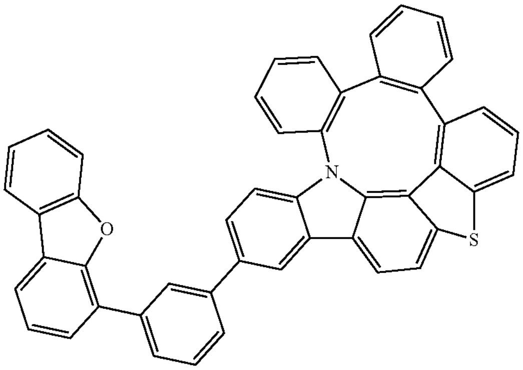
,
Compound 269
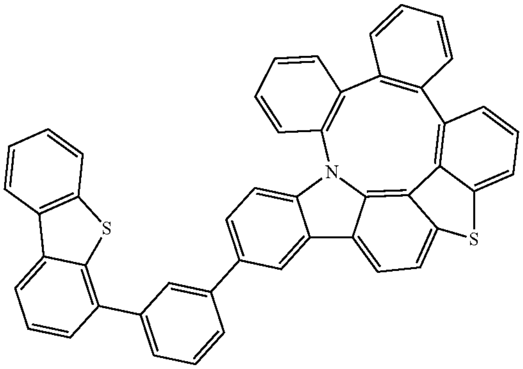
,
Compound 270
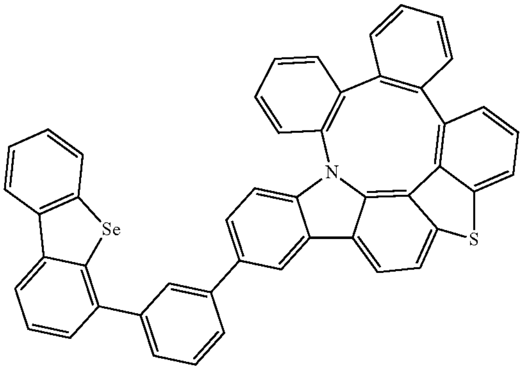
, -continued
Compound 271
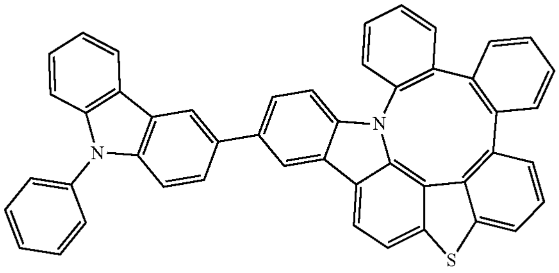
,
Compound 272
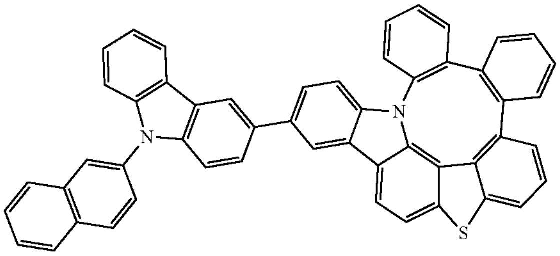
,
Compound 273
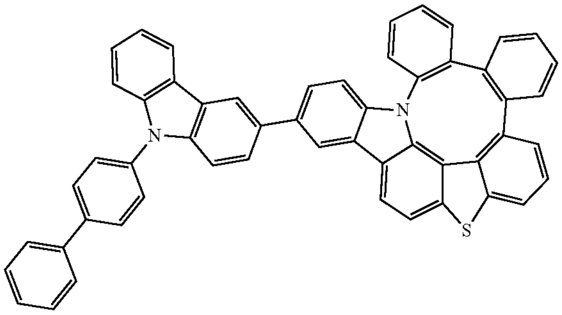
,
Compound 274
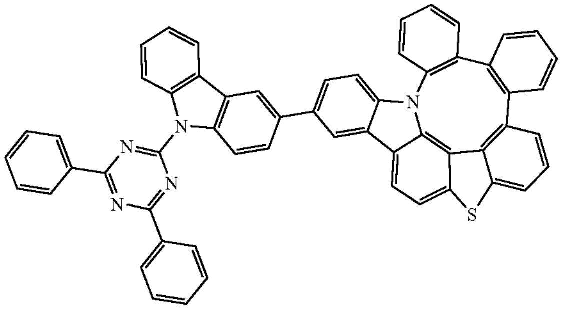
,
Compound 275
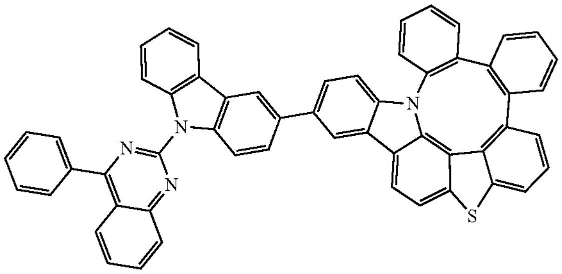
,
-continued
Compound 276
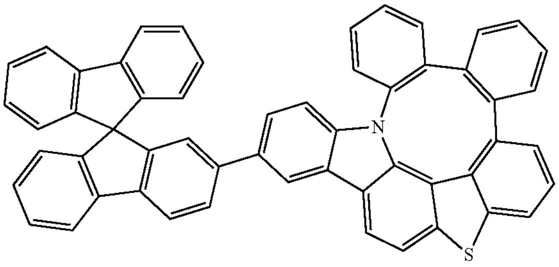
,
Compound 277
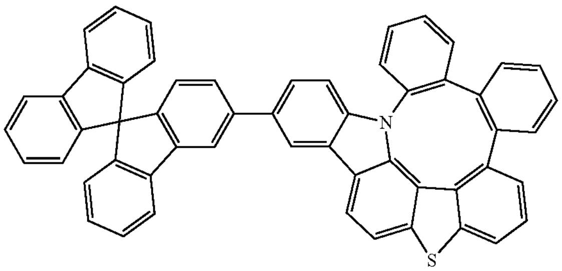
,
Compound 278
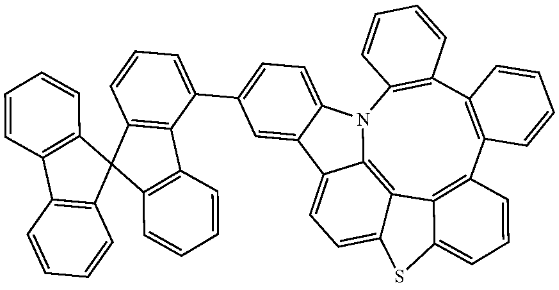
,
Compound 279
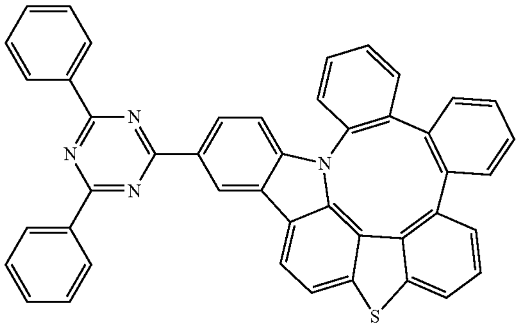
, -continued
Compound 280
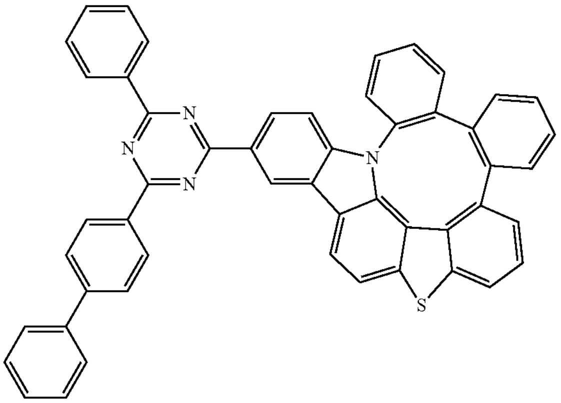
,
Compound 281
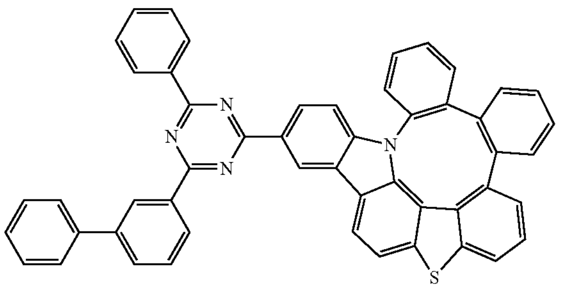
,
Compound 282
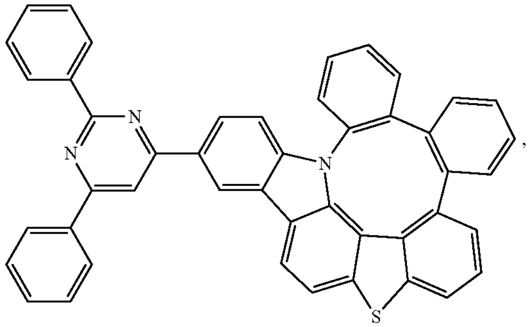
,
Compound 283
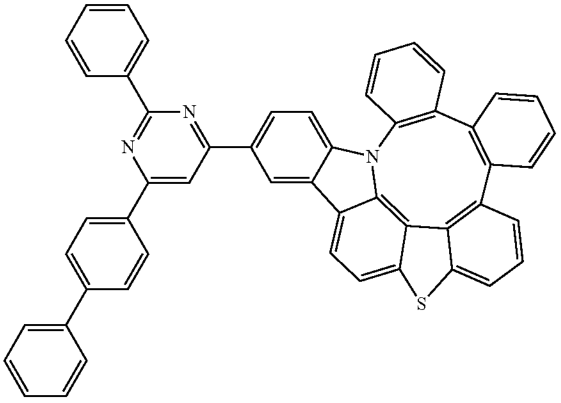
,
-continued
Compound 284
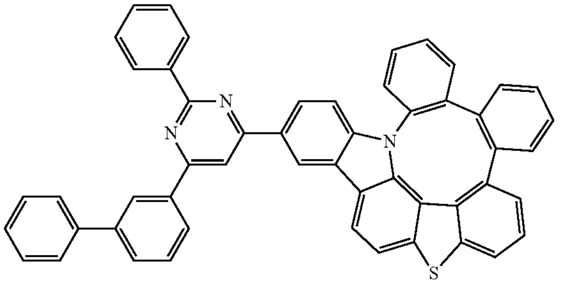
,
Compound 285
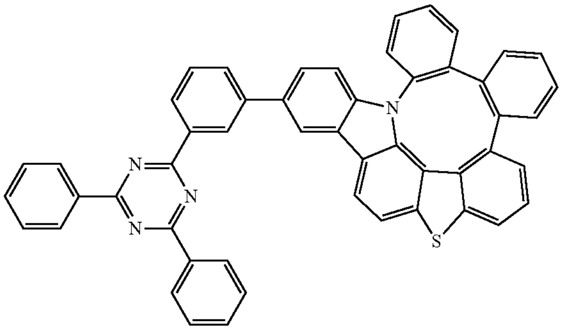
,
Compound 286
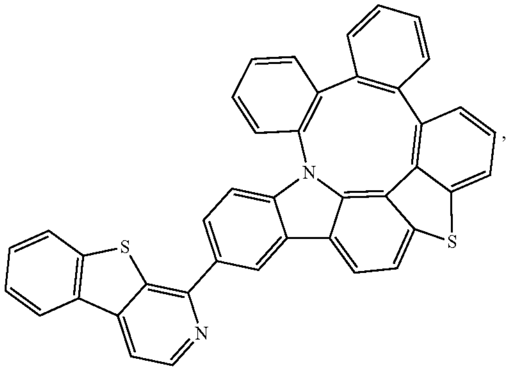
,
Compound 287
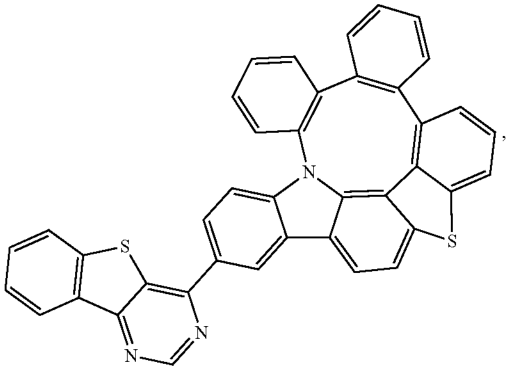
, -continued
Compound 288
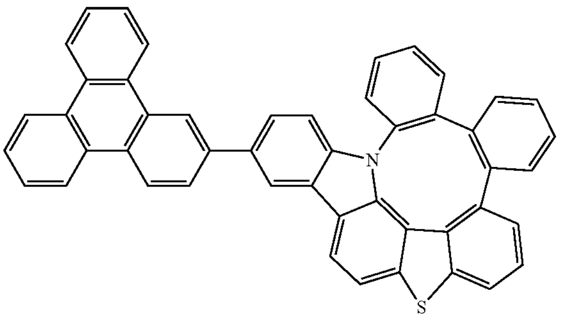
,
Compound 289
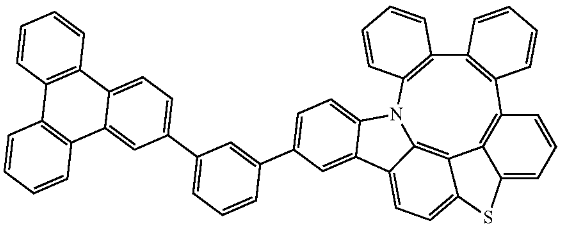
,
Compound 290
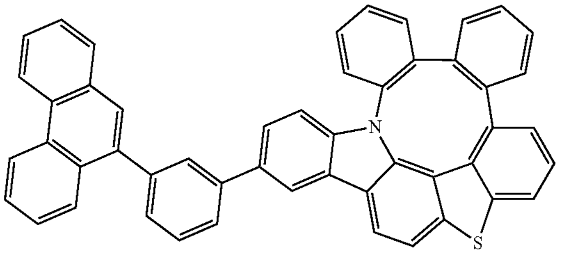
,
Compound 291
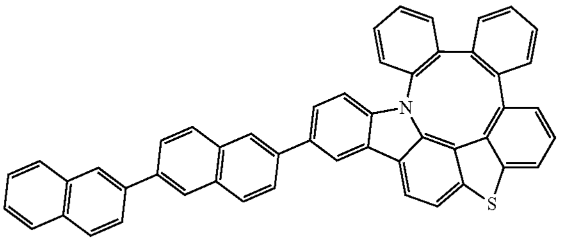
,
Compound 292
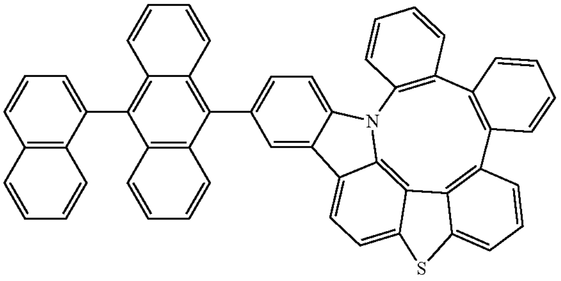
,
-continued
Compound 293
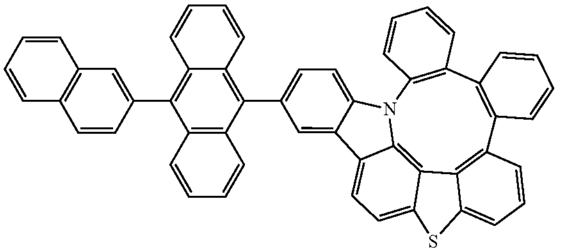
,
Compound 294
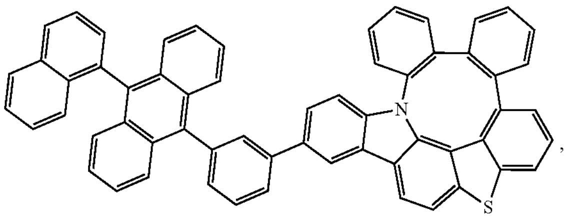
,
Compound 295
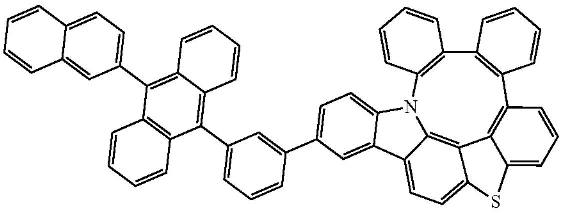
,
Compound 296
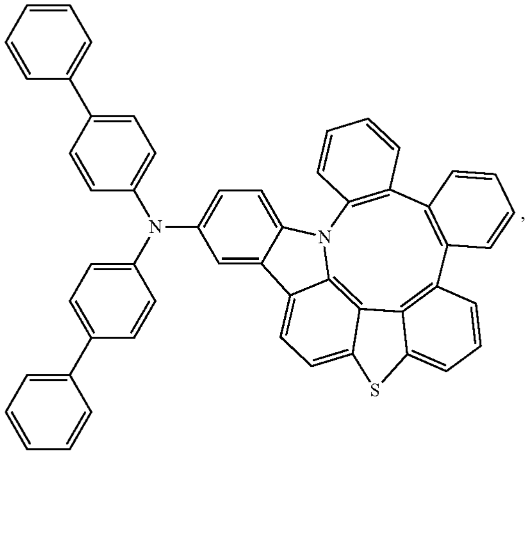
, -continued
Compound 297
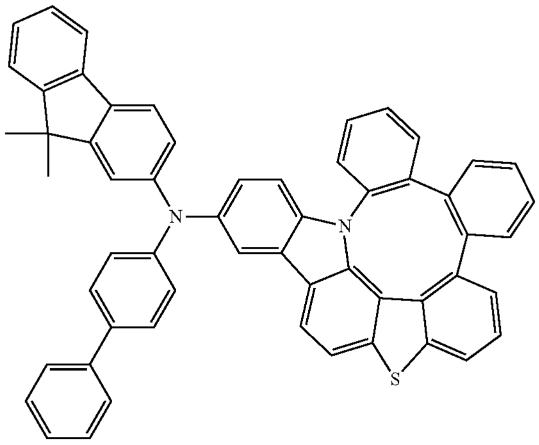
,
Compound 298
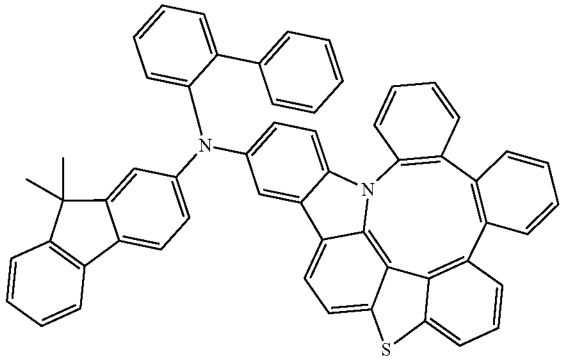
,
Compound 299
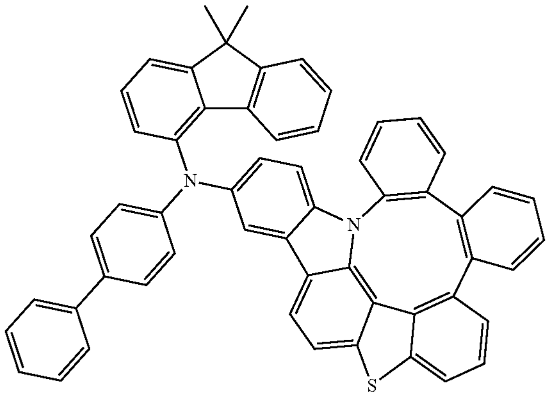
,
-continued
Compound 300
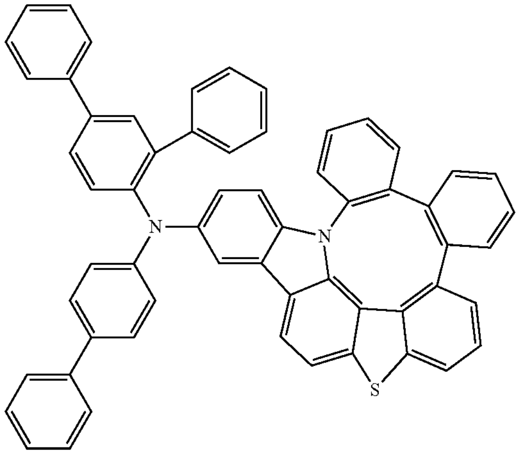
,
Compound 301
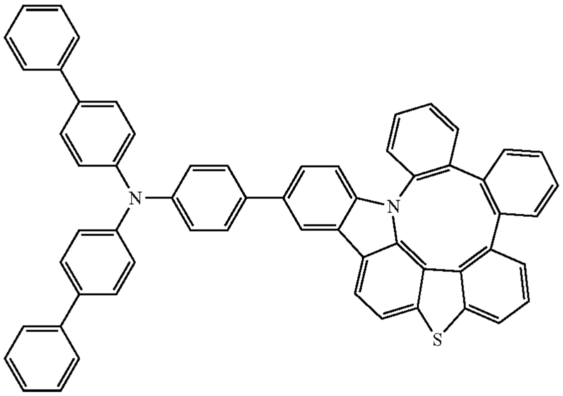
,
Compound 302
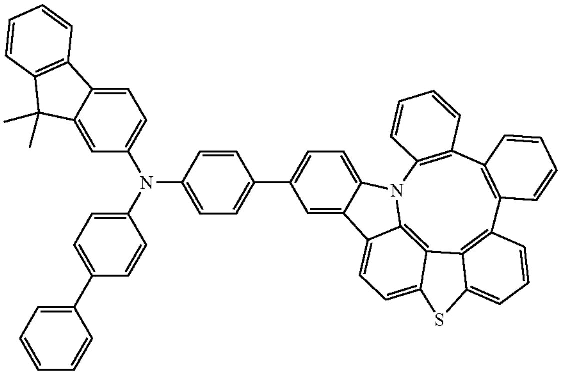
,
Compound 303
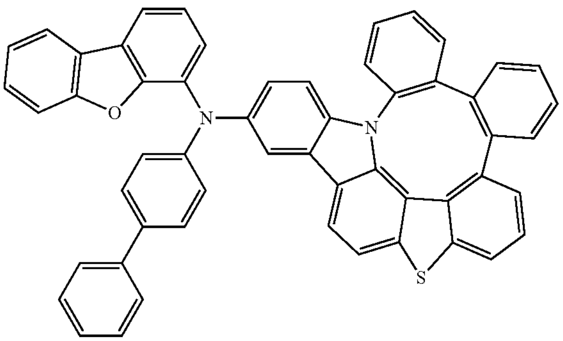
, -continued
Compound 304
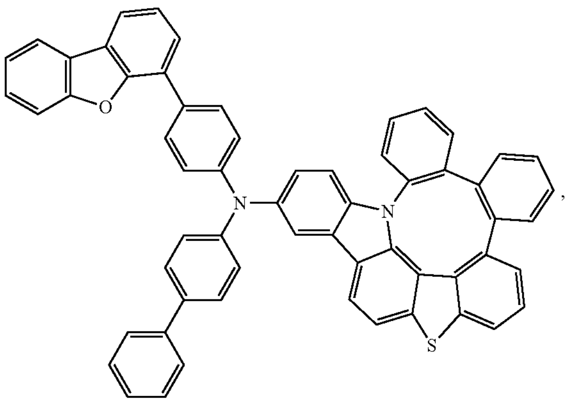
Compound 305
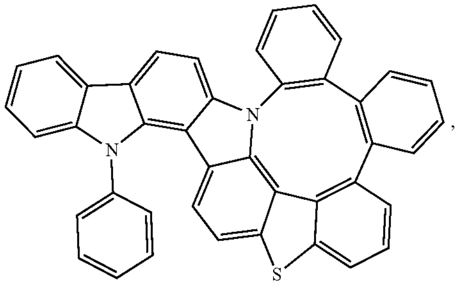
Compound 306
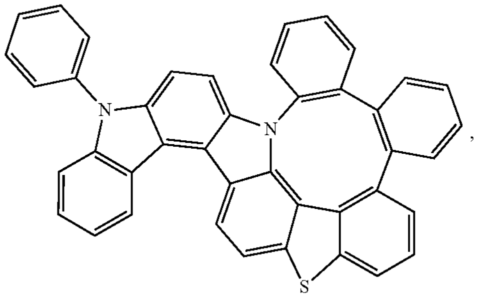
Compound 307
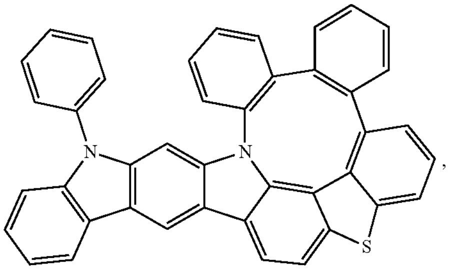
-continued
Compound 308
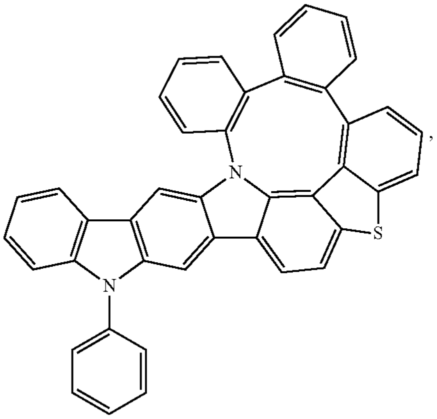
Compound 309
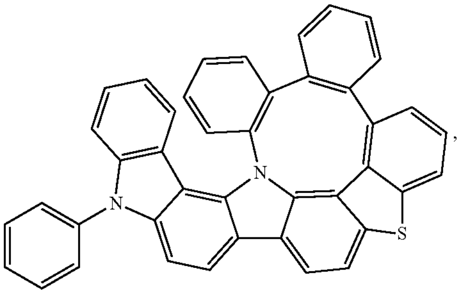
Compound 310
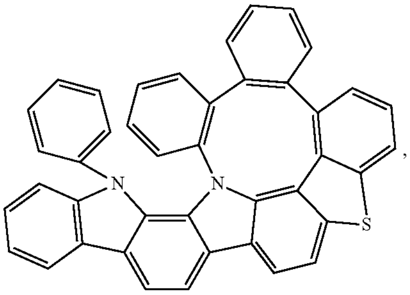
Compound 311
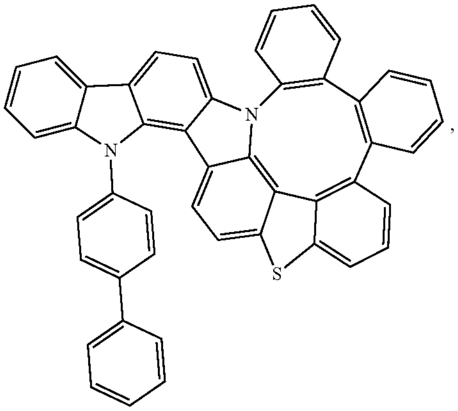

-continued
Compound 312
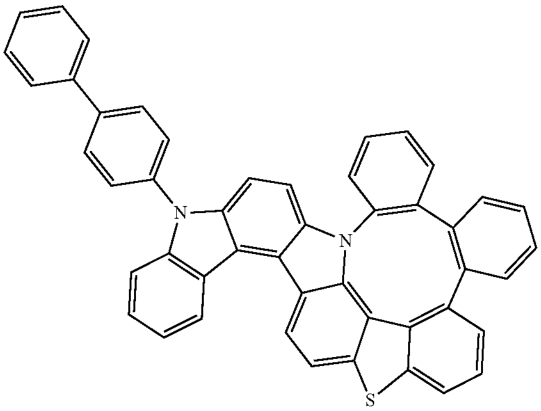
,
Compound 313
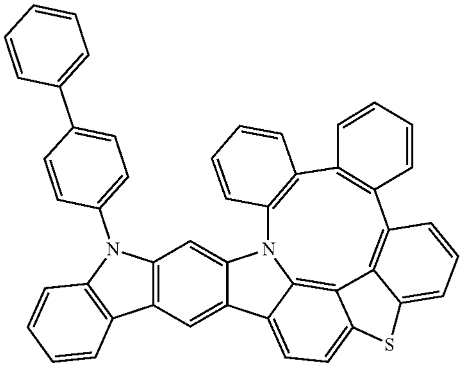
,
Compound 314
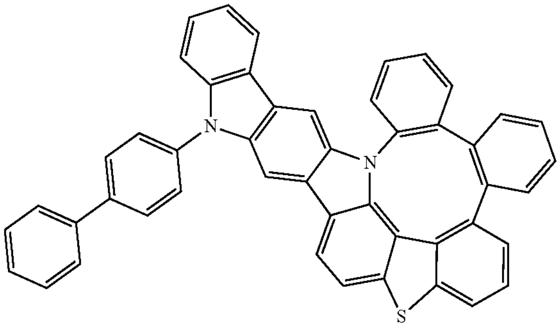
,
Compound 315
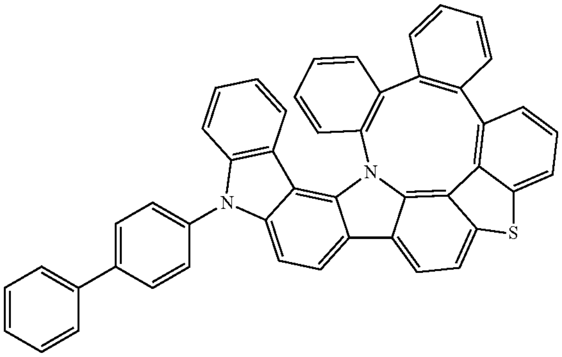
,
-continued
Compound 316
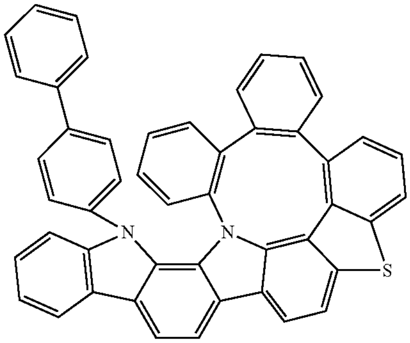
,
Compound 317
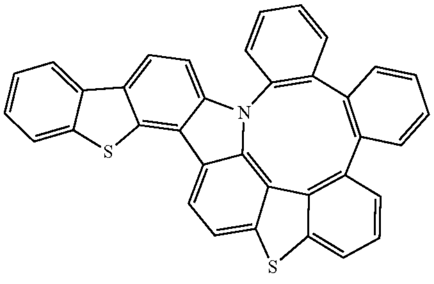
,
Compound 318
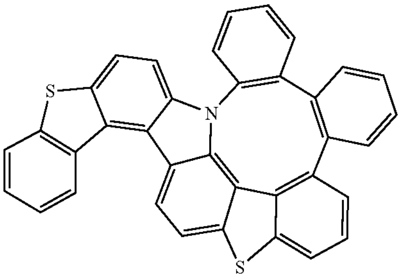
,
Compound 319
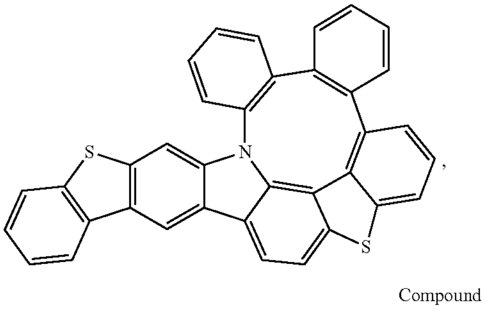
,
Compound 320
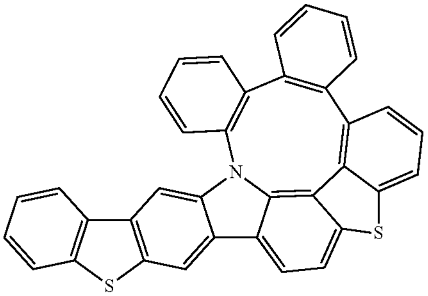
, -continued
Compound 321
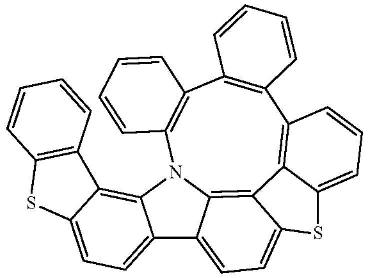,
Compound 322
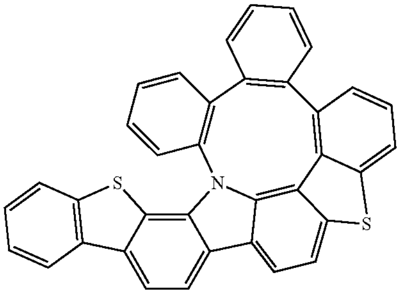,
Compound 323
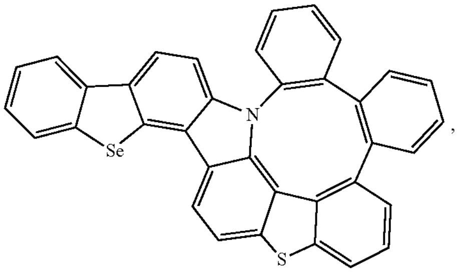,
Compound 324
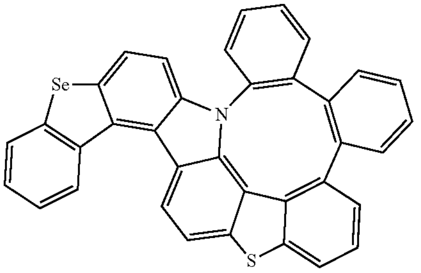,
Compound 325
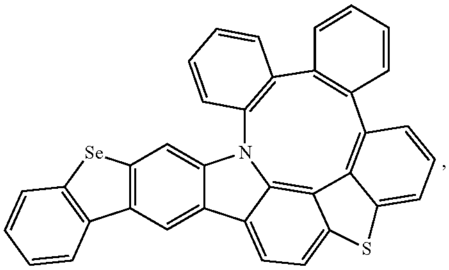,
-continued
Compound 326
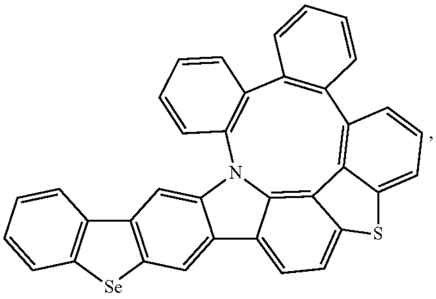,
Compound 327
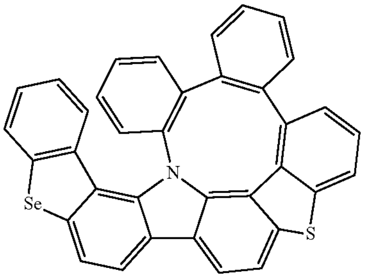,
Compound 328
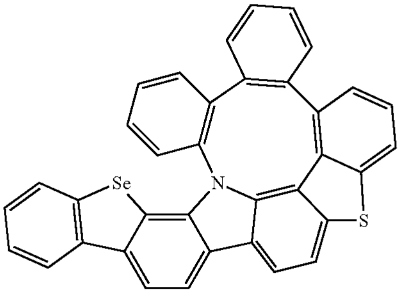,
Compound 329
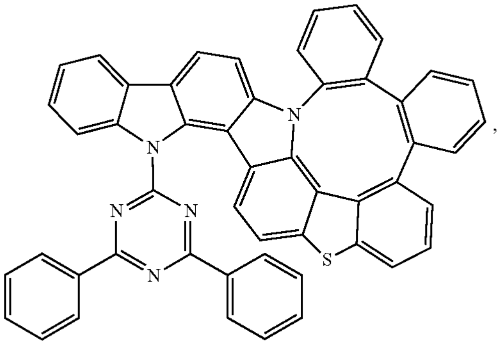, -continued
Compound 330
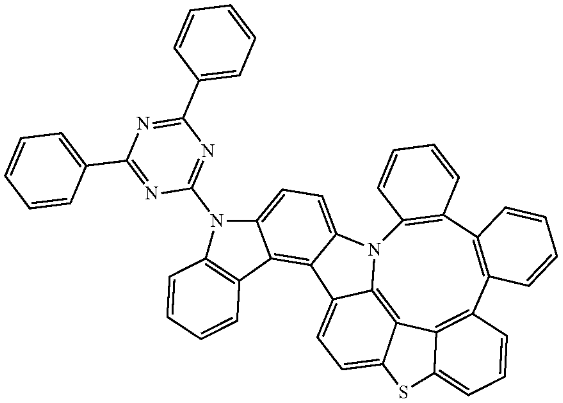
,
Compound 331
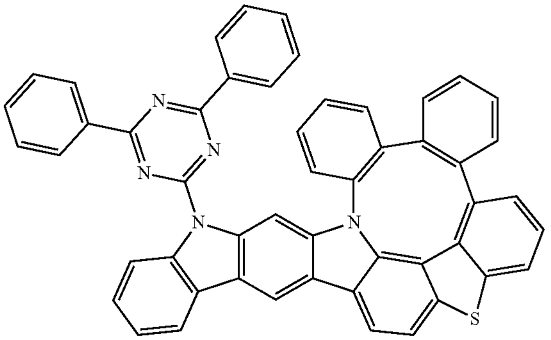
,
Compound 332
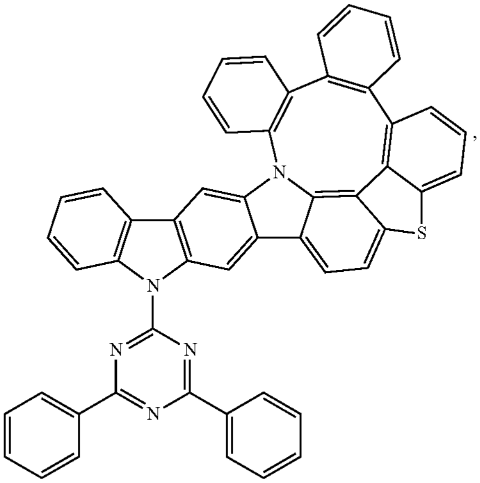
,
Compound 333
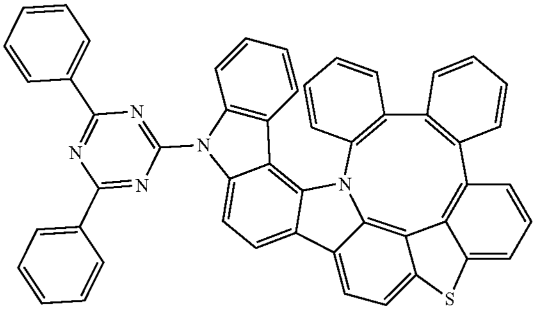
,
-continued
Compound 334
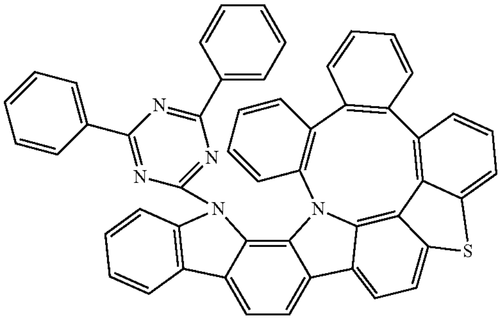
,
Compound 335
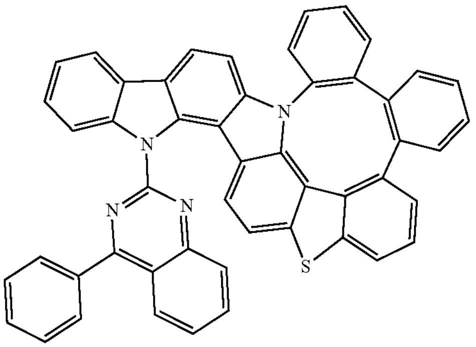
,
Compound 336
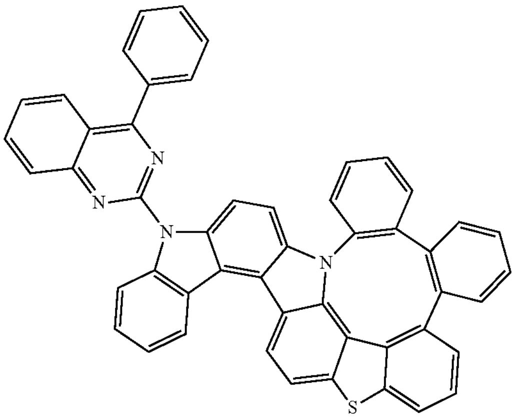
,
Compound 337
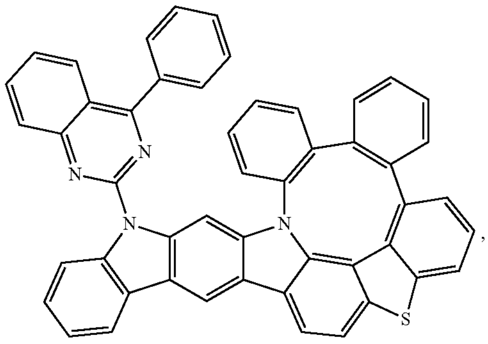
, -continued
Compound 338
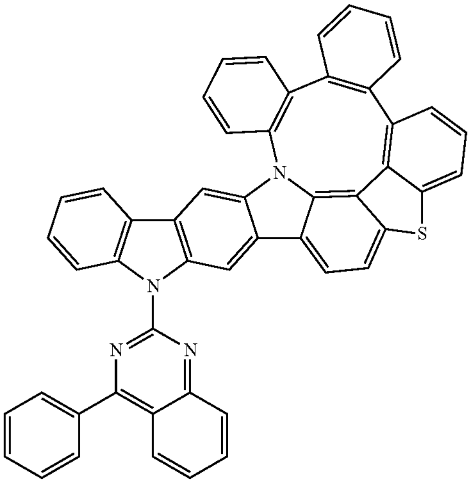
,
Compound 339
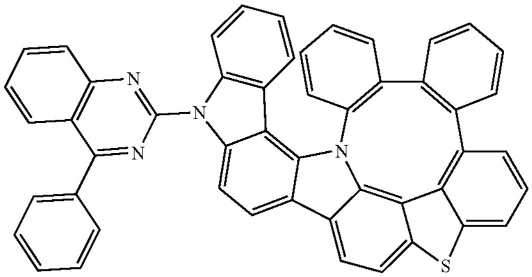
,
Compound 340
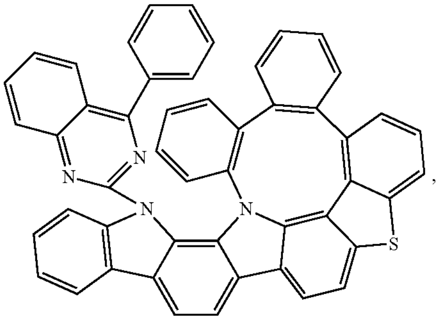
,
Compound 341
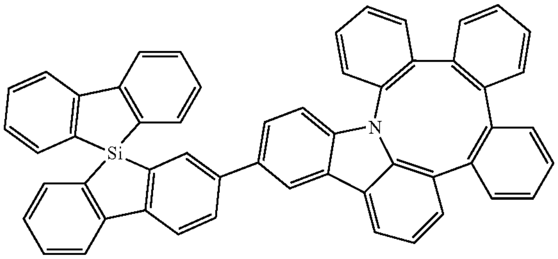
,
-continued
Compound 342
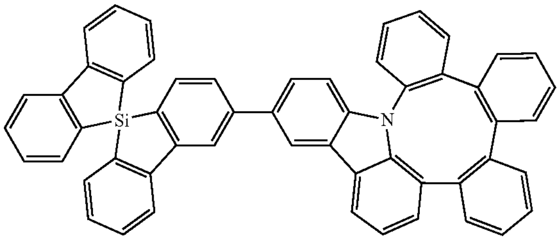
,
Compound 343
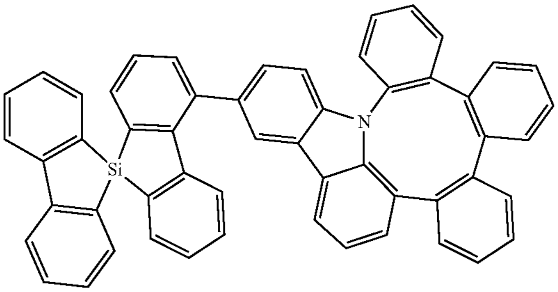
,
Compound 344
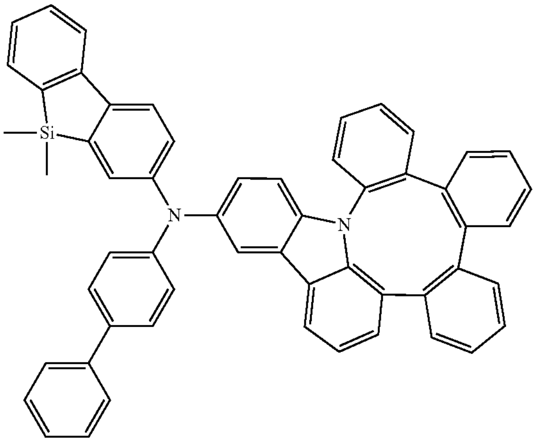
,
Compound 345
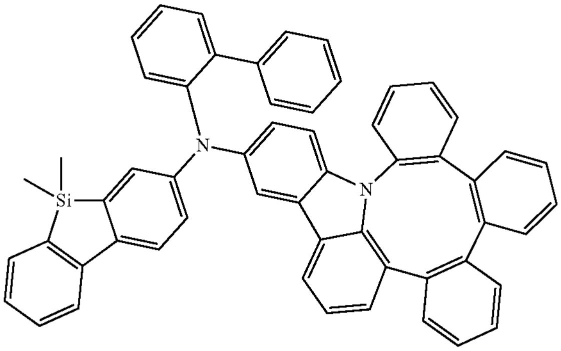
, -continued
Compound 346
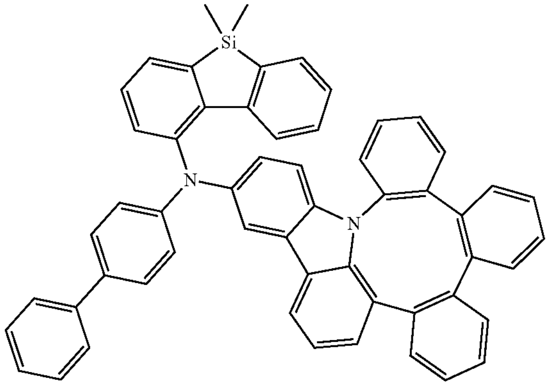
,
Compound 347
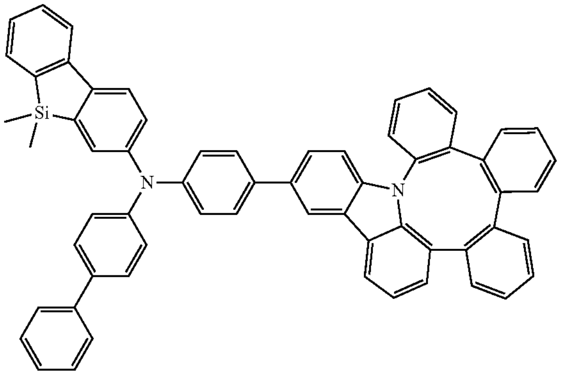
,
Compound 348
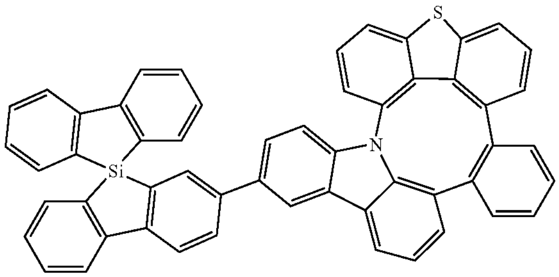
,
Compound 349
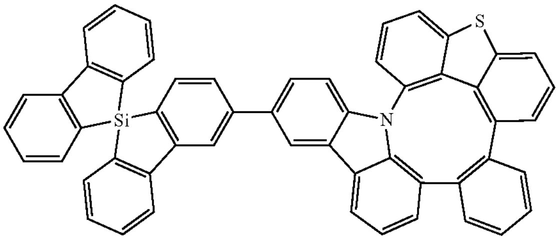
,
-continued
Compound 350
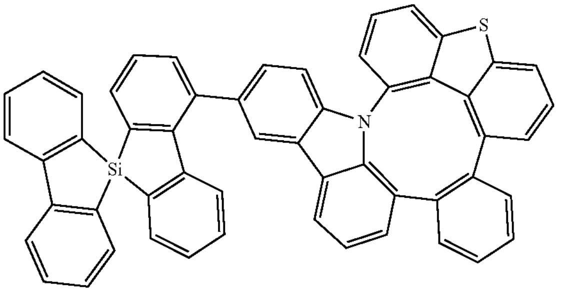
,
Compound 351
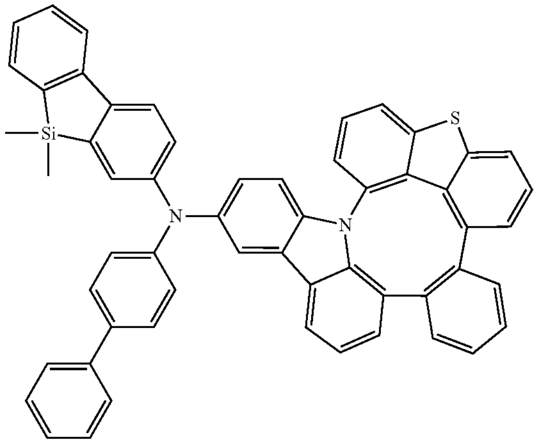
,
Compound 352
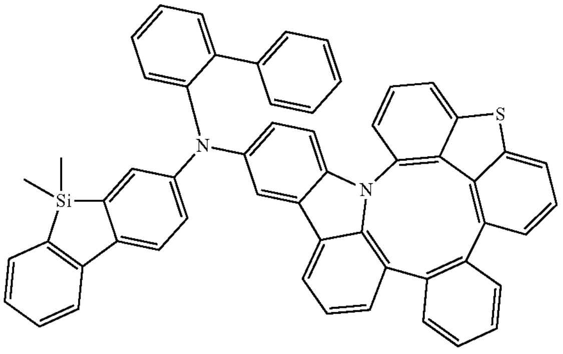
,
Compound 353
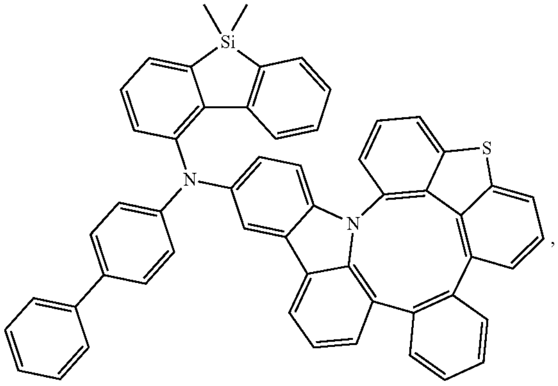
, -continued
Compound 354
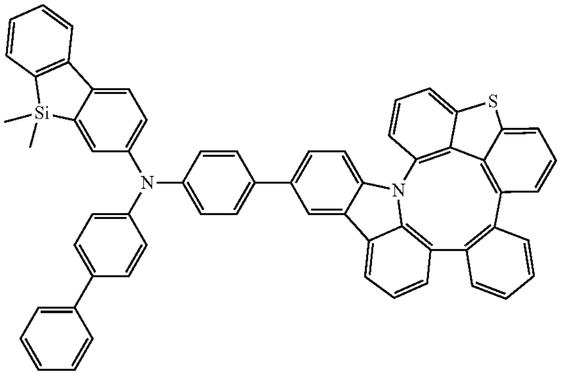
,
Compound 355
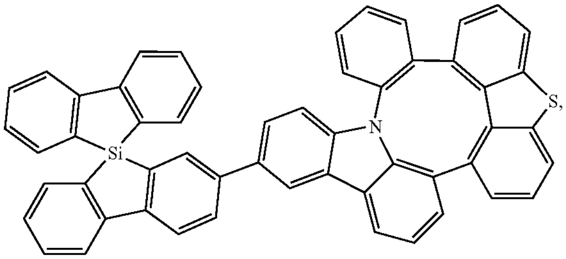
,
Compound 356
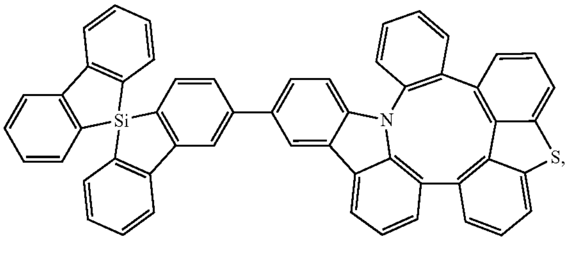
,
Compound 357
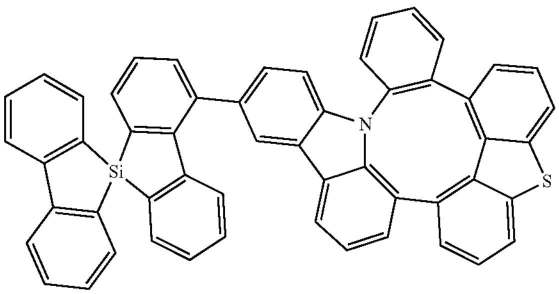
,
-continued
Compound 358
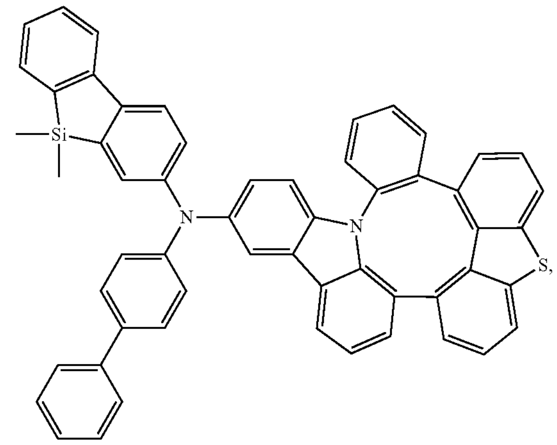
,
Compound 359
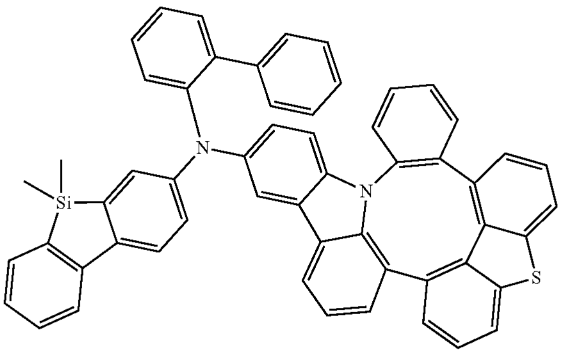
,
Compound 360
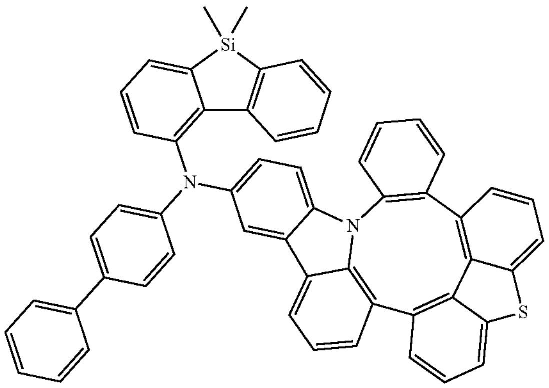
,
Compound 361
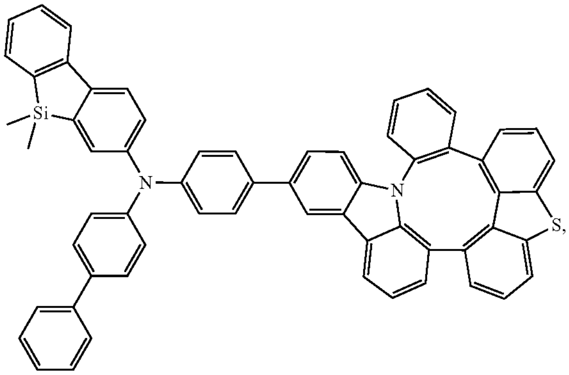
, -continued
Compound 362
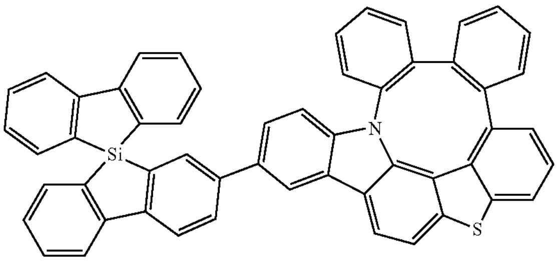
,
Compound 363
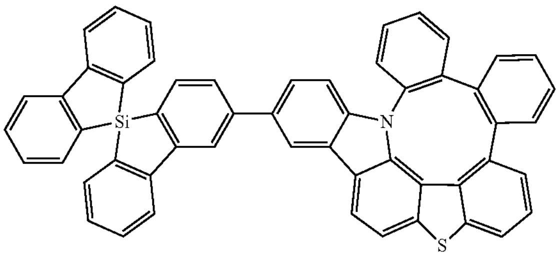
,
Compound 364
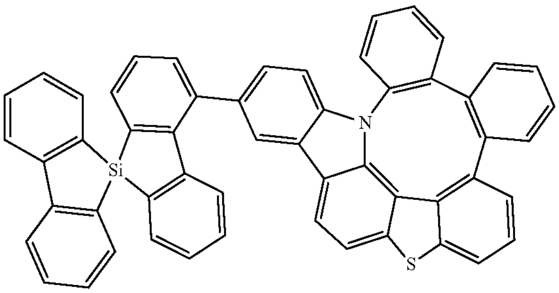
,
Compound 365
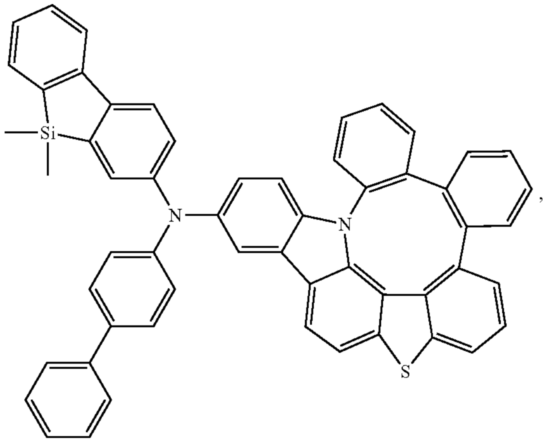
,
-continued
Compound 366
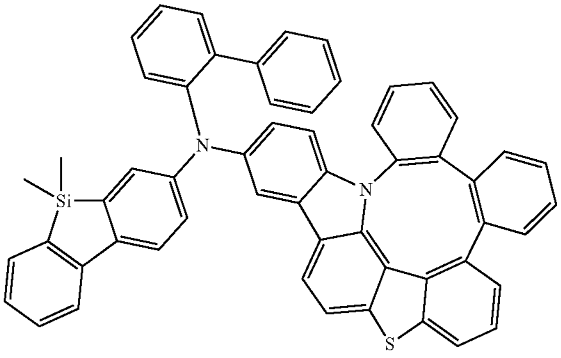
,
Compound 367
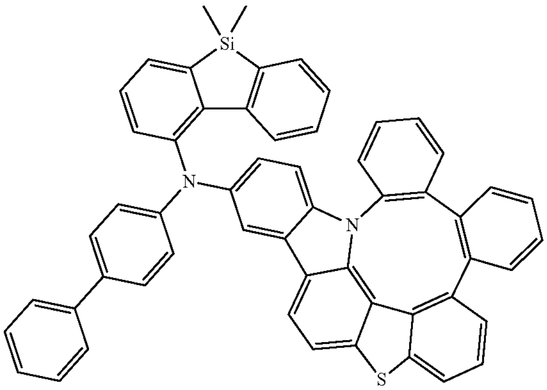
,
Compound 368
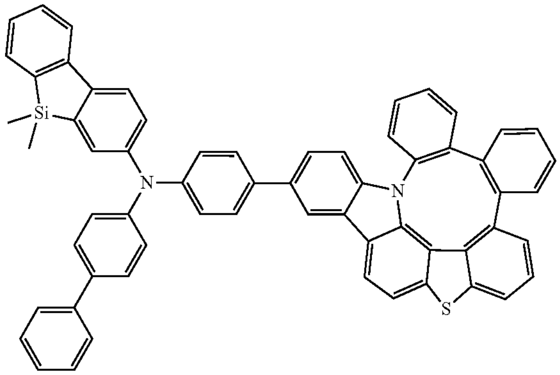
.

10. An electroluminescent device comprises:

an anode, a cathode, and an organic layer, disposed between the anode and the cathode, comprising a compound of Formula 1:

Formula 1

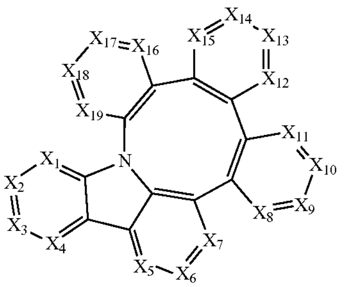

Wherein $X_1$ to $X_{19}$ are each independently selected from the group consisting of CR, and N;

Wherein R are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 50 carbon atoms, a substituted or unsubstituted heteroaryl group having 3 to 50 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring.

11. The device of claim 10, wherein the organic layer is a charge transporting layer.

12. The device of claim 10, wherein the organic layer is a charge blocking layer.

13. The device of claim 10, wherein the organic layer is an emissive layer and the compound is a host.

14. The device of claim 10, wherein the organic layer further comprises a phosphorescent emitter.

15. The device of claim 14, wherein the phosphorescent emitter is a metal complex having at least one ligand comprising any of the following structures:

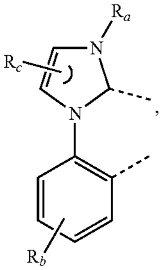,
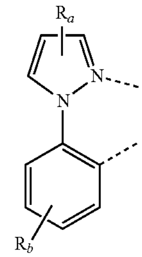,
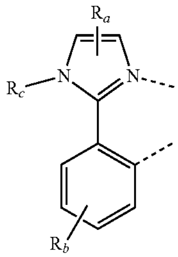,
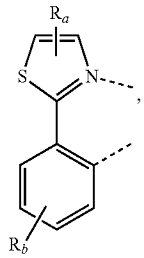,
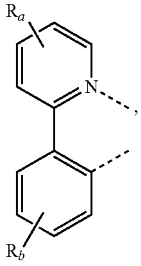,
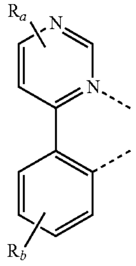,
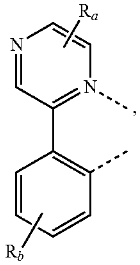,
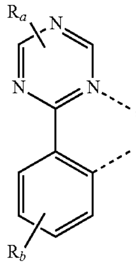,
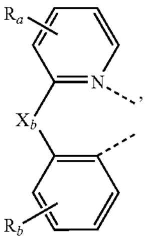,
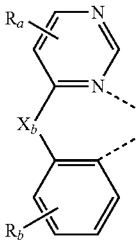,
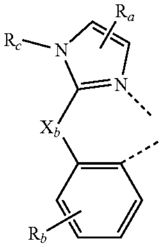, Wherein $R_a$, $R_b$, and $R_c$ can represent mono, multi substitution, or no substitution; said multi substitution refer to a range that includes di substitution, up to the maximum available substitutions of the formula;

$X_b$ is independently selected from the group consisting of O, S, Se, $NR_{N1}$, and $CR_{C1}R_{C2}$;

$R_a$, $R_b$, $R_c$, $R_{N1}$, $R_{C1}$ and $R_{C2}$ are each independently selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 50 carbon atoms, a substituted or unsubstituted heteroaryl group having 3 to 50 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, a nitrile group, an isonitrile group, a sulfanyl group, a sulfinyl group, a sulfonyl group, a phosphino group, and combinations thereof;

Any adjacent substitution can be optionally joined to form a ring.

16. The device of claim 10, wherein the organic layer is an emissive layer and the compound of Formula 1 is a thermally delayed fluorescent dopant.

17. A formulation comprising the compound of claim 1.

* * * * *